(12) United States Patent
Gopalsamy et al.

(10) Patent No.: US 11,014,908 B2
(45) Date of Patent: May 25, 2021

(54) CHEMICAL COMPOUNDS

(71) Applicant: Pfizer Inc., New York, NY (US)

(72) Inventors: Ariamala Gopalsamy, Lexington, MA (US); Arjun Venkat Narayanan, Cambridge, MA (US); Agustin Casimiro-Garcia, Concord, MA (US); Chulho Choi, Mystic, CT (US); David Hepworth, Concord, MA (US); David Walter Piotrowski, Waterford, CT (US); Hatice Gizem Yayla, Mystic, CT (US); Jayasankar Jasti, East Lyme, CT (US); Lee Richard Roberts, Belmont, MA (US); Lyn Howard Jones, Winchester, MA (US); Mihir Dineshkumar Parikh, East Greenwich, RI (US); Ming Zhu Chen, Mystic, CT (US); Olugbeminiyi Omezia Fadeyi, Harvard, MA (US); Ralph Pelton Robinson, Jr., Gales Ferry, CT (US); Robert Lee Dow, Quincy, MA (US); Shawn Cabral, Groton, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 16/695,709

(22) Filed: Nov. 26, 2019

(65) Prior Publication Data
US 2020/0172512 A1 Jun. 4, 2020

Related U.S. Application Data

(60) Provisional application No. 62/915,784, filed on Oct. 16, 2019, provisional application No. 62/772,815, filed on Nov. 29, 2018.

(51) Int. Cl.
| | | |
|---|---|---|
| *C07D 401/14* | (2006.01) | |
| *A61P 7/06* | (2006.01) | |
| *C07D 471/04* | (2006.01) | |
| *A61K 45/06* | (2006.01) | |

(52) U.S. Cl.
CPC .............. *C07D 401/14* (2013.01); *A61P 7/06* (2018.01); *C07D 471/04* (2013.01); *A61K 45/06* (2013.01)

(58) Field of Classification Search
CPC ................................ A61P 7/06; C07D 471/04
USPC ......................................................... 514/300
See application file for complete search history.

(56) References Cited

U.S. PATENT DOCUMENTS

| | | | |
|---|---|---|---|
| 7,169,797 B2 | 1/2007 | Xin et al. | |
| 8,916,593 B2 | 12/2014 | Bunnage et al. | |
| 8,952,171 B2 | 2/2015 | Xu et al. | |
| 9,422,279 B2 | 8/2016 | Metcalf et al. | |
| 9,458,139 B2 | 10/2016 | Xu et al. | |
| 9,604,999 B2 | 3/2017 | Harris et al. | |
| 9,776,960 B2 | 10/2017 | Xu et al. | |
| 9,981,939 B2 | 5/2018 | Metcalf et al. | |
| 10,017,491 B2 | 7/2018 | Metcalf et al. | |
| 10,100,040 B2 | 10/2018 | Li et al. | |
| 2004/0167188 A1 | 8/2004 | Xin et al. | |
| 2004/0214870 A1 | 10/2004 | Xin et al. | |
| 2008/0207584 A1 | 8/2008 | Habashita et al. | |
| 2013/0190315 A1 | 7/2013 | Metcalf et al. | |
| 2013/0190316 A1 | 7/2013 | Metcalf et al. | |
| 2013/0196952 A1* | 8/2013 | Bunnage .............. | C07D 401/04 514/89 |
| 2014/0271591 A1* | 9/2014 | Sinha ..................... | A61K 35/18 424/93.73 |
| 2014/0275008 A1 | 9/2014 | Xu et al. | |
| 2014/0275152 A1 | 9/2014 | Metcalf et al. | |
| 2014/0275176 A1* | 9/2014 | Xu ........................ | C07D 413/04 514/341 |
| 2014/0275181 A1 | 9/2014 | Harris et al. | |

(Continued)

FOREIGN PATENT DOCUMENTS

| | | |
|---|---|---|
| CN | 102206172 | 10/2011 |
| CN | 102206172 | 2/2015 |

(Continued)

OTHER PUBLICATIONS

Abdelsattar; Molecules 2016, 21(8), 1057. (Year: 2016).*

(Continued)

*Primary Examiner* — Daniel R Carcanague
(74) *Attorney, Agent, or Firm* — Richard V. Zanzalari

(57) ABSTRACT

The invention relates to pyrazole derivatives, to their use in medicine, to compositions containing them, to processes for their preparation and to intermediates used in such processes.

More particularly the invention relates to HbS modulators of formula (I)

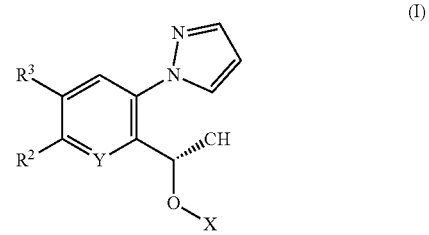

or tautomers thereof, or pharmaceutically acceptable salts of said modulators or tautomers thereof, wherein X, Y, $R^2$ and $R^3$ are as defined in the description.

HbS modulators are potentially useful in the treatment of a wide range of disorders, including sickle cell disease (SCD).

28 Claims, 3 Drawing Sheets

(56) References Cited

U.S. PATENT DOCUMENTS

| | | |
|---|---|---|
| 2015/0133430 A1 | 5/2015 | Xu et al. |
| 2015/0209443 A1* | 7/2015 | Metcalf ............... A61K 31/444 424/9.2 |
| 2016/0031865 A1 | 2/2016 | Li et al. |
| 2016/0031904 A1 | 2/2016 | Li et al. |
| 2016/0046613 A1 | 2/2016 | Metcalf et al. |
| 2016/0083343 A1 | 3/2016 | Xu et al. |
| 2016/0083348 A1 | 3/2016 | Xu et al. |
| 2016/0152602 A1 | 6/2016 | Xu et al. |
| 2017/0174654 A1 | 6/2017 | Metcalf et al. |
| 2017/0355713 A1 | 12/2017 | Harris et al. |
| 2018/0201577 A1 | 7/2018 | Xu et al. |
| 2019/0177278 A1 | 6/2019 | Sintim |
| 2019/0330181 A1 | 10/2019 | Jin et al. |

FOREIGN PATENT DOCUMENTS

| | | |
|---|---|---|
| JP | 2007176799 | 7/2007 |
| WO | 2006001463 | 5/2006 |
| WO | 2006003923 | 12/2006 |
| WO | 2009011889 | 1/2009 |
| WO | 2011015524 | 2/2011 |
| WO | 2011138751 | 11/2011 |
| WO | 2012037204 | 3/2012 |
| WO | 2012129562 | 9/2012 |
| WO | 2013102142 | 7/2013 |
| WO | 2013102145 | 7/2013 |
| WO | 2014150258 | 9/2014 |
| WO | 2014150268 | 9/2014 |
| WO | 2014150276 | 9/2014 |
| WO | 2014150289 | 9/2014 |
| WO | 2015193506 | 12/2015 |
| WO | 2016043849 | 3/2016 |
| WO | 2017096230 | 6/2017 |
| WO | 2017218960 | 12/2017 |
| WO | 2018035072 | 2/2018 |

OTHER PUBLICATIONS

Ashley-Koch; Am J Epidemiol. 2000, 151, 839-845. (Year: 2000).*
Huang; J. Med. Chem. 2014, 57, 4, 1170-1187. (Year: 2014).*
Johnson; J. Med. Chem. 2014, 57, 11, 4720-4744. (Year: 2014).*
Metcalf; ACS Med. Chem. Lett. 2017, 8, 3, 321-326. (Year: 2017).*
Nakagawa; ACS Chem. Biol. 2014, 9, 10, 2318-2325. (Year: 2014).*
Nakagawa; Mol. Pharmaceutics 2018, 15, 5, 1954-1963. (Year: 2018).*
Park; J. Med. Chem. 2003, 46, 6, 936-953 (Year: 2003).*
Piel; N. Engl. J. Med. 2017, 376, 1561-1573. (Year: 2017).*
Poillon; Biochemistry 1982, 21, 6, 1400-1406. (Year: 1982).*
Xu; Mol. Pharmaceutics 2017, 14, 10, 3499-3511. (Year: 2017).*
Zaugg; J. Biol. Chem. 1977, 252, 8542-8548. (Year: 1977).*
International Written Opinion Report dated Apr. 2, 2020 for Application No. PCT/IB2019/060171, filed on Nov. 26, 2019, 6 pages.
Metcalf, Brian W., et al., "Discovery of GBT440, Bioavailable R-State Stabilizer of Sickle Cell Hemoglobin", ACS Medicinal Chemistry Letters, Jan. 23, 2017, pp. 321-326, 8(3).
Oksenberg, Donna, et al., "GBT440 increases haemoglobin oxygen affinity, reduces sickling and prolongs RBC calf-life in a murine model of sickle cell disease", British Journal of Haematology, Oct. 2016, pp. 141-153, 175(1).
Hankins, Jane, et al., "Phamacotherapy in sickle cell disease-state of the art and future prospects", British Journal of Haematology, May 2009, pp. 296-308, 145(3).

* cited by examiner

CHEMICAL COMPOUNDS

This application is a Non-Provisional application under 35 U.S.C. 119(e) which claims the benefit of U.S. Provisional Patent Application 62/915,784 filed Oct. 16, 2019 and to U.S. Provisional Patent Application 62/772,815 filed Nov. 29, 2018.

The invention relates to pyrazole derivatives, to their use in medicine, to compositions containing them, to processes for their preparation and to intermediates used in such processes. More especially the invention relates to modulators of hemoglobin (Hb), in particular sickle hemoglobin (HbS), and their use in the treatment of diseases mediated by HbS, such as sickle cell disease (SCD).

SCD is a multisystem disorder. While carriers of HbS are protected from malaria infection (which may explain the high incidence of SCD in people of Mediterranean and African descent), people with SCD suffer from significant medical complications, including chronic anemia, acute chest syndrome, stroke, splenic and renal dysfunction, pain crises and susceptibility to bacterial infections, and those affected exhibit early mortality (Am J Epidemiol Vol. 151, No. 9, 2000, 839-845).

Moreover SCD is a significant, and growing, global health problem. In 2017 it was estimated that approximately 300,000 infants are born with sickle cell anemia every year and that this could rise to 400,000 by 2050. While early diagnosis of SCD, coupled with treatments such as penicillin prophylaxis, blood transfusion, hydroxyurea and hematopoietic stem-cell transplantation can improve survival and quality of life for some SCD patients, there is a need for treatments that are convenient (e.g. a tablet for oral administration), effective and inexpensive (N Engl J Med 2017, 376(16), 1561-1571).

Hb is a tetrameric protein in red blood cells (RBCs) that transports oxygen from the lungs to tissues and body organs, and returns carbon dioxide from tissues and body organs to the lungs. Hb binds and releases oxygen through conformational changes: oxygen is not bound to Hb in its tense (T) state, whereas oxygen is bound to Hb in its relaxed (R) state. The two states of Hb are in an equilibrium under allosteric regulation, wherein certain compounds such as 2,3-bisphosphoglycerate (2,3-BPG), carbon dioxide and proton sources stabilize Hb in its de-oxygenated T state, while oxygen stabilizes Hb in its oxygenated R state (Contin Educ Anaesth Crit Care Pain 2012, 12, 251-256).

The cause of SCD is a single gene mutation of the β-globin gene called HbS, where hydrophilic glutamic acid residue βGlu6 has been exchanged for a hydrophobic βVal6, thereby creating a hydrophobic region on the outside of the protein. Under low oxygen conditions HbS polymerizes via the mutated βVal6, whereby the hydrophobic region on one HbS tetramer binds to a hydrophobic cavity formed by the amino acid residues β1Ala70, β1Phe85, and β1Leu88 from an adjacent HbS tetramer. These polymers result in RBCs losing their ability to deform and taking on a sickle-like shape. The sickle-shaped RBCs are unable to pass through narrow capillaries, resulting in painful vaso-occlusive crises, and undergo hemolysis, leading to a shortened lifespan and anemia (ACS Med Chem Lett 2017, 8, 321-326; N Engl J Med 1997, 337(11), 762-769; Lancet 2010, 376, 2018-2031).

One approach to treating SCD would be to modulate the behaviour of HbS so as to maintain HbS in its R (i.e. oxygenated) state and thereby prevent polymerization, since polymerization of HbS only occurs when HbS is in its T (i.e. deoxygenated) state.

In addition to being of use in the treatment of SCD, HbS modulators would be of use in the treatment of any disorder or condition which would benefit from the presence of HbS in its R state, such as: disorders or conditions associated with oxygen deficiency in tissue (e.g. cancers resistant to radiotherapy and/or chemotherapy, because of the low levels of oxygen in the cell), or disorders or conditions which would benefit from increased tissue oxygenation (e.g. altitude sickness and pulmonary insufficiency).

HbS modulators potentially suitable for the treatment of, inter alia, SCD are known. WO2013/102142 and WO2013/102145 respectively disclose substituted benzaldehyde and substituted heteroaryl aldehydes. By their very nature, however, these aldehydes are reactive species and indeed covalently bind to HbS by a reversible Schiff-base linkage (i.e. by reacting with an available amino group, to form an imine). Use of such reactive species poses the real and substantial risk of unwanted modification of, or interference with, other pharmacological processes (i.e. 'off-target' effects), particularly where administration is chronic and at higher dose levels.

There is therefore an ongoing need to provide new HbS modulators that are good drug candidates, in particular new HbS modulators employing a non-covalent approach to HbS modulation.

According to a first aspect of the invention there is provided a compound of formula (I)

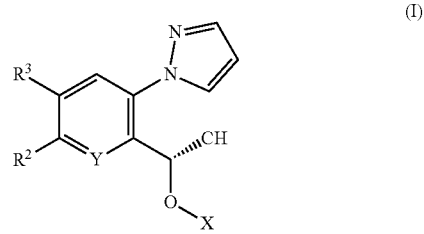

(I)

or a tautomer thereof, or a pharmaceutically acceptable salt of said compound or tautomer thereof, wherein
X is an amino substituted naphthyridine or quinoline selected from

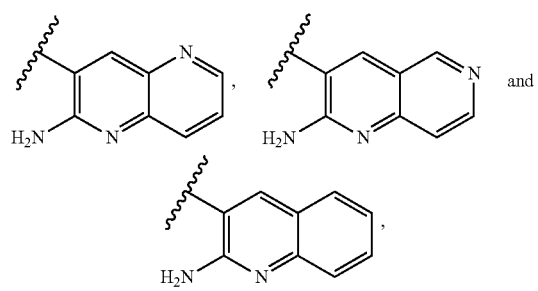

wherein the right-hand-side ring of said naphthyridine is optionally substituted by $R^1$, and wherein the right-hand-side ring of said quinoline is optionally independently substituted by one or two $R^1$;
Y is CH or N;
each $R^1$ is independently halogen; CN; $(C_1-C_4)$alkyl, optionally substituted by OH; or $CONR^4R^5$;
$R^2$ and $R^3$ together with the carbon atoms to which they are attached form a 5-membered heteroaryl containing one or two N, optionally substituted by $R^6$; or $R^2$ is H; OH; $(C_1-C_4)$alkyl, optionally substituted by OH or $CO_2R^4$; $(C_1-C_4)$alkyloxy, optionally substituted by OH or $CO_2R^4$; $CO_2R^4$; $CONR^4R^5$; $SO_2NR^4R^4$; $NR^4SO_2(C_1-C_4)$alkyl; or oxadiazolone;

$R^3$ is H or halogen;

each $R^4$ is independently H or $(C_1-C_4)$alkyl;

each $R^5$ is independently H; $(C_1-C_4)$alkyl, optionally substituted by OH, $O(C_1-C_4)$alkyl or $CO_2R^4$; $SO_2(C_1-C_4)$alkyl; or $(C_3-C_6)$cycloalkyl, optionally substituted by OH; and $R^6$ is $(C_1-C_4)$alkyl, optionally substituted by OH, $CO_2R^4$ or $CONR^4R^5$.

Described below are a number of embodiments (E1) of this first aspect of the invention, where for convenience E1 is identical thereto.

E1 A compound of formula (I) or a tautomer thereof, or a pharmaceutically acceptable salt of said compound or tautomer thereof, as defined above.

E2 A compound according to embodiment E1 or a tautomer thereof, or a pharmaceutically acceptable salt of said compound or tautomer thereof, wherein X is an amino substituted quinoline selected from

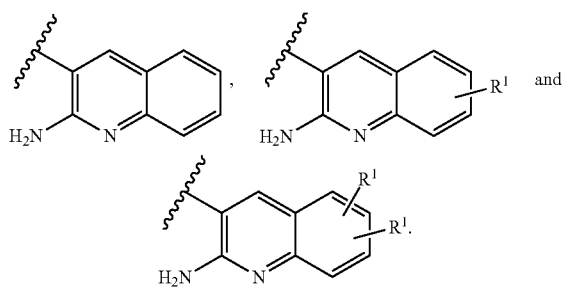

E3 A compound according to embodiment E2 or a tautomer thereof, or a pharmaceutically acceptable salt of said compound or tautomer thereof, wherein X is an amino substituted quinoline selected from

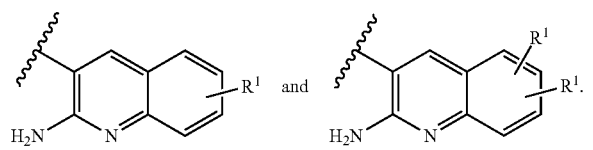

E4 A compound according to embodiment E3 or a tautomer thereof, or a pharmaceutically acceptable salt of said compound or tautomer thereof, wherein X is the amino substituted quinoline

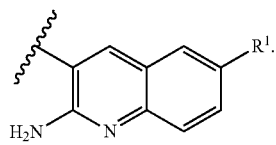

E5 A compound according to embodiment E3 or a tautomer thereof, or a pharmaceutically acceptable salt of said compound or tautomer thereof, wherein X is an amino substituted quinoline selected from

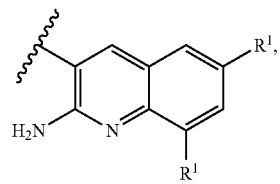

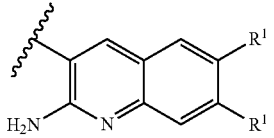 and 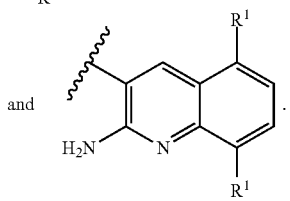

E6 A compound according to embodiment E5 or a tautomer thereof, or a pharmaceutically acceptable salt of said compound or tautomer thereof, wherein X is the amino substituted quinoline

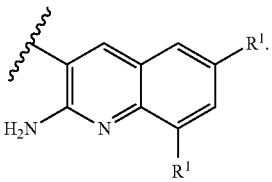

E7 A compound according to embodiment E1 or a tautomer thereof, or a pharmaceutically acceptable salt of said compound or tautomer thereof, wherein X is an amino substituted naphthyridine selected from

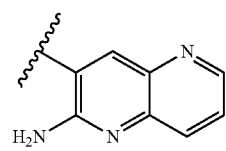 and 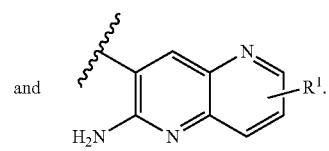

E8 A compound according to embodiment E7 or a tautomer thereof, or a pharmaceutically acceptable salt of said compound or tautomer thereof, wherein X is the amino substituted naphthyridine

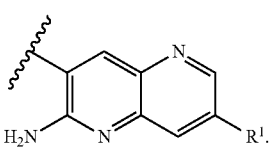

E9 A compound according to any one of embodiments E1 to E8 or a tautomer thereof, or a pharmaceutically acceptable salt of said compound or tautomer thereof, wherein each $R^1$ is independently F, Cl, Br, CN, $CH_3$ or $CONH_2$.

E10 A compound according to embodiment E9 or a tautomer thereof, or a pharmaceutically acceptable salt of said compound or tautomer thereof, wherein each $R^1$ is independently F, Cl or $CONH_2$.

E11 A compound according to embodiment E10 or a tautomer thereof, or a pharmaceutically acceptable salt of said compound or tautomer thereof, wherein each $R^1$ is F.

E12 A compound according to any one of embodiments E1 to E11 or a tautomer thereof, or a pharmaceutically acceptable salt of said compound or tautomer thereof, wherein Y is CH.

E13 A compound according to any one of embodiments E1 to E11 or a tautomer thereof, or a pharmaceutically acceptable salt of said compound or tautomer thereof, wherein Y is N.

E14 A compound according to either embodiment E12 or E13 or a tautomer thereof, or a pharmaceutically acceptable salt of said compound or tautomer thereof, wherein $R^2$ and $R^3$ together with the carbon atoms to which they are attached form a 5-membered heteroaryl selected from

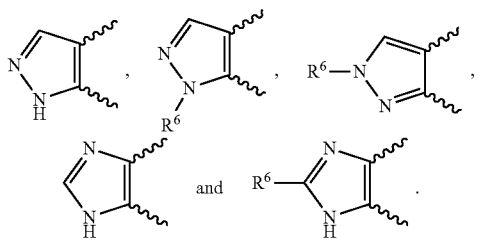

E15 A compound according to embodiment E14 or a tautomer thereof, or a pharmaceutically acceptable salt of said compound or tautomer thereof, wherein $R^2$ and $R^3$ together with the carbon atoms to which they are attached form a pyrazolyl selected from

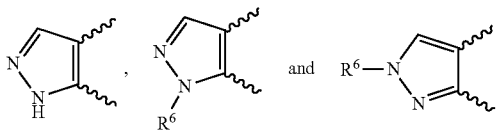

E16 A compound according to embodiments E14 or E15 or a tautomer thereof, or a pharmaceutically acceptable salt of said compound or tautomer thereof, wherein $R^6$ is $(C_1-C_4)$alkyl substituted by OH, $CO_2H$ or $CONH_2$.

E17 A compound according to embodiment E16 or a tautomer thereof, or a pharmaceutically acceptable salt of said compound or tautomer thereof, wherein $R^6$ is $(C_1-C_2)$alkyl substituted by OH, $CO_2H$ or $CONH_2$.

E18 A compound according to embodiments E12 or a tautomer thereof, or a pharmaceutically acceptable salt of said compound or tautomer thereof, wherein $R^2$ is $(C_1-C_4)$alkyl substituted by $CO_2R^4$; $(C_1-C_4)$alkyloxy substituted by $CO_2R^4$; $CO_2R^4$; $CONR^4R^5$; $SO_2NR^4R^4$; or oxadiazolone.

E19 A compound according to embodiments E18 or a tautomer thereof, or a pharmaceutically acceptable salt of said compound or tautomer thereof, wherein $R^2$ is $(C_1-C_2)$alkyl substituted by $CO_2R^4$; $(C_1-C_2)$alkyloxy substituted by $CO_2R^4$; $CO_2R^4$; $CONR^4R^5$; $SO_2NR^4R^4$;

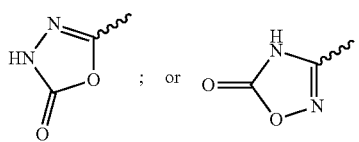

E20 A compound according to embodiment E13 or a tautomer thereof, or a pharmaceutically acceptable salt of said compound or tautomer thereof, wherein $R^2$ is H; OH; $(C_1-C_4)$alkyl substituted by OH; $(C_1-C_4)$alkyloxy; $(C_1-C_4)$alkyloxy substituted by OH or $CO_2R^4$; $CO_2R^4$; or $CONR^4R^5$.

E21 A compound according to embodiment E20 or a tautomer thereof, or a pharmaceutically acceptable salt of said compound or tautomer thereof, wherein $R^2$ is H; OH; $(C_1-C_2)$alkyl substituted by OH; $(C_1-C_2)$alkyloxy; $(C_1-C_2)$alkyloxy substituted by OH or $CO_2R^4$; $CO_2R^4$; or $CONR^4R^5$.

E22 A compound according to embodiment E21 or a tautomer thereof, or a pharmaceutically acceptable salt of said compound or tautomer thereof, wherein $R^2$ is H; OH; $(C_1-C_2)$alkyloxy; $(C_1-C_2)$alkyloxy substituted by OH or $CO_2R^4$; $CO_2R^4$; or $CONR^4R^5$.

E23 A compound according to any one of embodiments E1 to E22 or a tautomer thereof, or a pharmaceutically acceptable salt of said compound or tautomer thereof, wherein $R^3$ is H or F.

E24 A compound according to embodiment E23 or a tautomer thereof, or a pharmaceutically acceptable salt of said compound or tautomer thereof, wherein $R^3$ is H.

E25 A compound according to any one of embodiments E1 to E24 or a tautomer thereof, or a pharmaceutically acceptable salt of said compound or tautomer thereof, wherein $R^4$ is H or methyl.

E26 A compound according to embodiment E25 or a tautomer thereof, or a pharmaceutically acceptable salt of said compound or tautomer thereof, wherein $R^4$ is H.

E27 A compound according to any one of embodiments E1 to E26 or a tautomer thereof, or a pharmaceutically acceptable salt of said compound or tautomer thereof, wherein $R^5$ is H or methyl.

E28 A compound according to embodiment E27 or a tautomer thereof, or a pharmaceutically acceptable salt of said compound or tautomer thereof, wherein $R^5$ is H.

E29 A compound according to embodiment E1 or a tautomer thereof, or a pharmaceutically acceptable salt of said compound or tautomer thereof, selected from:

5-{(1S)-1-[(2-amino-6-fluoroquinolin-3-yl)oxy]ethyl}-2-fluoro-4-(1H-pyrazol-1-yl)benzamide;

5-{(1S)-1-[(2-amino-7-chloro-6-fluoroquinolin-3-yl)oxy]ethyl}-2-fluoro-4-(1H-pyrazol-1-yl)benzamide;

3-{(1S)-1-[(2-amino-6-bromoquinolin-3-yl)oxy]ethyl}-4-(1H-pyrazol-1-yl)benzamide;

3-{(1S)-1-[(2-amino-6-fluoroquinolin-3-yl)oxy]ethyl}-4-(1H-pyrazol-1-yl)benzoic acid;

Potassium 3-{(1S)-1-[(2-amino-6-fluoroquinolin-3-yl)oxy]ethyl}-4-(1H-pyrazol-1-yl)benzoate;

5-[3-{(1S)-1-[(2-amino-6-fluoroquinolin-3-yl)oxy]ethyl}-4-(1H-pyrazol-1-yl)phenyl]-1,3,4-oxadiazol-2(3H)-one;

methyl 3-{(1S)-1-[(2-amino-6-fluoroquinolin-3-yl)oxy]ethyl}-4-(1H-pyrazol-1-yl)benzoate;

3-{(1S)-1-[(2-amino-6-fluoroquinolin-3-yl)oxy]ethyl}-4-(1H-pyrazol-1-yl)benzenesulfonamide;

[3-{(1S)-1-[(2-amino-6-fluoroquinolin-3-yl)oxy]ethyl}-4-(1H-pyrazol-1-yl)phenyl]acetic acid;

5-{(1S)-1-[(2-amino-6-fluoroquinolin-3-yl)oxy]ethyl}-2-fluoro-4-(1H-pyrazol-1-yl)benzoic acid;

N-[3-{(1S)-1-[(2-amino-6-fluoroquinolin-3-yl)oxy]ethyl}-4-(1H-pyrazol-1-yl)benzoyl]glycine;

3-{(1S)-1-[(2-amino-6-fluoroquinolin-3-yl)oxy]ethyl}-N-(2-methoxyethyl)-4-(1H-pyrazol-1-yl)benzamide;

3-{(1S)-1-[(2-amino-6-fluoroquinolin-3-yl)oxy]ethyl}-N-(2-hydroxyethyl)-4-(1H-pyrazol-1-yl)benzamide;

3-{(1S)-1-[(2-amino-6-fluoroquinolin-3-yl)oxy]ethyl}-N-(3-hydroxypropyl)-4-(1H-pyrazol-1-yl)benzamide;
3-{(1S)-1-[(2-amino-6-fluoroquinolin-3-yl)oxy]ethyl}-N-(trans-3-hydroxycyclobutyl)-4-(1H-pyrazol-1-yl)benzamide;
[3-{(1S)-1-[(2-amino-6-fluoroquinolin-3-yl)oxy]ethyl}-4-(1H-pyrazol-1-yl)phenoxy]acetic acid;
3-[3-{(1S)-1-[(2-amino-6-fluoroquinolin-3-yl)oxy]ethyl}-4-(1H-pyrazol-1-yl)phenyl]propanoic acid;
3-[3-{(1S)-1-[(2-amino-6-fluoroquinolin-3-yl)oxy]ethyl}-4-(1H-pyrazol-1-yl)phenyl]-1,2,4-oxadiazol-5(4H)-one;
N-[3-{(1S)-1-[(2-amino-6-fluoroquinolin-3-yl)oxy]ethyl}-4-(1H-pyrazol-1-yl)phenyl]methanesulfonamide;
3-{(1S)-1-[(2-amino-5,8-difluoroquinolin-3-yl)oxy]ethyl}-4-(1H-pyrazol-1-yl)benzoic acid;
methyl 3-{(1S)-1-[(2-amino-6,8-difluoroquinolin-3-yl)oxy]ethyl}-4-(1H-pyrazol-1-yl)benzoate;
3-{(1S)-1-[(2-amino-6,8-difluoroquinolin-3-yl)oxy]ethyl}-4-(1H-pyrazol-1-yl)benzoic acid;
3-{(1S)-1-[(2-amino-7-methyl-1,6-naphthyridin-3-yl)oxy]ethyl}-4-(1H-pyrazol-1-yl)benzoic acid;
5-{(1S)-1-[(2-amino-6,8-difluoroquinolin-3-yl)oxy]ethyl}-2-fluoro-4-(1H-pyrazol-1-yl)benzoic acid;
3-{(1S)-1-[(2-amino-6,8-difluoroquinolin-3-yl)oxy]ethyl}-N-(methylsulfonyl)-4-(1H-pyrazol-1-yl)benzamide;
6-bromo-3-{(1S)-1-[5-fluoro-3-(1H-pyrazol-1-yl)pyridin-2-yl]ethoxy}quinolin-2-amine;
2-amino-3-{(1S)-1-[5-fluoro-3-(1H-pyrazol-1-yl)pyridin-2-yl]ethoxy}quinoline-6-carbonitrile;
2-amino-3-{(1S)-1-[5-fluoro-3-(1H-pyrazol-1-yl)pyridin-2-yl]ethoxy}quinoline-6-carboxamide;
6-bromo-3-{(1S)-1-[3-(1H-pyrazol-1-yl)pyridin-2-yl]ethoxy}quinolin-2-amine;
7-chloro-6-fluoro-3-{(1S)-1-[3-(1H-pyrazol-1-yl)pyridin-2-yl]ethoxy}quinolin-2-amine;
2-amino-3-{(1S)-1-[3-(1H-pyrazol-1-yl)pyridin-2-yl]ethoxy}quinoline-6-carboxamide;
7-chloro-6-fluoro-3-{(1S)-1-[5-fluoro-3-(1H-pyrazol-1-yl)pyridin-2-yl]ethoxy}quinolin-2-amine;
6-{(1S)-1-[(2-amino-7-chloro-6-fluoroquinolin-3-yl)oxy]ethyl}-5-(1H-pyrazol-1-yl)pyridine-2-carboxamide;
6-fluoro-3-{(1S)-1-[5-fluoro-3-(1H-pyrazol-1-yl)pyridin-2-yl]ethoxy}quinolin-2-amine;
2-amino-7-fluoro-3-{(1S)-1-[5-fluoro-3-(1H-pyrazol-1-yl)pyridin-2-yl]ethoxy}quinoline-6-carboxamide;
2-amino-8-fluoro-3-{(1S)-1-[5-fluoro-3-(1H-pyrazol-1-yl)pyridin-2-yl]ethoxy}quinoline-6-carboxamide;
3-{(1S)-1-[5-fluoro-3-(1H-pyrazol-1-yl)pyridin-2-yl]ethoxy}-7-methyl-1,6-naphthyridin-2-amine;
6-{(1S)-1-[(2-amino-6-fluoroquinolin-3-yl)oxy]ethyl}-5-(1H-pyrazol-1-yl)pyridine-2-carboxylic acid;
6,8-difluoro-3-{(1S)-1-[5-fluoro-3-(1H-pyrazol-1-yl)pyridin-2-yl]ethoxy}quinolin-2-amine;
6-{(1S)-1-[(2-amino-6-fluoroquinolin-3-yl)oxy]ethyl}-3-fluoro-5-(1H-pyrazol-1-yl)pyridine-2-carboxylic acid;
{[6-{(1S)-1-[(2-amino-6-fluoroquinolin-3-yl)oxy]ethyl}-5-(1H-pyrazol-1-yl)pyridin-2-yl]oxy}acetic acid;
2-{[6-{(1S)-1-[(2-amino-6-fluoroquinolin-3-yl)oxy]ethyl}-5-(1H-pyrazol-1-yl)pyridin-2-yl]oxy}ethanol;
2-amino-3-{(1S)-1-[6-(2-hydroxyethoxy)-3-(1H-pyrazol-1-yl)pyridin-2-yl]ethoxy}quinoline-6-carboxamide;
5,8-difluoro-3-{(1S)-1-[5-fluoro-3-(1H-pyrazol-1-yl)pyridin-2-yl]ethoxy}quinolin-2-amine;
2-amino-3-{(1S)-1-[6-hydroxy-3-(1H-pyrazol-1-yl)pyridin-2-yl]ethoxy}quinoline-6-carboxamide;
3-{(1S)-1-[5-fluoro-3-(1H-pyrazol-1-yl)pyridin-2-yl]ethoxy}quinolin-2-amine;
6-{(1S)-1-[(2-amino-7-methyl-1,6-naphthyridin-3-yl)oxy]ethyl}-5-(1H-pyrazol-1-yl)pyridin-2-ol;
6-{(1S)-1-[(2-amino-1,5-naphthyridin-3-yl)oxy]ethyl}-5-(1H-pyrazol-1-yl)pyridin-2-ol;
6-{(1S)-1-[(2-amino-7-fluoro-1,5-naphthyridin-3-yl)oxy]ethyl}-5-(1H-pyrazol-1-yl)pyridin-2-ol;
6-[(1S)-1-{[2-amino-6-(hydroxymethyl)quinolin-3-yl]oxy}ethyl]-5-(1H-pyrazol-1-yl)pyridin-2-ol;
6-[(1S)-1-{[2-amino-6-(2-hydroxypropan-2-yl)quinolin-3-yl]oxy}ethyl]-5-(1H-pyrazol-1-yl)pyridin-2-ol;
6-[(1S)-1-({2-amino-6-[(1R)-1-hydroxyethyl]quinolin-3-yl}oxy)ethyl]-5-(1H-pyrazol-1-yl)pyridin-2-ol;
6-[(1S)-1-({2-amino-6-[(1S)-1-hydroxyethyl]quinolin-3-yl}oxy)ethyl]-5-(1H-pyrazol-1-yl)pyridin-2-ol;
6-{(1S)-1-[(2-amino-6,8-difluoroquinolin-3-yl)oxy]ethyl}-5-(1H-pyrazol-1-yl)pyridin-2-ol;
6-{(1S)-1-[(2-amino-6-methyl-1,5-naphthyridin-3-yl)oxy]ethyl}-5-(1H-pyrazol-1-yl)pyridin-2-ol;
2-amino-3-{(1S)-1-[6-(hydroxymethyl)-3-(1H-pyrazol-1-yl)pyridin-2-yl]ethoxy}quinoline-6-carboxamide;
6,8-difluoro-3-{(1S)-1-[6-methoxy-3-(1H-pyrazol-1-yl)pyridin-2-yl]ethoxy}quinolin-2-amine;
6-fluoro-3-{(1S)-1-[6-methoxy-3-(1H-pyrazol-1-yl)pyridin-2-yl]ethoxy}quinolin-2-amine;
6-{(1S)-1-[(2-amino-6-fluoroquinolin-3-yl)oxy]ethyl}-5-(1H-pyrazol-1-yl)pyridin-2-ol;
6-fluoro-3-{(1S)-1-[5-(1H-pyrazol-1-yl)-1H-indazol-6-yl]ethoxy}quinolin-2-amine;
7-chloro-6-fluoro-3-{(1S)-1-[5-(1H-pyrazol-1-yl)-1H-indazol-6-yl]ethoxy}quinolin-2-amine;
2-amino-3-{(1S)-1-[5-(1H-pyrazol-1-yl)-1H-indazol-6-yl]ethoxy}quinoline-6-carboxamide;
2-amino-3-{(1S)-1-[5-(1H-pyrazol-1-yl)-1H-pyrazolo[3,4-b]pyridin-6-yl]ethoxy}quinoline-6-carboxamide;
6-fluoro-3-{(1S)-1-[5-(1H-pyrazol-1-yl)-1H-benzimidazol-6-yl]ethoxy}quinolin-2-amine;
6-fluoro-3-{(1S)-1-[2-methyl-5-(1H-pyrazol-1-yl)-1H-benzimidazol-6-yl]ethoxy}quinolin-2-amine;
2-amino-7-fluoro-3-{(1R)-1-[5-(1H-pyrazol-1-yl)-1H-indazol-6-yl]ethoxy}quinoline-6-carboxamide;
tert-butyl (S)-2-(6-(1-((2-amino-6-fluoroquinolin-3-yl)oxy)ethyl)-5-(1H-pyrazol-1-yl)-1H-indazol-1-yl)acetate;
[6-{(1S)-1-[(2-amino-6-fluoroquinolin-3-yl)oxy]ethyl}-5-(1H-pyrazol-1-yl)-1H-indazol-1-yl]acetic acid;
6-fluoro-3-{(1S)-1-[5-(1H-pyrazol-1-yl)-1H-pyrazolo[3,4-b]pyridin-6-yl]ethoxy}quinolin-2-amine;
[6-{(1S)-1-[(2-amino-6,8-difluoroquinolin-3-yl)oxy]ethyl}-5-(1H-pyrazol-1-yl)-1H-indazol-1-yl]acetic acid;
2-[6-{(1S)-1-[(2-amino-6-fluoroquinolin-3-yl)oxy]ethyl}-5-(1H-pyrazol-1-yl)-1H-indazol-1-yl]acetamide;
[6-{(1S)-1-[(2-amino-6-fluoroquinolin-3-yl)oxy]ethyl}-5-(1H-pyrazol-1-yl)-2H-indazol-2-yl]acetic acid;
2-[6-{(1S)-1-[(2-amino-6,8-difluoroquinolin-3-yl)oxy]ethyl}-5-(1H-pyrazol-1-yl)-1H-indazol-1-yl]ethanol;
2-[6-{(1S)-1-[(2-amino-6-fluoroquinolin-3-yl)oxy]ethyl}-5-(1H-pyrazol-1-yl)-1H-indazol-1-yl]ethanol;
2-amino-3-{(1S)-1-[1-(2-hydroxyethyl)-5-(1H-pyrazol-1-yl)-1H-indazol-6-yl]ethoxy}quinoline-6-carboxamide;
7-methyl-3-{(1S)-1-[5-(1H-pyrazol-1-yl)-1H-pyrazolo[3,4-b]pyridin-6-yl]ethoxy}-1,6-naphthyridin-2-amine;
2-amino-7-fluoro-3-{(1S)-1-[5-(1H-pyrazol-1-yl)-1H-pyrazolo[3,4-b]pyridin-6-yl]ethoxy}quinoline-6-carboxamide, and
2-[6-{(1S)-1-[(2-amino-7-methyl-1,6-naphthyridin-3-yl)oxy]ethyl}-5-(1H-pyrazol-1-yl)-1H-pyrazolo[3,4-b]pyridin-1-yl]ethanol.

E30 A compound according to any one of embodiments E1 to E29, or a pharmaceutically acceptable salt thereof.

E31 The compound according to embodiment E29 which is 3-{(1S)-1-[(2-amino-6,8-difluoroquinolin-3-yl)oxy]ethyl}-4-(1H-pyrazol-1-yl)benzoic acid, or a tautomer thereof.

E32 The compound according to embodiment E31 which is 3-{(1S)-1-[(2-amino-6,8-difluoroquinolin-3-yl)oxy]ethyl}-4-(1H-pyrazol-1-yl)benzoic acid tris(hydroxymethyl)aminomethane salt, or a tautomer thereof.

E33 The compound according to embodiment E29 which is 6-{(1S)-1-[(2-amino-6-fluoroquinolin-3-yl)oxy]ethyl}-5-(1H-pyrazol-1-yl)pyridin-2-ol, or a tautomer thereof.

E34 The compound according to embodiment E29 which is (S)-6-(1-((2-amino-6-fluoroquinolin-3-yl)oxy)ethyl)-5-(1H-pyrazol-1-yl)pyridin-2(1H)-one, or a tautomer thereof.

E35 The compound according to embodiment E29 which is 2-amino-7-fluoro-3-{(1S)-1-[5-(1H-pyrazol-1-yl)-1H-pyrazolo[3,4-b]pyridin-6-yl]ethoxy}quinoline-6-carboxamide, or a tautomer thereof.

E36 A compound according to any one of embodiments E31 to E35.

Figure 1:
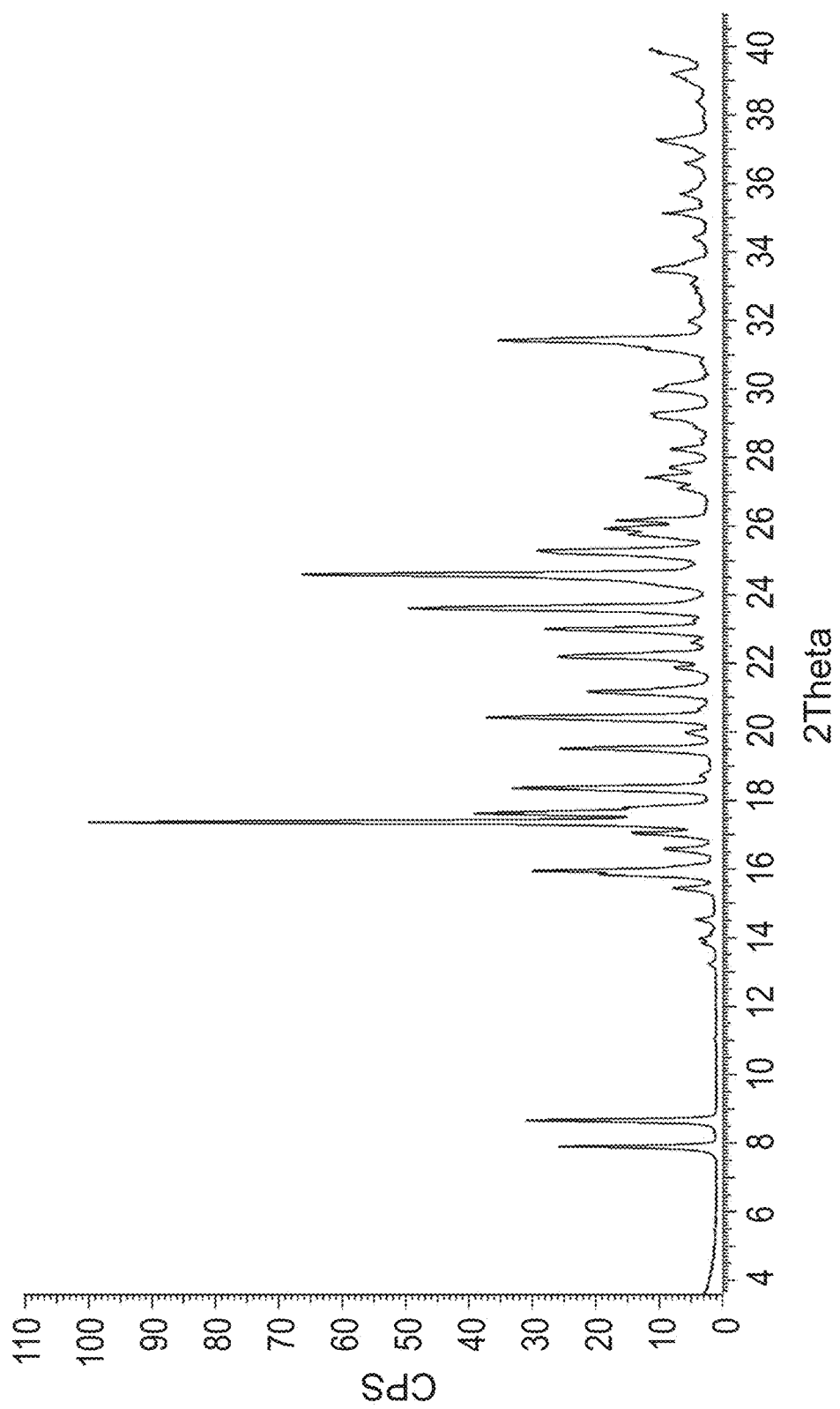
FIG. 1 is a PXRD pattern for the crystalline form (Form 1) of (S)-6-(1-((2-amino-6-fluoroquinolin-3-yl)oxy)ethyl)-5-(1H-pyrazol-1-yl)pyridin-2(1H)-one.

In compounds of formula (I) and tautomers thereof:

Alkyl means a straight or branched chain hydrocarbon group of formula —$C_nH_{(2n+1)}$. Examples of alkyl include methyl, ethyl, n-propyl, i-propyl, n-butyl, i-butyl, sec-butyl and t-butyl.

Alkyloxy means an alkyl substituent attached through an oxygen atom. Examples of alkyloxy include methoxy, ethoxy, n-propoxy, i-propoxy, n-butoxy, i-butoxy, sec-butoxy and t-butoxy.

Cycloalkyl means a cyclic hydrocarbon group of formula —$C_nH_{(2n-1)}$ containing at least three carbon atoms. Examples of Cycloalkyl include cyclopropyl, cyclobutyl, cyclopentyl and cyclohexyl.

Examples of halogen include fluoro (F), chloro (Cl), bromo (Br) and iodo (I).

Examples of 5-membered heteroaryl containing one or two N include pyrrolyl, pyrazolyl and imidazoyl.

Hereinafter, all references to compounds of the invention include compounds of formula (I) or tautomers thereof, or pharmaceutically acceptable salts, solvates, or multi-component complexes of said compounds or tautomers thereof, or pharmaceutically acceptable solvates or multi-component complexes of pharmaceutically acceptable salts of compounds of formula (I) or tautomers thereof, as discussed in more detail below.

Preferred compounds of the invention are compounds of formula (I) or tautomers thereof, or pharmaceutically acceptable salts of said compounds or tautomers thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, 1,5-naphathalenedisulfonate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, benzathine, calcium, choline, diethylamine, diolamine, glycine, lithium, lysine, magnesium, meglumine, olamine, potassium, sodium, tromethamine and zinc salts.

Hemisalts of acids and bases may also be formed, for example, hemisulphate and hemicalcium salts.

The skilled person will appreciate that the aforementioned salts include ones wherein the counterion is optically active, for example d-lactate or l-lysine, or racemic, for example dl-tartrate or dl-arginine.

For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of formula (I) or tautomers thereof may be prepared by one or more of three methods:

(i) by reacting the compound of formula (I) or tautomer thereof with the desired acid or base;

(ii) by removing an acid- or base-labile protecting group from a suitable precursor of the compound of formula (I) or tautomer thereof using the desired acid or base; or (iii) by converting one salt of the compound of formula (I) or tautomer thereof to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of formula (I) or tautomers thereof, or pharmaceutically acceptable salts of said compounds or tautomers thereof, may exist in both unsolvated and solvated forms. The term 'solvate' is used herein to describe a molecular complex comprising a compound of formula (I) or tautomer thereof, or a pharmaceutically acceptable salt of said compound or tautomer thereof and one or more pharmaceutically acceptable solvent molecules, for example, ethanol. The term 'hydrate' is employed when said solvent is water. Pharmaceutically acceptable solvates in accordance with the invention include those wherein the solvent of crystallization may be isotopically substituted, e.g. $D_2O$, $d_6$-acetone and $d_6$-DMSO.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995), incorporated herein by reference. Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

Also included within the scope of the invention are multi-component complexes (other than salts and solvates) of compounds of formula (I) or tautomers thereof, or pharmaceutically acceptable salts of said compounds or tautomers thereof, wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889-1896, by O. Almarsson and M. J. Zaworotko (2004), incorporated herein by reference. For a general review of multi-component complexes, see J Pharm Sci, 64 (8), 1269-1288, by Haleblian (August 1975), incorporated herein by reference.

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO$^-$Na$^+$, —COO—K$^+$, or —SO$_3^-$Na$^+$) or non-ionic (such as —N$^-$N$^+$(CH$_3$)$_3$) polar head group. For more information, see *Crystals and the Polarizing Microscope* by N. H. Hartshorne and A. Stuart, 4th Edition (Edward Arnold, 1970), incorporated herein by reference.

The compounds of the invention may be administered as prodrugs. Thus certain derivatives of compounds of formula (I) or tautomers thereof which may have little or no pharmacological activity themselves can, when administered into or onto the body, be converted into compounds of formula (I) or tautomers thereof having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

Prodrugs can, for example, be produced by replacing appropriate functionalities present in a compound of formula (I) or a tautomer thereof with certain moieties known to those skilled in the art as 'pro-moieties' as described, for example, in "Design of Prodrugs" by H Bundgaard (Elsevier, 1985).

Examples of prodrugs include phosphate prodrugs, such as dihydrogen or dialkyl (e.g. di-tert-butyl) phosphate prodrugs. Further examples of replacement groups in accordance with the foregoing examples and examples of other prodrug types may be found in the aforementioned references.

Also included within the scope of the invention are metabolites of compounds of formula (I) or tautomers thereof, that is, compounds formed in vivo upon administration of the drug. Some examples of metabolites in accordance with the invention include, where the compound of formula (I) or tautomer thereof contains a phenyl (Ph) moiety, a phenol derivative thereof (-Ph>-PhOH).

Formula (I) contains an asymmetric carbon atom and is stereospecifically defined.

The skilled person will also appreciate that one or more substituents in formula (I) may introduce one or more additional asymmetric carbon atoms. Compounds of the invention containing said one or more additional asymmetric carbon atoms can exist as two or more stereoisomers; included within the scope of the invention are all such stereoisomers (including epimers) of the compounds of the invention and mixtures of two or more thereof.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) or tautomer thereof contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

Chiral chromatography using sub- and supercritical fluids may be employed. Methods for chiral chromatography useful in some embodiments of the present invention are known; see, for example, Smith, Roger M., Loughborough University, Loughborough, UK; Chromatographic Science Series (1998), 75 (Supercritical Fluid Chromatography with Packed Columns), pp. 223-249 and references cited therein.

Mixtures of stereoisomers may be separated by conventional techniques known to those skilled in the art; see, for example, "Stereochemistry of Organic Compounds" by E. L. Eliel and S. H. Wilen (Wiley, New York, 1994).

Where structural isomers are interconvertible via a low energy barrier, tautomeric isomerism ('tautomerism') and conformational isomerism can occur.

Tautomerism can take the form of proton tautomerism in compounds of formula (I) containing, for example, an amide group (i.e. amide-imidic acid tautomerism), or so-called valence tautomerism in compounds which contain an aromatic moiety. With reference to Examples 58, 58a and 58b, an example of such tautomerism is shown below:

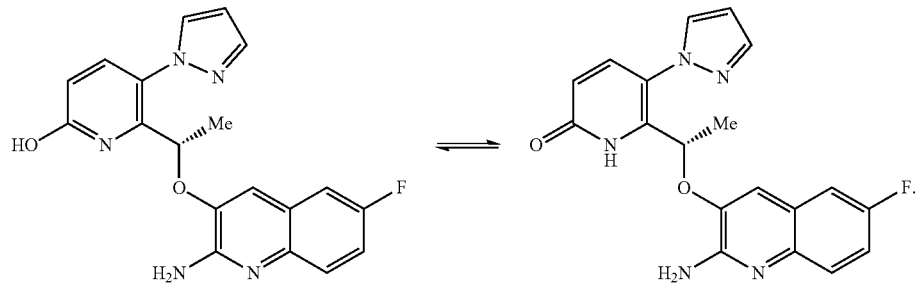 [SMILES: C[C@H](Oc1cc2cc(F)ccc2nc1N)c1nc(O)ccc1-n1cccn1 ; C[C@H](Oc1cc2cc(F)ccc2nc1N)c1[nH]c(=O)ccc1-n1cccn1]

The skilled person will appreciate that, in addition to Examples 58-58b, amide-imidic acid tautomerism can take place in the compounds of Examples 44, 46-54 and 78. While, for conciseness, the compounds of formula (I) have been drawn herein in a single tautomeric form, all possible tautomeric forms, especially those arising from proton tautomerism, and in particular amide-imidic acid tautomers and all mixtures thereof, are included within the scope of the invention.

Conformational isomerism is a form of stereoisomerism in which the isomers can be interconverted exclusively by rotations about single bonds. Such isomers are generally referred to as conformational isomers or conformers and, specifically, as rotamers. While, for conciseness, the compounds of formula (I) and tautomers thereof have been drawn in a single conformational form, all possible conformers are included within the scope of the invention.

The scope of the invention includes all crystal forms of the compounds of the invention, including racemates and racemic mixtures (conglomerates) thereof. Stereoisomeric conglomerates may also be separated by the conventional techniques described herein just above.

The scope of the invention includes all pharmaceutically acceptable isotopically-labelled compounds of the invention wherein one or more atoms are replaced by atoms having the same atomic number, but an atomic mass or mass number different from the atomic mass or mass number which predominates in nature.

Examples of isotopes suitable for inclusion in the compounds of the invention include isotopes of: hydrogen, such as $^{2}H$ and $^{3}H$; carbon, such as $^{11}C$, $^{13}C$ and $^{14}C$; nitrogen, such as $^{13}N$ and $^{15}N$; and oxygen, such as $^{15}O$, $^{17}O$ and $^{18}O$.

Certain isotopically-labelled compounds of the invention, for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection. Substitution with heavier isotopes such as deuterium (D), i.e. $^{2}H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{15}O$ and $^{13}N$, can be useful in Positron Emission Topography (PET) studies for examining substrate receptor occupancy.

Isotopically-labeled compounds of formula (I) and tautomers thereof can generally be prepared by conventional techniques known to those skilled in the art or by processes analogous to those described in the accompanying examples and preparations using an appropriate isotopically-labeled reagent in place of the non-labeled reagent previously employed.

Also within the scope of the invention are intermediate compounds or tautomers thereof as hereinafter defined, all salts, solvates and complexes thereof and all solvates and complexes of salts thereof as defined hereinbefore for compounds of formula (I). The invention includes all polymorphs of the aforementioned species and crystal habits thereof.

When preparing a compound of formula (I) or a tautomer thereof in accordance with the invention, a person skilled in the art may routinely select the form of intermediate which provides the best combination of features for this purpose. Such features include the melting point, solubility, processability and yield of the intermediate form and the resulting ease with which the product may be purified on isolation.

The compounds of the invention may be prepared by any method known in the art for the preparation of compounds of analogous structure. In particular, the compounds of the invention can be prepared by the procedures described by reference to the schemes that follow, or by the specific methods described in the examples, or by similar processes to either.

The skilled person will appreciate that the experimental conditions set forth in the schemes that follow are illustrative of suitable conditions for effecting the transformations shown, and that it may be necessary or desirable to vary the precise conditions employed for the preparation of compounds of formula (I) or tautomers thereof. It will be further appreciated that it may be necessary or desirable to carry out the transformations in a different order from that described in the schemes, or to modify one or more of the transformations, to provide the desired compound of the invention.

In addition, the skilled person will appreciate that it may be necessary or desirable at any stage in the synthesis of compounds of the invention to protect one or more sensitive groups, so as to prevent undesirable side reactions. In particular, it may be necessary or desirable to protect hydroxyl, carboxyl and/or amino groups. The protecting groups used in the preparation of the compounds of the invention may be used in conventional manner; see, for example, those described in 'Greene's Protective Groups in Organic Synthesis' by Theodora W Greene and Peter G M Wuts, fifth edition, (John Wiley and Sons, 2014), incorporated herein by reference, and in particular chapters 2, 5 and 7 respectively, which also describes methods for the removal of such groups.

In the following general processes:
- X, Y and $R^1$ to $R^6$ are as previously defined for a compound of formula (I) or a tautomer thereof unless otherwise stated;
- $Z^1$ and $Z^2$ are selected from CH or N, and the ring bearing $Z^1$ and $Z^2$ may be appropriately substituted by one or two $R^1$, so as to provide a compound of formula (I) or tautomer thereof wherein X is as previously defined;
- PG is a suitable amino protecting group such as a carbamate, alkyl, benzyl or phthaloyl group, and is preferably, Boc, tBu, benzyl, PMB or phthaloyl;
- Hal is halogen, preferably chloro (Cl) in Scheme 6 and iodo (I) in Scheme 8; and
- LG is a leaving group, such as Cl, mesylate or tosylate (preferable mesylate).

According to a first process, compounds of Formula (I) or tautomers thereof may be prepared from alcohols of Formulae (II) and (III) as illustrated by Scheme 1

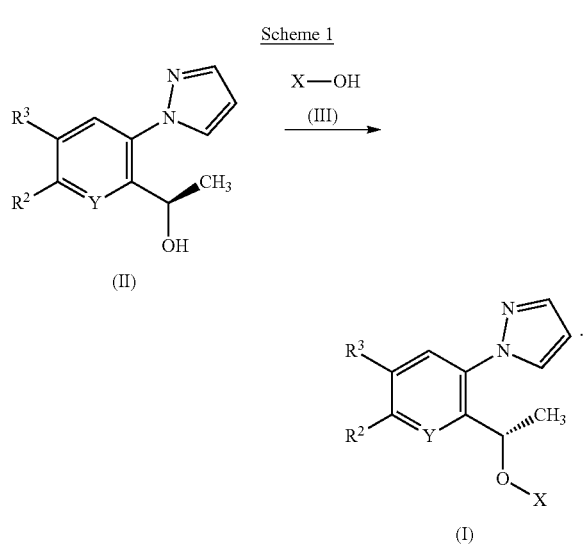

Compounds of Formula (I) or tautomers thereof may be prepared from alcohols of Formulae (II) and (III) under Mitsunobu reaction conditions—i.e. in the presence of an excess of azodicarboxylate and trialkyl or triaryl phosphine and in a polar aprotic solvent such as THF or DMF. Preferred conditions comprise reaction of the alcohols of Formulae (II) and (III) in the presence of excess DIAD and $PPh_3$ or $P(nBu)_3$ in THF, optionally with DMF as co-solvent, at between 0° C. and 50° C.

According to a second process, compounds of Formula (I) or tautomers thereof may be prepared from compounds of Formulae (III), (IV) and (V) as illustrated by Scheme 2

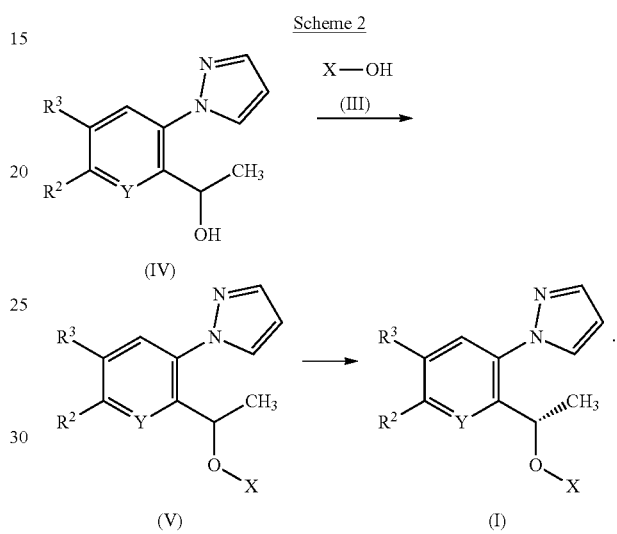

Compounds of Formula (V) may be prepared from alcohols of Formulae (III) and (IV) under Mitsunobu reaction conditions as described previously in Scheme 1.

Compounds of Formula (I) or tautomers thereof may be prepared by chiral purification of compounds of Formula (V) using methods well known to the skilled person, such as SFC, HPLC or recrystallization.

According to a third process, compounds of Formula (I) or tautomers thereof may be prepared from compounds of Formulae (II), (VI), (VII), (VIII) and (IX) as illustrated by Scheme 3

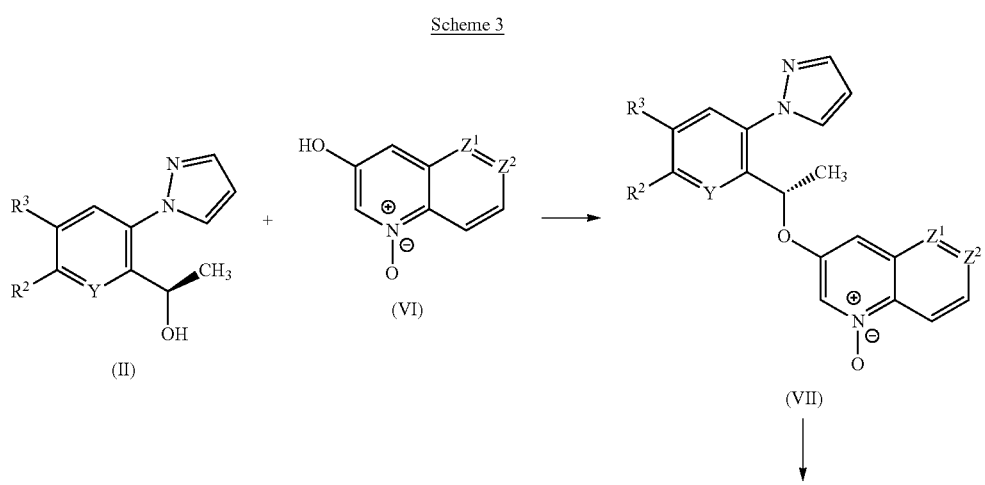

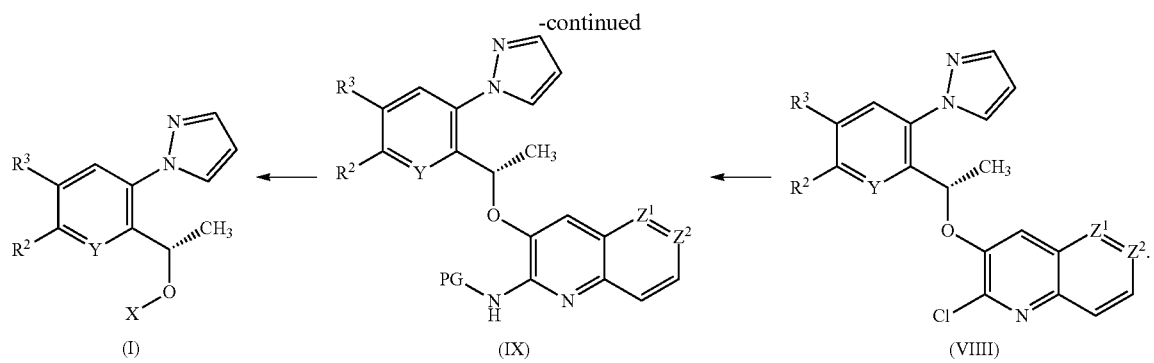

Compounds of Formula (VII) may be prepared from alcohols of Formulae (II) and (VI) under Mitsunobu reaction conditions as described previously in Scheme 1.

Chlorides of Formula (VIII) may be prepared by treating compounds of Formula (VII) with a chlorinating agent such as TsCl, in the presence of an organic base such as DIPEA, in a solvent such as DCM and at rt.

Compounds of Formula (IX) may be prepared by reaction of chlorides of Formula (VIII) with PGNH$_2$ such as PMB-NH$_2$, in the presence of an organic base such as DIPEA or Et$_3$N, in a polar aprotic solvent such as THF and at elevated temperature such as 70° C.

Compounds of Formula (I) or tautomers thereof may be prepared by the deprotection of compounds of Formula (IX) under conditions well known to the skilled person, such as treatment with anisole in the presence of TFA at rt. The skilled person will appreciate that there are many alternative methods for the removal of an appropriate amino protecting group.

According to a fourth process, compounds of Formula (I) or tautomers thereof wherein R$^2$ is OH; (C$_1$-C$_4$)alkyloxy, optionally substituted by OH or CO$_2$R$^4$; or CO$_2$R$^4$; may be prepared from compounds of Formulae (X), (XI), (XII) and (XIII) as illustrated by Scheme 4

Scheme 4

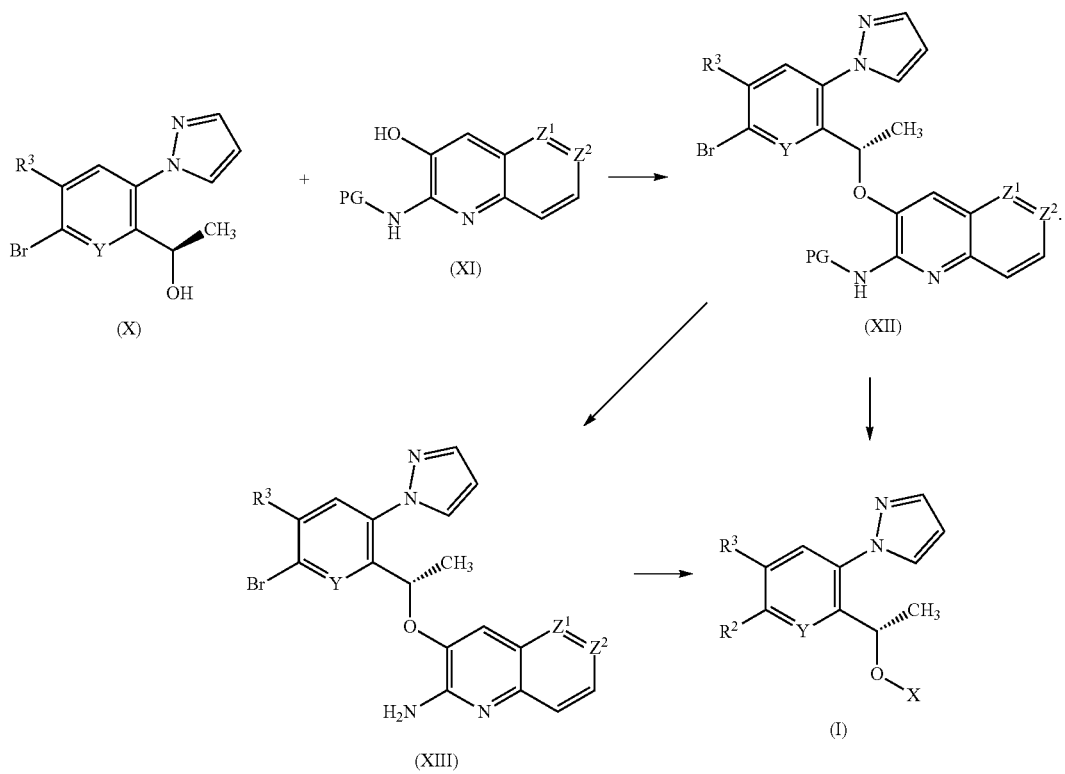

Compounds of Formula (XII) may be prepared from alcohols of Formulae (X) and (XI) under Mitsunobu reaction conditions as described previously in Scheme 1.

Compounds of Formula (XIII) may be prepared by deprotection of compounds of Formula (XII) under conditions well known to the skilled person. For example, when PG is Boc, typical conditions comprise treatment with a strong acid such as HCl or preferably TFA, in a suitable solvent such as DCM and at between 0° C. and rt. When PG is phthalimidyl, typical conditions comprise reaction with either hydrazine in EtOH at elevated temperatures such as 85° C., or NH₃ in THF at between −60° C. and rt.

Compounds of Formula (I) or tautomers thereof may be prepared from compounds of Formulae (XII) or (XIII) under conditions well known to those skilled in the art for the transformation of aryl bromides. For example, when R² is OH, transition metal catalyzed hydroxylation of an aryl bromide may be effected in the presence of a Pd catalyst such as Pd₂dba₃, together with a ligand such as tBuXPhos, in the presence of a base such as KOH, in a solvent such as dioxane/H₂O and at rt to 80° C. (followed by deprotection steps, as required).

Alternatively compounds of Formula (I) or tautomers thereof may be prepared in one step from the compound of Formula (XII) without the isolation of the compound of Formula (XIII).

According to a fifth process, compounds of Formula (XIII) may also be prepared from compounds of Formulae (VI) and (X) as illustrated by Scheme 5

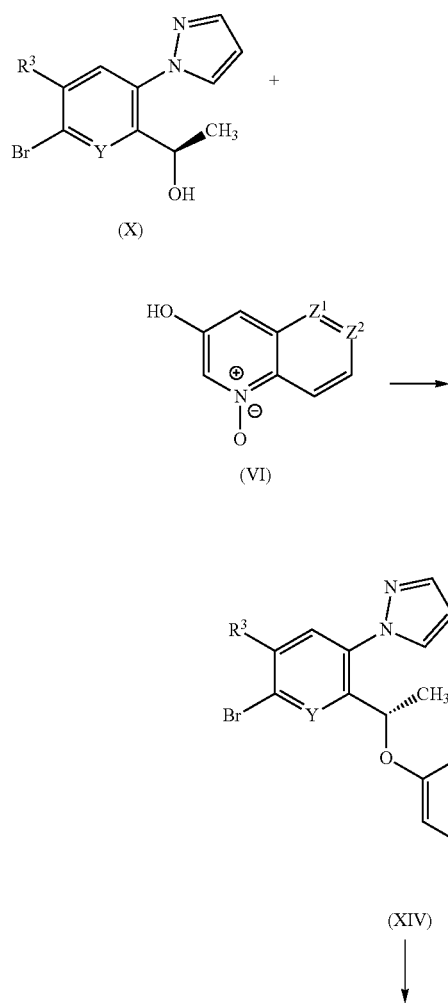

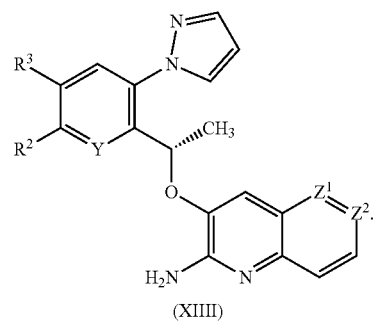

Compounds of Formula (XIV) may be prepared from alcohols of Formulae (X) and (VI) under Mitsunobu reaction conditions as described previously in Scheme 1.

Compounds Formula (XIII) may be prepared from compounds of Formula (XIV) by treatment with an activating agent such as TsCl, an organic base such as DIPEA, an amine source such as NH₄PF₆ and in a solvent such as DCM, or by analogy with the methods of Couturier et al (*Org. Lett.* 2006, 8, (9), 1929-1932), or Ferrell et. al (*Org. Lett.* 2013, 15 (1), 168-171). Typical conditions comprise reaction of the compound of formula (XIII) with excess TsCl in the presence of NH₄PF₆, DIPEA and DCM, at between −5° C. and rt.

According to a sixth process, compounds of Formula (VII) may also be prepared from compounds of Formulae (XV), (XVI) and (XVII) as illustrated by Scheme 6

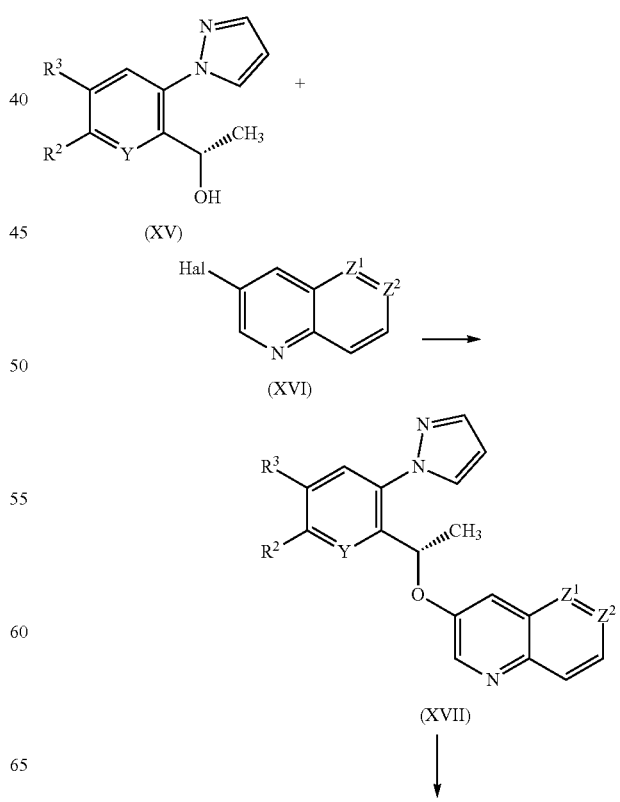

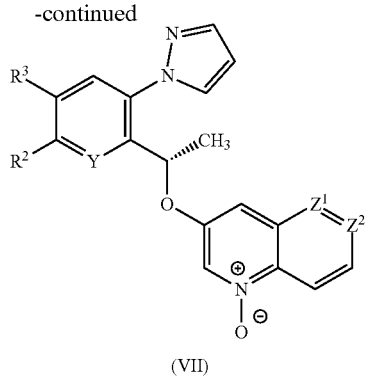

(VII)

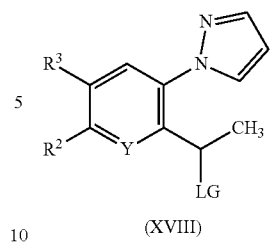

(XVIII)

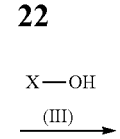

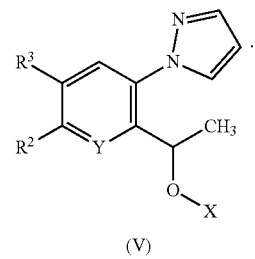

(V)

Compounds of Formula (XVII) may be prepared from compounds of Formulae (XV) and (XVI) using a palladium cross-coupling reagent such as the allyl palladium chloride dimer (S)-1-[($R_P$)-2-(dicyclohexylphosphino)ferrocenyl] ethyldi-tert-butylphosphine, in the presence of a base such as $Cs_2CO_3$ or $K_2CO_3$, in a solvent such as toluene, and at a temperature between rt and 105° C. The skilled person will appreciate that alternative organometallic coupling strategies may be used involving alternative coupling ligands, metals and solvent combinations.

Compounds of Formula (VII) may be prepared from compounds of Formula (XVII) by oxidation in the presence of a suitable oxidising agent such as MCPBA, in a solvent such as DCM and at rt.

According to a seventh process, compounds of Formula (V), may be prepared from compounds of Formulae (XVIII) and (III) as illustrated by Scheme 7

Scheme 7

Compounds of Formula (V) may be prepared by reaction of alcohols of Formula (III) with compounds of Formula (XVIII) in the presence of an inorganic base, in a solvent and at between 0° C. and 100° C. Preferred conditions comprise reaction of the compounds of Formulae (XVIII) and (III) in the presence of $Cs_2CO_3$ in MeCN at 60° C.

According to an eighth process, compounds of Formula (I) or tautomers thereof may be prepared from compounds of Formulae (XV), (XIX), (XX), (XXI), (XXII) and (XXIII) as illustrated by Scheme 8

Scheme 8

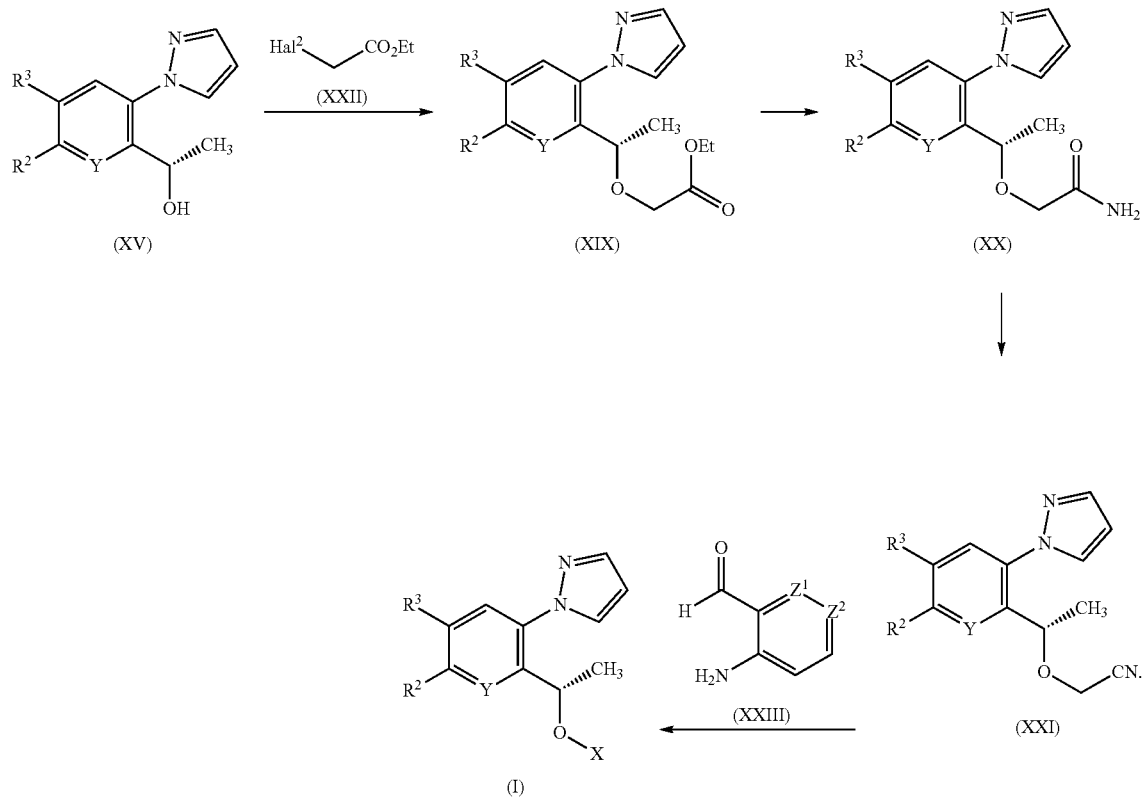

Esters of Formula (XIX) may be prepared by reaction of compounds of Formula (XV) with haloalkylesters of Formula (XXII) in the presence of a strong base such as NaH, in a polar aprotic solvent such as THF and at elevated temperature, such as 60° C.

Amides of Formula (XX) may be prepared by amidation of esters of Formula (XIX) by treatment with aqueous $NH_3$, optionally in the presence of an alcoholic solvent such as EtOH or preferably MeOH, in a sealed container and at elevated temperature, such as 90° C.

Nitriles of Formula (XXI) may be prepared by dehydration of amides of Formula (XX) using a dehydrating agent such as TFAA, in the presence of an organic base such as $Et_3N$, in a solvent such as pyridine and at between 0° C. and rt.

Compounds of Formula (I) or tautomers thereof may be prepared by condensation of aldehydes of Formula (XXI II) and the nitriles of Formula (XXI) in the presence of a strong base such as KOtBu, in a polar aprotic solvent such as DMSO and at rt.

According to a ninth process, compounds of Formula (IX) may be prepared from the compounds of Formula (X) and (XI) as illustrated by Scheme 9

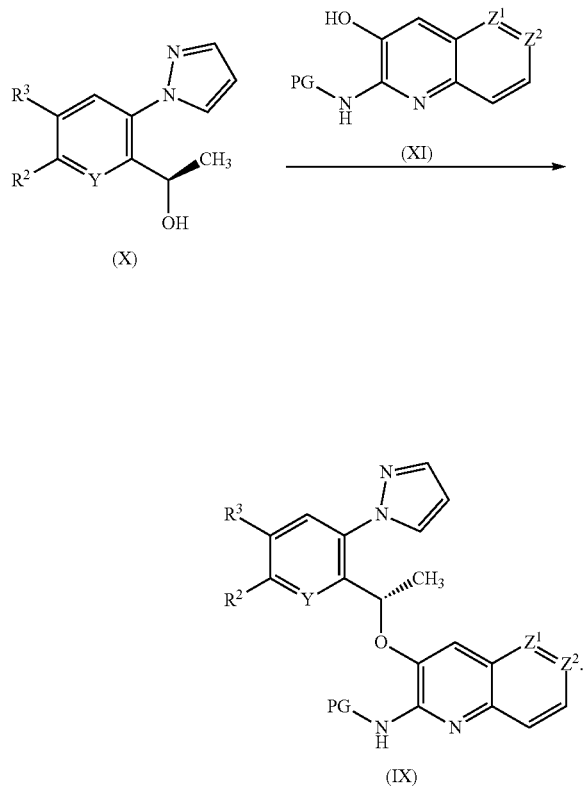

Compounds of Formula (IX) may be prepared from alcohols of Formulae (X) and (XI) under Mitsunobu reaction conditions as described previously in Scheme 1.

According to a tenth process, compounds of Formula (II) and (XV), may be prepared from compounds of Formula (XXIV) as illustrated by Scheme 10

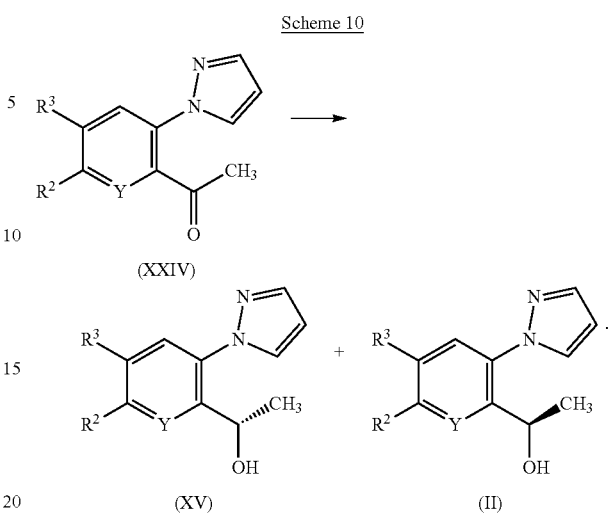

Alcohols of Formulae (XV) and (II) may be prepared by reduction of ketones of Formula (XXIV) with a reducing agent in a polar solvent at between 0° C. and rt. Preferred conditions comprise (i) treatment with $NaBH_4$, in EtOH or MeOH, optionally with THF as co-solvent, at between 0° C. and rt, followed by separation of the enantiomers under conditions described above in Scheme 2 (the skilled person will appreciate that Formula (IV) denotes a mixture, such as a racemic mixture, of the enantiomers of Formulae (II) and (XV); or (ii) biocatalytic reduction utilising (+) glucose, NADP+, GDH-CDX901 and an appropriate ketoreductase in pH7 phosphate buffer at rt.

Compounds of Formula (I) or tautomers thereof may be transformed to alternative compounds of Formula (I) or tautomers thereof by functional group interconversions known to those skilled in the art. For example: a $CO_2(C_1$-$C_4)$alkyl ester may be converted to its corresponding carboxylic acid by acid or base catalysed hydrolysis, preferably using aq NaOH in THF or MeOH; a benzonitrile compound may be hydrolyzed to a benzamide by treatment with $K_2CO_3$ and $H_2O_2$ in DMSO; a carboxylic acid may be converted to a carboxamide by reaction with $NH_4Cl$, a coupling agent such as HATU in the presence of a organic base such as $Et_3N$ in THF, at rt; a $CO_2(C_1$-$C_4)$alkyl ester may be converted to an amide by treatment with methanolic $NH_3$ at 80° C. in a sealed vessel; a $CO_2(C_1$-$C_4)$alkyl ester may be reduced using $NaBH_4$ in MeOH/THF, or $LiAlH_4$ in THF; and a $CO_2(C_1$-$C_4)$alkyl ester or nitrile may be converted to an oxadiazolone, respectively via formation of a hydrazide or an N-hydroxycarbamimidoyl, under conditions well known to the skilled person for oxadiazolone formation.

Compounds of Formulae (III), (V), (IX), (XI), (XII), (XIII) and (XVII) may likewise also be interconverted to alternative compounds of Formulae (III), (V), (IX), (XI), (XII), (XIII) and (XVII) as described above, to facilitate preparation of further compounds of Formula (I) or tautomers thereof. Examples include the transformation of: Br to a $CO_2(C_1$-$C_4)$alkyl ester, as shown in Preparations 2 and 116; Br to OH, as shown in Preparation 3; Br to an alkyl group, optionally substituted by $CO_2(C_1$-$C_4)$alkyl ester, as shown in Preparation 5; Br to an optionally protected amino group, as shown in Preparation 7; Br to CN, as shown in Preparations 30 and 33; Cl to CN, as shown in Preparation 32; Br to an alkyl ether, as shown in Preparation 55; and CN to carboxamide, as shown in Example 3.

Alternatively such interconversions may be achieved by analogy with methods described in the literature such as those found in Buchwald-Hartwig amination (Name Reactions for Functional Group Transformations (2007), 564-609), Palladium-Catalyzed carbonylation Reactions-A Reaction coming of Age (Organometallics, vol 27, issue 21, 5402) and Levin et al (ACS Cent. Sci 2016, 2, 5, 293).

Compounds of Formulae (III), (VI), (X), (XI), (XVI), (XVIII), (XXII) and (XXIV) may be: acquired from commercial sources; prepared by analogy with literature methods, such as described by M. G.-A. Shvekhgeimer, Chemistry of Heterocyclic Compounds, Vol. 40, No. 3, 2004, 257 or S. A. Yamashkin and E. A. Oreshkina, Chemistry of Heterocyclic Compounds, Vol. 42, No. 6, 2006, 701; or obtained by the methods described in the Experimental section below, or variations of the same well known to the skilled person.

All new processes for preparing compounds of formula (I) or tautomers thereof, and corresponding new intermediates employed in such processes, form further aspects of the present invention.

Compounds of the invention intended for pharmaceutical use may be administered as crystalline or amorphous products or may exist in a continuum of solid states ranging from fully amorphous to fully crystalline. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention. The choice of excipient will to a large extent depend on factors such as the particular mode of administration, the effect of the excipient on solubility and stability, and the nature of the dosage form.

In another aspect the invention provides a pharmaceutical composition comprising a compound of the invention and a pharmaceutically acceptable excipient.

Pharmaceutical compositions suitable for the delivery of compounds of the present invention and methods for their preparation will be readily apparent to those skilled in the art. Such compositions and methods for their preparation may be found, for example, in "Remington's Pharmaceutical Sciences", 19th Edition (Mack Publishing Company, 1995).

The compounds of the invention may be administered orally, such as by means of solid or liquid dosage forms. Oral administration may involve swallowing, so that the compound enters the gastrointestinal tract, or buccal or sublingual administration (such as may be achieved by means of a lozenge), so that the compound enters the bloodstream directly from the mouth.

Solid dosage forms for oral administration of compounds of the invention include, for example, tablets, hard or soft capsules, lozenges, granules or powders, each containing at least one compound of the invention. In such solid dosage forms the compound of the invention is ordinarily combined with one or more pharmaceutically acceptable excipients. Solid dosage forms for oral administration such as tablets and capsules may be prepared with enteric coatings.

Liquid dosage forms for oral administration include, for example, pharmaceutically acceptable emulsions, solutions, suspensions, syrups, and elixirs containing inert diluents commonly used in the art (e.g., water). Such compositions also may comprise excipients, such as wetting, emulsifying, suspending, flavoring (e.g., sweetening), and/or perfuming agents.

The compounds of the invention may be administered parenterally, i.e. directly into the blood stream, into muscle, or into an internal organ.

Intravenous administration represents a convenient means for administering the compounds of the invention. Other suitable means for parenteral administration include intraarterial, intraperitoneal, intrathecal, intraventricular, intraurethral, intrasternal, intracranial, intramuscular and subcutaneous.

Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) and tautomers thereof used in the preparation of parenteral solutions may be increased by the use of appropriate formulation techniques, such as the incorporation of solubility-enhancing agents.

Formulations for oral and parenteral administration may be formulated to be immediate and/or modified release. Conveniently compounds of the invention are formulated for immediate release Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and poly(dl-lactic-coglycolic) acid (PGLA) microspheres.

Other modes of administration include topical, inhaled/intranasal, rectal/intravaginal and ocular/aural administration. Formulations suitable for these modes of administration include immediate and/or modified release. Modified release formulations include delayed-, sustained-, pulsed-, controlled-, targeted and programmed release.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, including hydroxypropyl beta cyclodextrin and sodium sulphobutylether beta cyclodextrin, examples of which may be found in International Patent Applications Nos. WO 91/11172, WO 94/02518 and WO 98/55148.

For administration to human patients, the total daily dose of the compounds of the invention is typically in the range 1 mg to 10 g, such as 60 mg to 6 g, for example 100 mg to 1.5 g, or 100 mg to 1.0 g, depending, of course, on the mode of administration and efficacy. For example, administration may require a total daily dose of from 250 mg to 1 g, such as from 400 mg to 800 mg. The total daily dose may be administered in single or divided doses and may, at the physician's discretion, fall outside of the typical range given herein. These dosages are based on an average human subject having a weight of about 60 kg to 70 kg. The physician will readily be able to determine doses for subjects whose weight falls outside this range, such as infants and the elderly.

As noted above, the compounds of the invention are useful because they exhibit pharmacological activity in animals, i.e. HbS modulation. More particularly, the compounds of the invention are of use in the treatment of disorders for which a HbS modulator is indicated. Preferably the animal is a mammal, more preferably a human.

In a further aspect of the invention there is provided a compound of the invention for use as a medicament.

In a further aspect of the invention there is provided a compound of the invention for use in the treatment of a disorder for which a HbS modulator is indicated.

In a further aspect of the invention there is provided use of a compound of the invention for the preparation of a medicament for the treatment of a disorder for which a HbS modulator is indicated.

In a further aspect of the invention there is provided a method of treating a disorder in an animal (preferably a mammal, more preferably a human) for which a HbS modulator is indicated, comprising administering to said animal a therapeutically effective amount of a compound of the invention.

Disorders or conditions for which a HbS modulator is indicated include:
  disorders or conditions associated with oxygen deficiency in tissue whereby a delay, or reduction, in Hb deoxygenation would be beneficial, such as: SCD and its variants; and cancers resistant to radiotherapy and/or chemotherapy because of low cell-oxygen levels; and
  disorders or conditions which would benefit from increased tissue oxygenation whereby an increased affinity of Hb for oxygen would contribute to greater saturation of Hb with oxygen as it transits the lung (thereby allowing for increased transit of oxygen to body tissues), such as: altitude sickness and related disorders (e.g. high altitude pulmonary edema (HARE) and high altitude cerebral edema (HACE)); pulmonary insufficiency and related disorders (e.g. chronic obstructive pulmonary disease (COPD), acute respiratory distress syndrome (ARDS) and asthma); wound healing (e.g. ulcers and pressure sores); and stroke (e.g. silent infarct).

A disorder of particular interest is SCD.

There are many different Hb genotypes that in turn give rise to variants of SCD (Lancet 2010, 376, 2018-2031). Common SCD variants include sickle cell anemia (HbS/S), sickle-hemoglobin C disease (HbS/C), sickle beta-plus-thalassaemia (HbS/δ+) and sickle beta-zero-thalassaemia(HbS/δ°. Relatively rare, to very rare, variants include HbS/O Arab, HbS/CHarlem and HbC/S Antilles. All such variants of SCD are within the scope of the invention.

In one embodiment the SCD variant is HbS/S. In another embodiment the SCD variant is HbS/C.

A HbS modulator may be usefully combined with another pharmacologically active compound, or with two or more other pharmacologically active compounds. Such combinations offer the possibility of significant advantages, including patient compliance, ease of dosing and synergistic activity.

In such combinations the compound of the invention may be administered simultaneously (e.g. in a single dosage form, such as a capsule or tablet), sequentially or separately in combination with the other therapeutic agent or agents.

The one or more additional therapeutic agents may be selected from any of the agents or types of agent that follow:
1) agents that increase the level of favorable hemoglobins (e.g. fetal hemoglobin, hemoglobin A, etc.) within red blood cells (RBCs), such as: hydroxyurea; butyrate derivatives (e.g. sodium butyrate); decitabine; thalidomide derivatives (e.g. pomalidomide or lenalidomide); and lentiglobin (an ex-vivo gene therapy delivered by autologous hematopoietic stem transplant);
2) agents that disrupt the unfavorable cellular adhesive interactions associated with sickle cell disease variants, such as: a selectin inhibitor, including a pan-selectin inhibitor (e.g. rivipansel), an E-Selectin inhibitor or a P-Selectin inhibitor (e.g. crizanlizumab); a poloxamer (e.g. poloxamer 188); and Nix-0999 (Nicosan®);
3) agents that improve hydration of sickle RBCs, such as: gardos channel blockers (e.g. senicapoc or clotrimazole); and magnesium supplements (e.g. magnesium pidolate);
4) agents that contribute to vasodilation, such as: inhaled nitric oxide; arginine; glutamic acid; and PDE5 inhibitors (e.g. sildenafil or tadalafil);
5) anti-inflammatory agents, such as: a phospholipase A2 inhibitor (e.g. varespladib); a corticosteroid (e.g. methylprednisolone); and intravenous immunoglobulin; and
6) agents that increase cGMP levels, leading to a reduction in the formation of heterotypic blood cell aggregates and a reduced inflammatory state, such as a PDE9 inhibitor (e.g. 1,5-dihydro-6-[(3S,4S)-4-methyl-1-(2-pyrimidinyl-methyl)-3-pyrrolidinyl]-1-(tetrahydro-2H-pyran-4-yl)-4H-pyrazolo[3,4-d]pyrimidin-4-one).

It is within the scope of the invention that two or more pharmaceutical compositions, at least one of which contains a compound of the invention, may conveniently be combined in the form of a kit suitable for coadministration of the compositions. Thus the kit of the invention comprises two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like. The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

In another aspect the invention provides a pharmaceutical product (such as in the form of a kit) comprising a compound of the invention together with one or more additional therapeutically active agents as a combined preparation for simultaneous, separate or sequential use in the treatment of a disorder for which a HbS modulator is indicated.

It is to be appreciated that all references herein to treatment include curative, palliative and prophylactic treatment.

In the non-limiting Examples and Preparations that illustrate the invention and that are set out later in the description, and in the aforementioned Schemes, the following the abbreviations, definitions and analytical procedures may be referred to:
° 2θ is degrees 2-theta;
AcCl is acetyl chloride;
AcOH is acetic acid;
ADH-101 is alcohol dehydrogenase 101;
APCI is atmospheric pressure chemical ionization;
aq is aqueous;
$BH_3Me_2S$ is (dimethyl sulphide)trihydroboron;
BINAP is 1,1'-binaphthalene-2,2'-diyl)bis(diphenylphosphine;
Bn is benzyl;
Boc is tert-butoxycarbonyl;
$Boc_2O$ is di-tert-butyl dicarbonate;
br is broad;
tBu is tert-butyl;
tBuOH is tert-butanol;
tBuOK is potassium tert-butoxide;
tBuXPhos is 2-di-tert-butylphosphino-2',4',6'-triisopropylbiphenyl,
tBuXPhos-Pd Gen-3 is [(2-di-tert-butylphosphino-2',4',6'-triisopropyl-1,1'-biphenyl)-2-(2'-amino-1,1'-biphenyl)] palladium(II) methanesulfonate;
° C. is degrees celcius;
$CDCl_3$ is deutero-chloroform,
CDl is 1,1'-carbonyldiimidazole;
δ is chemical shift;
d is doublet;
dd is doublet of doublets;
ddd is doublet of doublet of doublets;
dt is doublet of triplets;
DCE is 1,2-dichloroethane;
DCM is dichloromethane; methylene chloride;
DIAD is diisopropyl azodicarboxylate;
(–)-DIP-Chloride™ is (–)-B-chlorodiisopinocampheylborane;
DIPEA is N-ethyldiisopropylamine, also known as N,N-diisopropylethylamine;
DMA is N,N-dimethylacetamide;
DME is 1,2-dimethoxyethane;
DMAP is 4-dimethylaminopyridine;
DMF is N,N-dimethylformamide;
DMSO is dimethyl sulfoxide;
DMSO-$d_6$ is deuterodimethylsulfoxide;
DPPP is 1,3-bis(diphenylphosphino)propane;
EDC is N-(3-dimethylaminopropyl)-N'-ethylcarbodiimide;
EDC. HCl is N-(3-dimethylaminopropyl)-N'-ethylcarbodiimide hydrochloride;
ESI is electrospray ionization;
$Et_2O$ is diethyl ether;
EtOAc is ethyl acetate;
EtOH is ethanol;
$Et_3N$ is triethylamine;
g is gram;
HATU is 1-[bis(dimethylamino)methylene]-1H-1,2,3-triazolo[4,5-b]pyridinium 3-oxid hexafluorophosphate;
HPLC is high pressure liquid chromatography;
HOBt is 1-hydroxybenzotriazole hydrate;
hr(s) is hour(s);
IPA is isopropyl alcohol;
iPrOAc is isopropyl acetate;
Ir[dF($CF_3$)ppy]$_2$(dtbpy)$PF_6$ is [4,4'-bis(1,1-dimethylethyl)-2,2'-bipyridine-N1,N1']bis[3,5-difluoro-2-[5-(trifluoromethyl)-2-pyridinyl-N]phenyl-C]iridium(III) hexafluorophosphate;
KRED101 is ketoreductase 101 enzyme;
L is liter;
LCMS is liquid chromatography mass spectrometry;
m is multiplet;
M is molar;
m-CPBA is 3-chloroperbenzoic acid;
MeCN is acetonitrile;
MeMgBr is methylmagnesium bromide;
MeNHOMe HCl is N,O-dimethylhydroxylamine hydrochloride;
MeOD_$d_4$ is deuterated methanol;
MeOH is methanol;
2-MeTHF is 2-methyl tetrahydrofuran;
mg is milligram;
MHz is mega Hertz;
min(s) is minute(s);
mL is milliliter;
mmol is millimole;
mol is mole;
MS (m/z) is mass spectrum peak;
MsCl is mesyl chloride;
MTBE is tert-butyl methyl ether;
NADP+ is nicotinamide adenine dinucleotide phosphate;
$NiCl_2$.glyme is nickel (II) chloride ethylene glycol dimethyl ether complex;
NMR is nuclear magnetic resonance;
ODS is octadecyl-silica;
ORTEP is Oak Ridge Thermal Ellipsoid Plot;
Pd(tBu$_3$P)$_2$ is bis(tri-tert-butylphosphine)palladium(0);
Pd/C is palladium on carbon;
Pd$_2$(dba)$_3$ is palladium tris(dibenzylideneacetone)dipalladium(0);
Pd(dppf)Cl$_2$ is [1,1'-bis(diphenylphophino)ferrocene]dichloropalladium(II);
Pd(PPh$_3$)$_4$ is tetrakis(triphenylphosphine)palladium(0);
Pet. ether is the petroleum fraction consisting of aliphatic hydrocarbons and boiling in the range 35-60° C.;
PMB is para-methoxybenzyl;
PMB-$NH_2$ is para-methoxybenzylamine;
Polycat 5 ® is bis(2-dimethylaminoethyl)(methyl)amine
PPh$_3$ is triphenylphosphine;
pH is power of hydrogen;
ppm is parts per million;
PSD is position sensitive detector;
psi is pounds per square inch;
PXRD is powder X-ray diffraction;
q is quartet;
rt is room temperature;
RT is retention time;
s is singlet;
SEM-Cl is 2-(trimethylsilyl)ethoxymethyl chloride;
SFC is supercritical fluid chromatography;
t is triplet;
$T_3P$ is propylphosphonic anhydride;
TBAF is tert-butyl ammonium fluoride;
TBDMSCl is tert-butyldimethylsilyl chloride;
TFA is trifluoroacetic acid;
THF is tetrahydrofuran;
TLC is thin layer chromatography;

TMEDA is N,N,N'N'-tetramethylethylenediamine;
TMSCl is trimethylsilyl chloride;
TMSCN is trimethylsilyl cyanide;
TMSCHN$_2$ is (diazomethyl)trimethylsilane;
TsCl is p-toluenesulfonyl chloride;
Ts$_2$O is p-toluenesulfonic anhydride;
μL is microliter;
μmol is micromole; and
Xantphos is 4,5-bis(diphenylphosphno)-9,9-dimethylxanthene $^1$H Nuclear NMR spectra were in all cases consistent with the proposed structures. Characteristic δ are given in parts-per-million downfield from tetramethylsilane (for $^1$HNMR) using conventional abbreviations for designation of major peaks. Where appropriate, tautomers may be recorded within the NMR data and some exchangeable protons may not be visible.

Mass spectra were recorded using either ESI or APCI. Where relevant and unless otherwise stated the m/z data provided are for isotopes $^{19}$F, $^{35}$Cl, $^{79}$Br and $^{127}$I.

Where preparative TLC or silica gel chromatography have been used, the skilled person will appreciate that any suitable solvent or solvent combination may be employed to purify the desired compound.

EXAMPLE 1

5-{(1S)-1-[(2-amino-6-fluoroquinolin-3-yl)oxy]ethyl}-2-fluoro-4-(1H-pyrazol-1-yl)benzamide

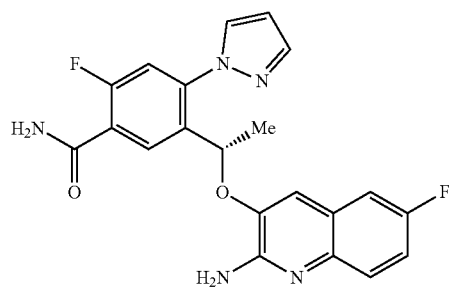 [SMILES: C[C@H](Oc1cc2cc(F)ccc2nc1N)c1cc(C(N)=O)c(F)cc1-n1cccn1]

To a solution of 5-[(1S)-1-{[2-(1,3-dioxo-1,3-dihydro-2H-isoindol-2-yl)-6-fluoroquinolin-3-yl]oxy}ethyl)-2-fluoro-4-(1H-pyrazol-1-yl)benzamide (Preparation 161, 222 mg, 0.411 mmol) in MeOH (10 mL) was added N$_2$H$_4$.H$_2$O (2.5 mL) at 20° C. The resulting reaction mixture was stirred at 70° C. for 3 hrs in a sealed vial and afterwards partitioned between DCM (80 mL) and H$_2$O (100 mL) and extracted with DCM (3×80 mL). The organic extracts were washed with H$_2$O (2×60 mL), dried (Na$_2$SO$_4$), filtered and evaporated to dryness in vacuo to provide a residue that was purified by preparative HPLC (DuraShell; 0.225% aq HCO$_2$H/MeCN; 10-55%) to afford the title compound as a white solid (78.5 mg, 46.6%). LCMS m/z=410 [M+H]$^+$.
$^1$HNMR (MeOH-d$_4$, 400 MHz) δ: 1.73 (3H, d), 5.96 (1H, q), 6.71 (1H, t), 7.00 (1H, s), 7.05-7.20 (2H, m), 7.41 (1H, d), 7.44 (1H, dd), 7.97 (1H, s), 8.15-8.20 (2H, m), 8.29 (1H, br s).

EXAMPLE 2

5-{(1S)-1-[(2-amino-7-chloro-6-fluoroquinolin-3-yl)oxy]ethyl}-2-fluoro-4-(1H-pyrazol-1-yl)benzamide

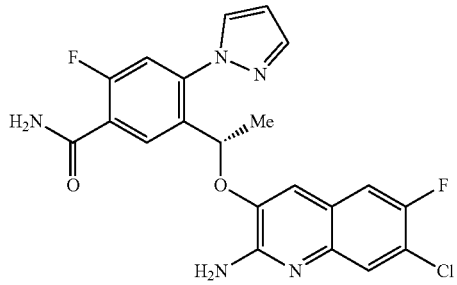 [SMILES: C[C@H](Oc1cc2cc(F)c(Cl)cc2nc1N)c1cc(C(N)=O)c(F)cc1-n1cccn1]

N$_2$H$_4$.H$_2$O (2.5 mL) was added to a solution of 5-[(1S)-1-{[7-chloro-2-(1,3-dioxo-1,3-dihydro-2H-isoindol-2-yl)-6-fluoroquinolin-3-yl]oxy}ethyl)-2-fluoro-4-(1H-pyrazol-1-yl)benzamide (Preparation 162; 160 mg, 0.279 mmol) in MeOH (10 mL) at 20° C. The sample vial was sealed and stirred at 70° C. for 3 hrs. The reaction mixture was partitioned between DCM (80 mL) and H$_2$O (100 mL) and further extracted with DCM (3×80 mL). The organic extracts were washed (H$_2$O, 2×60 mL), dried (Na$_2$SO$_4$) and evaporated to dryness in vacuo. The residue was purified by preparative HPLC (DuraShell, 0.05% aq NH$_4$OH/MeCN) to afford the title compound as a white solid (30.2 mg, yield: 24.4%).
LCMS m/z=444 [M+H]$^+$. $^1$HNMR (DMSO-d$_6$, 400 MHz) δ: 1.66 (3H, d), 5.76 (1H, q), 6.64 (1H, s), 6.70-6.80 (3H, m), 7.27 (1H, d), 7.49 (1H, d), 7.53 (1H, d), 7.80 (2H, br s), 7.98 (1H, d), 8.01 (1H, d), 8.41 (1H, d).

EXAMPLE 3

3-{(1S)-1-[(2-amino-6-bromoquinolin-3-yl)oxy]ethyl}-4-(1H-pyrazol-1-yl)benzamide

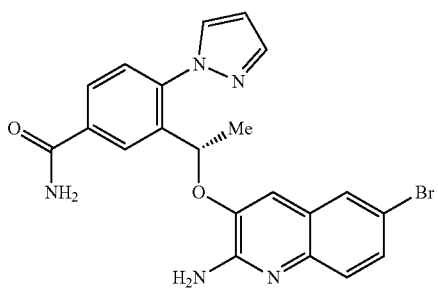 [SMILES: C[C@H](Oc1cc2cc(Br)ccc2nc1N)c1cc(C(N)=O)ccc1-n1cccn1]

Part 1.
K$_2$CO$_3$ (197 mg, 1.43 mmol) was added to a solution of 3-(1-{[6-bromo-2-(tert-butylamino)quinolin-3-yl]oxy}ethyl)-4-(1H-pyrazol-1-yl)benzonitrile (Preparation 156, 100.0 mg, 0.204 mmol) in DMSO (6.0 mL) and stirred for 10 mins. To this mixture was added H$_2$O$_2$ (1.00 mL) and the reaction mixture stirred for 1 hr. The reaction was extracted into EtOAc (20 mL), washed with brine, dried (Na$_2$SO$_4$) and evaporated to dryness in vacuo. The residue was purified by silica gel chromatography (pet. ether:E- tOAc=1:0 to 0:1) to give a white solid which was used without further purification in the following step.

Part 2.

To a solution the compound of Part 1 (above) in DCE (2 mL) was added TFA (0.5 mL) and the reaction mixture stirred at 70° C. for 16.0 hrs. The reaction mixture was diluted with DCM (20 mL) and quenched with NaHCO$_3$ (aq 10 mL). The combined organic extracts were washed (brine, 20 mL), dried (Na$_2$SO$_4$) and evaporated to dryness in vacuo. The residue was purified by silica gel chromatography to afford a yellow solid which was further purified using SFC (Chiralpak AS-H, 0.1% NH$_4$OH in EtOH, 40%) to afford the title compound (Peak 2) as a light yellow solid (20.7 mg, 17%). LCMS m/z=410 [M+H]$^+$. $^1$HNMR (CDCl$_3$, 400 MHz) δ: 1.68 (3H, d), 5.25 (2H, br s), 6.24 (1H, t), 6.90 (1H, s), 7.37-7.50 (4H, m), 7.7507.85 (2H, m), 7.89 (1H, s), 8.06 (1H, d).

EXAMPLE 4

3-{(1S)-1-[(2-amino-6-fluoroquinolin-3-yl)oxy]ethyl}-4-(1H-pyrazol-1-yl)benzoic Acid

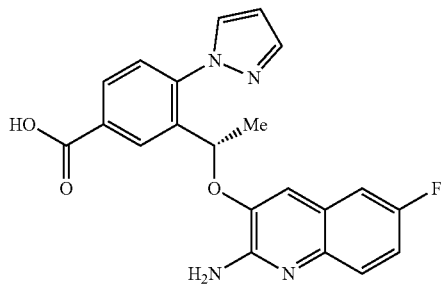

2M NaOH (53.3 mL, 107 mmol) was added to a solution of methyl 3-[(1S)-1-{[2-(1,3-dioxo-1,3-dihydro-2H-isoindol-2-yl)-6-fluoroquinolin-3-yl]oxy}ethyl]-4-(1H-pyrazol-1-yl)benzoate (Preparation 145, 4400 mg, 8.201 mmol) in MeOH (100 mL) and THF (50 mL) and the mixture stirred at 25° C. for 20 hrs. N$_2$H$_2$.H$_2$O (20.0 mL) was added and the mixture stirred at 40° C. for 60 hrs. The reaction mixture was evaporated in vacuo and the resulting aqueous mixture acidified with 3N HCl (pH=5~6). The resulting precipitate was collected by filtration and the filter cake washed with MeOH (2×20 mL) and dried under vacuum to give a solid (2.6 g) which was purified by further precipitation. The solid was stirred in a mixture of MeOH/DCM/H$_2$O (60 mL, 1:1:1) at 15° C. for 3 hrs. The solid was removed by filtration and dried under vacuum to afford a pale yellow solid (2.3 g) which was dissolved in warm DMSO (20 mL) to give a clear solution. MeOH (30 mL) was added and the mixture stirred at 15° C. for 2 hrs. The resulting solid was removed by filtration and the filter cake was dried afford the title compound as a white solid (1870 mg, 58%).

LCMS m/z=393 [M+H]$^+$. $^1$H NMR (DMSO-d$_6$, 400 MHz) δ: 1.67 (3H, d), 5.76 (1H, q), 6.49-6.65 (3H, m), 6.67-6.75 (1H, m), 7.02 (1H, dd), 7.15 (1H, dt), 7.37 (1H, dd), 7.58 (1H, d), 7.92-8.02 (2H, m), 8.25 (1H, d), 8.42 (1H, d).

EXAMPLE 4a

Potassium 3-{(1S)-1-[(2-amino-6-fluoroquinolin-3-yl)oxy]ethyl}-4-(1H-pyrazol-1-yl)benzoate

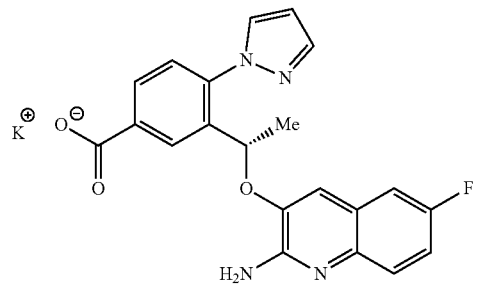 [SMILES: [K+] ; C[C@H](Oc1cc2cc(F)ccc2nc1N)c1cc(C(=O)O)ccc1-n1cccn1]

1M NaOH solution (2.3 mL, 2.3 mmol) was added to a solution of methyl 3-[(1S)-1-{[2-(1,3-dioxo-1,3-dihydro-2H-isoindol-2-yl)-6-fluoroquinolin-3-yl]oxy}ethyl]-4-(1H-pyrazol-1-yl)benzoate (Preparation 145, 120 mg, 0.224 mmol) in MeOH (3 mL) and the reaction stirred at 70° C. for 40 hrs. The cooled reaction was concentrated in vacuo and the residue diluted with MeCN (2 mL) and acidified to pH 3-4 using 1N HCl. The resulting precipitate was collected by filtration, rinsed with 50% MeCN/H$_2$O (6 mL), MeOH (2 mL), and dried in a vacuum oven to afford a white solid, 96 mg. The solid was combined with additional batches of product prepared according to the above process (194 mg, total, 0.49 mmol), suspended in IPA (5 mL), 1M KOH (0.5 mL, 0.5 mmol) added, and the mixture stirred for 4 hrs. The mixture was concentrated in vacuo, azeotroping with heptane (3×30 mL), and the resulting solid dried to afford the title compound as a white solid, 207 mg. LCMS m/z=393 [M+H]$^+$

EXAMPLE 5

5-[3-{(1S)-1-[(2-amino-6-fluoroquinolin-3-yl)oxy]ethyl}-4-(1H-pyrazol-1-yl)phenyl]-1,3,4-oxadiazol-2(3H)-one

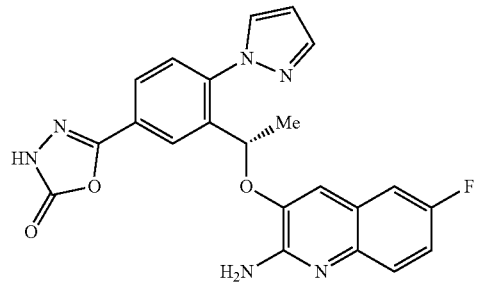 [SMILES: C[C@H](Oc1cc2cc(F)ccc2nc1N)c1cc(-c2n[nH]c(=O)o2)ccc1-n1cccn1]

CDI (108 mg, 0.664 mmol) was added to a solution of 3-{(1S)-1-[(2-amino-6-fluoroquinolin-3-yl)oxy]ethyl}-4-(1H-pyrazol-1-yl)benzohydrazide (Preparation 163, 90 mg, 0.22 mmol), Et$_3$N (0.5 mL, 4 mmol) in THF (3 mL) and stirred at rt for 1 hr. The reaction mixture was evaporated to dryness and purified using column chromatography (12 g silica gel, MeOH:DCM=0-5%) to afford a residue that was purified by preparative HPLC (Boston Green ODS, 0.05% aq HCl)/MeCN, 5-95%) to give the title compound as a white solid (62 mg, 65%). LCMS m/z=433 [M+H]⁺. ¹H NMR (DMSO-d₆, 400 MHz) δ: 1.72 (3H, d), 5.90 (1H, q), 6.66-6.74 (1H, m), 7.12 (1H, s), 7.35 (1H, dd), 7.44 (1H, dt), 7.59-7.72 (2H, m), 7.87 (1H, dd), 7.99 (1H, d), 8.15 (1H, d), 8.41 (1H, d), 8.74 (2H, br s), 12.76 (1H, s).

EXAMPLE 6 methyl 3-{(1S)-1-[(2-amino-6-fluoroquinolin-3-yl)oxy]ethyl}-4-(1H-pyrazol-1-yl)benzoate

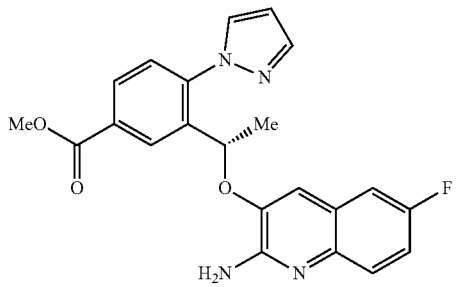 [SMILES: COC(=O)c1ccc(-n2cccn2)c([C@H](C)Oc2cc3cc(F)ccc3nc2N)c1]

TMSCHN₂ (2.04 mL, 2M in hexane) was added dropwise to a solution of 3-{(1S)-1-[(2-amino-6-fluoroquinolin-3-yl)oxy]ethyl}-4-(1H-pyrazol-1-yl)benzoic acid (Example 4, 400 mg, 1.02 mmol) in DMSO (10 mL) at 15° C. and then stirred at 15° C. for 90 mins. The reaction was quenched with H₂O (20 mL) and extracted with EtOAc (2×20 mL). The combined organic extracts were washed with H₂O (30 mL), brine (30 mL), dried (Na₂SO₄) and evaporated to dryness in vacuo. The residue was purified by column chromatography (12 g silica gel, EtOAc:Pet. ether=10-100%) to give a residue that was further purified by preparative HPLC (Agela Durashell C18, 0.05% aq NH₄OH/MeCN, 53-73%) to afford the title compound as a white solid (35 mg, 8.4%). LCMS m/z=407 [M+H]⁺.

¹H NMR (CHCl₃-di, 400 MHz) δ: 1.72 (3H, br d), 3.92 (3H, s), 5.17 (2H, br s), 5.97 (1H, q), 6.63 (1H, br s), 6.82 (1H, s), 6.89-7.03 (1H, m), 7.06-7.17 (1H, m), 7.42 (1H, d), 7.51 (1H, br dd), 7.74-7.94 (2H, m), 8.05 (1H, br d), 8.30 (1H, s).

EXAMPLE 7

3-{(1S)-1-[(2-amino-6-fluoroquinolin-3-yl)oxy]ethyl}-4-(1H-pyrazol-1-yl)benzenesulfonamide

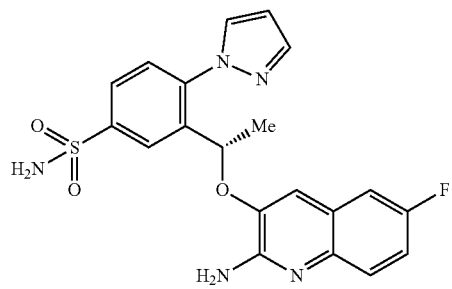 [SMILES: C[C@H](Oc1cc2cc(F)ccc2nc1N)c1cc(S(N)(=O)=O)ccc1-n1cccn1]

A mixture of 3-[1-{[2-(1,3-dioxo-1,3-dihydro-2H-isoindol-2-yl)-6-fluoroquinolin-3-yl]oxy}ethyl]-N,N-bis(4-methoxybenzyl)-4-(1H-pyrazol-1-yl)benzenesulfonamide (Preparation 153, 53 mg, 0.066 mmol), anisole (25.1 mg, 0.232) and TFA (1 mL) was stirred at rt for 18 hrs. The reaction mixture was evaporated to dryness in vacuo and stirred in 7 M NH₃ in MeOH (15 mL) at rt for 18 hrs. The reaction mixture was concentrated in vacuo and the residue purified by column chromatography (10% MeOH in DCM). The residue was further purified by chiral SFC (Chiral Technologies OD-H, 0.2% NH₄OH in MeOH, 17%) to afford the title compound. LCMS m/z=428 [M+H]⁺

EXAMPLE 8

[3-{(1S)-1-[(2-amino-6-fluoroquinolin-3-yl)oxy]ethyl}-4-(1H-pyrazol-1-yl)phenyl]acetic Acid

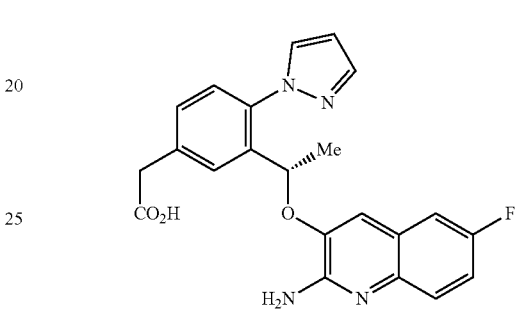

2M NaOH (53.3 mL, 107 mmol) was added to a solution of methyl {3-[1-{[2-(1,3-dioxo-1,3-dihydro-2H-isoindol-2-yl)-6-fluoroquinolin-3-yl]oxy}ethyl]-4-(1H-pyrazol-1-yl)phenyl}acetate (Preparation 146, 186.0 mg, 0.338 mmol) in MeOH and THF. The reaction mixture stirred at 44° C. for 20 hrs and then heated to 70° C. for 2 days. The mixture was concentrated in vacuo and the residue dissolved in H₂O/MeOH (3 mL) and acidified to pH 3 with 1M HCl. The resulting white solid was collected by filtration and the filter cake washed with 1:1 MeCN:H₂O and H₂O (1 mL each). The solid was further purified using SFC chromatography (Lux Amylose, 0.2% NH₄OH in MeOH, 20%) to afford the title compound (peak 1) as a glass (22.6 mg, 16.5%). LCMS m/z=407 [M+H]⁺. ¹H NMR (DMSO-d₆, 400 MHz) δ: 1.65 (3H, d), 3.65 (2H, s), 5.55 (1H, q), 6.60-6.85 (4H, m), 7.20-7.48 (5H, m), 7.55-7.78 (3H, m), 7.90 (1H, s), 8.30 (1H, s).

EXAMPLE 9

5-{(1S)-1-[(2-amino-6-fluoroquinolin-3-yl)oxy]ethyl}-2-fluoro-4-(1H-pyrazol-1-yl)benzoic Acid

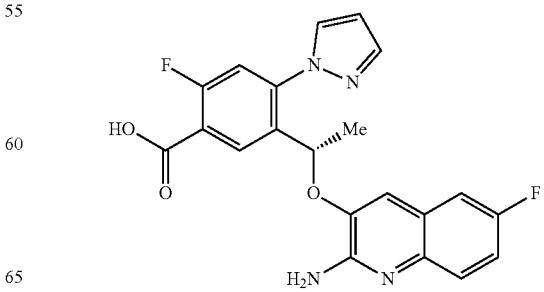

2M NaOH (2.48 mL, 4.97 mmol) was added to a solution of methyl 5-[(1S)-1-{[2-(1,3-dioxo-1,3-dihydro-2H-isoindol-2-yl)-6-fluoroquinolin-3-yl]oxy}ethyl]-2-fluoro-4-(1H-pyrazol-1-yl)benzoate (Preparation 149, 551 mg, 0.994 mmol) in MeOH (2 mL) and THF (6 mL) and stirred at 27° C. for 16 hrs. Hydrazine hydrate (2.90 mL, 59.6 mmol) was added and the solution heated at 40° C. for 5 hrs. Additional hydrazine hydrate (2.0 mL, 41 mmol) was added and heating continued for a further 18 hrs. The reaction mixture was concentrated in vacuo and the residue acidified to ~pH 6 using 4M HCl to afford a precipitate which was dissolved in DMSO (0.5 mL containing 1-2 drops of aqueous NH$_4$OH) and purified by HPLC (DuraShell, 0.05% aq NH$_4$OH/MeCN, 19%-39%). The title compound was obtained as a white solid (240 mg, 59%). LCMS m/z=411 [M+H]$^+$. $^1$H NMR (DMSO-d$_6$, 400 MHz) δ: 1.66 (3H, d), 5.82 (1H, q), 6.57 (3H, d), 6.71-6.74 (1H, m), 7.02 (1H, dd), 7.15 (1H, dt), 7.38 (1H, dd), 7.53 (1H, d), 7.99 (1H, d), 8.15 (1H, d), 8.45 (1H, d).

EXAMPLE 10

N-[3-{(1S)-1-[(2-amino-6-fluoroquinolin-3-yl)oxy]ethyl}-4-(1H-pyrazol-1-yl)benzoyl]glycine

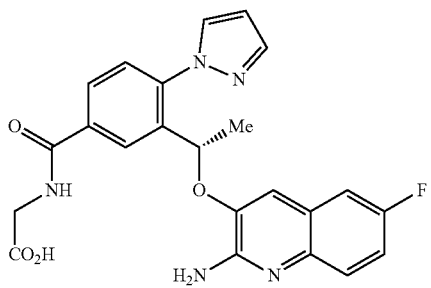 [SMILES: C[C@H](Oc1cc2cc(F)ccc2nc1N)c1cc(C(=O)NCC(=O)O)ccc1-n1cccn1]

T$_3$P (53 mg, 0.084 mmol, 0.050 mL) was added to a mixture of potassium 3-{(1S)-1-[(2-amino-6-fluoroquinolin-3-yl)oxy]ethyl}-4-(1H-pyrazol-1-yl)benzoate (Example 4a, 30 mg, 0.070 mmol), glycine methyl ester.HCl (11 mg, 0.088 mmol) and DIPEA (36.0 mg, 0.279 mmol) in DMF (0.5 mL), and the mixture stirred at rt overnight. Additional glycine methyl ester.HCl (6 mg, 0.044 mmol) and DIPEA (18.0 mg, 0.14 mmol) were added and stirring continued for 18 hrs. The reaction mixture was evaporated to dryness in vacuo. The residue was re-dissolved in MeOH (1 mL) and aqueous NaOH (10 mg, 0.4 mmol, 0.350 mL, 1 M) and the resulting solution stirred at rt. The reaction mixture was acidified to pH2-3 and evaporated to dryness in vacuo to afford a residue which was purified by HPLC (Waters Atlantis dC18, 0.05% TFA in H$_2$O/0.05% TFA in MeCN, 95/5 to 5/95) to afford the title compound (26 mg, 76%) as the TFA salt. LCMS m/z=450 [M+H]$^+$

EXAMPLE 11

3-{(1S)-1-[(2-amino-6-fluoroquinolin-3-yl)oxy]ethyl}-N-(2-methoxyethyl)-4-(1H-pyrazol-1-yl)benzamide

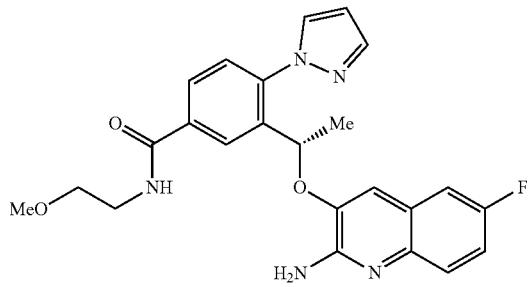 [SMILES: COCCNC(=O)c1ccc(-n2cccn2)c([C@H](C)Oc2cc3cc(F)ccc3nc2N)c1]

T$_3$P (53.2 mg, 0.0836 mmol) was added to a mixture potassium 3-{(1S)-1-[(2-amino-6-fluoroquinolin-3-yl)oxy]ethyl}-4-(1H-pyrazol-1-yl)benzoate (Example 4a, 20 mg, 0.046 mmol), 2-methoxyethylamine (6.98 mg, 0.0929 mmol) and DIPEA (36.0 mg, 0.279 mmol) in DMF (0.5 mL), and the mixture stirred at rt for 18 hrs. The reaction mixture was diluted with saturated aq NaHCO$_3$ (3 mL) and DCM (10 mL) and stirred at rt for 10 mins. The organic extracts were collected and evaporated to dryness in vacuo and the residue purified by HPLC (Waters Atlantis dC18, 0.05% TFA in H$_2$O/0.05% TFA in MeCN, 95/5 to 5/95) to afford the title compound (13.8 mg, 66%) as the TFA salt. LCMS m/z=450 [M+H]$^+$

EXS 12-14

Examples 12-14 in the table below were prepared according to the method described for Example 11 above using the appropriate amine.

| Ex | Name, Structure | Data |
| --- | --- | --- |
| 12 | 3-{(1S)-1-[(2-amino-6-fluoroquinolin-3-yl)oxy]ethyl}-N-(2-hydroxyethyl)-4-(1H-pyrazol-1-yl)benzamide as TFA salt 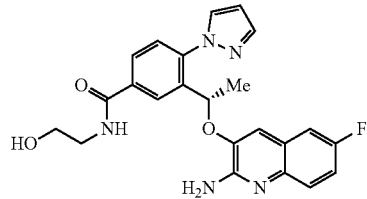 [SMILES: C[C@H](Oc1cc2cc(F)ccc2nc1N)c1cc(C(=O)NCCO)ccc1-n1cccn1] | 8.4 mg, 33% LCMS m/z = 436 [M + H]$^+$ |
| 13 | 3-{(1S)-1-[(2-amino-6-fluoroquinolin-3-yl)oxy]ethyl}-N-(3-hydroxypropyl)-4-(1H-pyrazol-1-yl)benzamide as TFA salt 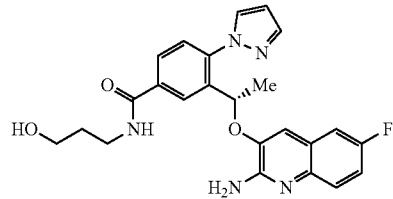 [SMILES: C[C@H](Oc1cc2cc(F)ccc2nc1N)c1cc(C(=O)NCCCO)ccc1-n1cccn1] | 13.1 mg, 51% LCMS m/z = 450 [M + H]$^+$ |

| Ex | Name, Structure | Data |
|---|---|---|
| 14 | 3-{(1S)-1-[(2-amino-6-fluoroquinolin-3-yl)oxy]ethyl}-N-(trans-3-hydroxycyclobutyl)-4-(1H-pyrazol-1-yl)benzamide as TFA salt | 15.7 mg, 59% LCMS m/z = 462 [M + H]⁺ |

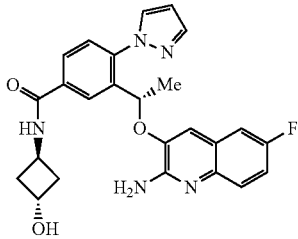 [SMILES: C[C@H](Oc1cc2cc(F)ccc2nc1N)c1cc(C(=O)N[C@H]2C[C@H](O)C2)ccc1-n1cccn1]

EXAMPLE 15

[3-{(1S)-1-[(2-amino-6-fluoroquinolin-3-yl)oxy]ethyl}-4-(1H-pyrazol-1-yl)phenoxy]acetic Acid

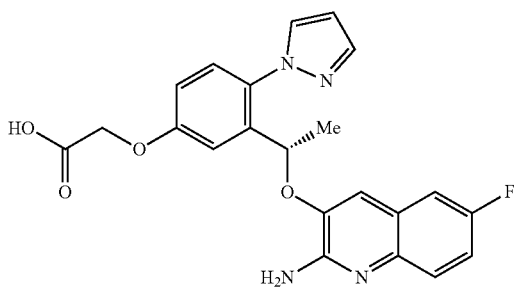 [SMILES: C[C@H](Oc1cc2cc(F)ccc2nc1N)c1cc(OCC(=O)O)ccc1-n1cccn1]

A solution of tert-butyl {3-[(1S)-1-({2-[(tert-butoxycarbonyl)amino]-6-fluoroquinolin-3-yl}oxy)ethyl]-4-(1H-pyrazol-1-yl)phenoxy}acetate (Preparation 154, 260 mg, 0.394 mmol) in TFA (2 mL) was stirred at 20° C. for 1 hr. The reaction mixture was evaporated to dryness in vacuo, the residue dissolved in MeCN (3 mL), washed with NH₄OH (~1 mL) and purified by preparative HPLC (Agela Durashell C18, 0.05% aq NH₄OH/MeCN, 11-51%) to afford the title compound as a white solid (71 mg, 43%). LCMS m/z=423 [M+H]⁺. ¹H NMR (DMSO-d₆, 400 MHz) δ: 1.62 (3H, d), 4.66 (2H, s), 5.42 (1H, q), 6.52 (2H, s), 6.63 (1H, t), 6.78 (1H, s), 6.92 (1H, dd), 7.09 (1H, dd), 7.16 (1H, dt), 7.27 (1H, d), 7.33 (1H, d), 7.39 (1H, dd), 7.89 (1H, d), 8.21 (1H, d).

EXAMPLE 16

3-[3-{(1S)-1-[(2-amino-6-fluoroquinolin-3-yl)oxy]ethyl}-4-(1H-pyrazol-1-yl)phenyl]propanoic Acid

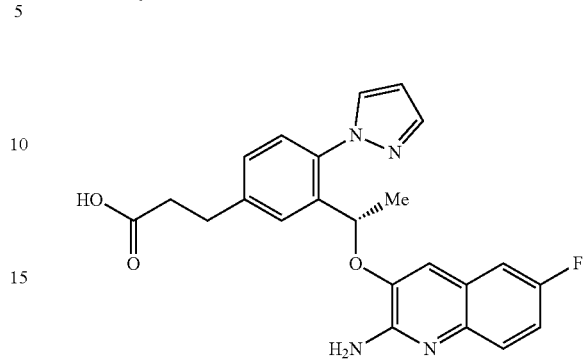

To a solution of tert-butyl 3-{3-[(1S)-1-{[2-(1,3-dioxo-1,3-dihydro-2H-isoindol-2-yl)-6-fluoroquinolin-3-yl]oxy}ethyl]-4-(1H-pyrazol-1-yl)phenyl}propanoate (Preparation 147, 113 mg, 0.186 mmol) in MeOH (4 mL) and THF (2 mL) was added 1M NaOH (7 mL) and the mixture stirred at rt for 64 hrs. The reaction mixture was heated to 70° C. for 8 hrs. The solvent was removed in vacuo and the slurry acidified to pH 3 with 1M HCl. The solid was collected by filtration and further purified by HPLC (Waters Atlantis dC18, 0.05% TFA in H₂O/0.05% TFA in MeCN, 95/5 to 5/95) to afford the title compound (10 mg, 13%).
LCMS m/z=421 [M+H]⁺

EXAMPLE 17

3-[3-{(1S)-1-[(2-amino-6-fluoroquinolin-3-yl)oxy]ethyl}-4-(1H-pyrazol-1-yl)phenyl]-1,2,4-oxadiazol-5(4H)-one

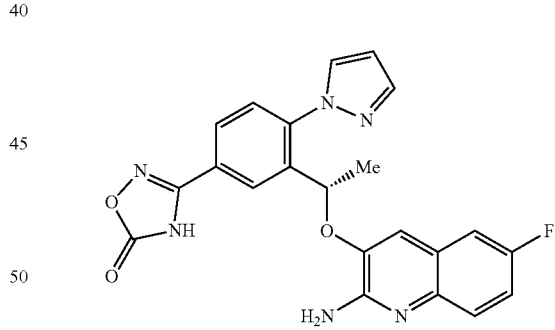

Part 1
To a solution of tert-butyl (6-fluoro-3-{(1S)-1-[5-(N-hydroxycarbamimidoyl)-2-(1H-pyrazol-1-yl)phenyl]ethoxy}quinolin-2-yl)carbamate (Preparation 164, 146 mg, 0.288 mmol) in 1,4-dioxane (4 mL) was added CDI (93.5 mg, 0.576 mmol). The mixture was heated to 100° C. for 16 hrs. The reaction was quenched with H₂O (5 mL) and extracted with EtOAc (3×15 mL). The combined organic extracts were washed with H₂O (5 mL), brine (5 mL), dried (Na₂SO₄), filtered and evaporated to dryness in vacuo to give crude tert-butyl (6-fluoro-3-{(1S)-1-[5-(5-oxo-4,5-dihydro-1,2,4-oxadiazol-3-yl)-2-(1H-pyrazol-1-yl)phenyl]ethoxy}quinolin-2-yl)carbamate as a brown oil which was used without further purification.

Part 2

TFA (1 mL) was added to a brown solution of tert-butyl (6-fluoro-3-{(1S)-1-[5-(5-oxo-4,5-dihydro-1,2,4-oxadiazol-3-yl)-2-(1H-pyrazol-1-yl)phenyl]ethoxy}quinolin-2-yl)carbamate from Part 1 in DCM (2 mL) and the reaction mixture stirred at rt (24° C.) for 1 hr. The reaction mixture was evaporated to dryness in vacuo, dissolved in MeOH (2.5 mL) and NH$_4$OH (0.5 mL), filtered, and purified by preparative HPLC (DuraShell, 0.05% aq NH$_4$OH/MeCN, 21-41%) to afford the title compound as a white solid (19.4 mg, 14%). LCMS m/z=433 [M+H]$^+$. $^1$H NMR (DMSO-d$_6$, 400 MHz) δ: 1.68 (3H, d), 5.80 (1H, q), 6.52 (2H, br s), 6.66-6.78 (2H, m), 7.07 (1H, dd), 7.16 (1H, dt), 7.39 (1H, dd), 7.68 (1H, d), 7.85 (1H, dd), 7.98 (1H, d), 8.21 (1H, d), 8.41 (1H, d), 8.88 (1H, s).

EXAMPLE 18

N-[3-{(1S)-1-[(2-amino-6-fluoroquinolin-3-yl)oxy]ethyl}-4-(1H-pyrazol-1-yl)phenyl]methanesulfonamide

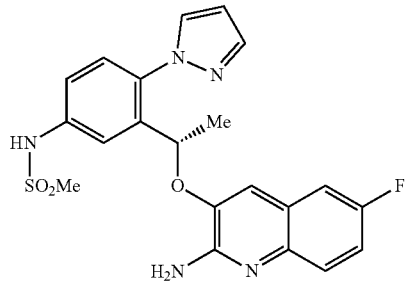 [SMILES: C[C@H](Oc1cc2cc(F)ccc2nc1N)c1cc(NS(C)(=O)=O)ccc1-n1cccn1]

Part 1

Et$_3$N (17.4 mg, 0.172 mmol) was added to a solution of 2-(3-{(1S)-1-[5-amino-2-(1H-pyrazol-1-yl)phenyl]ethoxy}-6-fluoroquinolin-2-yl)-1H-isoindole-1,3(2H)-dione (Preparation 160, 50 mg, 0.086 mmol) in anhydrous DCM (3 mL) at 0° C. The reaction mixture was stirred at 0° C. for 10 mins before methansulfonyl chloride (19.7 mg, 0.172 mmol) was added. The reaction mixture was stirred at 0° C. for 2 hrs and then at 30° C. for 18 hrs. The reaction mixture was cooled to 0° C. and Et$_3$N (17.4 mg, 0.172 mmol), followed by MsCl (19.7 mg, 0.172 mmol), were added and the mixture was stirred at 30° C. for 16 hrs. The reaction mixture was cooled to 0° C. and further portions of Et$_3$N (17.4 mg, 0.172 mmol), followed by MsCl (19.7 mg, 0.172 mmol), were added and the mixture was stirred at 30° C. for 2 hrs. The reaction mixture was diluted with DCM (20 mL), washed with H$_2$O (2 mL), brine (2 mL), and dried (Na$_2$SO$_4$). The organic extracts were evaporated to dryness under reduced pressure to give N-{3-[(1S)-1-{[2-(1,3-dioxo-1,3-dihydro-2H-isoindol-2-yl)-6-fluoroquinolin-3-yl]oxy}ethyl]-4-(1H-pyrazol-1-yl)phenyl}methanesulfonamide which was used in the following step without further purification.

Part 2

To a solution of N-{3-[(1S)-1-{[2-(1,3-dioxo-1,3-dihydro-2H-isoindol-2-yl)-6-fluoroquinolin-3-yl]oxy}ethyl]-4-(1H-pyrazol-1-yl)phenyl}methanesulfonamide from Part 1 in anhydrous MeOH (5 ml) was added NH$_2$NH$_2$.H$_2$O (2.52 mg, 0.0427 mmol) at 30° C. and the mixture was stirred at 30° C. for 10 mins. The reaction mixture was evaporated to dryness under reduced pressure and the residue diluted with DCM (10 mL). The resulting solid was removed by filtration and the filter cake washed with DCM (2×5 mL). The combined organic extracts were washed with H$_2$O (2 mL), brine (2 mL), dried (Na$_2$SO$_4$) and evaporated to dryness in vacuo. The resultant residue was purified by preparative HPLC (DuraShell, 0.05% aq NH$_4$OH/MeCN, 28%-58%) to afford a white solid which was further purified by SFC (Chiralcel OJ, 0.1% NH$_4$OH in EtOH, 30%). The title compound was obtained as light red solid (5 mg, 27%). LCMS m/z=442 [M+H]$^+$. $^1$H NMR (DMSO-d$_6$, 400 MHz) δ: 1.68 (3H, d), 2.82-2.88 (3H, m), 5.62 (1H, q), 6.66 (1H, t), 7.02 (1H, s), 7.11-7.17 (2H, m), 7.27-7.32 (1H, m), 7.40 (1H, d), 7.46 (1H, dd), 7.52 (1H, d), 7.90 (1H, d), 8.02 (1H, d).

EXAMPLE 19

3-{(1S)-1-[(2-amino-5,8-difluoroquinolin-3-yl)oxy]ethyl}-4-(1H-pyrazol-1-yl)benzoic Acid

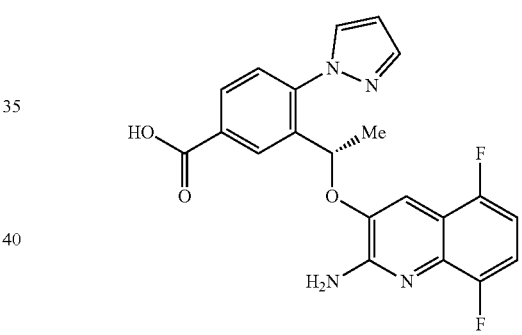

A solution of methyl 3-[(1S)-1-({5,8-difluoro-2-[(4-methoxybenzyl)amino]quinolin-3-yl}oxy)ethyl]-4-(1H-pyrazol-1-yl)benzoate (Preparation 157, 240 mg, 0.441 mmol) in TFA (5 mL) was stirred at 65° C. for 16 hrs. The reaction mixture was evaporated to dryness in vacuo and co-evaporated with MeOH to afford methyl 3-{(1S)-1-[(2-amino-5,8-difluoroquinolin-3-yl)oxy]ethyl}-4-(1H-pyrazol-1-yl)benzoate as yellow gum, which gum was dissolved in MeOH (4 mL), treated with aq NaOH (2M, 3.3 mL, 6.61 mmol) and stirred at 30° C. for 1.5 hrs. The reaction mixture was neutralised with 4M HCl to pH=6-7 and evaporated to dryness in vacuo. The residue was purified using preparative SFC chromatography (Chiralcel OJ, 0.1% NH$_4$OH in EtOH, 25%) to afford the title compound as a white solid (152 mg, 84%). LCMS m/z=411 [M+H]$^+$. $^1$H NMR (DMSO-d$_6$, 400 MHz) δ=1.67 (3H, d), 5.86 (1H, q), 6.67 (1H, t), 6.74-6.88 (2H, m), 6.99-7.17 (3H, m), 7.53 (1H, d), 7.89-7.99 (2H, m), 8.19-8.29 (2H, m).

EXAMPLE 20 methyl 3-{(1S)-1-[(2-amino-6,8-difluoroquinolin-3-yl)oxy]ethyl}-4-(1H-pyrazol-1-yl)benzoate

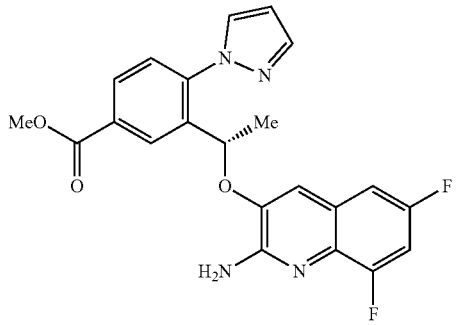 [SMILES: COC(=O)c1ccc(-n2cccn2)c([C@H](C)Oc2cc3cc(F)cc(F)c3nc2N)c1]

p-Toluene sulphonyl chloride (18000 mg, 94.414 mmol) in dichloromethane (100 mL) was added to a suspension of methyl 3-{(1S)-1-[(6,8-difluoro-1-oxidoquinolin-3-yl)oxy]ethyl}-4-(1H-pyrazol-1-yl)benzoate (Preparation 159, 20000 mg, 47.016 mmol), ammonium hexafluorophosphate (31000 mg, 190.18 mmol) and DIPEA (37000 mg, 290 mmol, 50 mL) in DCM (500 mL) at −0.6° C. The internal temperature was of the mixture was maintained below 1.5° C. during the addition and then the mixture was stirred at 0° C. to rt over 4 hrs. The mixture was then stirred at rt for 16 hrs. Further ammonium hexafluorophosphate (3100 mg, 19.0 mmol), and p-toluene sulphonyl chloride (1800 mg, 9.4 mmol) in DCM (30 mL), was added at rt and the mixture stirred at rt for 2 hrs. The reaction mixture was concentrated in vacuo, the residue partitioned between toluene (400 mL) and 2M sodium carbonate (100 mL) and the aqueous layer was extracted with toluene (100 mL). The combined organic extracts were washed with 10% citric acid (100 mL), brine (100 mL), dried (MgSO$_4$) and evaporated to dryness in vacuo. The residue was triturated with Et$_2$O (50 mL) and the resulting solid collected by filtration. The filter cake was washed with Et$_2$O (15 mL) and dried under high vacuum to afford the title compound as a pale yellow solid (12257 mg, 61%). LCMS m/z=425 [M+H]$^+$. $^1$H NMR (CDCl$_3$, 400 MHz) b=1.68 (3H, d), 3.90 (3H, s), 5.52 (2H, br s), 5.98 (1H, q), 6.60 (1H, s), 6.78-6.94 (3H, m), 7.40 (1H, d), 7.80 (1H, s), 7.88 (1H, s), 8.04 (1H, d), 8.30 (1H, s).

EXAMPLE 21

3-{(1S)-1-[(2-amino-6,8-difluoroquinolin-3-yl)oxy]ethyl}-4-(1H-pyrazol-1-yl)benzoic Acid

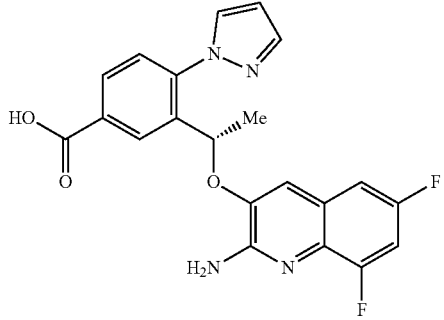 [SMILES: C[C@H](Oc1cc2cc(F)cc(F)c2nc1N)c1cc(C(=O)O)ccc1-n1cccn1]

Aqueous NaOH (4400 mg, 110 mmol, 55 mL, 2.0 M) was added to a solution of methyl 3-{(1S)-1-[(2-amino-6,8-difluoroquinolin-3-yl)oxy]ethyl}-4-(1H-pyrazol-1-yl)benzoate (Example 20, 11770 mg, 27.733 mmol) in THF (200 mL) at rt and the resulting mixture stirred at rt for 16 hrs. The reaction mixture was concentrated in vacuo to remove the organic solvent and the aqueous layer was extracted with MTBE (100 mL). The aqueous layer was acidified to pH 3 using 2N HCl (42 mL). The resulting suspension was removed by filtration and the solid washed with H$_2$O (100 mL). The solid was filtered under nitrogen then slurried with H$_2$O (200 mL) at 45° C. for 16 hrs. The solid was collected by filtration and the filter cake dried in vacuo at 60° C. for 16 hrs to give the title compound (10627 mg, 93%). LCMS m/z=411 [M+H]$^+$. $^1$H NMR (DMSO-d$_6$, 400 MHz) δ: 1.68 (3H, d), 5.78 (1H, q), 6.64-6.92 (5H, m), 7.16 (1H, t), 7.58 (1H, d), 7.90-8.00 (2H, m), 8.24 (1H, s), 8.40 (1H, s), 13.28 (1H, s).

EXAMPLE 21a

3-{(1S)-1-[(2-amino-6,8-difluoroquinolin-3-yl)oxy]ethyl}-4-(1H-pyrazol-1-yl)benzoic Acid tris(hydroxymethyl)aminomethane Salt

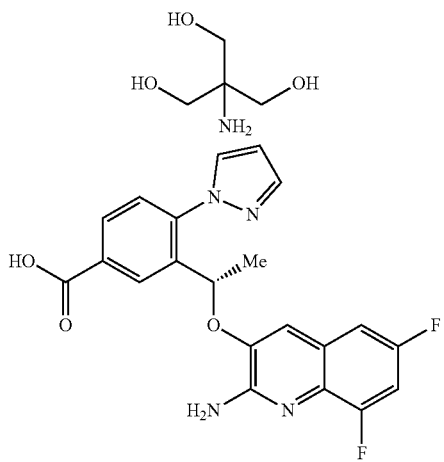

Part 1

To a vial was added 3-{(1S)-1-[(2-amino-6,8-difluoroquinolin-3-yl)oxy]ethyl}-4-(1H-pyrazol-1-yl)benzoic acid (27.1 mg) and THF (0.500 mL). The mixture was heated to 60° C., whereupon the mixture became homogenous. An aqueous solution of tris(hydroxymethyl)aminomethane (26.76 µL, 1.03 eq) was added to the mixture. The mixture was cooled to 21° C. at a rate of −0.05° C./min with stirring. The mixture was stripped of its solvent with $N_2$ and the residue dried in vacuo for about 10 mins. Dioxane (0.400 mL) was added to the residue. The mixture was heated to 70° C. and then cooled to 21° C. at a rate of −0.1° C./min with stirring. After stirring overnight in dioxane, the mixture was very thick with solid. The solid was collected with centrifuge filtration and dried. Seed crystals were formed by heating the solid in an open pan. The material was heated to 150° C. at a rate of 10° C./min and held isothermal for 5 mins, then analyzed by polarized light microscopy. The crystalline particles were birefringent with extinction and used in Part 2 as set out below.

Part 2

3-{(1S)-1-[(2-amino-6,8-difluoroquinolin-3-yl)oxy]ethyl}-4-(1H-pyrazol-1-yl)benzoic acid (0.50 g, 1.22 mmol), 9.1 mL acetonitrile and 0.32 mL water were mixed in a 30 mL vial. The mixture was heated at 60° C. for 5 mins to give an off-white/light-yellow suspension. Tris(hydroxymethyl)aminomethane (0.15 g, 1.26 mmol) was dissolved in 0.58 mL water and the resulting aq solution added to the suspension of 3-{(1S)-1-[(2-amino-6,8-difluoroquinolin-3-yl)oxy]ethyl}-4-(1H-pyrazol-1-yl)benzoic acid. The mixture became clear. The mixture was heated for about 3 mins at 60° C. then 5.3 mg of seed crystals of 3-{(1S)-1-[(2-amino-6,8-difluoroquinolin-3-yl)oxy]ethyl}-4-(1H-pyrazol-1-yl)benzoic acid tris(hydroxymethyl)aminomethane salt from Part 1 were added. The mixture was cooled and stirred at rt. After 16 hrs the mixture was filtered, the solids were washed with acetonitrile (3×1 mL) and then dried in vacuo to afford 499 mg (77%) of the title compound as a white solid. $^1$H NMR ($D_2O$, 400 MHz) δ: 1.69 (3H, d), 3.68 (6H, s), 5.17 (q, 1H), 6.18 (1H, s), 6.53-6.49 (1H, m), 6.62 (1H, t), 6.72 (1H, ddd), 7.36 (1H, d), 7.83 (1H, dd), 7.88-7.86 (2H, m), 8.10 (1H, d).

EXAMPLE 22

3-{(1S)-1-[(2-amino-7-methyl-1,6-naphthyridin-3-yl)oxy]ethyl}-4-(1H-pyrazol-1-yl)benzoic Acid

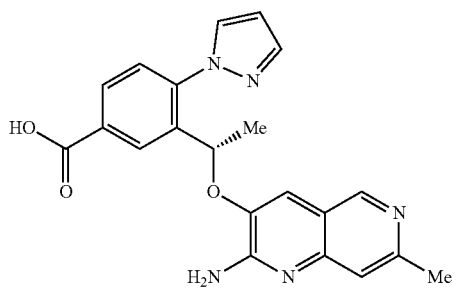 [SMILES: Cc1cc2nc(N)c(O[C@@H](C)c3cc(C(=O)O)ccc3-n3cccn3)cc2cn1]

DIAD (111 mg, 0.548 mmol) was added dropwise to a solution of methyl 3-[(1R)-1-hydroxyethyl]-4-(1H-pyrazol-1-yl)benzoate (Preparation 28, 45 mg, 0.18 mmol), tert-butyl (3-hydroxy-7-methyl-1,6-naphthyridin-2-yl)carbamate (Preparation 141, 50 mg, 0.18 mmol) and $PPh_3$ (144 mg, 0.548 mmol) in dry THF (0.5 mL) at 10° C. The resulting mixture was stirred at 25° C. for 3 hrs and then aq NaOH (21.9 mg NaOH in 0.5 mL $H_2O$, 0.548 mmol) was added. The reaction mixture was stirred at 25° C. for 16 hrs. The reaction mixture was evaporated to dryness in vacuo. The residue was dissolved in DCM (0.5 mL) and TFA (0.5 mL) added at 25° C. and the resulting mixture was stirred at 25° C. for 2 hrs. The reaction mixture was evaporated to dryness in vacuo and the residue purified by preparative HPLC (DuraShell, 0.05% aq $NH_4OH$/MeCN, 11%-31%) to give the title compound as a white solid (19 mg, 27%). LCMS m/z=390 [M+H]$^+$. $^1$H NMR (DMSO-$d_6$, 400 MHz) δ: 1.65 (3H, d), 2.43 (3H, s), 5.81 (1H, q), 6.68 (1H, s), 6.70-6.74 (1H, m), 7.05 (1H, s), 7.12 (2H, br s), 7.57 (1H, d), 7.93-8.01 (2H, m), 8.26 (1H, d), 8.35-8.43 (2H, m).

EXAMPLE 23

5-{(1S)-1-[(2-amino-6,8-difluoroquinolin-3-yl)oxy]ethyl}-2-fluoro-4-(1H-pyrazol-1-yl)benzoic Acid

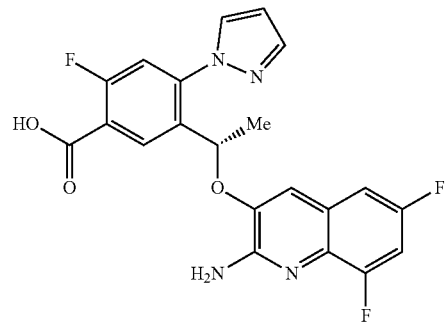 [SMILES: C[C@H](Oc1cc2cc(F)cc(F)c2nc1N)c1cc(C(=O)O)c(F)cc1-n1cccn1]

2M NaOH (0.33 mL, 0.66 mmol, 5.0 eq.) was added to a solution of methyl 5-[(1S)-1-{[2-(1,3-dioxo-1,3-dihydro-2H-isoindol-2-yl)-6,8-difluoroquinolin-3-yl]oxy}ethyl]-2-fluoro-4-(1H-pyrazol-1-yl)benzoate (Preparation 150, 75.8 mg, 0.132 mmol) in THF (1.5 mL) and MeOH (0.3 mL) and the solution stirred at 26° C. for 3 hrs. $N_2H_4 \cdot H_2O$ (0.4 mL, 8 mmol, 60 eq.) was added and the reaction mixture stirred at 27° C. for 6 hrs. Additional $N_2H_4 \cdot H_2O$ (0.5 mL, 10 mmol, 80 eq.) was then added and the reaction mixture was heated to 40° C. for 1.5 hrs, before stirring at 27° C. for 16 hrs. The solvent was removed in vacuo and the aqueous solution acidified with 4M HCl to pH 7 and then purified by preparative HPLC (DuraShell, 0.05% aq $NH_4OH$/MeCN, 20%-40%) to afford the title compound as a white solid (20 mg, 37%). LCMS m/z=429 [M+H]$^+$. $^1$H NMR (DMSO-$d_6$, 400 MHz) δ: 1.65 (3H, d), 5.80 (1H, q), 6.64 (1H, s), 6.69-6.73 (1H, m), 6.83 (2H, br s), 6.90 (1H, dd), 7.17 (1H, dt), 7.48 (1H, d), 7.97 (1H, d), 8.11 (1H, d), 8.42 (1H, d).

EXAMPLE 24

3-{(1S)-1-[(2-amino-6,8-difluoroquinolin-3-yl)oxy]ethyl}-N-(methylsulfonyl)-4-(1H-pyrazol-1-yl)benzamide

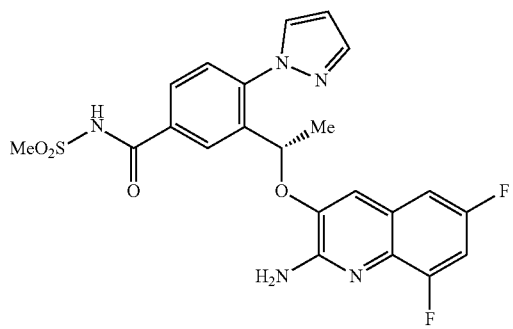 [SMILES: C[C@H](Oc1cc2cc(F)cc(F)c2nc1N)c1cc(C(=O)NS(C)(=O)=O)ccc1-n1cccn1]

DIPEA (87.9 mg, 0.12 mL, 0.680 mmol) was added to a solution of 3-{(1S)-1-[(2-amino-6,8-difluoroquinolin-3-yl)oxy]ethyl}-4-(1H-pyrazol-1-yl)benzoic acid (Example 21, 42.3 mg, 0.103 mmol), methanesulfonamide (23.4 mg, 0.246 mmol) and HATU (46.1 mg, 0.121 mmol) in DMF (1 mL). The reaction mixture was stirred at rt overnight. Additional methanesulfonamide (26.5 mg) and HATU (33 mg) was added and the mixture stirred at rt for 24 hrs. The solvent was removed using a vigorous $N_2$ stream and the residue purified by HPLC (Waters Atlantis dC18, 0.05% TFA in $H_2O$/0.05% TFA in MeCN, 95/5 to 5/95) to afford the title compound (26.4 mg, 52%). LCMS m/z=488 [M+H]$^+$. $^1$H NMR (DMSO-d$_6$, 400 MHz) δ: 1.66 (3H, d), 3.32 (2H, br s), 3.38 (3H, s), 5.82 (1H, q), 6.64-7.20 (6H, m), 7.60 (1H, d), 7.92 (1H, s), 8.00 (1H, d), 8.30 (1H, s), 8.40 (1H, s).

EXAMPLE 25

6-bromo-3-{(1S)-1-[5-fluoro-3-(1H-pyrazol-1-yl)pyridin-2-yl]ethoxy}quinolin-2-amine

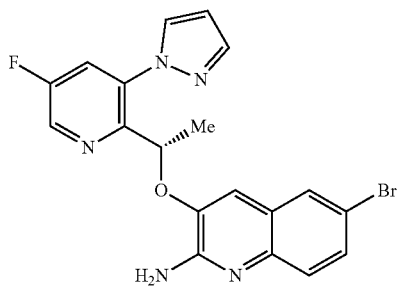 [SMILES: C[C@H](Oc1cc2cc(Br)ccc2nc1N)c1ncc(F)cc1-n1cccn1]

A solution of 6-bromo-N-tert-butyl-3-{1-[5-fluoro-3-(1H-pyrazol-1-yl)pyridin-2-yl]ethoxy}quinolin-2-amine (Preparation 186, 180.0 mg, 0.372 mmol) in anisole (40.2 mg, 0.372 mmol, 0.0404 mL) and TFA (2.2 mL) was heated to 70° C. for 3 hrs. The solution was evaporated to give an oil which was partitioned between $H_2O$ (5 mL) and DCM (20 mL) and the pH adjusted to 10 with 50% aq NaOH (4 mL). The aqueous layer was extracted with DCM (4×20 mL), evaporated to dryness in vacuo and purified by chromatography using 1 to 5% MeOH/DCM to give afford a solid, which was further purified by chiral SFC (Lux-Amylose-1, 0.2% $NH_4OH$ in MeOH, 20%) to give the title compound as a solid (60 mg, 38%). LCMS m/z=428 [M+H]$^+$. $^1$H NMR (CDCl$_3$, 400 MHz) δ: 1.78 (3H, d), 5.51 (2H, s), 5.83-5.94 (1H, m), 6.58 (1H, t), 6.69 (1H, s), 7.39 (2H, s), 7.41 (1H, d), 7.44 (1h, s), 7.67 (1H, d), 7.84-7.89 (1H, m), 8.56 (1H, d).

EXAMPLE 26

2-amino-3-{(1S)-1-[5-fluoro-3-(1H-pyrazol-1-yl)pyridin-2-yl]ethoxy}quinoline-6-carbonitrile

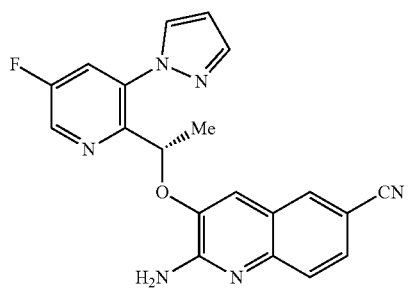 [SMILES: C[C@H](Oc1cc2cc(C#N)ccc2nc1N)c1ncc(F)cc1-n1cccn1]

Following the procedure of Example 25 and using 2-(tert-butylamino)-3-{1-[5-fluoro-3-(1H-pyrazol-1-yl)pyridin-2-yl]ethoxy}quinoline-6-carbonitrile (Preparation 190) the title compound was prepared as a solid (46 mg, 23%). LCMS m/z=375 [M+H]$^+$. $^1$H NMR (CDCl$_3$, 400 MHz) δ: 1.79 (3H, d), 5.79 (2H, br s), 5.95 (1H, q), 6.59-6.66 (1H, m), 6.79 (1H, s), 7.43-7.47 (1H, m), 7.49-7.53 (2H, m), 7.65 (1H, s), 7.72 (1H, d), 7.90 (1H, d), 8.56 (1H, d).

EXAMPLE 27

2-amino-3-{(1S)-1-[5-fluoro-3-(1H-pyrazol-1-yl)pyridin-2-yl]ethoxy}quinoline-6-carboxamide

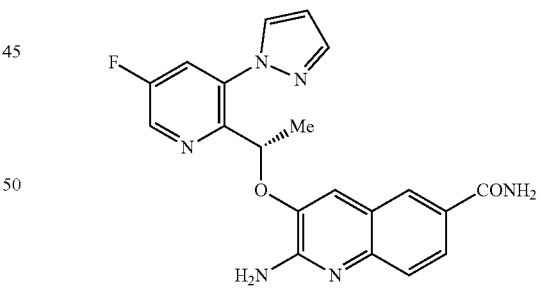

A solution of 2-(tert-butylamino)-3-{(1S)-1-[5-fluoro-3-(1H-pyrazol-1-yl)pyridin-2-yl]ethoxy}quinoline-6-carbonitrile (Preparation 190, 207 mg, 0.481 mmol) in DMSO (10 mL) was cooled to 0° C., $K_2CO_3$ (225 mg, 1.44 mmol) and $H_2O_2$ (81.8 mg, 0.721 mmol, 0.0737 mL) was added, and the mixture was stirred at 0° C. for 4 hrs. The reaction was quenched with saturated aq $Na_2S_2O_3$ solution and saturated aq $NaHCO_3$ and extracted with DCM (3×). The combined organic extracts were washed with $H_2O$ (3×), dried ($Na_2SO_4$) and concentrated in vacuo. Anisole (52.0 mg, 0.481 mmol, 52.0 uL) was added to the crude mixture and dissolved with TFA (20 mL) and the mixture heated at 70°

C. overnight. The mixture was concentrated in vacuo and quenched with H₂O and saturated aq NaHCO₃ and extracted with DCM (4×). The combined organic extracts were dried (Na₂SO₄) and evaporated to dryness in vacuo. The residue was purified by chromatography on silica gel (100% to 80% DCM/MeOH) to afford a white solid which was further purified by chiral SFC (Chiral Tech AS-H, 0.2% isopropanolamine in IPA, 20%) to give the title compound (9.4 mg). LCMS m/z=393 [M+H]⁺. ¹H NMR (CDCl₃, 400 MHz) δ: 1.63 (3H, d), 5.39 (2H, br s), 5.74 (1H, q), 6.57 (1H, t), 7.07 (1H, dt), 7.10 (1H, ss), 7.23-7.27 (1H, m), 7.33 (1H, dd), 7.58 (1H, d), 7.70-7.76 (2H, m), 7.84 (1H, d), 7.97 (1H, d).

EXAMPLE 28

6-bromo-3-{(1S)-1-[3-(1H-pyrazol-1-yl)pyridin-2-yl]ethoxy}quinolin-2-amine

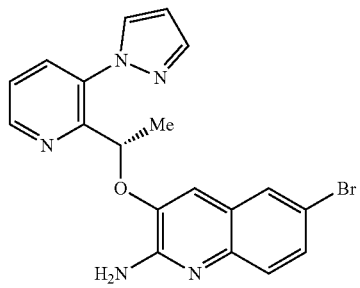 [SMILES: C[C@H](Oc1cc2cc(Br)ccc2nc1N)c1ncccc1-n1cccn1]

The title compound was obtained as a pale solid (42.2 mg, 44.5% yield) by chiral SFC separation (Chiralcel AD, 0.1% NH₄OH in EtOH) of 6-bromo-3-{1-[3-(1H-pyrazol-1-yl)pyridin-2-yl]ethoxy}quinolin-2-amine (Preparation 191). LCMS m/z=410 [M+H]⁺. ¹H NMR (MeOH-d₄, 400 MHz) δ: 1.79 (3H, d), 5.98 (1H, q), 6.70 (1H, t), 7.11 (1H, s), 7.44 (1H, d), 7.54-7.60 (2H, m), 7.65 (1H, d), 7.94-7.96 (2H, m), 8.11 (1H, d), 8.73 (1H, d).

EXAMPLE 29

7-chloro-6-fluoro-3-{(1S)-1-[3-(1H-pyrazol-1-yl)pyridin-2-yl]ethoxy}quinolin-2-amine

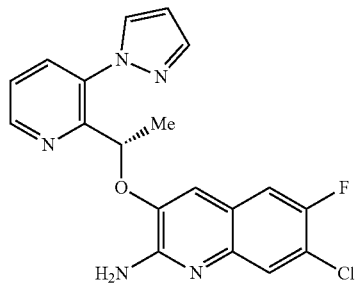 [SMILES: C[C@H](Oc1cc2cc(F)c(Cl)cc2nc1N)c1ncccc1-n1cccn1]

To a solution of 1-[3-(1H-pyrazol-1-yl)pyridin-2-yl]ethanol (Preparation 46, 267 mg, 1.41 mmol) in dry THF (4 mL) was added 2-amino-7-chloro-6-fluoroquinolin-3-ol (Preparation 140, 150 mg, 0.706 mmol) and PPh₃ (428 mg, 2.12 mmol) under N2. The mixture was stirred at 20° C., DIAD (555 mg, 2.12 mmol) added dropwise under N2, and then stirred at 20° C. for 24 hrs. The solvent was evaporated in vacuo to dryness and the residue partially purified by column chromatography (pet. ether:EtOAc 100:0 to 0:100) to give a yellow solid, which was further purified by preparative HPLC (DuraShell, 0.225% aq HCO₂H/MeCN, 38%-58%) to give a solid. The solid was still further purified by chiral SFC (Chiralcel-AD, 0.1% NH₄OH in MeOH, 50%) to afford the title compound as a solid (16.5 mg, 38%). LCMS m/z=384 [M+H]⁺. ¹H NMR (MeOH-d₄, 400 MHz) δ: 1.79 (3H, d), 5.88 (1H, q), 6.70 (1H, t), 6.88 (1H, s), 7.20 (1H, d), 7.50 (1H, d), 7.55-7.59 (1H, m), 7.92-7.95 (2H, m), 8.10 (1H, d), 8.72 (1H, q).

EXAMPLE 30

2-amino-3-{(1S)-1-[3-(1H-pyrazol-1-yl)pyridin-2-yl]ethoxy}quinoline-6-carboxamide

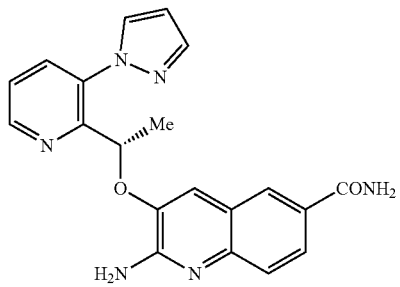 [SMILES: C[C@H](Oc1cc2cc(C(N)=O)ccc2nc1N)c1ncccc1-n1cccn1]

To a solution of 2-amino-3-{1-[3-(1H-pyrazol-1-yl)pyridin-2-yl]ethoxy}quinoline-6-carbonitrile (Preparation 192, 270 mg, 0.758 mmol) in DMSO (4 mL) was added potassium carbonate (209.0 mg, 1.52 mmol). The mixture was cooled to 10° C. and H₂O₂ (30% solution in H₂O, 0.380 mL, 3.79 mmol) added dropwise whilst keeping the internal temperature of the mixture below 40° C. After the addition was complete the reaction mixture was stirred at 40° C. for 30 mins. The reaction was quenched with saturated aq Na₂SO₃ solution and H₂O (50 mL). The solid was collected by filtration and the filter cake washed with H₂O (2×10 mL). The solid was purified by silica gel chromatography (DCM: MeOH; 100:0 to 85:15) to give a yellow solid 220.0 mg, 77.6%). The solid was further purified by chiral SFC (Chiralcel OD-H, 0.1% NH₄OH in EtOH, 40%) to afford the title compound as a white solid (101.0 mg, 46%). LCMS m/z=375 [M+H]⁺. ¹H NMR (MeOH-d₄, 400 MHz) δ: 1.81 (3H, d), 5.90 (1H, q), 6.72 (1H, t), 6.97 (1H, s), 7.47 (1H, d), 7.52-7.60 (1H, m), 7.81 (1H, d), 7.90-7.97 (3H, m), 8.12 (1H, d).

EXAMPLE 31

7-chloro-6-fluoro-3-{(1S)-1-[5-fluoro-3-(1H-pyrazol-1-yl)pyridin-2-yl]ethoxy}quinolin-2-amine

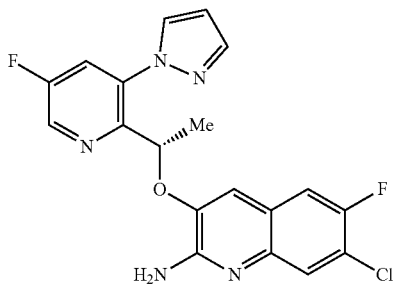 [SMILES: C[C@H](Oc1cc2cc(F)c(Cl)cc2nc1N)c1ncc(F)cc1-n1cccn1]

A solution of 1-[5-fluoro-3-(1H-pyrazol-1-yl)pyridin-2-yl]ethyl methanesulfonate (Preparation 58, 200 mg, 0.701 mmol), 2-amino-7-chloro-6-fluoroquinolin-3-ol (Preparation 140, 149 mg, 0.701 mmol) and $Cs_2CO_3$ (685 mg, 2.10 mmol) in MeCN (10 mL) was stirred at 70° C. for 16 hrs. The reaction mixture was evaporated to dryness in vacuo and the residue purified by silica gel chromatography (pet. ether:EtOAc=100:0 to 50:50) to give an off-white solid. The solid was further purified by chiral SFC (Chiralpak AD-H, 0.1% $NH_4OH$ in EtOH, 45%) to afford the title compound as an off-white solid (23.2 mg, 24%). LCMS m/z=402 [M+H]$^+$. $^1$H NMR (CDCl$_3$, 400 MHz) δ: 1.81 (3H, d), 5.21 (2H, br s), 5.92 (1H, q), 6.63 (1H, s), 6.73 (1H, s), 7.07 (1H, d), 7.47 (1H, dd), 7.60 (1H, d), 7.91 (1H, s), 8.60 (1H, d).

EXAMPLE 32

6-{(1S)-1-[(2-amino-7-chloro-6-fluoroquinolin-3-yl)oxy]ethyl}-5-(1H-pyrazol-1-yl)pyridine-2-carboxamide

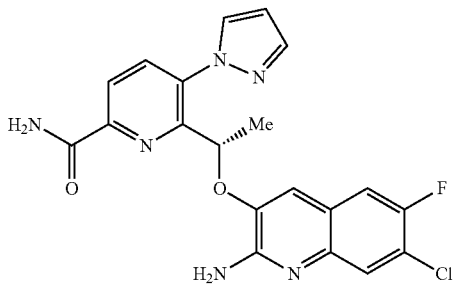 [SMILES: C[C@H](Oc1cc2cc(F)c(Cl)cc2nc1N)c1nc(C(N)=O)ccc1-n1cccn1]

The title compound was prepared following the procedure of Example 31 from 1-[6-carbamoyl-3-(1H-pyrazol-1-yl)pyridin-2-yl]ethyl methanesulfonate (Preparation 60, 350 mg, 1.13 mmol) and 2-amino-7-chloro-6-fluoroquinolin-3-ol (Preparation 140, 264 mg, 1.24 mmol), employing preparative SFC (Chiralcel AD, 0.1% $NH_4OH$ in EtOH, 40%), as a white solid (40 mg). LCMS m/z=427 [M+H]$^+$. $^1$H NMR (MeOH-d$_4$, 400 MHz) δ: 1.82 (3H, d), 6.19 (1H, q), 6.69 (1H, t), 6.96 (1H, s), 7.21 (1H, d), 7.49 (1H, d), 7.94 (1H, s), 8.03 (1H, d), 8.12 (1H, d), 8.18 (1H, d).

EXAMPLE 33

6-fluoro-3-{(1S)-1-[5-fluoro-3-(1H-pyrazol-1-yl)pyridin-2-yl]ethoxy}quinolin-2-amine

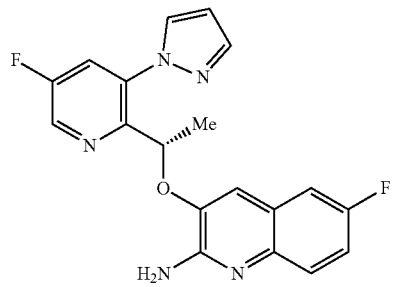 [SMILES: C[C@H](Oc1cc2cc(F)ccc2nc1N)c1ncc(F)cc1-n1cccn1]

A solution of tert-butyl (6-fluoro-3-{(1S)-1-[5-fluoro-3-(1H-pyrazol-1-yl)pyridin-2-yl]ethoxy}quinolin-2-yl)carbamate (Preparation 167, 250 mg, 0.535 mmol) in TFA/DCM (3 mL/3 mL) was stirred at rt (~24° C.) for 0.5 hour. The reaction mixture was evaporated in vacuo to dryness and purified by preparative HPLC (Agela Durashell C18, 0.05% aq $NH_4OH$/MeCN, 29%-69%) to give the title compound as a white solid (120 mg, 61%).

LCMS m/z=368 [M+H]$^+$. $^1$H NMR (CDCl$_3$, 400 MHz) δ: 1.80 (3H, d), 4.92-5.29 (2H, m), 5.89 (1H, q), 6.60 (1H, t), 6.71 (1H, s), 6.97 (1H, dd), 7.12 (1H, dt), 7.44 (1H, dd), 7.50 (1H, dd), 7.68 (1H, d), 7.88 (1H, d), 8.58 (1H, d).

EXAMPLE 34

2-amino-7-fluoro-3-{(1S)-1-[5-fluoro-3-(1H-pyrazol-1-yl)pyridin-2-yl]ethoxy}quinoline-6-carboxamide

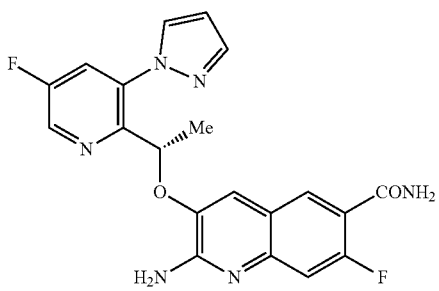 [SMILES: C[C@H](Oc1cc2cc(C(N)=O)c(F)cc2nc1N)c1ncc(F)cc1-n1cccn1]

A mixture of 2-amino-7-fluoro-3-{1-[5-fluoro-3-(1H-pyrazol-1-yl)pyridin-2-yl]ethoxy}quinoline-6-carboxylic acid (Preparation 195, 111 mg, 0.27 mmol), HOBt (72.9 mg, 0.540 mmol), EDCl (103 mg, 0.540 mmol) and Et$_3$N (81.9 mg, 0.810 mmol) in DMF (3 mL) was stirred at 20° C. for 0.5 hrs. NH$_4$Cl (43.3 mg, 0.810 mmol) was added and the mixture was stirred at 20° C. for 15 hrs under N2. The reaction mixture was evaporated to dryness in vacuo to give a residue that was purified by HPLC (Agela DuraShell, 0.05% aq $NH_4OH$/MeCN, 20-50%) to afford 30 mg of a white solid. This was combined with the product (20 mg) obtained by following the above procedure, starting from 45 mg (0.11 mmol) of precursor acid. The combined solid was purified by chiral SFC to afford the title compound as a white solid (17.9 mg, 36%). LCMS m/z=411 [M+H]⁺. ¹H NMR (CDCl₃, 400 MHz) δ: 1.79 (3H, d), 5.45 (2H, br s), 5.72 (1H, br s), 5.95 (1H, q), 6.63 (1H, t), 6.75 (1H, br d), 6.84 (1H, s), 7.22 (1H, d), 7.43 (1H, d), 7.71 (1H, d), 7.88 (1H, d), 8.16 (1H, d), 8.56 (1H, d).

EXAMPLE 35

2-amino-8-fluoro-3-{(1S)-1-[5-fluoro-3-(1H-pyrazol-1-yl)pyridin-2-yl]ethoxy}quinoline-6-carboxamide

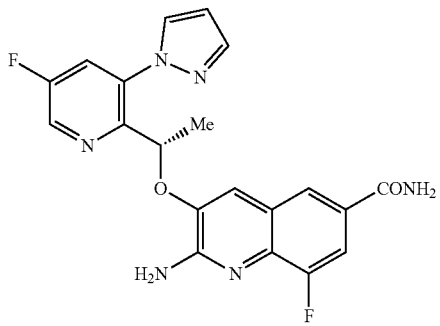 [SMILES: C[C@H](Oc1cc2cc(C(N)=O)cc(F)c2nc1N)c1ncc(F)cc1-n1cccn1]

A 50 mL Parr reactor with a glass insert was charged with CaCl₂ (344 mg, 3.10 mmol), methyl 2-(1,3-dioxo-1,3-dihydro-2H-isoindol-2-yl)-8-fluoro-3-{(1S)-1-[5-fluoro-3-(1H-pyrazol-1-yl)pyridin-2-yl]ethoxy}quinoline-6-carboxylate (Preparation 169, 860.0 mg, 1.55 mmol) and NH₃ in MeOH (3000 mg, 200 mmol, 25.0 mL, 7.0 M). The reaction mixture was stirred at 110° C. for 30 hrs and then at rt for 30 hrs. At 110° C., the internal pressure reached 140 psi. The reaction mixture was filtered through a pad of Celite®, washed with MeOH and 50:50 MeOH/DCM, and the combined organic extracts evaporated to dryness in vacuo. The residue was purified by chromatography (RediSep GOLD 120 g, heptane/DCM/MeOH, 25/67.5/7.5) to afford an off-white solid. The solid was dissolved in MeOH (4 mL) by gently heating before 2 drops of H₂O were added and white crystals precipitated immediately. The crystals were removed by filtration to afford the title compound as white crystals (156 mg). LCMS m/z=411 [M+H]⁺. ¹H NMR (DMSO-d₆, 400 MHz) δ: 1.70 (3H, d), 5.90 (1H, q), 6.65-6.90 (4H, m), 7.35 (1H, br s), 7.55 (1H, d), 7.70 (1H, d), 7.90-7.96 (2H, m), 8.10 (1H, dd), 8.35 (1H, d), 8.75 (1H, d).

EXAMPLE 36

3-{(1S)-1-[5-fluoro-3-(1H-pyrazol-1-yl)pyridin-2-yl]ethoxy}-7-methyl-1,6-naphthyridin-2-amine

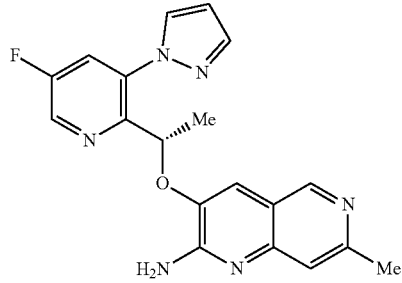 [SMILES: Cc1cc2nc(N)c(O[C@@H](C)c3ncc(F)cc3-n3cccn3)cc2cn1]

A mixture of (1R)-1-[5-fluoro-3-(1H-pyrazol-1-yl)pyridin-2-yl]ethyl methanesulfonate (Preparation 59, 71.7 mg, 0.251 mmol), 2-amino-7-methyl-1,6-naphthyridin-3-ol trifluoroacetate (Preparation 138. 44 mg, 0.25 mmol) and Cs₂CO₃ (175 mg, 0.537 mmol) in MeCN (2 mL) was stirred overnight at 60° C. The mixture was diluted with DCM (10 mL), the inorganic solids removed by filtration and washed with DCM (10 mL). The combined organic extracts were evaporated in vacuo to dryness and the residue purified by RediSep GOLD 12 g (0-60% EtOH/EtOAc) to afford the title compound as a white solid (31 mg, 34%). LCMS m/z=365 [M+H]⁺. ¹H NMR (MeOH-d₄, 400 MHz) δ: 1.78 (3H, d), 2.55 (3H, s), 5.55 (1H, s), 6.00 (1H, q), 6.65 (1H, s), 6.92 (1H, s), 7.18 (1H, s), 7.82 (1H, d), 7.90 (1H, s), 8.10 (1H, s), 8.43 (1H, s), 8.62 (1H, s).

EXAMPLE 37

6-{(1S)-1-[(2-amino-6-fluoroquinolin-3-yl)oxy]ethyl}-5-(1H-pyrazol-1-yl)pyridine-2-carboxylic Acid

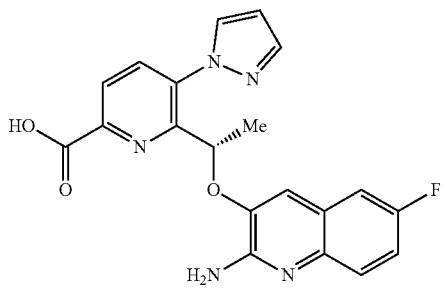 [SMILES: C[C@H](Oc1cc2cc(F)ccc2nc1N)c1nc(C(=O)O)ccc1-n1cccn1]

To a solution of methyl 6-[(1S)-1-{[2-(1,3-dioxo-1,3-dihydro-2H-isoindol-2-yl)-6-fluoroquinolin-3-yl]oxy}ethyl]-5-(1H-pyrazol-1-yl)pyridine-2-carboxylate, Preparation 174, 120 mg, 0.223 mmol) in MeOH (2.0 mL) and THF (1.0 mL) was added 2 M NaOH (116 mg, 2.0 mL, 2.9 mmol) and the reaction mixture was stirred at 25° C. for 36 hrs. N₂H₄ (2 mL, 40 mmol) was added and the reaction solution was stirred at 45° C. for 3 days. The reaction mixture was evaporated to dryness in vacuo and purified by preparative HPLC (DuraShell, 0.05% aq HCl/MeCN, 15-31%) to afford the title compound as a white solid (11 mg, 13). LCMS m/z=394 [M+H]⁺. ¹H NMR (DMSO-d₆, 400 MHz) δ: 1.75 (3H, d), 6.18 (1H, q), 6.61 (1H, t), 7.38 (1H, s), 7.40-7.50 (2H, m), 7.68 (1H, dd), 7.82 (1H, d), 8.15 (2H, q), 8.31 (1H, d), 8.56 (2H, br s).

EXAMPLE 38

6,8-difluoro-3-{(1S)-1-[5-fluoro-3-(1H-pyrazol-1-yl)pyridin-2-yl]ethoxy}quinolin-2-amine

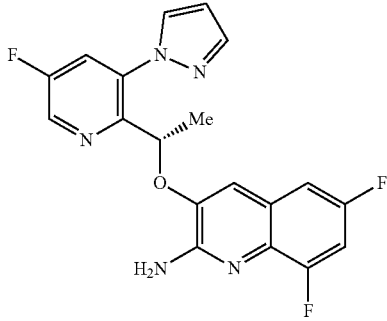 [SMILES: C[C@H](Oc1cc2cc(F)cc(F)c2nc1N)c1ncc(F)cc1-n1cccn1]

To a solution of 2-(6,8-difluoro-3-{(1S)-1-[5-fluoro-3-(1H-pyrazol-1-yl)pyridin-2-yl]ethoxy}quinolin-2-yl)-1H-isoindole-1,3(2H)-dione (Preparation 168, 120 mg, 0.233 mmol) in MeOH (2.0 mL) was added NH₂NH₂·H₂O (0.4 mL) and the mixture stirred at rt (25-30° C.) for 1 hr. The mixture was filtered and purified by preparative HPLC to afford the title compound as a white solid (34.5 mg, 39%). LCMS m/z=386 [M+H]⁺. ¹H NMR (DMSO-d₆, 400 MHz) δ: 1.71 (3H, d), 5.85 (1H, q), 6.52 (2H, br s), 6.63-6.72 (2H, m), 6.95 (1H, dt), 7.17 (1H, dt), 7.92 (1H, d), 8.07 (1H, dd), 8.37 (1H, d), 8.74 (1H, d).

EXAMPLE 39

6-{(1S)-1-[(2-amino-6-fluoroquinolin-3-yl)oxy]ethyl}-3-fluoro-5-(1H-pyrazol-1-yl)pyridine-2-carboxylic Acid

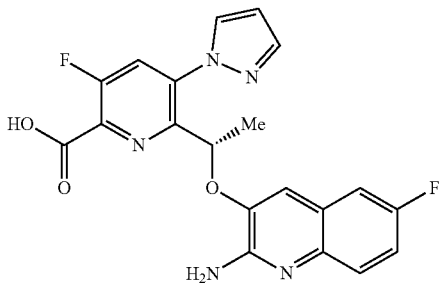 [SMILES: C[C@H](Oc1cc2cc(F)ccc2nc1N)c1nc(C(=O)O)c(F)cc1-n1cccn1]

To a solution of methyl 6-[(1S)-1-{[2-(1,3-dioxo-1,3-dihydro-2H-isoindol-2-yl)-6-fluoroquinolin-3-yl]oxy}ethyl]-3-fluoro-5-(1H-pyrazol-1-yl)pyridine-2-carboxylate (Preparation 180, 73.00 mg, 0.131 mmol) in THF (1.5 mL) was added 2M NaOH aq (0.329 mL, 0.657 mmol, 5.0 eq.) and the resulting solution stirred at rt for 3 hrs. NH₂NH₂·H₂O (0.4 mL, 8 mmol, 60 eq.) was added and stirred at rt for 19 hrs. The mixture was evaporated to dryness in vacuo and purified by preparative HPLC (DuraShell C18, 0.05% aq NH₄OH/MeCN, 20%-40%) to afford the title compound as a white solid (15.5 mg, 29%). LCMS m/z=412 [M+H]⁺. ¹H NMR (DMSO-d₆, 400 MHz) δ: 1.75 (3H, d), 5.91-6.02 (1H, m), 6.28 (2H, br s), 6.66-6.77 (2H, m), 7.08-7.21 (2H, m), 7.39 (1H, dd), 7.93 (1H, d), 8.17 (1H, d), 8.39 (1H, d).

EXAMPLE 40

{[6-{(1S)-1-[(2-amino-6-fluoroquinolin-3-yl)oxy]ethyl}-5-(1H-pyrazol-1-yl)pyridin-2-yl]oxy}acetic Acid

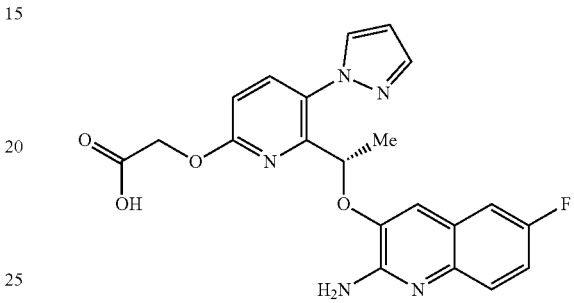

A solution of tert-butyl ({6-[(1S)-1-({2-[(tert-butoxycarbonyl)amino]-6-fluoroquinolin-3-yl}oxy)ethyl]-5-(1H-pyrazol-1-yl)pyridin-2-yl}oxy)acetate (Preparation 176, 110 mg, 0.19 mmol) in TFA (1.5 mL) was stirred at 25° C. for 30 mins. The reaction mixture was evaporated to dryness in vacuo and the residue purified by preparative HPLC (DuraShell C18, 0.05% aq NH₄OH/MeCN, 22%-42%) to afford the title compound as a white solid (27 mg, 34%). LCMS m/z=424 [M+H]⁺. ¹H NMR (DMSO-d₆, 400 MHz) δ: 1.65 (3H, d), 4.76-5.00 (2H, m), 5.56 (1H, q), 6.13 (2H, br s), 6.59 (1H, d), 6.77 (1H, s), 7.00 (1H, d), 7.08-7.23 (2H, m), 7.38 (1H, dd), 7.77-7.91 (2H, m), 8.13 (1H, d).

EXAMPLE 41

2-{[6-{(1S)-1-[(2-amino-6-fluoroquinolin-3-yl)oxy]ethyl}-5-(1H-pyrazol-1-yl)pyridin-2-yl]oxy}ethanol

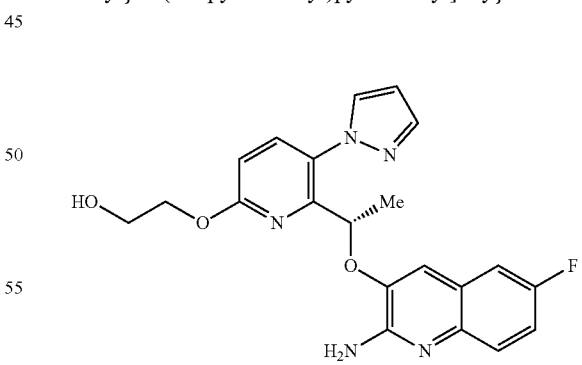

Hydrazine hydrate (0.4 mL, 8 mmol) in MeOH (1 mL) was added dropwise to a solution of 2-({6-[(1S)-1-{[2-(1,3-dioxo-1,3-dihydro-2H-isoindol-2-yl]-6-fluoroquinolin-3-yl]oxy}ethyl]-5-(1H-pyrazol-1-yl)pyridin-2-yl}oxy)ethyl acetate (Preparation 177, 130 mg, 0.224 mmol) in THF/MeOH (1 mL/1 mL) and then the reaction mixture stirred at 22° C. for 1.5 hrs. The reaction solution was transferred from 4 mL vial to flask and concentrated in vacuo. EtOH (10 mL) was added, the solids removed by filtration and the filtrate washed with EtOH. The combined filtrate was evaporated to dryness in vacuo and the residue purified by preparative HPLC (DuraShell, 0.05% aq NH$_4$OH/MeCN, 35%-65%) to afford the title compound as a white solid (45 mg, 49%). LCMS m/z=410 [M+H]$^+$. $^1$H NMR (DMSO-d$_6$, 400 MHz) δ: 1.69 (3H, d), 3.61-3.76 (2H, m), 4.24-4.40 (2H, m), 4.84 (1H, t), 5.53 (1H, q), 6.22 (2H, br s), 6.62 (1H, s), 6.74 (1H, s), 6.88 (1H, d), 7.05-7.20 (2H, m), 7.38 (1H, dd), 7.78 (1H, d), 7.88 (1H, s), 8.19 (1H, d).

EXAMPLE 42

2-amino-3-{(1S)-1-[6-(2-hydroxyethoxy)-3-(1H-pyrazol-1-yl)pyridin-2-yl]ethoxy}quinoline-6-carboxamide

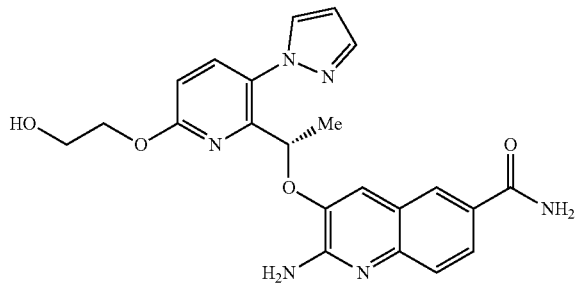 [SMILES: C[C@H](Oc1cc2cc(C(N)=O)ccc2nc1N)c1nc(OCCO)ccc1-n1cccn1]

A solution of methyl 3-[(1S)-1-{6-[2-(acetyloxy)ethoxy]-3-(1H-pyrazol-1-yl)pyridin-2-yl}ethoxy]-2-(1,3-dioxo-1,3-dihydro-2H-isoindol-2-yl)quinoline-6-carboxylate (Preparation 178, 220 mg, 0.354 mmol) in NH$_3$/MeOH (~8 M, 20 mL) was stirred at 80° C. in a steel tube for 72 hrs. The reaction mixture was evaporated to dryness in vacuo and the residue purified by preparative HPLC (DuraShell, 0.05% aq NH$_4$OH/MeCN, 14%-44%) to afford the title compound as a pink solid (13 mg, 8.5%).

LCMS m/z=435 [M+H]$^+$. $^1$H NMR (DMSO-d$_6$, 400 MHz) δ: 1.66 (3H, d), 3.57-3.74 (2H, m), 4.22-4.37 (2H, m), 4.83 (1H, t), 5.56 (1H, q), 6.52 (2H, br s), 6.59-6.65 (1H, m), 6.87 (2H, d), 7.22 (1H, br s), 7.36 (1H, d), 7.73-7.81 (2H, m), 7.85-7.90 (3H, m), 8.17 (1H, d).

EXAMPLE 43

5,8-difluoro-3-{(1S)-1-[5-fluoro-3-(1H-pyrazol-1-yl)pyridin-2-yl]ethoxy}quinolin-2-amine

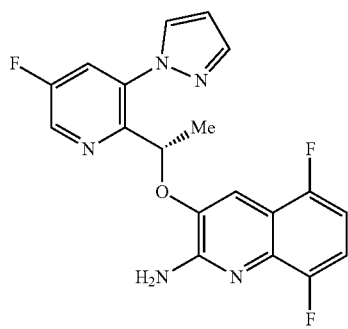 [SMILES: C[C@H](Oc1cc2c(F)ccc(F)c2nc1N)c1ncc(F)cc1-n1cccn1]

To a solution of 5,8-difluoro-3-{(1S)-1-[5-fluoro-3-(1H-pyrazol-1-yl)pyridin-2-yl]ethoxy}quinoline 1-oxide (Preparation 185, 300 mg, 0.777 mmol) and NH$_4$OH (0.5 mL) in DCM (8 mL) was added a solution of TsCl (740 mg, 3.88 mmol) in DCM (2 mL) at 0° C. The resulting suspension was stirred at 15° C. for 16 hrs. The suspension was diluted with DCM (10 mL) and the organic extracts were washed with brine (2 mL), dried (Na$_2$SO$_4$) and evaporated to dryness in vacuo. The residue was purified using a CombiFlash (silica gel, 20 g, eluting with EtOAc/Pet. ether=20-80%) to afford a light yellow solid. The title compound was obtained after chiral SFC (Chiralpak AD-H, 0.1% NH$_4$OH in EtOH) as a white solid (110 mg, 37%). LCMS m/z=386 [M+H]$^+$. $^1$H NMR (DMSO-d$_6$, 400 MHz) δ: 1.72 (3H, d), 5.99 (1H, q), 6.63-6.71 (1H, m), 6.71-7.03 (4H, m), 7.08 (1H, dt), 7.93 (1H, d), 8.08 (1H, dd), 8.30 (1H, d), 8.73 (1H, d).

EXAMPLE 44

2-amino-3-{(1S)-1-[6-hydroxy-3-(1H-pyrazol-1-yl)pyridin-2-yl]ethoxy}quinoline-6-carboxamide

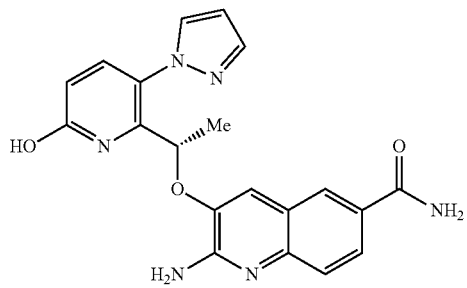 [SMILES: C[C@H](Oc1cc2cc(C(N)=O)ccc2nc1N)c1nc(O)ccc1-n1cccn1]

To a solution of 2-amino-3-{(1S)-1-[6-hydroxy-3-(1H-pyrazol-1-yl)pyridin-2-yl]ethoxy}quinoline-6-carboxylic acid (Preparation 193, 360 mg, 0.92 mmol) in DMF (4 mL) was added NH$_4$Cl (148 mg, 2.76 mmol), DIPEA (713 mg, 5.52 mmol) and HATU (525 mg, 1.38 mmol), and the resulting mixture stirred at rt for 2 hrs. The mixture was diluted with H$_2$O (5 mL) and extracted with EtOAc (3×15 mL). The combined organic extracts were evaporated to dryness in vacuo and purified by preparative HPLC (XBridge, 0.05% aq NH$_4$OH/MeCN, 0%-35%) to afford the title compound as a white solid (187 mg, 52%). LCMS m/z=391 [M+H]$^+$. $^1$H NMR (DMSO-d$_6$, 400 MHz) δ: 1.69 (3H, d), 5.27 (1H, q), 6.37 (1H, br s), 6.65 (1H, s), 6.73-7.04 (3H, m), 7.26 (1H, br s), 7.39 (1H, d), 7.51 (1H, br s), 7.76-7.84 (1H, m), 7.86-8.01 (3H, m), 8.16 (1H, d), 12.04 (1H, br s).

EXAMPLE 45

3-{(1S)-1-[5-fluoro-3-(1H-pyrazol-1-yl)pyridin-2-yl]ethoxy}quinolin-2-amine

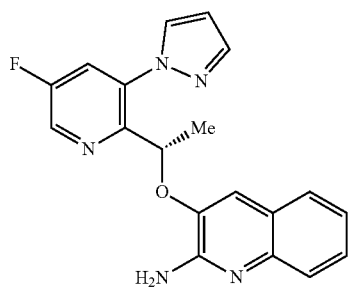 [SMILES: C[C@H](Oc1cc2ccccc2nc1N)c1ncc(F)cc1-n1cccn1]

A mixture of 6-bromo-3-{(1S)-1-[5-fluoro-3-(1H-pyrazol-1-yl)pyridin-2-yl]ethoxy}quinolin-2-amine (Example 25, 15.16 g, 35.40 mmol), Zn(CN)$_2$ (8.31 g, 70.8 mmol), Zn (463 mg, 7.08 mmol), Pd$_2$(dba)$_3$ (3.24 g, 3.54 mmol) and tBuXPhos (3.01 g, 7.08 mmol) in DMA (177 mL) was heated under N$_2$ at 100° C. for 2.5 hrs. The mixture was cooled to rt, diluted with EtOAc, filtered through pressed Celite® and washed with pH7 buffered H$_2$O, pH7 buffered brine, dried (Na$_2$SO$_4$), and then evaporated to dryness in vacuo to afford a caramel oil. The oil was dissolved in MeOH (259 mL) and treated with H$_2$O$_2$ (4.01 mL, 38.9 mmol) and DMSO (2.21 mL) and stirred for 1 hr. The MeOH was removed in vacuo and the residue slurried in H$_2$O (100 mL) for 1 hr and the solid collected by filtration. The solid was slurried in 30% H$_2$O/MeCN (22 mL) at 50° C. overnight. The slurry was cooled to rt, diluted with 30% H$_2$O/MeCN (~10 mL) and the solid removed by filtration and washed with 30% H$_2$O/MeCN. The combined filtrates were evaporated to dryness and the residue purified on a 120 g column with a gradient of DCM/EtOH to afford a residue which was further purified by HPLC (Waters Atlantis dC18, 0.05% TFA in H$_2$O/0.05% TFA in MeCN, 95/5 to 5/95) to afford the title compound (43 mg). LCMS m/z=350 [M+H]$^+$

EXAMPLE 46

6-{(1S)-1-[(2-amino-7-methyl-1,6-naphthyridin-3-yl)oxy]ethyl}-5-(1H-pyrazol-1-yl)pyridin-2-ol

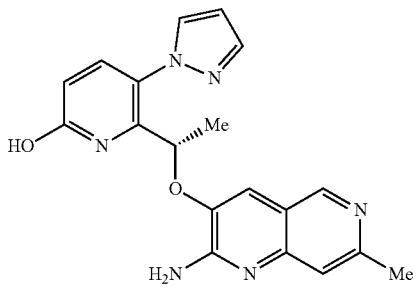 [SMILES: Cc1cc2nc(N)c(O[C@@H](C)c3nc(O)ccc3-n3cccn3)cc2cn1]

To a solution of tert-butyl (3-{(1S)-1-[6-bromo-3-(1H-pyrazol-1-yl)pyridin-2-yl]ethoxy}-7-methyl-1,6-naphthyridin-2-yl)carbamate (Preparation 182, 90 mg, 0.17 mmol) and KOH (28.8 mg, 0.514 mmol) in dioxane/H$_2$O (7 mL/3 mL) was added tBuXPhos (7.27 mg, 0.0171 mmol) and Pd$_2$(dba)$_3$ (7.84 mg, 0.00856 mmol) under N2. The resulting mixture was stirred at 90° C. for ~3 hrs and then evaporated to dryness in vacuo. The residue was acidified to pH 6 with 1N HCl, diluted with MeOH and purified by preparative HPLC (DuraShell C18, 0.05% aq NH$_4$OH/MeCN, 8%-28%) to afford the title compound as a white solid (10 mg, 16%). LCMS m/z=363 [M+H]$^+$. $^1$H NMR (DMSO-d$_6$, 400 MHz) δ: 1.69 (3H, d), 2.46 (3H, s), 5.29 (1H, q), 6.40 (1H, d), 6.64 (1H, t), 6.83 (1H, s), 7.09 (3H, s), 7.50 (1H, d), 7.90 (1H, d), 8.14 (1H, d), 8.46 (1H, s).

EXAMPLE 47

6-{(1S)-1-[(2-amino-1,5-naphthyridin-3-yl)oxy]ethyl}-5-(1H-pyrazol-1-yl)pyridin-2-ol

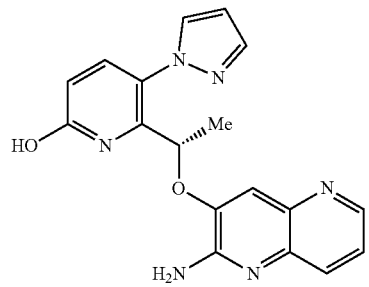 [SMILES: C[C@H](Oc1cc2ncccc2nc1N)c1nc(O)ccc1-n1cccn1]

The title compound was prepared following the procedure of Example 46 from tert-butyl (3-{(1S)-1-[6-bromo-3-(1H-pyrazol-1-yl)pyridin-2-yl]ethoxy}-1,5-naphthyridin-2-yl)carbamate (Preparation 181, 270 mg, 0.528 mmol), employing HPLC: DuraShell C18, 0.05% aq NH$_4$OH/MeCN, 8%-40%), as a yellow solid (58.9 mg, 32%). LCMS m/z=349 [M+H]$^+$. $^1$H NMR (DMSO-d$_6$, 400 MHz) δ: 1.70 (3H, d), 5.38 (1H, d), 6.41 (1H, br s), 6.63 (1H, t), 6.84 (2H, br s), 6.97 (1H, s), 7.34 (1H, dd), 7.54 (1H, d), 7.74 (1H, dd), 7.86 (1H, d), 8.10 (1H, d), 8.42 (1H, dd), 11.96 (1H, br s).

EXAMPLE 48

6-{(1S)-1-[(2-amino-7-fluoro-1,5-naphthyridin-3-yl)oxy]ethyl}-5-(1H-pyrazol-1-yl)pyridin-2-ol

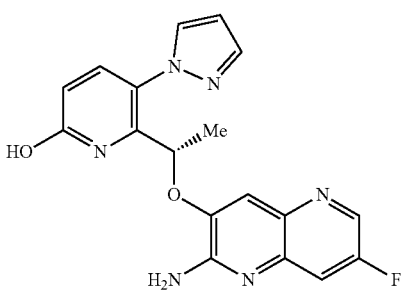 [SMILES: C[C@H](Oc1cc2ncc(F)cc2nc1N)c1nc(O)ccc1-n1cccn1]

The title compound was prepared following the procedure of Example 46 from tert-butyl (3-{(1S)-1-[6-bromo-3-(1H-pyrazol-1-yl)pyridin-2-yl]ethoxy}-7-fluoro-1,5-naphthyridin-2-yl)carbamate (Preparation 184, 85 mg, 0.16 mmol), employing HPLC: DuraShell C18, 0.05% aq NH$_4$OH/MeCN, 7%-47%), as a white solid (7.5 mg, 13%). LCMS m/z=367 [M+H]⁺. ¹H NMR (DMSO-d₆, 400 MHz) δ: 1.87 (3H, d), 5.57 (1H, q), 6.41 (2H, br s), 6.57-6.71 (2H, m), 7.20 (1H, s), 7.38 (1H, br d), 7.48-7.56 (1H, m), 7.74 (1H, d), 7.86 (1H, d), 8.42 (1H, d).

EXAMPLE 49

6-[(1S)-1-{[2-amino-6-(hydroxymethyl)quinolin-3-yl]oxy}ethyl]-5-(1H-pyrazol-1-yl)pyridin-2-ol

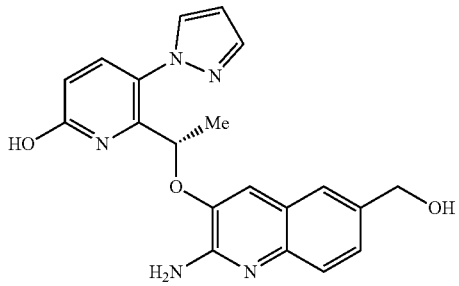 [SMILES: C[C@H](Oc1cc2cc(CO)ccc2nc1N)c1nc(O)ccc1-n1cccn1]

BH₃Me₂S (0.1 mL, 12 M) was added to a suspension of 2-amino-3-{(1S)-1-[6-hydroxy-3-(1H-pyrazol-1-yl)pyridin-2-yl]ethoxy}quinoline-6-carboxylic acid (Preparation 193, 60 mg, 0.15 mmol) in THF (10 mL) at 0° C. The resulting yellow suspension was stirred at 50° C. for ~4 hr before being quenched with MeOH (10 mL) and 1N HCl (5 mL). The resulting yellow solution was stirred at 25° C. for 10 minutes and evaporated to dryness in vacuo. The residue was purified by preparative HPLC to afford the title compound (12 mg, 21%) as a yellow solid. LCMS m/z=378 [M+H]⁺. ¹H NMR (DMSO-d₆, 400 MHz) δ: 1.81 (3H, d), 4.68 (2H, s), 5.40 (1H, q), 6.54 (1H, d), 6.67 (1H, t), 7.06 (1H, s), 7.39-7.43 (1H, m), 7.44-7.49 (2H, m), 7.58 (1H, d), 7.90 (1H, d), 7.96 (1H, d).

EXAMPLE 50

6-[(1S)-1-{[2-amino-6-(2-hydroxypropan-2-yl)quinolin-3-yl]oxy}ethyl]-5-(1H-pyrazol-1-yl)pyridin-2-ol

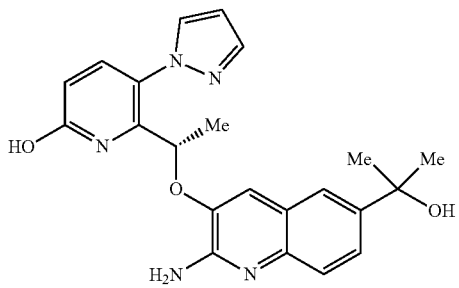 [SMILES: C[C@H](Oc1cc2cc(C(C)(C)O)ccc2nc1N)c1nc(O)ccc1-n1cccn1]

Step 1

MeNHOMe.HCl (77.1 mg, 0.575 mmol), DIPEA (297 mg, 2.3 mmol) and HATU (291 mg, 0.767 mmol) were added to a brown solution of 2-amino-3-{(1S)-1-[6-hydroxy-3-(1H-pyrazol-1-yl)pyridin-2-yl]ethoxy}quinoline-6-carboxylic acid (Preparation 193, 150 mg, 0.383 mmol) in DMF (3 mL). The reaction mixture was stirred at rt for 1 hr. The mixture was diluted with H₂O (5 mL) and extracted with EtOAc/THF (v/v=3/1; 5×15 mL). The combined organic extracts were dried (Na₂SO₄), and evaporated to dryness in vacuo to afford a yellow gum which was used in the following Step 2 without purification.

Step 2

To a solution of the compound of Step 1 in THF (10 mL) was added MeMgBr (4 mL, 3M) at 0° C. The reaction mixture was stirred at rt 6 hrs. The suspension was quenched with 1N HCl (3 mL) and evaporated to dryness in vacuo. The residue was diluted with H₂O (15 mL) and extracted with EtOAc/THF (v/v 2:1; 10×20 mL). The combined organic extracts were dried (Na₂SO₄) and evaporated to dryness in vacuo to give a yellow gum which was used in Step 3 without further purification.

Step 3

To a brown solution of the compound of Step 2 in THF (10 mL) was added MeMgBr (4 mL, 3M) at 0° C. The reaction mixture was stirred at rt for 1 hr. The reaction was quenched with 1N HCl (3 mL) and evaporated to dryness in vacuo. The residue was diluted with H₂O (30 mL) and extracted with EtOAc/THF (v/v=2/1, 10×20 mL). The combined organic extracts were dried (Na₂SO₄), evaporated to dryness in vacuo and the residue purified by preparative HPLC to afford the title compound as a yellow solid (15 mg, 9.6%). LCMS m/z=406 [M+H]⁺. ¹H NMR (MeOH-d₄, 400 MHz) δ: 1.59 (6H, s), 1.81 (3H, d), 5.42 (1H, br s), 6.54 (1H, br d), 6.65-6.70 (1H, m), 6.67 (1H, s), 7.05 (1H, s), 7.41-7.46 (1H, m), 7.51-7.61 (7.90 (1H, s), 7.97 (1H, s).

EXAMPLE 51 AND EXAMPLE 52, RESPECTIVELY

6-[(1S)-1-(1-({2-amino-6-[(1R)-1-hydroxyethyl]quinolin-3-yl}oxy)ethyl]-5-(1H-pyrazol-1-yl)pyridin-2-ol, and 6-[(1S)-1-(1-({2-amino-6-[(1S)-1-hydroxyethyl]quinolin-3-yl}oxy)ethyl]-5-(1H-pyrazol-1-yl)pyridin-2-ol

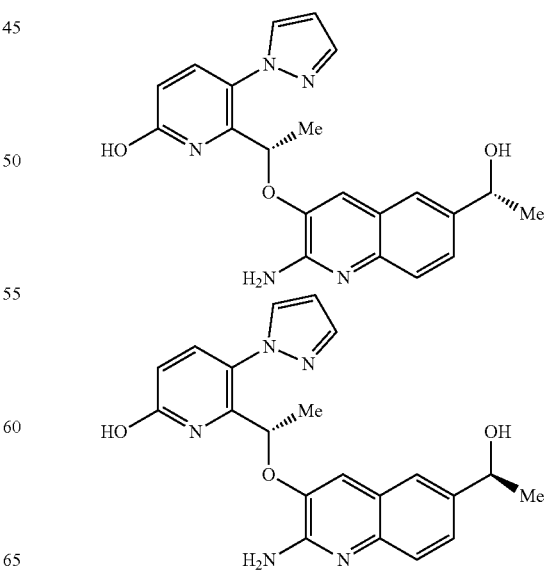

Step 1 of Example 50 was repeated to afford a yellow gum which was used in the following Step 2 without purification.

Step 2 of Example 50 was repeated to give a yellow gum which was used in Step 3 without further purification.

Step 3

To a solution of the compound of Step 2 in MeOH (10 mL) was added NaBH$_4$ (14.5 mg, 0.384 mmol) and the resulting solution stirred at 20° C. for 0.5 hr. The reaction mixture was acidified to pH 6 using 1N HCl and evaporated to dryness in vacuo. The residue was purified by preparative HPLC (XBridge. 0.05% aq NH$_4$OH/MeCN, 6%-46%) and then further purified by SFC (YMC Chiral Amylose-C, 0.1% NH$_4$OH in IPA, 40%) to afford 6-[(1S)-1-({2-amino-6-[(1R)-1-hydroxyethyl]quinolin-3-yl}oxy)ethyl]-5-(1H-pyrazol-1-yl)pyridin-2-ol as a pale yellow solid (13 mg, 46%). LCMS m/z=392 [M+H]$^+$. $^1$H NMR (DMSO-d$_6$, 400 MHz) δ: 1.35 (3H, d), 1.70 (3H, d), 4.70-4.82 (1H, m), 5.13 (1H, d), 5.26 (1H, q), 6.25-6.60 (3H, m), 6.66 (1H, t), 6.83 (1H, s), 7.25-7.41 (3H, m), 7.51 (1H, br s), 7.91 (1H, s), 8.14 (1H, d), 12.05 (1H, br d), and 6-[(1S)-1-({2-amino-6-[(1S)-1-hydroxyethyl]quinolin-3-yl}oxy)ethyl]-5-(1H-pyrazol-1-yl)pyridin-2-ol as a pale yellow solid (13 mg, 46%). LCMS m/z=392 [M+H]$^+$. $^1$H NMR (DMSO-d$_6$, 400 MHz) δ: 1.35 (3H, d), 1.71 (3H, d), 4.72-4.82 (1H, m), 5.14 (1H, d), 5.28 (1H, br d), 6.39 (1H, br s), 6.66 (3H, s), 6.86 (1H, s), 7.30-7.42 (3H, m), 7.53 (1H, br s), 7.91 (1H, s), 8.15 (1H, d), 12.06 (1H, br s).

EXAMPLE 53

6-{(1S)-1-[(2-amino-6,8-difluoroquinolin-3-yl)oxy]ethyl}-5-(1H-pyrazol-1-yl)pyridin-2-ol

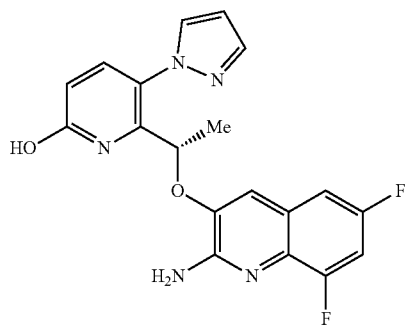 [SMILES: C[C@H](Oc1cc2cc(F)cc(F)c2nc1N)c1nc(O)ccc1-n1cccn1]

To a solution of 2-(3-{(1S)-1-[6-bromo-3-(1H-pyrazol-1-yl)pyridin-2-yl]ethoxy}-6,8-difluoroquinolin-2-yl)-1H-isoindole-1,3(2H)-dione (Preparation 172, 4000 mg, 6.94 mmol) and KOH (1170 mg, 20.8 mmol) in dioxane/H$_2$O (60 mL/30 mL) was added tBuXPhos (295 mg, 0.694 mmol) and Pd$_2$(dba)$_3$ (318 mg, 0.347 mmol) under N2. The resulting solution was heated at 90° C. for 16 hrs and evaporated to dryness in vacuo. The residue was dissolved in MeOH (30 mL) and N$_2$H$_4$.H$_2$O was added (30 mL, 85% purity) and stirred at 35° C. for 16 hrs. The suspension was removed by filtration and the filter cake washed with H$_2$O (30 mL). The filtrate was acidified to pH 10 with HCl (12 N) and extracted with DCM (2×100 mL). The combined extracts were dried (Na$_2$SO$_4$), evaporated to dryness in vacuo and the residue was purified by column chromatography (40 g, MeOH:DCM=0-5%) to obtain a solid which was slurried with MTBE:DCM to afford the title compound as a white solid (1 g, 37%). LCMS m/z=384 [M+H]$^+$. $^1$H NMR (DMSO-d$_6$, 400 MHz) δ: 1.70 (3H, d), 5.26 (1H, q), 6.38 (1H, br s), 6.64 (1H, t), 6.75-7.06 (4H, m), 7.16-7.31 (1H, m), 7.51 (1H, br s), 7.91 (1H, s), 8.17 (1H, d), 12.04 (1H, br s).

EXAMPLE 54

6-{(1S)-1-[(2-amino-6-methyl-1,5-naphthyridin-3-yl)oxy]ethyl}-5-(1H-pyrazol-1-yl)pyridin-2-ol

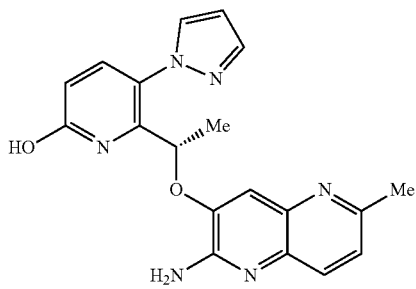 [SMILES: Cc1ccc2nc(N)c(O[C@@H](C)c3nc(O)ccc3-n3cccn3)cc2n1]

A mixture of tert-butyl (3-{(1S)-1-[6-bromo-3-(1H-pyrazol-1-yl)pyridin-2-yl]ethoxy}-6-methyl-1,5-naphthyridin-2-yl)carbamate (Preparation 183, 124.00 mg, 0.236 mmol), Pd$_2$(dba)$_3$ (10.8 mg, 0.0012 mmol), tBuXPhos (10.0 mg, 0.0236 mmol) and KOH (39.7 mg, 0.708 mmol) in dioxane/H$_2$O (2.0 mL/0.4 mL) was degassed and flushed with N$_2$ 3 times. The resulting suspension was heated at 80° C. for 1.5 hrs. Additional Pd$_2$(dba)$_3$ (10.8 mg, 0.0012 mmol), tBuXPhos (10.0 mg, 0.0236 mmol) and KOH (26.5 mg, 0.472 mmol) were added and the reaction mixture was again degassed and flushed with N$_2$ 3 times and then heated at 80° C. for 1.5 hrs. The reaction mixture was acidified to pH 6-7 with 4M HCl (drops) and evaporated to dryness in vacuo. TFA (1.0 mL) was added to a solution of the residue in DCM (3 mL) and the resulting solution stirred at rt for 2 hrs. The reaction mixture was evaporated to dryness in vacuo and the residue dissolved in MeOH/H$_2$O (2.5 mL/0.5 mL) and purified by preparative HPLC (Xtimate C18, 0.05% aq NH$_4$OH/MeCN, 6-46%) to afford the title compound as a white solid (15 mg, 18%). LCMS m/z=363 [M+H]$^+$. $^1$H NMR (DMSO-d$_6$, 400 MHz) δ: 1.67 (3H, d), 2.52 (3H, d), 5.37 (1H, q), 6.41 (1H, br s), 6.55-6.85 (3H, m), 6.93 (1H, s), 7.22 (1H, d), 7.54 (1H, br d), 7.65 (1H, d), 7.85 (1H, d), 8.08 (1H, d), 12.02 (1H, br s).

EXAMPLE 55

2-amino-3-{(1S)-1-[6-(hydroxymethyl)-3-(1H-pyrazol-1-yl)pyridin-2-yl]ethoxy}quinoline-6-carboxamide

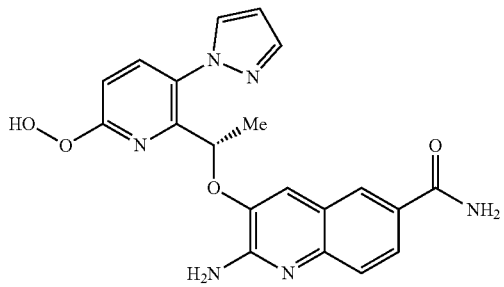 [SMILES: C[C@H](Oc1cc2cc(C(N)=O)ccc2nc1N)c1nc(OO)ccc1-n1cccn1]

2M NaOH (0.1 mL, 0.2 mmol) was added to a solution of 3-{(1S)-1-[6-({[tert-butyl(dimethyl)silyl]oxy}methyl)-3-(1H-pyrazol-1-yl)pyridin-2-yl]ethoxy}-2-(1,3-dioxo-1,3-dihydro-2H-isoindol-2-yl)quinoline-6-carbonitrile (Preparation 173, 66 mg, 0.1 mmol) in DMSO (0.3 mL) and the mixture stirred at 30° C. for 16 hrs. $N_2H_4.H_2O$ (0.4 mL) was added and stirring at 30° C. was continued for 16 hrs before heating at 50° C. for 48 hrs. The reaction mixture was evaporated to dryness in vacuo and purified by preparative HPLC (Xtimate C18, 0.225% aq $HCO_2H$/MeCN, 5-25%) to afford the title compound as a white solid (7 mg, 15%). LCMS m/z=427 [M+Na]$^+$. $^1$H NMR (DMSO-d$_6$, 400 MHz): δ=1.69 (3H, d), 4.53-4.66 (2H, m), 5.55 (1H, br t), 5.69 (1H, q), 6.52 (2H, br s), 6.60-6.69 (1H, m), 6.82 (1H, s), 7.22 (1H, br s), 7.35 (1H, d), 7.58 (1H, d), 7.71-7.79 (1H, m), 7.83-7.94 (4H, m), 8.14 (1H, s), 8.26 (1H, d).

EXAMPLE 56

6,8-difluoro-3-{(1S)-1-[6-methoxy-3-(1H-pyrazol-1-yl)pyridin-2-yl]ethoxy}quinolin-2-amine

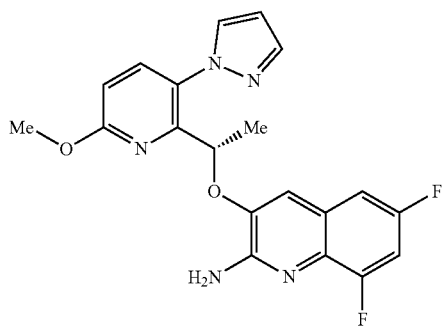 [SMILES: COc1ccc(-n2cccn2)c([C@H](C)Oc2cc3cc(F)cc(F)c3nc2N)n1]

$N_2H_4.H_2O$ (196 mg, 3.32 mmol) was added dropwise to a suspension of 2-(6,8-difluoro-3-{(1S)-1-[6-methoxy-3-(1H-pyrazol-1-yl)pyridin-2-yl]ethoxy}quinolin-2-yl)-1H-isoindole-1,3(2H)-dione (Preparation 175, 1030 mg, 1.7 mmol) in anhydrous MeOH (10 mL) at 10° C. and the reaction mixture stirred at 30° C. for 30 mins. The reaction mixture was evaporated to dryness in vacuo and the residue purified by column chromatography (EtOAc/pet. ether=0 to 40%) to give a yellow solid. The solid (470 mg) was diluted with MTBE (3 mL) and stirred at 10° C. for 16 hrs. The solid was collected by filtration and the filter cake washed with MTBE (3×0.5 mL) to afford the title compound as a yellow solid (395 mg, 60%).

LCMS m/z=398 [M+H]$^+$. $^1$H NMR (MeOH-d$_4$, 400 MHz) δ: 1.76 (3H, d), 3.93-3.99 (3H, m), 5.65 (1H, q), 6.61 (1H, t), 6.85 (1H, d), 6.94-7.04 (3H, m), 7.69 (1H, d), 7.86 (1H, d), 7.93 (1H, d).

EXAMPLE 57

6-fluoro-3-{(1S)-1-[6-methoxy-3-(1H-pyrazol-1-yl)pyridin-2-yl]ethoxy}quinolin-2-amine

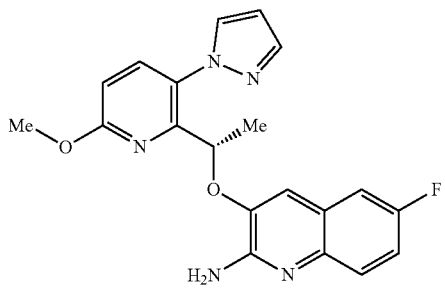 [SMILES: COc1ccc(-n2cccn2)c([C@H](C)Oc2cc3cc(F)ccc3nc2N)n1]

The title compound was obtained as a yellow solid (411.4 mg, 48%), following the procedure of Example 56, from 2-(6-fluoro-3-{(1S)-1-[6-methoxy-3-(1H-pyrazol-1-yl)pyridin-2-yl]ethoxy}quinolin-2-yl)-1H-isoindole-1,3(2H)-dione (Preparation 179). LCMS m/z=380 [M+H]$^+$. $^1$H NMR (DMSO-d$_6$, 400 MHz): δ=1.70 (3H, d), 3.88 (3H, s), 5.55 (1H, q), 6.23 (2H, br s), 6.62 (1H, d), 6.76 (1H, s), 6.89 (1H, d), 7.07-7.22 (2H, m), 7.38 (1H, dd), 7.78 (1H, d), 7.87 (1H, s), 8.18 (1H, d).

EXAMPLE 58

6-{(1S)-1-[(2-amino-6-fluoroquinolin-3-yl)oxy]ethyl}-5-(1H-pyrazol-1-yl)pyridin-2-ol (Prepared in Solid Form as its Amide Tautomer (S)-6-(1-((2-amino-6-fluoroquinolin-3-yl)oxy)ethyl)-5-(1H-pyrazol-1-yl)pyridin-2(1H)-one)

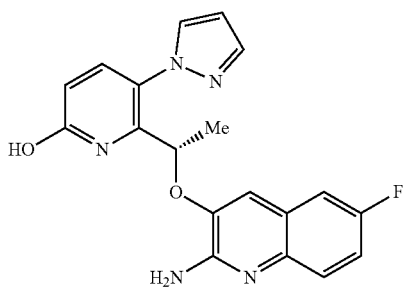

TMSCl (10300 mg, 94.5 mmol, 12.0 mL) was added to a fine suspension of 6-fluoro-3-{(1S)-1-[6-methoxy-3-(1H-pyrazol-1-yl)pyridin-2-yl]ethoxy}quinolin-2-amine (Example 57, 18600 mg, 49.025 mmol) and NaI (13000 mg, 86.730 mmol) in MeCN (300 mL) at rt and the mixture stirred at 65° C. for 3 hrs. The reaction mixture was cooled in an ice bath, saturated sodium thiosulfate (250 mL) added and the mixture stirred at 0° C. for 1.5 hrs, then filtered. The solid removed by filtration was added to H₂O (pH=7; 140 mL). The suspension was stirred at 40° C. and the pH continually adjusted to pH 7 with 1N sodium hydroxide (~34 mL) over 2 hrs. Once the pH stabilized at 7 the reaction mixture was cooled to rt and the solid removed by filtration, and dried in a vacuum oven, to afford the title compound as a colourless solid (7554 mg, 72%). LCMS m/z=366 [M+H]⁺. ¹H NMR (DMSO-d₆, 400 MHz) δ: 1.71 (3H, d), 5.25 (1H, q), 6.26-6.62 (3H, m), 6.65 (1H, t), 6.79 (1H, s), 7.10 (1H, dd), 7.20 (1H, dt), 7.41 (1H, dd), 7.51 (1H, br d), 7.91 (1H, d), 8.17 (1H, d), 12.00 (1H, br s). PXRD data are consistent with that obtained for the compound of Example 58a and confirm that the title compound was prepared in solid form as its amide tautomer.

EXAMPLE 58a (S)-6-(1-((2-amino-6-fluoroquinolin-3-yl)oxy)ethyl)-5-(1H-pyrazol-1-yl)pyridin-2(1H)-one

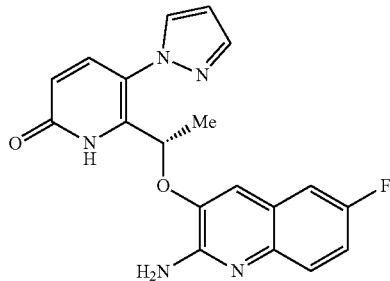 [SMILES: C[C@H](Oc1cc2cc(F)ccc2nc1N)c1[nH]c(=O)ccc1-n1cccn1]

Preparation

A 200 L reactor containing tetrahydrofuran (77.4 L, 9 L/kg) and aqueous 2.8 M potassium hydroxide solution (49.2 kg, 6.0 equiv, 120.5 mol) at 25° C. was sparged with nitrogen for 19 min. 3-{(1S)-1-[6-Bromo-3-(1H-pyrazol-1-yl)pyridin-2-yl]ethoxy}-6-fluoroquinolin-2-amine (Preparation 189, 8.60 kg, 1.0 equiv, 20.1 mol) was charged, and the reactor walls were rinsed with tetrahydrofuran (4.3 L, 0.5 L/kg). The resulting biphasic mixture was heated to 45° C. over 46 min. t-BuXPhos (172 g, 0.02 equiv, 0.40 mol) was charged, and the reaction mixture was held for 5 min. Tris(dibenzylideneacetone)dipalladium(0) (184 g, 0.01 equiv, 0.20 mol) was charged, and the reactor walls were rinsed with tetrahydrofuran (4.3 L, 0.5 L/kg). The mixture was heated to 60° C. over 18 min, held for 4 hr, and cooled to 45° C. Analysis of the mixture indicated the reaction was complete. The mixture was further cooled to 5° C. over 1 hr 15 min, and aqueous 6 M hydrochloric acid (18.6 kg, 5.2 equiv, 104.4 mol) was charged to neutralize the basic mixture while maintaining a batch temperature below 15° C. The mixture was warmed to 25° C. after the addition was complete. Next, aqueous 1 M sodium phosphate buffer (8.6 L, 1 L/kg) was charged over 10 min, and the mixture was held for 10 min. At this point, the pH of the aqueous layer was 7.5. The layers were separated, and the organic layer was distilled to ~26 L (3 L/kg) under vacuum. Fresh tetrahydrofuran (60.2 L, 7 L/kg) was charged, and the solution was distilled again to ~26 L (3 L/kg). The process was repeated twice, and fresh tetrahydrofuran (17.2 L, 2 L/kg) was charged after the final distillation. The batch temperature was adjusted to 20° C. At this point, the residual water content was 0.29%. The mixture was filtered through a pad of diatomaceous earth (2 kg) in a Nutsche filter to remove salts and palladium black that precipitated from the solution. The reactor and Nutsche filter were washed with tetrahydrofuran (17.2 L, 2 L/kg) and the washing was combined with the filtrate. The reactor and Nutsche filter were washed again with tetrahydrofuran (51.6 L, 6 L/kg), and the washing was collected in three separate fractions. The main filtrate and fractions containing the desired product were combined in the 200 L reactor, and the containers were rinsed with tetrahydrofuran (2 L) and charged to the reactor. Ultra Pure Si-Thiol silica gel (2.92 kg, 40 wt %) was charged. The mixture was held at 25° C. with agitation for 23 hr 35 min and filtered through a pad of diatomaceous earth (2 kg) in a Nutsche filter. The reactor and Nutsche filter were washed with 2:1 v/v tetrahydrofuran/ethanol mixture (8 L×4+11 L), collecting each washing in a separate container. The main filtrate and fractions containing the desired product were combined in the reactor. Each container was rinsed with 2:1 v/v tetrahydrofuran/ethanol mixture (2 L) and the rinse was charged to the reactor. The combined solution was distilled to ~17 L (2 L/kg), and ethanol (51.6 L, 6 L/kg) was charged. At this point, a robust slurry was formed. The slurry was distilled to ~17 L (2 L/kg), and ethanol (43.0 L, 5 L/kg) was charged. The batch temperature was adjusted to 25° C. At this point, the residual tetrahydrofuran content was 0.406 wt/wt %. The mixture was heated to 70° C., held for 1 hr 31 min, cooled to 25° C. over 1 hr 9 min, and held for 30 min. The mixture was further cooled to 0° C. over 42 min and held for 30 min. The slurry was filtered through a Nutsche filter, and the reactor and filter cake were washed with cold ethanol (8.6 L, 1 L/kg). The filter cake was blown with nitrogen for 8 hr 39 min. The material was transferred to tray dryers and dried at 45° C. under vacuum over 12 hr 14 min, affording the title compound as a white solid (6.266 kg, 85.4% yield).

An additional batch was run for the same process, giving the title compound as a white solid (6.236 kg, 85.1% yield). Purification with Si-Thiol Silica Gel To an ambient solution of 6-{(1S)-1-[(2-amino-6-fluoroquinolin-3-yl)oxy]ethyl}-5-(1H-pyrazol-1-yl)pyridin-2 (1H)-one obtained from the preceding step (12.48 kg, 1.0 equiv, 34.2 mol) in tetrahydrofuran (93.6 L, 7.5 L/kg) was charged Ultra Pure Si-Thiol silica gel (4.99 kg, 40 wt %). The reactor walls were rinsed with tetrahydrofuran (6.2 L, 0.5 L/kg). The mixture was heated to 50° C. over 50 min, held for 12 hr 17 min, and cooled to 25° C. over 43 min. The slurry was filtered through a pad of diatomaceous earth (1 kg) in a Nutsche filter. The reactor and Nutsche filter were washed with 2:1 v/v tetrahydrofuran/ethanol mixture (18 L×4+21.6 L), collecting each washing in a separate container. The main filtrate and fractions containing the desired product were combined in the reactor. Each container was rinsed with 2:1 v/v tetrahydrofuran/ethanol mixture (2 L) and the rinse was charged to the reactor. The combined solution was distilled to ~37 L (3 L/kg), and ethanol (87.4 L, 7 L/kg) was charged. At this point, a robust slurry was formed. The slurry was distilled to ~37 L (3 L/kg), and ethanol (87.4 L, 7 L/kg) was charged. The distillation/charging process was repeated once more. The batch temperature was adjusted to 25° C. At this point, the residual tetrahydrofuran content was 0.081 wt/wt %. The mixture was heated to 70° C., held for 1 hr 2 min, cooled to 25° C. over 1 hr 13 min, and held for 31 min. A sample of the slurry was extracted for solid form analysis by PXRD as set out in the section that follows entitled "PXRD analysis". The mixture was further cooled to 0° C. over 44 min and held for 30 min. The slurry was filtered through a Nutsche filter, and the reactor and filter cake were washed with cold ethanol (25.0 L, 2 L/kg). The filter cake was blown with nitrogen for 1 hr 8 min. The material was transferred to tray dryers and dried at 50° C. under vacuum over 40 hr 7 min, affording the title compound as a white solid (11.624 kg, 93.1% yield); PXRD data therefrom are consistent with that reported directly below for the slurry sample.

PXRD Analysis

PXRD analysis was conducted on the sample of the title compound extracted for solid form analysis in the preceding step using a Bruker AXS D8 Endeavor diffractometer equipped with a Cu radiation source. The divergence slit was set at 11 mm constant illumination. Diffracted radiation was detected by a LYNXEYE detector, with the PSD opening set at 2.949 degrees. The X-ray tube voltage and amperage were set to 40 kV and 40 mA respectively. Data was collected in the theta-theta goniometer at the Cu wavelength from 3.0 to 40.0° 2θ using a step size of 0.016 degrees and a time per step of 0.3 seconds.

The slurry sample was centrifuged and the isolated filtrate was placed in a silicon low background small divot sample holder and rotated during data collection. Data were analyzed in EVA diffract plus software. The peak selection carried out manually was carefully checked to ensure that all peaks below 30° 2θ had been captured and all peak positions had been accurately assigned. A typical error of ±0.2° 2θ in peak positions (USP-941) applies to this data. The minor error associated with this measurement can occur because of a variety of factors including: (a) sample preparation (e.g., sample height), (b) instrument characteristics, (c) instrument calibration, (d) operator input (e.g. in determining the peak locations), and (e) the nature of the material (e.g. preferred orientation and transparency effects). The PXRD profile for the crystalline form (Form 1) of the title compound is provided in FIG. 1. The corresponding peak list is provided in Table 1.

TABLE 1

PXRD peak list for the crystalline form (Form 1) of the title compound

| Angle, °2-Theta (°2θ) | Relative Intensity, % |
|---|---|
| 7.9* | 25 |
| 8.7* | 31 |
| 13.2 | 1 |
| 13.8 | 2 |
| 14.0 | 3 |
| 14.5 | 3 |
| 15.4 | 6 |
| 15.8 | 18 |
| 15.9 | 30 |
| 16.6 | 7 |
| 17.0 | 13 |
| 17.4* | 100 |
| 17.6 | 38 |
| 17.8 | 14 |
| 18.4* | 32 |
| 18.8 | 2 |
| 19.5 | 27 |
| 20.0 | 4 |
| 20.4* | 36 |
| 21.2 | 19 |
| 21.9 | 5 |
| 22.2 | 24 |
| 22.6 | 2 |
| 23.0 | 26 |
| 23.6 | 48 |
| 24.6 | 68 |
| 25.3 | 26 |
| 25.8 | 12 |

TABLE 1-continued

PXRD peak list for the crystalline form (Form 1) of the title compound

| Angle, °2-Theta (°2θ) | Relative Intensity, % |
|---|---|
| 25.9 | 16 |
| 26.2 | 15 |
| 27.1 | 5 |
| 27.4 | 10 |
| 27.7 | 6 |
| 28.3 | 6 |
| 29.2 | 8 |
| 30.0 | 9 |

PXRD peaks considered diagnostic for crystalline Form 1 are marked with an asterisk.

In one embodiment the invention provides the crystalline Form 1 of the title compound with PXRD peaks at 7.9°±0.2° 2θ, 8.7°±0.2° 2θ, 17.4° 1:0.2° 2θ, 18.4° 1:0.2° 2θ and 20.4°±0.2° 2θ.

In another embodiment the invention provides the crystalline Form 1 of the title compound with one, two, three or four PXRD peaks selected from the PXRD peaks at 7.9°±0.2° 2θ, 8.7°±0.2° 2θ, 17.4°±0.2° 2θ, 18.4°±0.2° 2θ and 20.4°±0.2° 2θ.

In another embodiment the invention provides the crystalline Form 1 of the title compound with PXRD peaks at 7.9°±0.2° 2θ and 8.7°±0.2° 2θ.

In another embodiment the invention provides the crystalline Form 1 of the title compound with PXRD peaks at 7.9°±0.2° 2θ, 8.7°±0.2° 2θ and 17.4°±0.2° 2θ.

In another embodiment the invention provides the crystalline Form 1 of the title compound with PXRD peaks at 7.9°±0.2° 2θ, 8.7°±0.2° 2θ, 17.4°±0.2° 2θ and 18.4°±0.2° 2θ.

In another embodiment the invention provides the crystalline Form 1 of the title compound with PXRD peaks at 7.9°±0.2° 2θ, 8.7°±0.2° 2θ, 17.4°±0.2° 2θ and 20.4°±0.2° 2θ.

EXAMPLE 58b (S)-6-(1-((2-amino-6-fluoroquinolin-3-yl)oxy)ethyl)-5-(1H-pyrazol-1-yl)pyridin-2(1H)-one Single Crystal Solution The title compound (4.577 g, 100 mass %, 12.53 mmol, 91.5% Yield, lot 711743-532-12) was isolated as a white crystalline solid following, at reduced scale, the process of Example 58a.

Single crystal data collection was performed on a Bruker D8 Venture diffractometer at room temperature. Data collection consisted of omega and phi scans. The structure was solved by intrinsic phasing using SHELX software suite in the Monoclinic class space group P21. The structure was subsequently refined by the full-matrix least squares method. All non-hydrogen atoms were found and refined using anisotropic displacement parameters. The final R-index was 2.9%. A final difference Fourier revealed no missing or misplaced electron density. Table 2 contains relevant structural data.

TABLE 2

Crystal structure data for crystalline form
(Form 1) of the title compound

| | |
|---|---|
| Empirical formula | C19 H16 F N5 O2 |
| Formula weight | 365.37 |
| Temperature | 296(2) K |
| Wavelength | 1.54178 Å |
| Crystal system | Monoclinic |
| Space group | P21 |
| Unit cell dimensions | a = 6.8257(6) Å    α = 90°. |
| | b = 22.3992(17) Å   β = 101.170(4)°. |
| | c = 11.7014(9) Å    γ = 90°. |
| Volume | 1755.1(2) Å3 |
| Z | 4 |
| Density (calculated) | 1.383 Mg/m3 |
| Goodness-of-fit on F2 | 1.034 |
| Final R indices [I > 2sigma(I)] | R1 = 0.0291, wR2 = 0.0684 |
| R indices (all data) | R1 = 0.0307, wR2 = 0.0696 |

Figure 2:
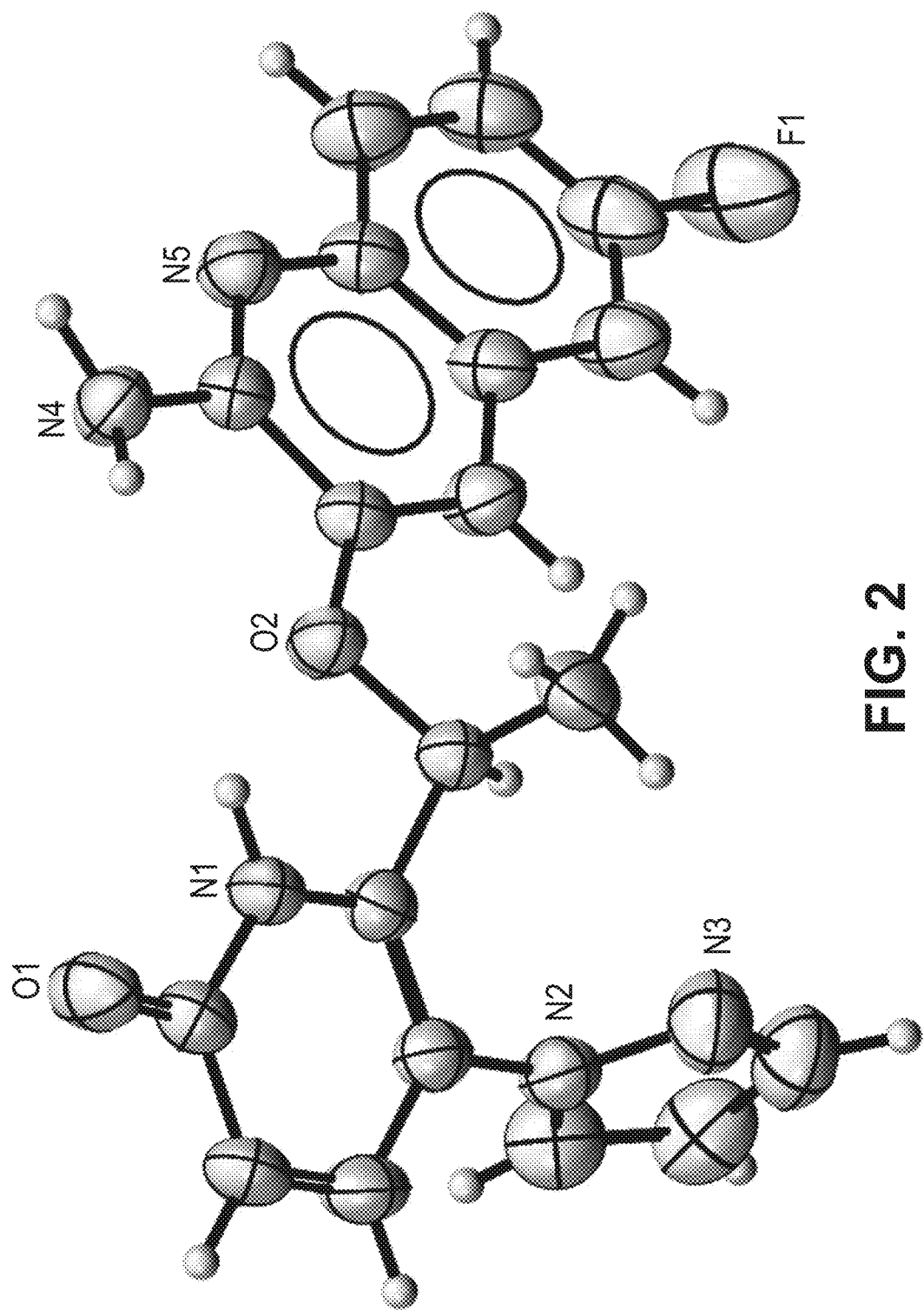
FIG. 2 is an X-ray crystal structure (ORTEP drawing) for the single crystal structure of the crystalline form (Form 1) of (S)-6-(1-((2-amino-6-fluoroquinolin-3-yl)oxy)ethyl)-5-(1H-pyrazol-1-yl)pyridin-2(1H)-one.

The absolute configuration (—S) and the tautomeric state of the title compound are confirmed via this solution. The ORTEP diagram for one of the molecules in the asymmetric unit for the solution is presented in FIG. 2. The peak position list for the simulated PXRD pattern from the single crystal structure is presented in Table 3.

TABLE 3

Peak position list for the simulated PXRD pattern from
the single crystal structure for Form 1 of the title compound

| Angle, °2-Theta (°2θ) | Relative Intensity, % |
|---|---|
| 7.9 | 80 |
| 8.7 | 23 |
| 13.2 | 6 |
| 13.8 | 9 |
| 14.0 | 12 |
| 14.5 | 13 |
| 15.4 | 15 |
| 15.8 | 18 |
| 16.0 | 7 |
| 16.1 | 24 |
| 16.5 | 20 |
| 17.0 | 21 |
| 17.4 | 39 |
| 17.6 | 57 |
| 17.8 | 35 |
| 18.4 | 100 |
| 18.7 | 2 |
| 19.5 | 15 |
| 20.0 | 8 |
| 20.4 | 94 |
| 20.7 | 3 |
| 21.1 | 61 |
| 21.8 | 12 |
| 22.2 | 15 |
| 22.2 | 16 |
| 22.6 | 2 |
| 23.0 | 36 |
| 23.7 | 23 |
| 24.3 | 15 |
| 24.5 | 6 |
| 24.5 | 15 |
| 24.8 | 1 |
| 25.1 | 4 |
| 25.3 | 19 |
| 25.7 | 11 |
| 25.9 | 21 |
| 26.2 | 5 |
| 27.1 | 7 |
| 27.4 | 12 |
| 27.7 | 14 |
| 28.2 | 1 |
| 28.9 | 3 |

TABLE 3-continued

Peak position list for the simulated PXRD pattern from
the single crystal structure for Form 1 of the title compound

| Angle, °2-Theta (°2θ) | Relative Intensity, % |
|---|---|
| 29.0 | 3 |
| 29.1 | 12 |
| 30.0 | 9 |

Comparison of the data in Table 1 with that presented in Table 3 for the simulated PXRD pattern of Form 1 of the title compound obtained from single crystal structure determination shows good peak correlation. The lack or loss of resolution of some peaks in the experimental data (Table 1 and FIG. 1) compared to the simulated pattern is to be expected and may be due to the inherent errors of the experimental PXRD data previously noted (i.e. errors associated with one or more of the factors (a) to (e)). It should also be noted that the peak list from the simulated pattern features two instances of two peaks at the same peak position (i.e. 22.2 and 24.5° 2θ). This is consequent on the precision (to one decimal place) to which the peak positions are quoted.

EXAMPLE 59

6-fluoro-3-{(1S)-1-[5-(1H-pyrazol-1-yl)-1H-indazol-6-yl]ethoxy}quinolin-2-amine

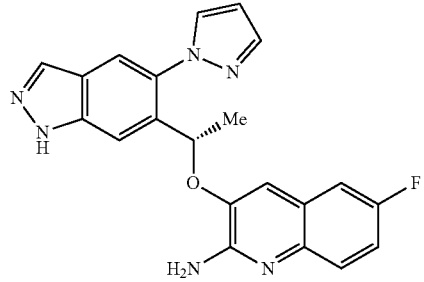 [SMILES: C[C@H](Oc1cc2cc(F)ccc2nc1N)c1cc2[nH]ncc2cc1-n1cccn1]

HCl/MeOH (0.5 mL, 4N) was added to a solution of 6-fluoro-3-{1-[5-(1H-pyrazol-1-yl)-1-(tetrahydro-2H-pyran-2-yl)-1H-indazol-6-yl]ethoxy}quinolin-2-amine (Preparation 196, 42 mg, 0.089 mmol) in MeOH (2 mL) at 5° C. The reaction mixture was allowed to warm to rt and stirred for 1.5 hrs before additional HCl/EtOAc (0.5 mL) was added and stirring continued at 25° C. 3 hrs. Additional HCl/EtOAc (0.3 mL) was added and the reaction mixture was stirred at 25° C. for further 1.5 hrs. The reaction mixture was evaporated to dryness in vacuo to give a light brown solid which was purified by preparative HPLC (DuraShell, 0.05% aq NH4OH/MeCN, 36-56%) to give a white solid, which was further purified by chiral SFC (Chiralcel AD, 0.1% NH4OH/EtOH, 30%) to afford the title compound (Peak 1) as a white solid (4.95 mg, 14%). LCMS m/z=389 [M+H]+. 1H NMR (MeCN-d3, 400 MHz): δ=1.66 (3H, d), 5.55-5.65 (3H, m), 6.61 (1H, t), 7.05-7.15 (3H, m), 7.45 (1H, dd), 7.81 (2H, s), 7.86 (1H, dd), 8.00 (1H, d), 8.09 (1H, s), 11.32 (1H, br s).

EXAMPLE 60

7-chloro-6-fluoro-3-{(1S)-1-[5-(1H-pyrazol-1-yl)-1H-indazol-6-yl]ethoxy}quinolin-2-amine

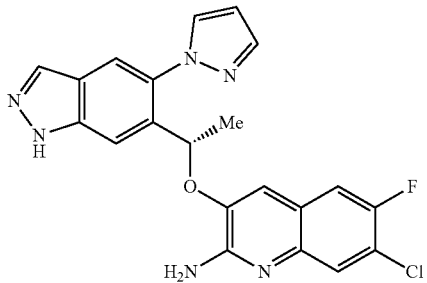 [SMILES: C[C@H](Oc1cc2cc(F)c(Cl)cc2nc1N)c1cc2[nH]ncc2cc1-n1cccn1]

The title compound was obtained as a white solid (6.15 mg) from 7-chloro-6-fluoro-3-{1-[5-(1H-pyrazol-1-yl)-1-(tetrahydro-2H-pyran-2-yl)-1H-indazol-6-yl]ethoxy}quinolin-2-amine (Preparation 197, 50 mg, 0.099 mmol) by following the procedure of Example 59, employing HPLC: DuraShell, 0.225% aq HCO$_2$H/MeCN, 38-58% and Chiral SFC: Chiralpak AD-H, 0.1% NH$_4$OH in EtOH, 30%). LCMS m/z=423 [M+H]$^+$. $^1$H NMR (MeOH-d$_4$, 400 MHz): δ=1.66 (3H, d), 4.62 (1H, br s), 5.60 (1H, q), 6.64 (1H, t), 7.17 (1H, s), 7.33 (1H, d), 7.51 (1H, d), 7.79 (1H, s), 7.90 (2H, br s), 8.07 (1H, d), 8.15 (1H, s).

EXAMPLE 61

2-amino-3-{(1S)-1-[5-(1H-pyrazol-1-yl)-1H-indazol-6-yl]ethoxy}quinoline-6-carboxamide

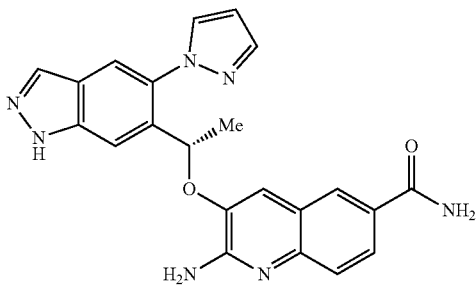 [SMILES: C[C@H](Oc1cc2cc(C(N)=O)ccc2nc1N)c1cc2[nH]ncc2cc1-n1cccn1]

To a yellow solution of 2-amino-3-{1-[5-(1H-pyrazol-1-yl)-1-(tetrahydro-2H-pyran-2-yl)-1H-indazol-6-yl]ethoxy}quinoline-6-carboxamide (Preparation 217, 600 mg, 1.21 mmol) in DCM (5 mL) was added TFA (3 mL) and the resulting solution stirred at 15° C. for ~2 hrs. The reaction mixture was evaporated to dryness in vacuo, partitioned between NaHCO$_3$(10 mL) and extracted with DCM (3×20 mL). The combined extracts were dried (Na$_2$SO$_4$) and evaporated to dryness in vacuo to give a residue which was purified by preparative HPLC (Xtimate C18, 0.05% aq NH$_4$OH/MeCN, 22-42%). The residue was further purified by chiral SFC (Chiral Tech IC, 0.2% isopropanol amine in IPA, 50%) to afford the title compound as an off-white solid (36.4 mg). LCMS m/z=414 [M+H]$^+$. $^1$H NMR (MeOH-d$_4$, 400 MHz): δ=1.64 (3H, d), 5.60 (1H, q), 6.62 (1H, s), 7.20 (1H, s), 7.48 (1H, d), 7.76-8.16 (7H, m).

EXAMPLE 62

2-amino-3-{(1S)-1-[5-(1H-pyrazol-1-yl)-1H-pyrazolo[3,4-b]pyridin-6-yl]ethoxy}quinoline-6-carboxamide

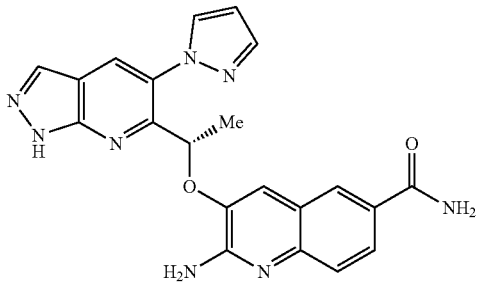 [SMILES: C[C@H](Oc1cc2cc(C(N)=O)ccc2nc1N)c1nc2[nH]ncc2cc1-n1cccn1]

A solution of 2-amino-3-[(1S)-1-{5-(1H-pyrazol-1-yl)-1-[(2S)-tetrahydro-2H-pyran-2-yl]-1H-pyrazolo[3,4-b]pyridin-6-yl}ethoxy]quinoline-6-carboxamide (Preparation 221, 00708245-1609-001, 971 mg 1.947 mmol) in TFA (5 mL) was stirred at 25° C. for ~2 hrs. The reaction mixture was evaporated to dryness in vacuo and the residue partitioned between DCM (50 mL) and aq NaHCO$_3$ (20 mL). The aqueous was extracted with DCM (3×20 mL), dried (Na$_2$SO$_4$) and evaporated to dryness in vacuo. The residue was purified by combiflash (SiO2, MeOH/DCM=0 to 10%) and the resulting solid recrystallized from DCM/EtOAc (5 mL/25 mL). The solid was then further purified by SFC (Phenomenex-Amylose-1, 0.1% NH$_4$OH in EtOH, 40%) to give the title compound as a yellow solid (135 mg, 16%). LCMS m/z=415 [M+H]$^+$. $^1$H NMR (DMSO-d$_6$, 400 MHz): δ=1.69 (3H, d), 5.56 (1H, q), 6.40-6.79 (3H, m), 6.96 (1H, s), 7.23 (1H, br s), 7.36 (1H, d), 7.75 (1H, dd), 7.82-8.00 (3H, m), 8.24 (1H, s), 8.31 (1H, d), 8.42 (1H, s), 14.00 (1H, s).

EXAMPLE 63

6-fluoro-3-{(1S)-1-[5-(1H-pyrazol-1-yl)-1H-benzimidazol-6-yl]ethoxy}quinolin-2-amine

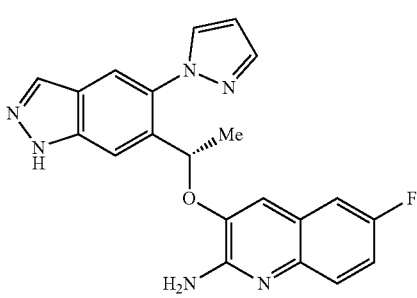 [SMILES: C[C@H](Oc1cc2cc(F)ccc2nc1N)c1cc2[nH]ncc2cc1-n1cccn1]

A yellow solution of 6-fluoro-3-{1-[5-(1H-pyrazol-1-yl)-1-{[2-(trimethylsilyl)ethoxy]methyl}-1H-benzimidazol-6-yl]ethoxy}quinolin-2-amine (Preparation 223, 240 mg, 0.463 mmol) and TBAF (1.0 M in THF, 3.0 mL, 3.0 mmol) was stirred at 55° C. for 1 h. The reaction mixture was evaporated to dryness in vacuo to give a yellow oil which was purified by preparative TLC (DCM:MeOH=15:1) to afford a white solid (72.4 mg). The title compound was obtained as a white solid (9.9 mg) as peak 1 from SFC separation (Chiralcel OJ, 0.1% NH$_4$OH in MeOH, 25%). LCMS m/z=389 [M+H]$^+$. $^1$H NMR (DMSO-d$_6$, 400 MHz): =1.69 (3H, d), 5.54 (1H, q), 6.64 (1H, s), 7.05-7.20 (3H, m), 7.42 (1H, q), 7.67 (1H, br s), 7.80-7.90 (2H, m), 8.54 (1H, s), 8.27 (1H, s).

EXAMPLE 64

6-fluoro-3-{(1S)-1-[2-methyl-5-(1H-pyrazol-1-yl)-1H-benzimidazol-6-yl]ethoxy}quinolin-2-amine

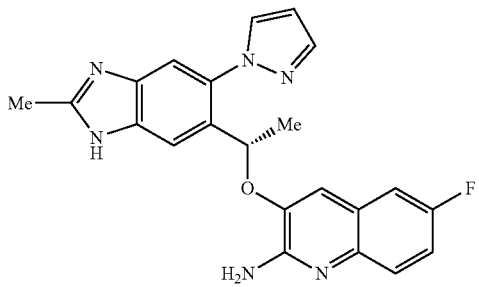 [SMILES: Cc1nc2cc(-n3cccn3)c([C@H](C)Oc3cc4cc(F)ccc4nc3N)cc2[nH]1]

To a solution of 6-fluoro-3-{1-[2-methyl-5-(1H-pyrazol-1-yl)-1-{[2-(trimethylsilyl)ethoxy]methyl}-1H-benzimidazol-6-yl]ethoxy}quinolin-2-amine (Preparation 225, 130 mg, 0.244 mmol) in dioxane (5 mL) was added HCl/dioxane (4 mL, 4M). The resulting solution was stirred at 25° C. for 16 hrs and evaporated to dryness in vacuo. The residue was basified by addition of saturated aq NaHCO$_3$ solution, extracted with EtOAc (3×15 mL), dried (Na$_2$SO$_4$) and evaporated to dryness in vacuo to afford a white gum, which was purified by preparative TLC (DCM/MeOH/NH$_4$OH, 10/1/0.5) to give a white solid. The title compound was obtained as a white solid (14.93 mg, 20%) after SFC purification (Chiralcel AD, 0.1% NH$_4$OH in MeOH, 30%). LCMS m/z=403 [M+H]$^+$. $^1$H NMR (MeOH-d$_4$, 400 MHz): δ=1.64 (3H, d), 2.55 (3H, s), 5.49 (1H, q), 6.65 (1H, t), 7.00-7.15 (3H, m), 7.41 (1H, dd), 7.52 (1H, br s), 7.73 (1H, br s), 7.89 (1H, d), 8.03 (1H, d).

EXAMPLE 65

2-amino-7-fluoro-3-{(1R)-1-[5-(1H-pyrazol-1-yl)-1H-indazol-6-yl]ethoxy}quinoline-6-carboxamide

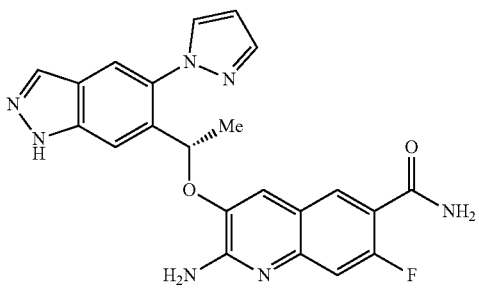 [SMILES: C[C@H](Oc1cc2cc(C(N)=O)c(F)cc2nc1N)c1cc2[nH]ncc2cc1-n1cccn1]

The title compound was obtained as a white solid (1.5 mg) from 2-amino-7-fluoro-3-{1-[5-(1H-pyrazol-1-yl)-1-{[2-(trimethylsilyl)ethoxy]methyl}-1H-indazol-6-yl] ethoxy}quinoline-6-carboxamide (Preparation 216, 50 mg, 0.89 mmol) by following the procedure of Example 64 and employing SFC: Chiralcel OJ, 0.1% NH$_4$OH in MeOH, 35%. LCMS m/z=432 [M+H]$^+$. $^1$H NMR (MeOH-d$_4$, 400 MHz): δ=1.68 (3H, d), 5.62 (1H, q), 6.65 (1H, t), 7.16 (1H, d), 7.25 (1H, s), 7.80 (1H, s), 7.85-7.95 (2H, m), 7.99 (1H, d), 8.08 (1H, s), 8.15 (1H, s).

EXAMPLE 66 tert-butyl (S)-2-(6-(1-((2-amino-6-fluoroquinolin-3-yl)oxy)ethyl)-5-(1H-pyrazol-1-yl)-1H-indazol-1-yl)acetate

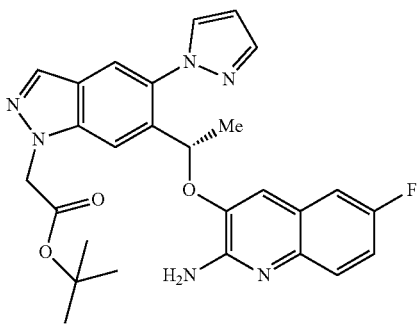 [SMILES: C[C@H](Oc1cc2cc(F)ccc2nc1N)c1cc2c(cnn2CC(=O)OC(C)(C)C)cc1-n1cccn1]

35% NH$_2$NH$_2$.H$_2$O (105 mg, 1.15 mmol) was added to a solution of tert-butyl {6-[(1S)-1-{[2-(1,3-dioxo-1,3-dihydro-2H-isoindol-2-yl)-6-fluoroquinolin-3-yl]oxy}ethyl]-5-(1H-pyrazol-1-yl)-1H-indazol-1-yl}acetate (Preparation 207, 145 mg, 0.229 mmol) in CDCl$_3$ (0.4 mL) and MeOH (1.6 mL) and the resulting thick white precipitate was allowed to stand at rt overnight. MeOH and EtOAc were added and the solid removed by filtration. The filtrate was diluted with EtOAc and washed with NaOH (1×5 mL), H$_2$O and brine. The previously filtered solids were partitioned between EtOAc and 1N NaOH. The aqueous layer was further extracted with EtOAc and the organic extracts combined, dried (MgSO$_4$) and evaporated to afford the title compound as an off-white solid (98 mg, 85%). LCMS m/z=503

EXAMPLE 67

[6-{(1S)-1-[(2-amino-6-fluoroquinolin-3-yl)oxy] ethyl}-5-(1H-pyrazol-1-yl)-1H-indazol-1-yl]acetic Acid

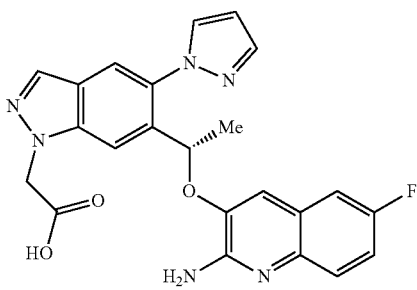 [SMILES: C[C@H](Oc1cc2cc(F)ccc2nc1N)c1cc2c(cnn2CC(=O)O)cc1-n1cccn1]

HCl (1 mL, 4M in dioxane) was added to a solution of tert-butyl (S)-2-(6-(1-((2-amino-6-fluoroquinolin-3-yl)oxy)ethyl)-5-(1H-pyrazol-1-yl)-1H-indazol-1-yl)acetate (Example 66, 98.3 mg, 0.196 mmol) in DCM (1 mL). An insoluble semi-solid formed which was solubilised by the addition of MeOH (~0.5 mL). The pH was adjusted to ~pH 12 with KOH (1N in MeOH) and the resulting mixture stirred at rt. The pH was adjusted to pH7 with 1N HCl and the reaction mixture evaporated to dryness in vacuo to give a solid which was azeotroped with heptane (2×). The solids were taken up in hot MeCN and filtered through a pad of Celite®. The filtrate was evaporated to dryness and azeotroped with heptane (2×) to give an off white solid that was purified by HPLC (Waters Atlantis dC18, 0.05% TFA in $H_2O$/0.05% TFA in MeCN, 95/5 to 5/95). The resulting solid was triturated with $Et_2O$, stirred vigorously and then allowed to stand unstirred overnight. The $Et_2O$ was decanted and the solids dissolved in warm EtOAc (~3 mL) and then filtered through a 0.2 μm nylon frit. The filtrate was allowed to slowly cool and partially evaporate to afford the title compound as a tan solid (10 mg, 11%). LCMS m/z=447 [M+H]$^+$. $^1$H NMR (MeOH-d$_4$, 400 MHz) δ: 1.68 (3H, d), 4.10 (1H, q), 5.52 (1H, q), 6.80 (1H, s), 7.02-7.38 (3H, m), 7.40 (1H, dd), 7.78-7.90 (3H, m), 8.00 (1H, s), 8.10 (1H, s).

EXAMPLE 68

6-fluoro-3-{(1S)-1-[5-(1H-pyrazol-1-yl)-1H-pyrazolo[3,4-b]pyridin-6-yl]ethoxy}quinolin-2-amine

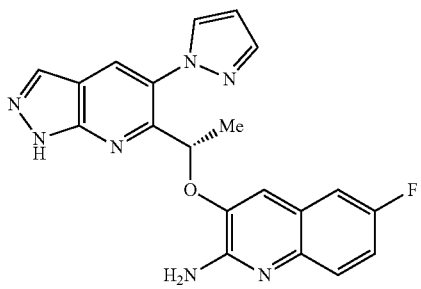 [SMILES: C[C@H](Oc1cc2cc(F)ccc2nc1N)c1nc2[nH]ncc2cc1-n1cccn1]

To a solution of 2-(6-fluoro-3-{(1S)-1-[5-(1H-pyrazol-1-yl)-1-{[2-(trimethylsilyl)ethoxy]methyl}-1H-pyrazolo[3,4-b]pyridin-6-yl]ethoxy}quinolin-2-yl)-1H-isoindole-1,3 (2H)-dione (Preparation 202, 288 mg, 0.443 mmol) in MeOH (3 mL) was added $N_2H_4.H_2O$ (1500 mg, 1.5 mL, 31 mmol) and the mixture stirred at rt for 2 hrs. The reaction mixture was evaporated to dryness in vacuo, treated with TFA (10 mL) and stirred at rt for 1 hr. The reaction mixture was evaporated to dryness and purified by preparative HPLC (DuraShell, 0.05% aq NH$_4$OH/MeCN; 23-63%) to afford the title compound as a white solid (63.3 mg, 37%).

LCMS m/z=390 [M+H]$^+$ $^1$H NMR (DMSO-d$_6$, 400 MHz): δ=1.68 (3H, d), 5.51 (1H, q), 6.60 (1H, t), 6.75 (2H, br s), 7.01 (1H, s), 7.07 (1H, d), 7.50 (2H, br d), 7.71 (1H, d), 7.88 (1H, s), 8.23 (1H, s), 8.28 (1H, d), 8.39 (1H, s), 13.98 (1H, s).

EXAMPLE 69

[6-{(1S)-1-[(2-amino-6,8-difluoroquinolin-3-yl)oxy]ethyl}-5-(1H-pyrazol-1-yl)-1H-indazol-1-yl]acetic Acid

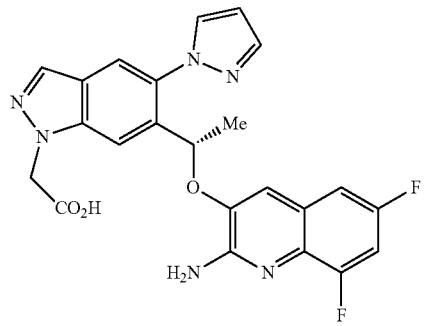 [SMILES: C[C@H](Oc1cc2cc(F)cc(F)c2nc1N)c1cc2c(cnn2CC(=O)O)cc1-n1cccn1]

To a solution of methyl {6-[(1S)-1-{[2-(1,3-dioxo-1,3-dihydro-2H-isoindol-2-yl)-6,8-difluoroquinolin-3-yl]oxy}ethyl]-5-(1H-pyrazol-1-yl)-1H-indazol-1-yl}acetate (Preparation 198, 949 mg, 0.94 mmol) in MeOH (10 mL) and THF (5 mL) was added aq NaOH (2N, 5 mL) and the resulting mixture was stirred at rt for 1.5 hrs. $N_2H_4.H_2O$ (4 mL) was added to the mixture and stirring continued at rt for 37 hrs. The reaction mixture was evaporated to dryness in vacuo and the residue partitioned between $H_2O$ (10 mL) and EtOAc (15 mL). The pH of the aqueous layer was adjusted to pH=5-6 with 1N HCl and extracted with EtOAc (15 mL×3). The combined organic extracts were evaporated to dryness in vacuo and purified by preparative HPLC (DuraShell; 0.05% aq NH$_4$OH/MeCN, 15-35%) to afford the title compound as a white solid (258.5 mg, 36%). LCMS m/z=465 [M+H]$^+$. $^1$H NMR (DMSO-d$_6$, 400 MHz): δ=1.62 (3H, d), 5.13-5.00 (2H, m), 5.42 (1H, q), 6.61 (1H, t), 6.77 (2H, br s), 6.97 (1H, s), 7.01 (1H, dt), 7.16 (1H, ddd), 7.82 (1H, s), 7.88 (1H, d), 7.99 (1H, s), 8.11 (1H, d), 8.24 (1H, d).

EXAMPLE 70

2-[6-{(1S)-1-[(2-amino-6-fluoroquinolin-3-yl)oxy]ethyl}-5-(1H-pyrazol-1-yl)-1H-indazol-1-yl]acetamide

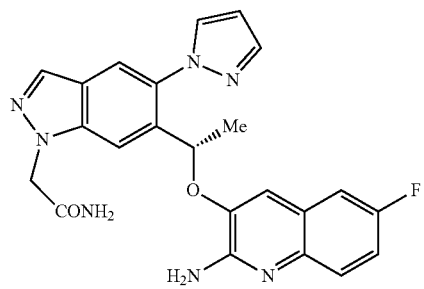 [SMILES: C[C@H](Oc1cc2cc(F)ccc2nc1N)c1cc2c(cnn2CC(N)=O)cc1-n1cccn1]

A solution of methyl {6-[(1S)-1-{[2-(1,3-dioxo-1,3-dihydro-2H-isoindol-2-yl)-6-fluoroquinolin-3-yl]oxy}ethyl]-5-(1H-pyrazol-1-yl)-1H-indazol-1-yl}acetate (Preparation 201, 295 mg, 0.499 mmol) in NH$_3$/MeOH (~8M, 10 mL)

was stirred at 80° C. in a steel tube for 48 hrs. The reaction mixture was evaporated to dryness in vacuo and the residue purified by HPLC (DuraShell C18, 0.05% aq NH$_4$OH/MeCN, 22-62%) and then SFC (Chiralcel OD-H, 0.1% NH$_4$OH in EtOH, 45%) to afford the title compound as a white solid (51 mg, 23%). LCMS m/z=446 [M+H]$^+$. $^1$H NMR (DMSO-d$_6$, 400 MHz): δ=1.64 (3H, d), 5.08 (2H, d), 5.43 (1H, d), 6.46 (2H, s), 6.63 (1H, t), 6.92 (1H, s), 7.08-7.20 (2H, m), 7.29 (1H, s), 7.38 (1H, br d), 7.61 (1H, s), 7.84 (1H, s), 7.90 (1H, d), 8.03 (1H, s), 8.15 (1H, d), 8.26 (1H, d).

EXAMPLE 71

[6-{(1S)-1-[(2-amino-6-fluoroquinolin-3-yl)oxy]ethyl}-5-(1H-pyrazol-1-yl)-2H-indazol-2-yl]acetic Acid

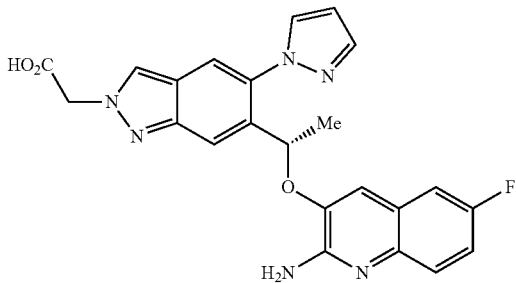 [SMILES: C[C@H](Oc1cc2cc(F)ccc2nc1N)c1cc2nn(CC(=O)O)cc2cc1-n1cccn1]

A solution of {6-[(1S)-1-({2-[(tert-butoxycarbonyl)amino]-6-fluoroquinolin-3-yl}oxy)ethyl]-5-(1H-pyrazol-1-yl)-2H-indazol-2-yl}acetic acid (Preparation 219, 80 mg, 0.15 mmol) in DCM/TFA (3 mL/2 mL) was stirred at 28° C. for 1 hr. The reaction mixture was concentrated in vacuo, THF (3×10 mL) added and the solution evaporated to dryness in vacuo to remove traces of TFA. The residue was purified by preparative HPLC (Phenomenex Gemini-NX, 0.05% aq NH$_4$OH/MeCN, 22-42%) to afford the title compound as a white solid (11.6 mg, 18%). LCMS m/z=447 [M+H]$^+$. $^1$H NMR (DMSO-d$_6$, 400 MHz): b=1.59 (3H, s), 5.24 (2H, d), 5.43 (1H, q), 6.54 (2H, s), 6.62 (1H, t), 6.94 (1H, s), 7.09-7.18 (2H, m), 7.38 (1H, dd), 7.83 (1H, s), 7.85-7.91 (2H, m), 8.27 (1H, d), 8.47 (1H, s).

EXAMPLE 72

2-[6-{(1S)-1-[(2-amino-6,8-difluoroquinolin-3-yl)oxy]ethyl}-5-(1H-pyrazol-1-yl)-1H-indazol-1-yl]ethanol

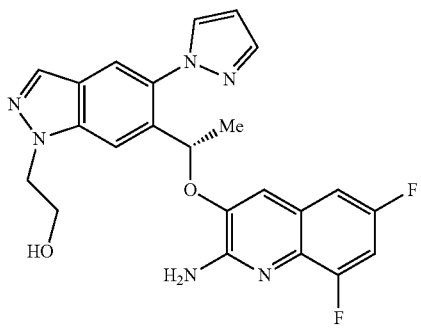 [SMILES: C[C@H](Oc1cc2cc(F)cc(F)c2nc1N)c1cc2c(cnn2CCO)cc1-n1cccn1]

To a solution of methyl {6-[(1S)-1-{[2-(1,3-dioxo-1,3-dihydro-2H-isoindol-2-yl)-6,8-difluoroquinolin-3-yl]oxy}ethyl]-5-(1H-pyrazol-1-yl)-1H-indazol-1-yl}acetate (Preparation 198, 328 mg, 0.555 mmol) in dry THF/MeOH (3 mL/3 mL) was added NaOH (222 mg, 5.55 mmol, 2 M aq). The resulting reaction mixture was stirred at 28° C. for 1 hr. N$_2$H$_4$.H$_2$O (0.5 mL) was added to the reaction mixture and the resulting reaction mixture stirred at ~25° C. for 16 hrs. Additional N$_2$H$_4$.H$_2$O (0.5 mL) was added and stirring continued for 22 hr at 40° C. The reaction mixture was evaporated to dryness in vacuo and the residue partitioned between H$_2$O (10 mL) and EtOAc (15 mL). The aqueous solution was acidified to pH4-5 with 1N HCl and then extracted with EtOAc (3×15 mL), dried (Na$_2$SO$_4$) and evaporated to dryness in vacuo to afford an off-white solid (143 mg). THF was added with cooling to afford an ice-cold THF solution, to which was added BH$_3$SMe$_2$ (0.308 mL, 3.08 mmol). The resulting reaction mixture was stirred at rt for ~1.5 hrs before an additional BH$_3$SMe$_2$ (0.5 mL, 5 mmol) was added and stirring continued at rt overnight (~16 hrs). MeOH was slowly added to the mixture, which was then evaporated to dryness in vacuo. The residue was partially purified using column chromatography (4 g silica gel column, EtOAc/pet. ether=50%/100%) to afford a residue that was further purified by Preparative HPLC (DuraShell, 0.05% aq NH$_4$OH/MeCN, 39-69%) and SFC (Chiralcel-OD; 0.1% NH$_4$OH in EtOH, 30%) to afford the title compound as a white solid (15 mg, 6%). LCMS m/z=451 [M+H]$^+$. $^1$H NMR (MeOH-d$_4$, 400 MHz): δ=1.68 (3H, d), 3.93 (2H, t), 4.50 (2H, t), 5.56 (1H, q), 6.61 (1H, t), 6.93-7.04 (2H, m), 7.16 (1H, d), 7.83 (1H, s), 7.87 (1H, d), 7.91 (1H, s), 8.01 (1H, d), 8.11 (1H, d).

EXAMPLE 73

2-[6-{(1S)-1-[(2-amino-6-fluoroquinolin-3-yl)oxy]ethyl}-5-(1H-pyrazol-1-yl)-1H-indazol-1-yl]ethanol

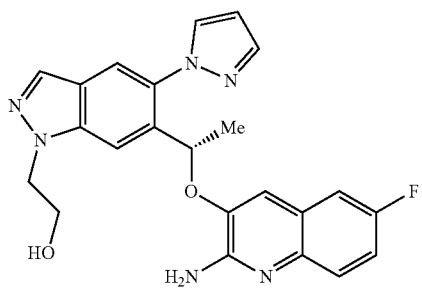 [SMILES: C[C@H](Oc1cc2cc(F)ccc2nc1N)c1cc2c(cnn2CCO)cc1-n1cccn1]

A solution of tert-butyl (6-fluoro-3-{(1S)-1-[1-(2-hydroxyethyl)-5-(1H-pyrazol-1-yl)-1H-indazol-6-yl]ethoxy}quinolin-2-yl)carbamate (Preparation 218, 79 mg, 0.15 mmol) in DCM/TFA (3 mL/2 mL) was stirred at rt for 1.5 hrs. The reaction mixture was evaporated to dryness in vacuo, azeotroped with THF (3×5 mL) and the residue purified by Preparative HPLC (Durashell, 0.05% aq NH$_4$OH/MeCN, 35-65%). The resulting material was combined with material from a second synthesis from carbamate (Preparation 218, 155 mg, 0.29 mmol) and purified by SFC (Chiralcel-OD, 0.1% NH$_4$OH in EtOH, 30%) to afford the title compound as a white solid (30 mg). LCMS m/z=433 [M+H]$^+$. $^1$H NMR (DMSO-d$_6$, 400 MHz): δ=1.67 (3H, d), 3.80 (2H, br s), 4.06 (1H, br s), 4.41-4.51 (2H, m), 4.86 (1H, br s), 5.46 (1H, q), 6.63 (1H, t), 7.01 (2H, s), 7.16-7.25 (2H, m), 7.44 (br dd), 7.83 (1H, s), 7.90 (1H, d), 8.05 (1H, s), 8.14 (1H, d), 8.25 (1H, d).

EXAMPLE 74

2-amino-3-{(1S)-1-[1-(2-hydroxyethyl)-5-(1H-pyrazol-1-yl)-1H-indazol-6-yl]ethoxy}quinoline-6-carboxamide

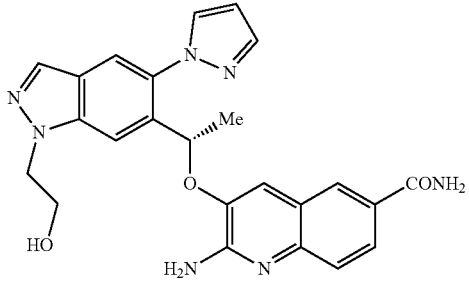 [SMILES: C[C@H](Oc1cc2cc(C(N)=O)ccc2nc1N)c1cc2c(cnn2CCO)cc1-n1cccn1]

To a solution of 2-amino-3-{1-[1-(2-{[tert-butyl(dimethyl)silyl]oxy}ethyl)-5-(1H-pyrazol-1-yl)-1H-indazol-6-yl]ethoxy}quinoline-6-carboxamide (Preparation 215, 2400 mg, 4.198 mmol) in dry DCM (50 mL) was added TFA (5 mL) at rt (15° C.) and the mixture stirred at rt for 5 hrs. The reaction mixture was evaporated to dryness in vacuo and the residue basified to pH=9 by the addition of saturated aqueous NaHCO₃. The resulting suspension was stirred for 10 mins, diluted with DCM/MeOH (50/1, 200 mL), washed with H₂O (10 mL) and then brine (10 mL), dried (Na₂SO₄) and then evaporated to dryness in vacuo. The residue was purified by SFC (Chiralcel-OJ, 0.1% NH₄OH in EtOH, 40%) to afford the title compound as a light yellow solid (peak 2, 650 mg, 33%). LCMS m/z=480 [M+Na]⁺. ¹H NMR (DMSO-d₆, 400 MHz): δ=1.63 (3H, d), 3.79 (2H, br s), 4.39-4.50 (2H, m), 4.86 (1H, br s), 5.48 (1H, d), 6.65 (1H, t), 6.81 (2H, br s), 7.02 (1H, s), 7.23 (1H, br s), 7.36 (1H, d), 7.76 (1H, dd), 7.84 (1H, s), 7.88 (2H, br d), 7.92 (1H, d), 8.03 (1H, s), 8.14 (1H, s), 8.25 (1H, d).

EXAMPLE 75

7-methyl-3-{(1S)-1-[5-(1H-pyrazol-1-yl)-1H-pyrazolo[3,4-b]pyridin-6-yl]ethoxy}-1,6-naphthyridin-2-amine

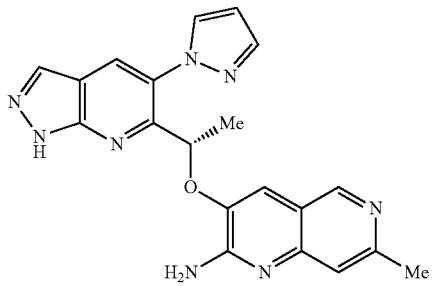 [SMILES: Cc1cc2nc(N)c(O[C@@H](C)c3nc4[nH]ncc4cc3-n3cccn3)cc2cn1]

A solution of tert-butyl (7-methyl-3-{(1S)-1-[5-(1H-pyrazol-1-yl)-1-{[2-(trimethylsilyl)ethoxy]methyl}-1H-pyrazolo[3,4-b]pyridin-6-yl]ethoxy}-1,6-naphthyridin-2-yl)carbamate (Preparation 205, 90 mg, 0.15 mmol) in DCM/TFA (1 mL/1 mL) was stirred at rt for 1 hr. The reaction mixture was evaporated to dryness in vacuo and the residue purified by preparative HPLC (DuraShell C18, 0.05% aq NH₄OH/MeCN, 10-50%) to afford the title compound as a yellow solid (10 mg, 18%). LCMS m/z=387 [M+H]⁺. ¹H NMR (DMSO-d₆, 400 MHz): δ=1.71 (3H, d), 2.40-2.47 (3H, m), 5.52-5.63 (1H, m), 6.56-6.64 (1H, m), 6.91 (2H, s), 7.05 (1H, s), 7.88 (1H, d), 8.25 (1H, s), 8.30 (1H, d), 8.40 (1H, s), 8.47 (1H, s), 14.01 (1H, s).

EXAMPLE 76

2-amino-7-fluoro-3-{(1S)-1-[5-(1H-pyrazol-1-yl)-1H-pyrazolo[3,4-b]pyridin-6-yl]ethoxy}quinoline-6-carboxamide

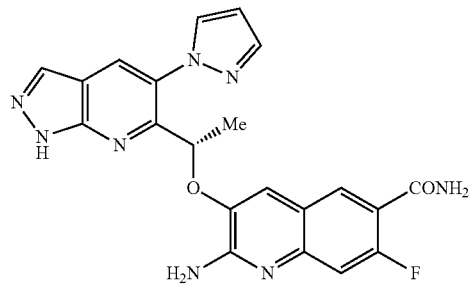 [SMILES: C[C@H](Oc1cc2cc(C(N)=O)c(F)cc2nc1N)c1nc2[nH]ncc2cc1-n1cccn1]

The title compound was prepared from 2-amino-7-fluoro-3-{(1S)-1-[5-(1H-pyrazol-1-yl)-1-{[2-(trimethylsilyl)ethoxy]methyl}-1H-pyrazolo[3,4-b]pyridin-6-yl]ethoxy}quinoline-6-carboxamide (Preparation 222, 95.7 mg, 0.17 mmol) as a white solid (13.49 mg, 18%) by following the procedure of Example 75.

LCMS m/z=433 [M+H]⁺

¹H NMR (DMSO-d₆, 400 MHz): δ=1.68 (3H, d), 5.51 (1H, q), 6.60 (1H, t), 6.75 (2H, br s), 7.01 (1H, s), 7.07 (1H, d), 7.50 (2H, br d), 7.71 (1H, d), 7.88 (1H, d), 8.23 (1H, s), 8.28 (1H, d), 8.39 (1H, s), 13.98 (1H, s).

EXAMPLE 76a 2-amino-7-fluoro-3-{(1S)-1-[5-(1H-pyrazol-1-yl)-1H-pyrazolo[3,4-b]pyridin-6-yl]ethoxy}quinoline-6-carboxamide A solution of 2-amino-7-fluoro-3-{(1S)-1-[5-(1H-pyrazol-1-yl)-1-{[2-(trimethylsilyl)ethoxy]methyl}-1H-pyrazolo[3,4-b]pyridin-6-yl]ethoxy}quinoline-6-carboxamide (Preparation 222, 1800 mg, 3.2 mmol) in TFA (5 mL) was stirred at rt for 1 hr. The reaction mixture was evaporated to dryness in vacuo and the residue was purified by Combi-Flash (silica gel, DCM/MeOH=100/0 to 20/1) to give the partially purified product (1100 mg) as a yellow solid. The solid was dissolved in dioxane (40 mL) and NH₄OH (10 mL) and the yellow solution was stirred at 20° C. for 2 hr. The yellow solution was concentrated and purified by preparative HPLC (DAICEL CHIRALPAK AS, 0.1% NH₄OH/ EtOH, 40%) to afford the title compound as a yellow solid (475 mg, 34%).

The solid was taken up in EtOH (5 mL) in an 8 dram vial and heated to 65° C. for 30 mins. The mixture was cooled to rt and the slurry stirred for 60 hrs. The mixture was then filtered, washed with ethanol (2 mL) and dried under vacuum for 1 hr. The solid was collected and dried further using high vacuum and heating to 55° C. for 16 hrs, then kept under high vacuum without heat for three additional days to provide the title compound as a crystalline solid, which was then analysed by PXRD.

PXRD analysis was conducted using a Bruker AXS D8 Endeavor diffractometer equipped with a Cu radiation source. The divergence slit was set at 11 mm continuous illumination. Diffracted radiation was detected by a PSD-Lynx Eye detector, with the detector PSD opening set at 2.949 degrees. The X-ray tube voltage and amperage were set to 40 kV and 40 mA respectively. Data was collected in the Theta-Theta goniometer at the Cu wavelength (CuKα̅ λ=1.5418 Å) from 3.0 to 40.0 degrees 2-Theta using a step size of 0.016 degrees and a step time of 0.3 second. A 0.012 mm thickness nickel Kβ filter was used. The antiscatter screen was set to an automatic mode. Samples were prepared by placing them in a silicon low background sample holder and rotated during data collection. Data were collected using Bruker DIFFRAC Plus software and analysis was performed by EVA diffract plus software.

Figure 3:
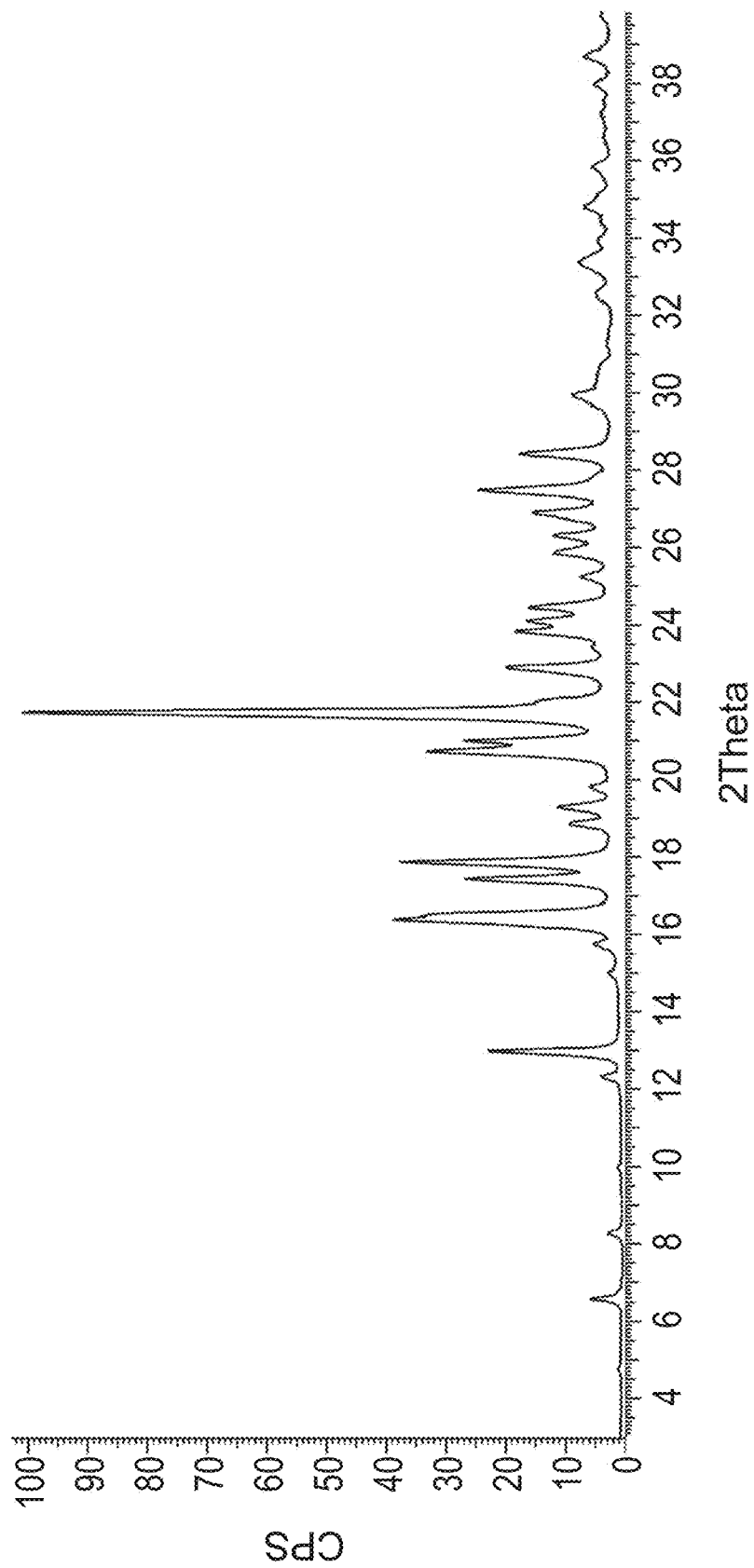
FIG. 3 is a PXRD pattern for the crystalline form (Form 1) of 2-amino-7-fluoro-3-{(1S)-1-[5-(1H-pyrazol-1-yl)-1H-pyrazolo[3,4-b]pyridin-6-yl]ethoxy}quinoline-6-carboxamide.

The PXRD profile for the crystalline form (Form 1) of the title compound is provided in FIG. 3.

EXAMPLE 77

2-[6-{(1S)-1-[(2-amino-7-methyl-1,6-naphthyridin-3-yl)oxy]ethyl}-5-(1H-pyrazol-1-yl)-1H-pyrazolo[3,4-b]pyridin-1-yl]ethanol

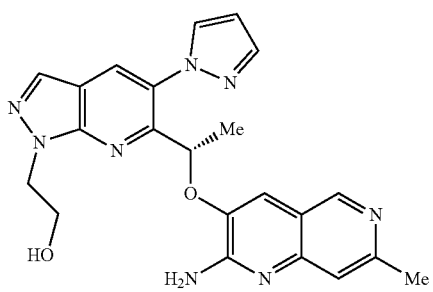 [SMILES: Cc1cc2nc(N)c(O[C@@H](C)c3nc4c(cnn4CCO)cc3-n3cccn3)cc2cn1]

TFA (1 mL) was added to a solution of tert-butyl (3-{(1S)-1-[1-(2-hydroxyethyl)-5-(1H-pyrazol-1-yl)-1H-pyrazolo[3,4-b]pyridin-6-yl]ethoxy}-7-methyl-1,6-naphthyridin-2-yl)carbamate (Preparation 220, 114 mg, 0.215 mmol) in DCM (2 mL) at 10° C. and stirred for 1 hr. The reaction mixture was evaporated to dryness in vacuo and the residue purified by preparative HPLC (DuraShell, 0.05% aq NH₄OH/MeCN, 23-43%) to afford the title compound (7.8 mg, 43%). LCMS m/z=431 [M+H]⁺. ¹H NMR (DMSO-d₆, 400 MHz): b=1.80 (3H, d), 2.53 (3H, s), 4.02 (2H, dt), 4.64-4.70 (2H, m), 5.82 (1H, q), 6.59 (1H, t), 7.19 (2H, d), 7.86 (1H, d), 8.00 (1H, d), 8.19 (1H, s), 8.53 (1H, s).

EXAMPLE 78

(S)-6-(1-((2-amino-6-fluoroquinolin-3-yl)oxy)ethyl-1,2,2,2-d₄)-5-(1H-pyrazol-1-yl)pyridin-2-ol

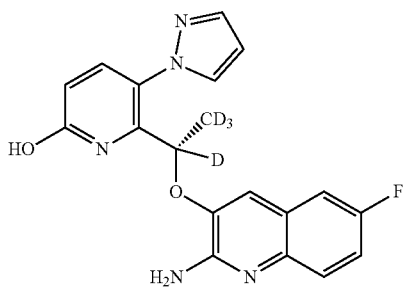 [SMILES: [2H]C([2H])([2H])[C@]([2H])(Oc1cc2cc(F)ccc2nc1N)c1nc(O)ccc1-n1cccn1]

A 250 mL 3 neck flask under nitrogen was charged with tert-butyl (3-(1-(6-bromo-3-(1H-pyrazol-1-yl)pyridin-2-yl)ethoxy-1,2,2,2-d₄)-6-fluoroquinolin-2-yl)carbamate (Preparation 227, 2.8 g, 5.2 mmol) as suspension in 1,4-dioxane (50 mL) and water (25 mL). To this suspension potassium hydroxide (879 mg, 15.7 mmol), di-tert-butyl(2',4',6'-triisopropyl-[1,1'-biphenyl]-2-yl)phosphane (222 mg, 522.0 μmol) and Pd₂(dba)₃ (239 mg, 261.0 μmol) were added. The mixture was heated overnight at 90° C. resulting in a clear dark red solution. After cooling the mixture was concentrated under reduced pressure yielding a red solid with a brown suspension in water. To this mixture 50 mL saturated NH₄Cl (aq) was added to neutralize the base. The organic solvent was removed in vacuo. The resulting aqueous layer was dissolved in 300 mL DCM and 65 mL EtOH. The organic layer was separated, and the aqueous layer was extracted twice with 100 mL DCM/20 mL EtOH. The combined organics were dried over Na₂SO₄, filtered and partially concentrated under reduced pressure when a precipitate formed in the solution. This precipitate was isolated by filtration and was washed 3×5 mL EtOH. The residue was dried under reduced pressure until a constant weight to yield 6-(1-((2-amino-6-fluoroquinolin-3-yl)oxy)ethyl-1,2,2,2-d₄)-5-(1H-pyrazol-1-yl)pyridin-2-ol (1.25 g, 64.8%) as an off-white solid. LCMS m/z=370.0 [M+H]⁺. ¹H NMR (300 MHz, CDCl₃) δ 6.50 (d, 1H), 6.60-6.55 (m, 1H), 7.20-7.05 (m, 3H), 7.30-7.35 (m, 3H), 7.42 (d, 1H), 7.45-7.55 (m, 1H), 7.65 (s, 1H), 7.82 (s, 1H).

The title compound is isolated by preparative SFC on a chiral column.

EXAMPLE 79

(S)-3-(1-((2-amino-6,8-difluoroquinolin-3-yl)oxy)ethyl-1,2,2,2-d4)-4-(1H-pyrazol-1-yl)benzoic Acid

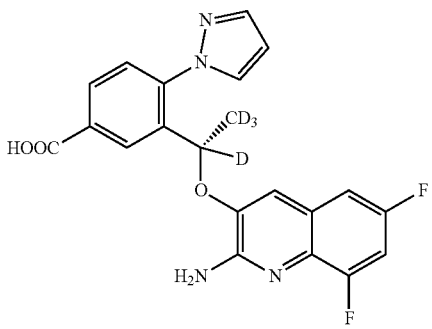 [SMILES: [2H]C([2H])([2H])[C@]([2H])(Oc1cc2cc(F)cc(F)c2nc1N)c1cc(C(=O)O)ccc1-n1cccn1]

To a stirred solution of methyl 3-(1-((2-(1,3-dioxoisoindolin-2-yl)-6,8-difluoroquinolin-3-yl)oxy)ethyl-1,2,2,2-d4)-4-(1H-pyrazol-1-yl)benzoate (Preparation 229, 1.35 g, 2.42 mmol) in a mixed solvent of MeOH (15 mL) and THF (10 mL) was added dropwise a solution of NaOH (966.76 mg, 24.17 mmol, 10 eq) in H₂O (15 mL) over a period of 15 min at 20° C. The internal temperature of the mixture was increased to 25° C. After 5 hrs, NH₂NH₂.H₂O (3.63 g, 72.53 mmol, 3.53 mL) was added then the mixture was heated to 30° C. After 16 hrs, the mixture was filtered, and the filtrate was acidified to pH 6 with 1 N aqueous HCl. The precipitate was filtered, and the filter cake was rinsed with MeOH (2×5 mL). The filter cake was suspended in distilled H₂O (20 mL) and lyophilized to give 3-(1-((2-amino-6,8-difluoroquinolin-3-yl)oxy)ethyl-1,2,2,2-d4)-4-(1H-pyrazol-1-yl)benzoic acid (518 mg, 50.5% yield) as a white solid. LCMS m/z 414.8 [M+H]⁺. ¹H NMR (400 MHz, DMSO-d6) δ 6.67 (s, 1H), 6.71 (t, 1H), 6.94-6.82 (m, 3H), 7.21-7.13 (m, 1H), 7.58 (d, 1H), 8.00-7.95 (m, 2H), 8.26 (d, 1H), 8.41 (d, 1H).

The title compound is isolated by preparative SFC on a chiral column.

EXAMPLE 80

(S)-3-(3-(1-((2-amino-6,8-difluoroquinolin-3-yl)oxy)ethyl)-4-(1H-pyrazol-1-yl)phenyl)-1,2,4-oxadiazol-5(4H)-one

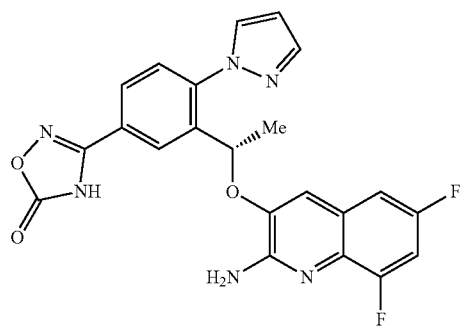 [SMILES: C[C@H](Oc1cc2cc(F)cc(F)c2nc1N)c1cc(-c2noc(=O)[nH]2)ccc1-n1cccn1]

Step 1

To a solution of (S)-3-(1-((2-(1,3-dioxoisoindolin-2-yl)-6,8-difluoroquinolin-3-yl)oxy)ethyl)-4-(1H-pyrazol-1-yl)benzonitrile (Preparation 230, 940 mg, 1.80 mmol) in anhydrous MeOH (8 mL) and THF (8 mL) was added NH₂OH.HCl (188 mg, 2.70 mmol) and Et₃N (547 mg, 5.41 mmol) at rt and the reaction mixture stirred for 16 hrs at 80° C. After cooling to rt, the reaction mixture was concentrated in vacuo to deliver the desired hydroxybenzimidamide (756 mg) as a yellow solid, which was used in the next step without further purification. LCMS m/z 424.8 [M+1]⁺

Step 2

To a solution of the hydroxybenzimidamide from Step 1 (756 mg) in 1,4-dioxane (16 mL) was added CDI (322 mg, 1.98 mmol). The mixture was heated to 100° C. for 16 hrs. After cooling to rt, the reaction mixture was concentrated in vacuo. The residue was purified twice by flash chromatography (silica gel) eluting with a gradient of DCM:MeOH (100:0 to 75:25) to deliver a yellow solid (540 mg). The yellow solid was further purified by SFC (Daicel ChiralPak AD, 250 mm×30 mm×10 μm, isocratic CO₂:EtOH (0.1% NH₄OH), 75:25) to deliver the title compound (240 mg, 30%) as a white solid. LCMS m/z 450.9 [M+1]⁺. ¹H NMR (400 MHz, DMSO-d6) E11.68 (d, 3H), 5.78 (q, 1H), 6.70 (pseudo t, 1H), 6.75 (s, 1H), 6.80 (br s, 2H), 6.97-6.93 (m, 1H), 7.21-7.15 (m, 1H), 7.64 (d, 1H), 7.85 (dd, 1H), 7.97 (d, 1H), 8.19 (d, 1H), 8.40 (d, 1H), 13.08 (br s, 1H).

Preparation 1

1-[5-bromo-2-(1H-pyrazol-1-yl)phenyl]ethanone

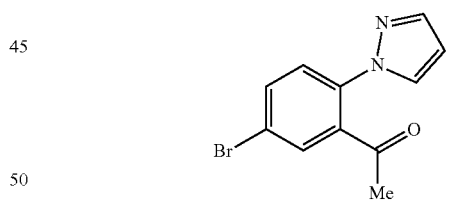

To a solution of 1-(5-bromo-2-fluorophenyl)ethanone (1100 g, 5.07 mol) and 1H-pyrazole (414 g, 6.08 mol) in DMF (7000 mL) was added K₂CO₃ (2099 g, 15.21 mol) and the resulting brown suspension stirred at 110° C. for 24 hrs. The mixture was filtered and the filtrate diluted with EtOAc (10 L) and H₂O (4 L). The organic layer was separated and washed with H₂O (3×3 L), dried over Na₂SO₄, filtered and concentrated in vacuo. The residue was re-crystallized from pet. ether: EtOAc (5:1), the filter cake washed with 100 mL of petr. ether: EtOAc (5:1) and dried to afford the title compound, 800 g (59%) as a solid. ¹H NMR (400 MHz, MeOD_d4) δ: 1.98 (s, 3H), 6.56-6.60 (m, 1H), 7.49 (d, 1H), 7.71-7.74 (m, 2H), 7.79 (dd, 1H), 8.07 (d, 1H).

Preparation 2 methyl 3-acetyl-4-(1H-pyrazol-1-yl)benzoate

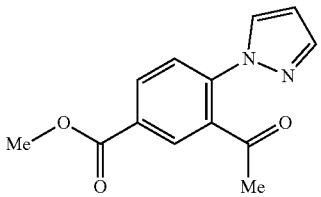 [SMILES: COC(=O)c1ccc(-n2cccn2)c(C(C)=O)c1]

A mixture of 1-[5-bromo-2-(1H-pyrazol-1-yl)phenyl]ethanone (Preparation 1, 350 g, 1.32 mol), DPPP (45 g, 0.11 mol), Pd(OAc)$_2$ (23.7 g, 0.11 mol) and Et$_3$N (307 g, 3.04 mol) in MeOH:DMF (1894 mL:494 mL) was stirred at 85° C. under a CO atmosphere (50 psi) for 20 hrs. The cooled mixture was filtered and the filtrate concentrated in vacuo under reduced pressure. The residue was suspended in EtOAc (5000 mL), the mixture filtered and the filtrate washed with H$_2$O (2×1000 mL), dried (Na$_2$SO$_4$) and filtered. The organic solution was concentrated in vacuo to 300 mL and cooled to 0° C. resulting in solid formation. The suspension was filtered and the solid dried in vacuo to afford the title compound, 260 g, 80%. $^1$H NMR (400 MHz, DMSO-d$_6$) δ: 2.05 (s, 3H), 3.90 (s, 3H), 6.65 (d, 1H), 7.82-7.84 (m, 2H), 8.02 (d, 1H), 8.16 (d, 1H), 8.48 (d, 1H).

Preparation 3

1-[5-hydroxy-2-(1H-pyrazol-1-yl)phenyl]ethanone

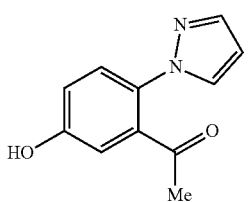 [SMILES: CC(=O)c1cc(O)ccc1-n1cccn1]

H$_2$O (10 mL) followed by a solution of 1-[5-bromo-2-(1H-pyrazol-1-yl)phenyl]ethanone (Preparation 1, 2000 mg, 7.54 mmol) in dioxane (15 mL) were added to a mixture of KOH (974 mg, 17.4 mmol), Pd$_2$(dba)$_3$ (345 mg, 0.38 mmol) and tBuXPhos (320 mg, 0.75 mmol) in a steel tube. The mixture was evacuated and stirred under an atmosphere of argon at 80° C. for 16 hrs. The mixture was allowed to cool to rt, washed with 3 M HCl to achieve a pH of 4-5, then extracted with EtOAc (3×30 mL), and the combined organic solutions were washed with brine (50 mL), dried over Na$_2$SO$_4$, filtered and evaporated. The resulting crude material was purified by column chromatography eluting with EtOAc: pet. ether (0:100 to 60:40) to afford the title compound as a yellow solid, 40%.

LCMS m/z=203 [M+H]$^+$

Preparation 4 tert-butyl [3-acetyl-4-(1H-pyrazol-1-yl)phenoxy]acetate

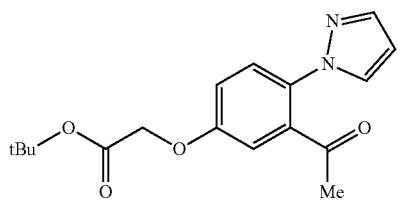 [SMILES: CC(=O)c1cc(OCC(=O)OC(C)(C)C)ccc1-n1cccn1]

tert-Butyl bromoacetate (1570 mg, 8.04 mmol) was added to a mixture of 1-[5-hydroxy-2-(1H-pyrazol-1-yl)phenyl]ethanone (Preparation 3, 650 mg, 3.21 mmol) and Cs$_2$CO$_3$ (3140 mg, 9.64 mmol) in MeCN (30 mL) at rt under N2, and the reaction mixture stirred for 16 hrs. The reaction mixture was diluted with H$_2$O (60 mL), extracted with EtOAc (2×60 mL) and the combined organic layers were dried over Na$_2$SO$_4$, filtered and concentrated in vacuo. The residue was purified by column chromatography eluting with EtOAc: pet. ether (0:100 to 30:70) to provide the title compound as a light yellow oil, 700 mg, 68.8%.

LCMS m/z=317 [M+H]$^+$

Preparation 5

Methyl 2-[3-acetyl-4-(1H-pyrazol-1-yl)phenyl]acetate

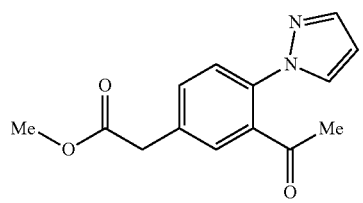 [SMILES: COC(=O)Cc1ccc(-n2cccn2)c(C(C)=O)c1]

A mixture of Ir[dF(CF$_3$)ppy]$_2$(dtbpy)PF$_6$ (25.4 mg, 0.023 mmol), 1-[5-bromo-2-(1H-pyrazol-1-yl)phenyl]ethanone (Preparation 1, 300 mg, 1.13 mmol), monochloroacetic acid methyl ester (184 mg, 1.7 mmol), tris(triethylsilyl)silane (848 mg, 2.26 mmol), and 2,6-lutidine (364 mg, 3.39 mmol) was purged with N2 in a sealed vial, then DME (1.5 mL) added. A solution of NiCl$_2$.glyme (12.4 mg, 0.057 mmol) and 4,4'-di-tert-butyl-2,2'-bipyridine (15.2 mg, 0.057 mmol) in DME (1 mL) was purged with N2 then added to the reaction vial and the mixture stirred under irradiation from blue Kessil LED lamps for 16 hrs. The reaction was quenched by exposure to air and concentrated in vacuo. The residue was partitioned between brine and EtOAc, the layers separated and the organic phase extracted with EtOAc (2×50 mL). The combined organic layers were dried (Na$_2$SO$_4$), filtered and evaporated under reduced pressure. The crude brown oil was purified by flash chromatography on silica gel eluting with EtOAc:heptanes (0:100 to 50:50) to afford the title compound, 165 mg, 56%. $^1$H NMR (400 MHz, CDCl$_3$) δ: 2.00 (s, 3H), 3.74 (s, 2H), 3.76 (s, 3H), 6.51-6.53 (m, 1H), 7.42-7.77 (m, 5H).

Preparation 6 tert-butyl 3-[3-acetyl-4-(1H-pyrazol-1-yl)phenyl]propanoate

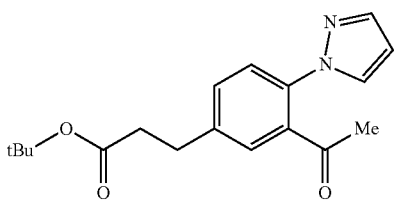 [SMILES: CC(=O)c1cc(CCC(=O)OC(C)(C)C)ccc1-n1cccn1]

The title compound was prepared in 77% yield (459 mg) from 1-[5-bromo-2-(1H-pyrazol-1-yl)phenyl]ethanone (Preparation 1) and tert-butyl 3-bromopropanoate, following the procedure described in Preparation 5, except tris(trimethylsilyl)silane was used in place of tris(triethylsilyl)silane. $^1$H NMR (400 MHz, CDCl$_3$) δ: 1.44 (s, 9H), 1.97 (s, 3H), 2.57-2.61 (m, 2H), 2.97-3.01 (m, 2H), 6.49-6.50 (m, 1H), 7.36-7.41 (m, 3H), 7.72-7.73 (m, 2H).

Preparation 7 tert-butyl [3-acetyl-4-(1H-pyrazol-1-yl)phenyl]carbamate

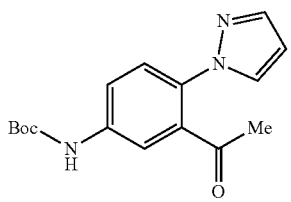 [SMILES: CC(=O)c1cc(NC(=O)OC(C)(C)C)ccc1-n1cccn1]

To a suspension of 1-[5-bromo-2-(1H-pyrazol-1-yl)phenyl]ethanone (Preparation 1, 1000 mg, 3.77 mmol), tert-butyl carbamate (663 mg, 5.66 mmol), Xantphos (437 mg, 0.75 mmol) and Cs$_2$CO$_3$ (2460 mg, 7.54 mmol) in anhydrous 1,4-dioxane (40 mL) was added Pd(OAc)$_2$ (84.7 mg, 0.38 mmol), the mixture degassed, then heated under N2 at 100° C. for 4 hrs. The cooled reaction mixture was diluted with H$_2$O (20 mL) and extracted with EtOAc (3×30 mL). The combined organic extracts were washed with brine (10 mL), dried over Na$_2$SO$_4$, filtered and concentrated under reduced pressure. The crude product was purified by silica gel chromatography eluting with EtOAc: pet. ether (0:100 to 25:75) to afford the title compound as a gray solid, 446 mg, 39.2%. LCMS m/z=302 [M+H]$^+$

Preparation 8

5-chloro-4-fluoro-2-hydrazinylbenzoic Acid Hydrochloride

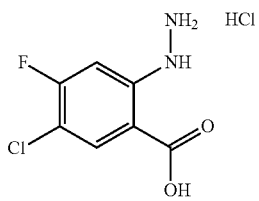 [SMILES: Cl ; NNc1cc(F)c(Cl)cc1C(=O)O]

A solution of sodium nitrite (57.3 g, 831 mmol) in H$_2$O (500 mL) was added drop wise to an ice-cooled mixture of 2-amino-5-chloro-4-fluorobenzoic acid (105 g, 554 mmol) in 12M HCl (420 mL) and H$_2$O (140 mL) so as to maintain the temperature below 5° C., and the reaction mixture then stirred for 30 mins. Tin(II) chloride dihydrate (1.79 g, 7.91 mmol) in 37% HCl (aq) (140 mL) was added drop wise so as to maintain the temperature below 5° C. and the resulting suspension stirred at rt for 20 hrs. The suspension was filtered, the solid washed with cold H$_2$O and Et$_2$O and dried to afford the title compound, 98.0 g, 86.5% as a yellow solid. $^1$H NMR (400 MHz, CDCl$_3$) δ: 7.25 (d, 1H), 8.01 (d, 1H), 9.30 (br s, 1H).

Preparation 9

5-bromo-4-fluoro-2-hydrazinylbenzoic Acid Hydrochloride

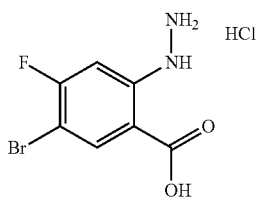 [SMILES: NNc1cc(F)c(Br)cc1C(=O)O ; Cl]

The title compound was prepared as a solid in 78% yield (10.7 g) from 2-amino-5-bromo-4-fluorobenzoic acid, following the procedure described in Preparation 8. $^1$H NMR (400 MHz, DMSO-d$_6$) δ: 7.12 (d, 1H), 7.98-8.13 (m, 1H), 9.05-9.53 (m, 1H).

Preparation 10

Ethyl 5-chloro-4-fluoro-2-(1H-pyrazol-1-yl)benzoate

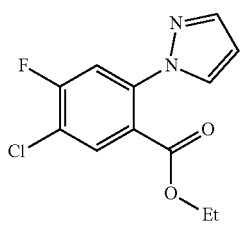 [SMILES: CCOC(=O)c1cc(Cl)c(F)cc1-n1cccn1]

1,1,3,3-Tetramethoxypropane (118 g, 719 mmol) was added to a solution of 5-chloro-4-fluoro-2-hydrazinylbenzoic acid hydrochloride (Preparation 8, 98.0 g, 479 mmol) in EtOH (1000 mL) and the reaction mixture stirred at 100° C. for 1 hr. The cooled reaction mixture was concentrated in vacuo and the residue purified twice by flash chromatography on silica gel eluting with pet. ether: EtOAc (0:100 to 80:20) to afford the title compound as a yellow solid, 44.0 g, 34.2% as a yellow solid. LCMS m/z=269 [M+H]+

Preparation 11

5-chloro-4-fluoro-2-(1H-pyrazol-1-yl)benzoic Acid

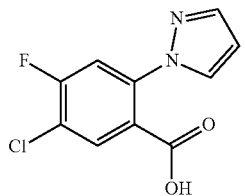

LiOH (4.22 g, 100 mmol) was added portion wise to a solution of ethyl 5-chloro-4-fluoro-2-(1H-pyrazol-1-yl)benzoate (Preparation 10, 13.5 g, 50.25 mmol) in EtOH/THF/H₂O (39 mL/60 mL/30 mL) and the reaction mixture stirred at rt for 1 hr. The mixture was concentrated in vacuo to remove the organic solvents, cooled in an ice bath and 1 N HCl added to achieve pH 3. The resulting suspension was filtered, the solid washed with H₂O and then co-evaporated with toluene and dried to provide the title compound as a pale solid, 11.3 g, 93.5%. $^1$H NMR (400 MHz, DMSO-$d_6$) δ: 6.55 (s, 1H), 7.75 (s, 1H), 7.82 (d, 1H), 7.96 (d, 1H), 8.23 (s, 1H), 13.24 (br s, 1H).

Preparation 12

5-bromo-4-fluoro-2-(1H-pyrazol-1-yl)benzoic Acid

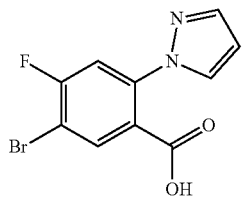 [SMILES: O=C(O)c1cc(Cl)c(F)cc1-n1cccn1]

A solution of 5-bromo-4-fluoro-2-hydrazinylbenzoic acid hydrochloride (Preparation 9, 9.2 g, 36.94 mmol) and 1,1,3,3-tetramethoxypropane (8.49 g, 51.7 mmol) in AcOH (30 mL) was stirred at 80° C. for 3 hrs and then at rt for 48 hrs. The reaction mixture was carefully washed with aq saturated NaHCO₃ (400×3 mL) and the combined aqueous solutions washed with DCM (2×200 mL). The combined aqueous layers were then acidified to pH 4 and extracted with DCM (3×200 mL). The combined organic layers were dried over Na₂SO₄ and evaporated under reduced pressure to give the title compound as a light yellow solid, 8.5 g, 80.7%. LCMS m/z=285, 287 [M+H]+

Preparation 13

5-chloro-4-fluoro-N-methoxy-N-methyl-2-(1H-pyrazol-1-yl)benzamide

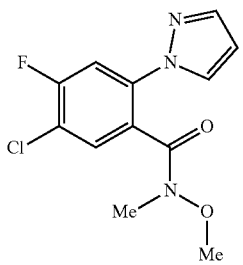

DIPEA (7.0 g, 72.07 mmol) was added to a solution of 5-chloro-4-fluoro-2-(1H-pyrazol-1-yl)benzoic acid (Preparation 11, 7.0 g, 29.09 mmol), N,O-dimethylhydroxylamine hydrochloride (3.41 g, 34.9 mmol) and HATU (16.6 g, 43.6 mmol) in DMF (80 mL) and the reaction mixture stirred at rt for 16 hrs. The mixture was poured into EtOAc (300 mL) and washed with brine (3×160 mL), the organic phase dried over Na₂SO₄ and concentrated in vacuo. The crude product was purified by flash chromatography on silica gel, eluting with pet. ether:EtOAc (100:0 to 70:30) to provide the title compound as a pale solid, 6.4 g, 78%. $^1$H NMR (400 MHz, CDCl₃) δ: 3.28 (s, 3H), 3.37 (s, 3H), 6.49 (s, 1H), 7.48 (d, 1H), 7.57 (d, 1H), 7.77 (s, 1H), 7.81 (s, 1H).

Preparation 14

5-bromo-4-fluoro-N-methoxy-N-methyl-2-(1H-pyrazol-1-yl)benzamide

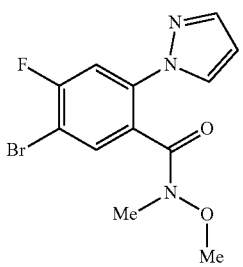 [SMILES: CON(C)C(=O)c1cc(Cl)c(F)cc1-n1cccn1]

To a solution of 5-bromo-4-fluoro-2-(1H-pyrazol-1-yl)benzoic acid (Preparation 12, 5.71 g, 20.03 mmol) in DCM (32 mL) and DMF (32 mL) were added HOBt (3.03 g, 22.4 mmol), EDC.HCl (4.30 g, 22.4 mmol), N,O-dimethylhydroxylamine hydrochloride (2.44 g, 25.0 mmol) and DIPEA (4.36 mL, 25.0 mmol) at rt and the reaction mixture stirred for 19 hrs. The reaction mixture was concentrated in vacuo then diluted with EtOAc (200 mL) and washed with H₂O (100 mL). The organic layer was separated and the aqueous phase extracted with EtOAc (2×80 mL). The combined organic extracts were washed with H₂O (80 mL) and brine (80 mL) then evaporated under reduced pressure. The crude was purified by silica gel column chromatography eluting with EtOAc:pet. ether (0:100 to 50:50) to afford the title compound as a yellow gum. $^1$H NMR (400 MHz, CDCl₃) δ:

3.24 (s, 3H), 3.33 (s, 3H), 6.46 (br s, 1H), 7.40 (d, 1H), 7.68 (d, 1H), 7.72 (s, 1H), 7.79 (s, 1H)

Preparation 15

1-[5-chloro-4-fluoro-2-(1H-pyrazol-1-yl)phenyl]ethanone

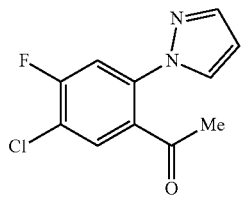 [SMILES: CC(=O)c1cc(Cl)c(F)cc1-n1cccn1]

MeMgBr (3.4 M in 2-MeTHF, 60.9 mL, 207 mmol) was added drop wise to an ice cooled solution of 5-chloro-4-fluoro-N-methoxy-N-methyl-2-(1H-pyrazol-1-yl)benzamide (Preparation 13, 23.5 g, 82.8 mmol) in THF (350 mL), the reaction mixture stirred for 10 mins, then allowed to warm to rt and stirred for a further 18 hrs. THF was removed under reduced pressure without heating and the residue partitioned between saturated NH₄Cl solution and EtOAc. The organic layer was washed with H₂O, brine, dried over Na₂SO₄, filtered and concentrated in vacuo to approx. ⅓ of its volume. The resulting solid was dissolved in DCM and the solution concentrated in vacuo to approx. ⅓ of its volume. The resulting suspension was filtered, the solid washed with hexane and Et₂O and dried to afford the title compound, 13.23 g. The filtrate was evaporated under reduced pressure and the yellow solid purified by silica gel chromatography on a Redisep® GOLD column, eluting with hexane:EtOAc (100:0 to 50:50) to afford additional compound, 2.3 g. ¹H NMR (400 MHz, CDCl₃) δ: 2.04 (s, 3H), 6.58 (s, 1H), 7.28 (d, 1H), 7.65-7.78 (m, 3H)

Preparation 16

1-[5-bromo-4-fluoro-2-(1H-pyrazol-1-yl)phenyl]ethanone

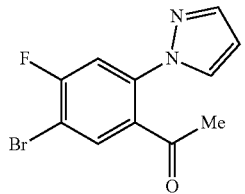

MeMgBr (21.5 mL, 64.5 mmol, 3.0 M in Et₂O) was added drop wise to a solution of 5-bromo-4-fluoro-N-methoxy-N-methyl-2-(1H-pyrazol-1-yl)benzamide (Preparation 14, 7.05 g, 21.48 mmol) in THF (221 mL) at −70° C. and the reaction mixture stirred at −70° C. for 30 mins and then allowed to warm to rt and stirred for 30 mins. The reaction was quenched with ice cold 1 N HCl solution (160 mL) and diluted with EtOAc (300 mL). The aqueous layer was extracted with EtOAc (2×100 mL) and the combined organic extracts evaporated under reduced pressure. The residue was purified by column chromatography (silica gel) eluting with EtOAc:pet. ether (0:100 to 80:20) to afford the title compound as a yellow solid, 3.38 g, 55.6%. LCMS m/z=283 [M+H]⁺

Preparation 17

3-acetyl-4-bromo-N,N-bis(4-methoxybenzyl)benzenesulfonamide

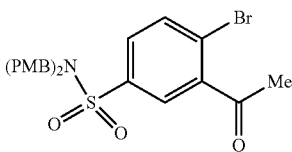

Bis(4-methoxybenzyl)amine (865 mg, 3.36 mmol) was added at 0° C. over 10 mins to a solution of 3-acetyl-4-bromobenzene-1-sulfonyl chloride (500 mg, 1.68 mmol) and Et₃N (340 mg, 3.36 mmol) in DCM (5 mL) and the reaction mixture stirred at rt for 16 hrs. The reaction mixture was diluted with EtOAc (50 mL) quenched with HCl (1 M, 10 mL) and the layers separated. The organic phase was washed with saturated NaHCO₃ (aq) solution (26 mL), dried (Na₂SO₄), filtered and concentrated in vacuo to give a white solid. This was purified by silica gel column chromatography, eluting with EtOAc:heptane to afford the title compound, 580 mg, 67%. ¹H NMR (400 MHz, CDCl₃) δ: 2.52 (s, 3H), 3.74 (s, 6H), 4.20 (s, 4H), 6.72 (d, 4H), 6.94 (d, 4H), 7.54-7.62 (m, 3H).

Preparation 18

3-acetyl-N,N-bis(4-methoxybenzyl)-4-(1H-pyrazol-1-yl)benzenesulfonamide

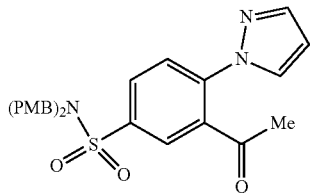

A mixture of 3-acetyl-4-bromo-N,N-bis(4-methoxybenzyl)benzenesulfonamide (Preparation 17, 450 mg, 0.87 mmol), K₂CO₃ (360 mg, 2.60 mmol), 1H-pyrazole (177 mg, 2.60 mmol), CuI (49.6 mg, 2.60 mmol) and (R,R)-(−)-N,N'-dimethyl-1,2-cyclohexanediamine (30.9 mg, 2.60 mmol) in DMF (3 mL) was stirred at 105° C. for 16 hrs under N2. The cooled mixture was concentrated in vacuo and the residue partitioned between DCM and aq NaHCO₃ solution and the layers separated. The aqueous phase was extracted with DCM (3×5 mL), the combined organic extracts dried over Na₂SO₄ and evaporated under reduced pressure. The crude material was purified on a silica gel column eluting with EtOAc:heptane (0:100 to 50:50) to afford the title compound, 305 mg, 70%. ¹H NMR (400 MHz, CDCl₃) δ: 2.10 (s, 3H), 3.81 (s, 6H), 4.32 (s, 4H), 6.59 (s, 1H), 6.80 (d, 4H), 7.08 (d, 4H), 7.45 (d, 1H), 7.82-7.95 (m, 4H).

Preparation 19

[5-bromo-2-(1H-pyrazol-1-yl)phenyl]ethanol

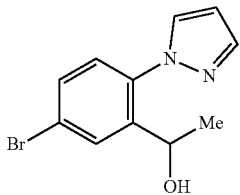 [SMILES: CC(O)c1cc(Br)ccc1-n1cccn1]

To an ice-cold solution of 1-[5-bromo-2-(1H-pyrazol-1-yl)phenyl]ethanone (Preparation 1, 20.0 g 75.44 mmol) in MeOH (200 mL) and THF (200 mL) was added NaBH$_4$ (3.43 g, 90.5 mmol) portion wise. The reaction mixture was stirred at 0° C. for 1 hr, then at rt for a further 30 mins. The mixture was diluted with HCl (1N, 30 mL) and H$_2$O (100 mL) and extracted with EtOAc (3×100 mL). The combined organic layers were dried over Na$_2$SO$_4$, filtered and concentrated in vacuo. The residue was purified by column chromatography (silica gel) eluting with EtOAc:pet. ether (0:100 to 60:40) to afford the title compound as a brown oily liquid, 17.76 g, 88%. $^1$H NMR (400 MHz, DMSO-d$_6$) δ: 1.14 (d, 3H), 4.73-4.84 (m, 1H), 5.37 (d, 1H), 6.47-6.54 (m, 1H), 7.28 (s, 1H), 7.57 (dd, 1H), 7.75 (d, 1H), 7.84 (d, 1H), 8.03 (d, 1H).

Preparations 20 to 23

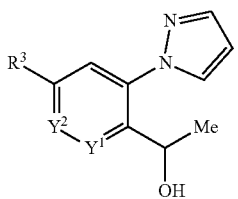

The alcohols in the table below were prepared by reducing the appropriate ethanone according to the procedure described in Preparation 19.

| | |
|---|---|
| 20 [A] | 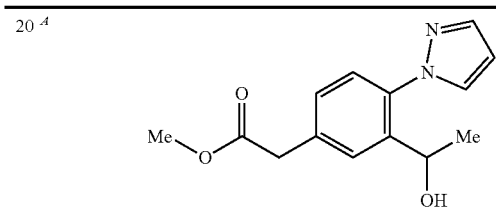<br>Methyl 2-[3-(1-hydroxyethyl)-4-(1H-pyrazol-1-yl)phenyl]acetate, 120 mg (74%) $^1$H NMR (400MHz, CDCl$_3$) δ: 1.41 (d, 3H), 3.72-3.75 (m, 5H), 4.68-4.73 (m, 1H), 5.10 (d, 1H), 6.51-6.53 (m, 1H), 7.28-7.35 (m, 3H), 7.52 (s, 1H), 7.55 (dd, 1H) |
| 21 [A] | 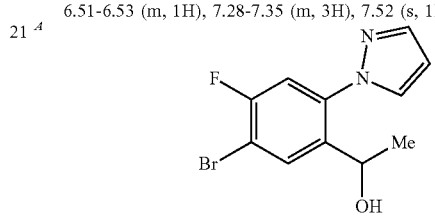<br>1-[5-bromo-4-fluoro-2-(1H-pyrazol-1-yl)phenyl]ethanol, yellow gum in quantitative yield; LCMS m/z = 267 [M—H$_2$O]$^+$ |
| 22 [A] | 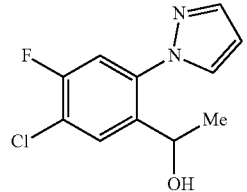<br>1-[5-chloro-4-fluoro-2-(1H-pyrazol-1-yl)phenyl]ethanol, 10.8 g (97%) as a colorless oil; $^1$H NMR (400MHz, CDCl$_3$) δ: 1.45 (d, 3H), 4.72-4.75 (m, 1H), 6.56 (s, 1H), 7.15 (d, 1H), 7.66-7.80 (m, 3H). |
| 23 | 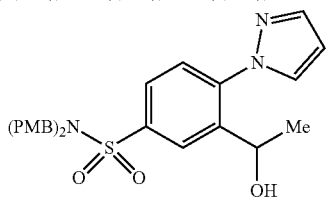<br>3-(1-hydroxyethyl)-N,N-bis(4-methoxybenzyl)-4-(1H-pyrazol-1-yl)benzenesulfonamide, 205 mg (67%) as a white solid; $^1$H NMR (400MHz, CDCl$_3$) δ: 1.43 (d, 3H), 3.81 (s, 6H), 4.34 (s, 4H), 4.72-4.75 (m, 1H), 6.58 (s, 1H), 6.80 (d, 4H), 7.08 (d, 4H), 7.42 (d, 1H), 7.82-7.85 (m, 3H), 8.08 (s, 1H). |

[A] MeOH was used as the reaction solvent

Preparations 24 to 26

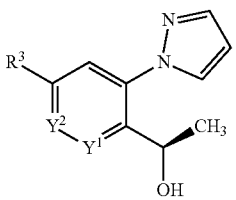

The alcohols in the table below were prepared by reducing the appropriate ethanone according to the procedure described in Preparation 19, and then were purified by SFC using the conditions described.

| | |
|---|---|
| 24 [B] | 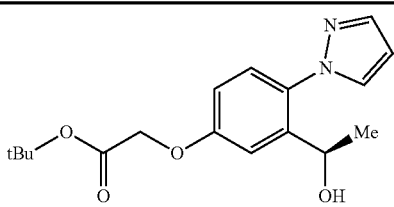<br>tert-butyl {3-[(2R)-1-hydroxyethyl]-4-(1H-pyrazol-1-yl)phenoxy}acetate, Column: Chiralpak AS-H, 85% CO$_2$, (15% MeOH + 0.1% 7N NH$_3$ in MeOH), Flow: 60 mL/min, Peak 1, 199 mg, 37.5% as a colorless oil $^1$H NMR (400MHz, CDCl$_3$) δ: 1.38 (d, 3H), 1.51 (s, 9H), 4.58 (s, 2H), 4.60-4.66 (m, 1H), 4.83 (d, 1H), 6.47 (dd, 1H), 6.87 (dd, 1H), 7.13 (d, 1H), 7.21 (d, 1H), 7.65 (d, 1H), 7.72 (d, 1H). |

25 [A]

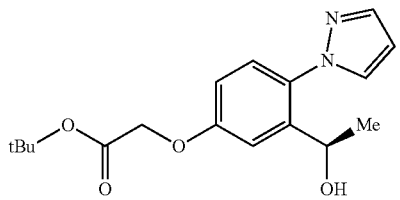 [SMILES: C[C@@H](O)c1cc(OCC(=O)OC(C)(C)C)ccc1-n1cccn1]

tert-butyl {3-[(1R)-1-hydroxyethyl]-4-(1H-pyrazol-1-yl)phenyl}
propanoate, Column: Chiral Tech IG 250 mm × 21.2 mm 5 μm,
80% $CO_2$, 20% (MeOH + 0.2% 7N $NH_3$ in MeOH),
Flow: 80 mL/min, Peak 1 isolated, 125 mg, 27% SFC
Analytical conditions: Chiral Tech IG 250 mm × 4.6 mm 5 pm
column $CO_2$: (MeOH + 0.2% 7N $NH_3$ in MeOH) from 5:95 to
40:60 over 8 mins, at 3 mL/min, RT = 5.542 min (peak 1)

26 [A]

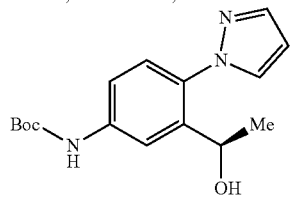

tert-butyl {3-[(1R)-1-hydroxyethyl]-4-(1H-pyrazol-1-yl)phenyl}
carbamate, Column: AD (250 mm × 30 mm 5 μm), 70% $CO_2$,
30% (MeOH + 0.2% 7N $NH_3$ in EtOH), Flow: 60 mL/min,
Peak 1 isolated, 235 mg, 38%, as a colorless liquid; $^1$H NMR
(400MHz, DMSO-$d_6$) δ: 1.13 (d, 3H), 1.50 (s, 9H), 4.60-4.69
(m, 1H), 5.16 (d, 1H), 6.47 (dd, 1H), 7.16 (d, 1H), 7.39 (dd, 1H),
7.68 (d, 1H), 7.86 (d, 1H), 7.91 (d, 1H), 8.54 (s, 1H).

[A] MeOH was used as the reaction solvent
[B] only 0.6 eq of $NaBH_4$ was used in the reaction Preparation 27 methyl 3-[(1S)-1-hydroxyethyl]-4-(1H-pyrazol-1-yl)
benzoate

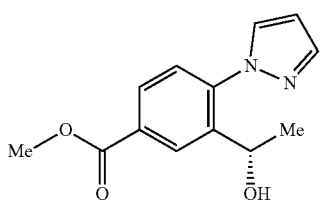 [SMILES: COC(=O)c1ccc(-n2cccn2)c([C@H](C)O)c1]

Methyl 3-acetyl-4-(1H-pyrazol-1-yl)benzoate (Preparation 2, 200 g, 0.81 mol) and DCM (0.8 L) was stirred for 20 mins and purged with N2. (−)-DIP-Cl (965 mL, 1.64 mol) was added drop wise to the reaction mixture at −50° C. over 2 hrs and the mixture then stirred at 15° C. The reaction mixture was concentrated under reduced pressure and the residue dissolved in MTBE (4 L). 2,2′-Iminodi-1-ethanol (350 g, 3.30 mol) was added and the solution stirred at 20° C. for 3 hrs. The mixture was filtered, the filtrate evaporated and the crude product purified by silica gel column eluting with pet. ether: EtOAc (90:10 to 80:20) to afford crude product. This was dissolved in MTBE (1 L) at 40° C., n-hexane (1.6 L) added, the suspension stirred at 20° C. for 12 hrs then filtered and the solid dried under vacuum at 30° C. to afford the title compound, 191 g, 47.6%. RT=3.274 mins (AD-3 150 mm×4.6 mm 3 μm column, $CO_2$:0.1% TFA in EtOH from 5:95 to 45:65 over 7.5 mins, at 2.5 mL/min).

$^1$H NMR (400 MHz, $CDCl_3$) δ: 1.46 (d, 3H), 3.95 (s, 3H), 4.81 (q, 1H), 5.15 (br s, 1H), 6.53 (s, 1H), 7.34 (d, 1H), 7.78 (s, 2H), 8.03 (d, 1H), 8.31 (s, 1H).

Alternative Method

A mixture of methyl 3-acetyl-4-(1H-pyrazol-1-yl)benzoate (Preparation 2, 30 g, 120 mmol) in DMSO (200 mL) was heated to 50° C. to form a solution, then allowed to cool to rt. KRED101 (12 g), ADH-101 (1 g) and NADP+ (500 mg) were dissolved in pH 7.5 potassium phosphate buffer (500 mL) and added to a 2 L reactor with overhead stirring at 35° C., washing in with additional buffer (250 mL). IPA (50 mL) was added, followed by slow addition of the ketone/DMSO solution and the reaction mixture stirred at 35° C. for 7 hrs. Additional ADH-101 (500 mg) and NADP+ (250 mg) in buffer (10 mL total) were added and the reaction mixture stirred for 14 hrs. Additional ADH-101 (500 mg) and NADP+ (250 mg) in buffer (10 mL total) were again added and the reaction mixture stirred for 8 hrs. Additional ADH-101 (250 mg) and NADP+ (125 mg) were again added and the reaction mixture stirred for a further 14 hrs. EtOAc (500 mL) was added to the cooled reaction mixture, and the mixture stirred for 30 mins. The contents of the reactor were transferred to a 2 L bottle, Celite® added, and the mixture stirred for another 30 mins. The mixture was filtered through $H_2O$-wetted Celite® washing through with EtOAc (100 mL). MeOH (20 mL) was added to the filtrate, the layers separated and the organic layer washed with brine (400 mL) and dried ($Na_2SO_4$). 10% (IPA/iPrOAc) (500 mL) was added to the aqueous phase and the mixture stirred vigorously, then filtered again through $H_2O$ wetted Celite®. MeOH (20 mL) was added to the filtrate, the layers separated and the organic layer washed with brine (400 mL) and dried ($Na_2SO_4$). The combined organic layers were filtered, the filtrates combined and concentrated under reduced pressure, azeotroping with heptane to afford 28 g of crude product. This was combined with an additional batch of crude product, 13.14 g, prepared according to the same method and the solids suspended in MTBE (120 mL). The suspension was heated under reflux and the hot mixture was filtered to remove insoluble material. The filtrate was cooled to 0° C., heptane added and the resulting suspension stirred for an hr, then allowed to warm to rt. The solid was filtered off and dried in vacuo to afford the title compound as a white solid, 35.2 g.

LCMS m/z=269 [M+Na]$^+$

Preparation 28 methyl 3-[(1R)-1-hydroxyethyl]-4-(1H-pyrazol-1-yl)
benzoate

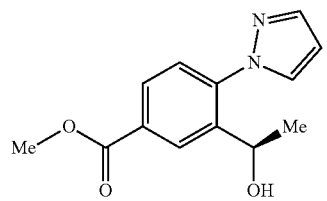 [SMILES: COC(=O)c1ccc(-n2cccn2)c([C@@H](C)O)c1]

Pd(OAc)$_2$ (1870 mg, 8.33 mmol) was added portion wise to a solution of 1-[5-bromo-2-(1H-pyrazol-1-yl)phenyl] ethanol (Preparation 19, 44.5 g, 166.6 mmol), Et$_3$N (116 mL, 833 mmol) and DPPP (6.87 g, 16.7 mmol) in MeOH (500 mL) and the reaction mixture stirred for 48 hrs at 80°

C. under CO (50 psi). The cooled reaction mixture was filtered and evaporated under reduced pressure. The residue was purified by column chromatography (silica gel) eluting with EtOAc:pet. ether (0:100 to 60:40) to afford a light brown liquid, 34.0 g, 83%. Some of the product was purified by SFC using a Chiralpak AD-H 250×30 5p column and eluting with 25% (0.1% aq NH₃ in EtOH) at a flow rate of 60 mL/min to afford the title compound (Peak 1) as a colorless oil, 454 mg, 47.8%. $^1$H NMR (400 MHz, DMSO-$d_6$) δ: 1.17 (d, 3H), 3.90 (s, 3H), 4.91-5.01 (m, 1H), 5.40 (d, 1H), 6.53-6.58 (m, 1H), 7.48 (d, 1H), 7.80 (d, 1H), 7.94 (dd, 1H), 8.14 (d, 1H), 8.35 (d, 1H).

Preparation 29 methyl 2-fluoro-5-[(1R)-1-hydroxyethyl]-4-(1H-pyrazol-1-yl)benzoate

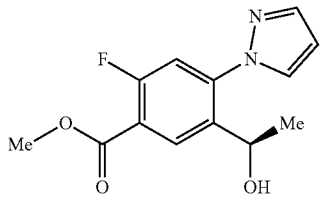

The title compound was prepared from 1-[5-bromo-4-fluoro-2-(1H-pyrazol-1-yl)phenyl]ethanol (Preparation 21) in 64% yield (2.0 g) as a white solid, according to the procedure described in Preparation 28. The product was further purified by SFC using an AY (250 mm×30 mm 10μ) column eluting with 20% (0.1% aq NH₃ in EtOH) at a flow rate of 50 mL/min to afford the title compound, 42.4% yield as a yellow solid. $^1$H NMR (400 MHz, CDCl₃) δ: 1.48 (d, 3H), 3.98 (s, 3H), 4.76-4.85 (m, 1H), 5.06 (d, 1H), 6.55-6.59 (m, 1H), 7.12 (d, 1H), 7.79-7.81 (m, 2H), 8.23 (d, 1H).

Preparations 30 and 31

3-(1-hydroxyethyl)-4-(1H-pyrazol-1-yl)benzonitrile and 3-[(1R)-1-hydroxyethyl]-4-(1H-pyrazol-1-yl) benzonitrile

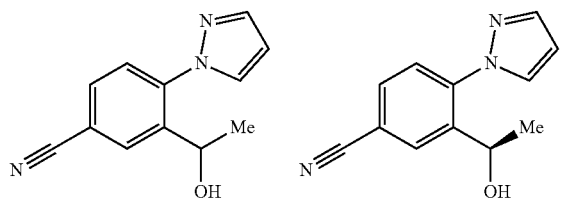 [SMILES: CC(O)c1cc(C#N)ccc1-n1cccn1 ; C[C@@H](O)c1cc(C#N)ccc1-n1cccn1]

A mixture of 1-[5-bromo-2-(1H-pyrazol-1-yl)phenyl]ethanol (Preparation 19, 1.8 g, 6.7 mmol), Zn(CN)₂ (2.37 g, 20.2 mmol), and Pd(PPh₃)₄ (779 mg, 0.674 mmol) in anhydrous DMF (15 mL) was bubbled with N₂(g) for 5 mins. The tube was sealed immediately and heated to 140° C. for 7 hrs. H₂O (20 mL) followed by EtOAc (40 mL) were added to the cooled mixture. The resulting suspension was filtered, the filtrate extracted with EtOAc (3×30 mL) and the combined organic layers washed with H₂O (20 mL) and brine (20 mL) then dried over Na₂SO₄, filtered, and concentrated in vacuo to give a brown oil. The crude product was purified by column chromatography (silica gel), eluting with EtOAc: pet. ether (0:100 to 30:70) to afford 3-(1-hydroxyethyl)-4-(1H-pyrazol-1-yl)benzonitrile (Preparation 30) as a colorless oil, 1320 mg, 92%. This was purified by SFC using a Chiralpak AD-H column eluting with 30% (0.1% aq NH₃ in EtOH) to provide 3-[(1R)-1-hydroxyethyl]-4-(1H-pyrazol-1-yl)benzonitrile (Preparation 31) as a colorless oil, 335 mg, 48%. $^1$H NMR (400 MHz, DMSO-$d_6$) δ: 1.17 (d, 3H), 4.97-5.00 (m, 1H), 5.47 (d, 1H), 6.58 (s, 1H), 7.57 (d, 1H), 7.82 (s, 1H), 7.88 (d, 1H), 8.10 (s, 1H), 8.18 (s, 1H).

Preparation 32

2-fluoro-5-[(1R)-1-hydroxyethyl]-4-(1H-pyrazol-1-yl)benzonitrile

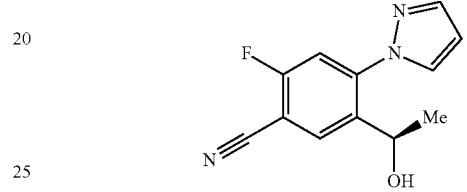

Dioxane (125 mL) and H₂O (125 mL) were added to a mixture of 1-[5-chloro-4-fluoro-2-(1H-pyrazol-1-yl)phenyl] ethanol (Preparation 22, 11.11 g, 46.2 mmol), K₄[Fe(CN)₆].3H₂O (11.7 g, 27.7 mmol), tBuXPhos-Pd Gen-3 pre-catalyst (220 mg, 0.28 mmol) and tBuXPhos (118 mg, 0.277 mmol) and the mixture degassed under N₂. The reaction mixture was heated at 100° C. for 18 hrs, then additional tBuXPhos-Pd Gen-3 pre-catalyst (110 mg, 0.14 mmol) and tBuXPhos (59 mg, 0.139 mmol) were added. The mixture was degassed and heated at 100° C. for a further 22 hrs. Additional K₄[Fe(CN)₆].3H₂O (11.7 g, 27.7 mmol), tBuXPhos-Pd Gen-3 pre-catalyst (220 mg, 0.28 mmol) and tBuXPhos (118 mg, 0.277 mmol) were added, the mixture degassed and the reaction mixture stirred at 100° C. for a further 24 hrs. The cooled mixture was concentrated in vacuo, the aqueous solution diluted with DCM, the resulting suspension filtered to remove the solid, and the layers separated. The organic phase was washed with brine, dried over Na₂SO₄, filtered and concentrated in vacuo. The crude product was purified by chromatography using a 80 g Redisep GOLD silica gel column, eluting with hexane: EtOAc, to afford the title compound as a light yellow oil 1.07 g. This was further purified by SFC to provide the title compound, 490 mg, 4.6%. RT=3.781 mins. (LUX Amylose-1 250 mm×4.6 mm 5 μm column) eluting with CO₂: 0.2% NHa+MeOH from 5:95 to 40:60 over 8 mins, at 3 mL/min.

Preparation 33

1-[3-(1H-pyrazol-1-yl)picolinonitrile

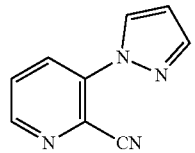 [SMILES: N#Cc1ncccc1-n1cccn1]

Cs₂CO₃ (26.7 g, 82 mmol) was added to a solution of 1H-pyrazole (11.2 g, 164 mmol) in DMF (250 mL) and the mixture stirred at rt for 45 mins. 3-Bromopicolinonitrile (10 g, 55 mmol), CuI (1.04 g, 5.46 mmol) and (R,R)-(−)-N,N′-dimethyl-1,2-cyclohexanediamine (0.466 g, 3.28 mmol) were added and the reaction mixture stirred at 130° C. for 12 hrs under N2. Aq NH₃ (300 mL), was added to the cooled reaction mixture and the mixture extracted with EtOAc (2×250 mL). The combined organic layers were washed with brine (3×500 mL), dried over Na₂SO₄ filtered and concentrated in vacuo. The crude product was purified by flash chromatography on silica gel eluting with pet. ether: EtOAc (100:0 to 50:50) to give the desired product as a white solid, 8.6 g, 92%. LCMS m/z=171 [M+H]⁺

Preparation 34

1-[6-bromo-3-(1H-pyrazol-1-yl)pyridin-2-yl]ethanone

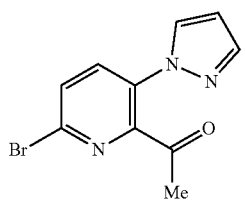 [SMILES: CC(=O)c1nc(Br)ccc1-n1cccn1]

K₂CO₃ (66.2 g, 479 mmol) was added to a suspension of 1-(6-bromo-3-fluoro-4-(triethylsilyl)pyridin-2-yl)ethanone (WO2016071211, 103 g, 160 mmol) and 1H-pyrazole (10.9 g, 160 mmol) in anhydrous MeCN (1300 mL) and the reaction mixture stirred at 80° C. for 16 hrs. The cooled mixture was filtered, washing through with MeCN (3×60 mL) and the combined filtrates evaporated under reduced pressure. The crude product was purified by flash chromatography on silica gel eluting with EtOAc:pet. ether (0:100 to 20:80) to provide the title compound as a brown oil, 14.8 g, 34.8%. LCMS m/z=268 [M+H]⁺

Preparation 35

5-fluoro-3-(1H-pyrazol-1-yl)picolinonitrile

A mixture of 3,5-difluoropicolinonitrile (21.59 g, 0.154 mol), 1H-pyrazole (10.5 g, 0.154 mol) and K₂CO₃ (53.2 g, 0.385 mol) in MeCN (1000 mL) was stirred at 20° C. for 16 hrs. The reaction mixture was filtered and the filtrate was concentrated in vacuo. The residue was purified via flash chromatography on silica gel, twice, eluting with pet. ether: EtOAc (100:0 to 50:50) to afford the title compound as a white solid, 15.2 g, 52.5%. ¹H NMR (400 MHz, CDCl₃) δ: 6.63 (dd, 1H), 7.87 (d, 1H), 8.09 (dd, 1H), 8.46 (d, 1H), 8.53 (d, 1H).

Preparation 36

1-[3-(1H-pyrazol-1-yl)pyridin-2-yl]ethanone

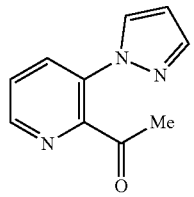 [SMILES: CC(=O)c1ncccc1-n1cccn1]

MeMgBr (3M in Et₂O, 49.9 mL, 150 mmol) was added to a stirred solution of 1-[3-(1H-pyrazol-1-yl)picolinonitrile (Preparation 33, 8.50 g, 49.95 mmol) in THF (250 mL) and the reaction mixture stirred at 25° C. for 16 hrs. The reaction was quenched with aq HCl and extracted with EtOAc (2×200 mL). The combined organic extracts were washed with saturated aq NaHCO₃ sol. (200 mL) and brine (3×200 mL), dried over Na₂SO₄, filtered and concentrated in vacuo to give a dark brown oil. This was purified by chromatography on silica gel, eluting with pet. ether: EtOAc (100:0 to 60:40) to afford the title compound as a yellow oil, 6.15 g, 65.8%. LCMS m/z=188 [M+H]⁺

Preparation 37 methyl 6-acetyl-5-(1H-pyrazol-1-yl)pyridine-2-carboxylate

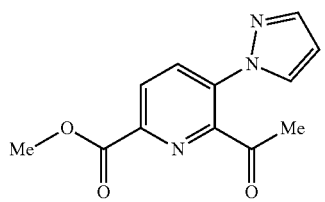 [SMILES: COC(=O)c1ccc(-n2cccn2)c(C(C)=O)n1]

To a suspension of 1-[6-bromo-3-(1H-pyrazol-1-yl)pyridin-2-yl]ethanone (Preparation 34, 5.30 g, 19.92 mmol) in MeOH (53 mL) was added DPPP (1640 mg, 3.99 mmol), Pd(OAc)₂ (447 mg, 1.99 mmol) and Et₃N (13.9 mL, 99.6 mmol) at rt. The mixture was degassed with N₂(g) and the reaction mixture heated at 80° C. under 50 psi of CO for 68 hrs. The cooled mixture was concentrated in vacuo and the residue purified by column chromatography (silica gel) eluting with EtOAc:pet. ether (0:100 to 100:0) to provide the title compound as a yellow solid, 3.7 g, 75.4%. ¹H NMR (400 MHz, DMSO-d₆) δ: 2.52 (s, 3H), 3.93 (s, 3H), 6.64 (dd, 1H), 7.83 (d, 1H), 8.29 (d, 1H), 8.40 (d, 1H), 8.51 (d, 1H).

Preparation 38

6-acetyl-5-(1H-pyrazol-1-yl)pyridine-2-carboxylic Acid

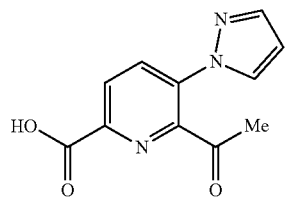 [SMILES: CC(=O)c1nc(C(=O)O)ccc1-n1cccn1]

LiOH (200 mg, 8.35 mmol) was added to a solution of methyl 6-acetyl-5-(1H-pyrazol-1-yl)pyridine-2-carboxylate (Preparation 37, 700 mg, 2.85 mmol) in THF/MeOH/H$_2$O (6 mL/6 mL/6 mL) and the reaction mixture stirred at 20° C. for 2 hrs. The reaction mixture was diluted with additional DCM/MeOH/H$_2$O (50 mL/5 mL/50 mL), the pH adjusted to 4 using conc. HCl and the layers separated. The aqueous phase was extracted with DCM/MeOH (5×50 mL/5 mL) and the combined organic phases filtered and evaporated under reduced pressure to yield the title compound as a light yellow solid, 660 mg, 100%.

LCMS m/z=232 [M+H]$^+$

Preparation 39

6-acetyl-5-(1H-pyrazol-1-yl)pyridine-2-carboxamide

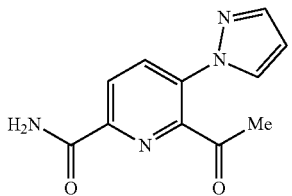 [SMILES: CC(=O)c1nc(C(N)=O)ccc1-n1cccn1]

A mixture of 6-acetyl-5-(1H-pyrazol-1-yl)pyridine-2-carboxylic acid (Preparation 38, 750 mg, 3.24 mmol), HOBT (877 mg, 6.49 mmol), EDC.HCl (1.24 g, 6.49 mmol) and Et$_3$N (1.41 mL, 9.73 mmol) in DMF (10 mL) was stirred at 20° C. for 0.5 hrs. NH$_4$Cl (521 mg, 9.73 mmol) was added and the reaction mixture stirred at 20° C. for 16 hrs. The reaction mixture was concentrated in vacuo and the residue purified by flash chromatography on silica gel eluting with EtOAc:MeOH (30:70) to afford the title compound as a yellow solid, 470 mg, 63%. LCMS m/z=231 [M+H]$^+$

Preparation 40

1-[5-fluoro-3-(1H-pyrazol-1-yl)pyridin-2-yl]ethanone

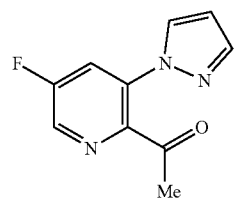 [SMILES: CC(=O)c1ncc(F)cc1-n1cccn1]

MeMgBr (213 mL, 638 mmol, 3 M in Et$_2$O) was added drop-wise to a colorless solution of 5-fluoro-3-(1H-pyrazol-1-yl)picolinonitrile (Preparation 35, 30.0 g, 159.4 mmol) in THF (1300 mL) at 0° C. and the reaction mixture stirred at rt for 3 hrs. The reaction mixture was poured into aq 1 M HCl (360 mL) in ice, the mixture stirred for 30 mins, then treated with 5 M NaOH until pH~7 to 8. The resulting solution was extracted with EtOAc (100 mL×2), the combined organic layers were dried over Na$_2$SO$_4$, filtered, and concentrated in vacuo. The orange gum was purified by column chromatography (silica gel) eluting with pet. ether: EtOAc (100:0 to 80:20) to provide the title compound as a yellow oil, 19.5 g, 60%. LCMS m/z=206 [M+H]$^+$

Preparation 41

1-[5-fluoro-1-oxido-3-(1H-pyrazol-1-yl)pyridin-2-yl]ethanone

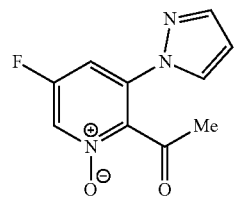 [SMILES: CC(=O)c1c(-n2cccn2)cc(F)c[n+]1[O-]]

m-CPBA (66.9 g, 330 mmol) was added to a solution of 1-[5-fluoro-3-(1H-pyrazol-1-yl)pyridin-2-yl]ethanone (Preparation 40, 27.05 g, 131.83 mmol) in DCM (400 mL) and the reaction mixture stirred at 45° C. for 64 hrs. The reaction mixture was filtered through a thin-pad of Celite® and washed with DCM (100 mL). 6M KOH aq solution (100 mL) was added to the filtrate and the solution stirred for 20 mins. The organic layer was separated, washed with saturated aq Na$_2$SO$_3$ solution (stirred at rt for 20 mins every time, 3×200 mL) and then concentrated in vacuo. The crude product was purified by column chromatography (120 g silica gel) eluting with EtOAc:pet. ether (15:85 to 100:0) twice, to afford the title compound as a yellow solid, 14.48 g, 50%. $^1$H NMR (400 MHz, CDCl$_3$) 3.14 (s, 3H), 6.51 (dd, 1H), 7.23 (dd, 1H), 7.70 (d, 1H), 7.81 (d, 1H), 8.08 (dd, 1H).

Preparation 42

1-[6-bromo-5-fluoro-3-(1H-pyrazol-1-yl)pyridin-2-yl]ethanone

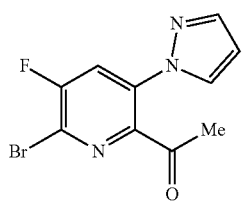

1-[5-fluoro-1-oxido-3-(1H-pyrazol-1-yl)pyridin-2-yl]ethanone (Preparation 41, 13.1 g, 59.23 mmol) in THF (300 mL) was heated at 75° C. for 15 mins until a solution was obtained. Fresh POBr₃ (34.0 g, 118 mmol) was added in three portions and the reaction mixture stirred at 75° C. for 1 hr. The cooled mixture was poured into saturated Na₂CO₃ solution (500 mL) and diluted with EtOAc (100 mL). The layers were separated, the aqueous layer was extracted with EtOAc (100 mL) and the organic phase concentrated in vacuo. The residue was purified by column chromatography (silica gel) eluting with EtOAc:pet. ether (0:100 to 25:75) twice, to provide the title compound as a white solid, 15.4%. LCMS m/z=284 [M+H]⁺

Preparation 43 methyl 6-acetyl-3-fluoro-5-(1H-pyrazol-1-yl)pyridine-2-carboxylate

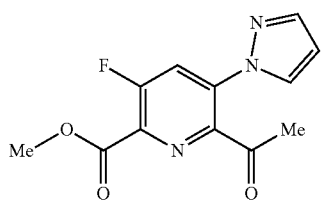 [SMILES: COC(=O)c1nc(C(C)=O)c(-n2cccn2)cc1F]

A mixture of 1-[6-bromo-5-fluoro-3-(1H-pyrazol-1-yl)pyridin-2-yl]ethanone (Preparation 42, 1000 mg, 3.52 mmol), DIPEA (1.84 mL, 10.6 mmol) and Pd(tBu₃P)₂ (198 mg, 0.387 mmol) in MeOH (70.4 mL) was stirred under CO (45 psi) at rt for 18 hrs. The reaction mixture was concentrated in vacuo and the residue purified by column chromatography (silica gel) eluting with, EtOAc:pet. ether (0:100 to 70:30) to afford the title compound as a red-yellow solid, 73%. LCMS m/z=264 [M+H]⁺

Preparation 44 tert-butyl {[6-acetyl-5-(1H-pyrazol-1-yl)pyridin-2-yl]oxy}acetate

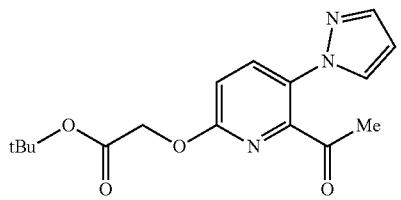 [SMILES: CC(=O)c1nc(OCC(=O)OC(C)(C)C)ccc1-n1cccn1]

A mixture of 1-[6-bromo-3-(1H-pyrazol-1-yl)pyridin-2-yl]ethanone (Preparation 34, 1.50 g, 5.64 mmol), tert-butyl 2-hydroxyacetate (1.49 g, 11.3 mmol), Cs₂CO₃ (9.18 g, 28.2 mmol), tBuXPhos (239 mg, 0.56 mmol) and tBuXPhos-Pd Gen-3 (224 mg, 0.28 mmol) in dioxane (15 mL) was degassed with N2 for 5 mins and stirred at 80° C. for 16 hrs. The cooled reaction mixture was diluted with EtOAc (60 mL) and washed with H₂O (60 mL). The organic layer was dried over Na₂SO₄ and evaporated under reduced pressure. The residue was purified by column chromatography (silica gel) eluting with EtOAc: pet. ether (0:100 to 50:50) to afford the title compound as a yellow oil, 990 mg, 55%. ¹H NMR (400 MHz, CDCl₃) δ: 1.48 (s, 9H), 2.54 (s, 3H), 4.85 (s, 2H), 6.46 (dd, 1H), 7.10 (d, 1H), 7.69 (dd, 2H), 7.79 (d, 1H)

Preparation 45

2-{[6-acetyl-5-(1H-pyrazol-1-yl)pyridin-2-yl]oxy}ethyl acetate

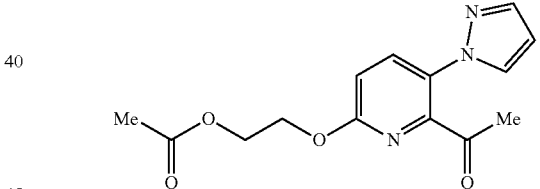

The title compound was obtained as a yellow gum, 138 mg, (13%) from 1-[6-bromo-3-(1H-pyrazol-1-yl)pyridin-2-yl]ethanone (Preparation 34) and 2-hydroxyethyl acetate, following the procedure described in Preparation 44. LCMS m/z=290 [M+H]⁺

Preparation 46

1-[3-(1H-pyrazol-1-yl)pyridin-2-yl]ethanol

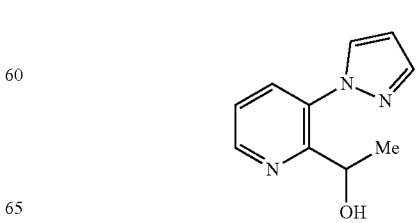

NaBH₄ (2450 mg, 64.9 mmol) was added to a solution of 1-[3-(1H-pyrazol-1-yl)pyridin-2-yl]ethanone (Preparation 36, 6.07 g, 32.43 mmol) in MeOH (162 mL), the solution purged with N2 and the reaction mixture stirred at 30° C. for 1 hr. The reaction was quenched with acetone, the mixture filtered and the filtrate concentrated in vacuo. The crude product was purified by column chromatography flash chromatography on silica gel eluting with pet. ether:EtOAc (100:0 to 80:20) to provide the title compound as a yellow oil, 4.1 g, 67%.

LCMS m/z=190 [M+H]⁺

Preparation 47

6-(1-hydroxyethyl)-5-(1H-pyrazol-1-yl)pyridine-2-carboxamide

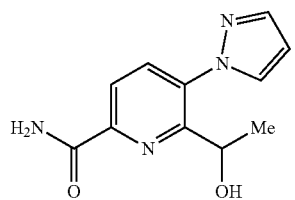 [SMILES: CC(O)c1nc(C(N)=O)ccc1-n1cccn1]

NaBH₄ (154 mg, 4.08 mmol) was added to a solution of 6-acetyl-5-(1H-pyrazol-1-yl)pyridine-2-carboxamide (Preparation 39, 0.47 g, 2.04 mmol) in dry EtOH (20 mL) and the reaction mixture stirred at 20° C. for 1 hr. The reaction mixture was concentrated in vacuo and the residue was purified by column chromatography on silica gel, eluting with MeOH:DCM (4:96) to afford the title compound as a white solid, 260 mg, 54.8%. LCMS m/z=233 [M+H]⁺

Preparation 48 to 50

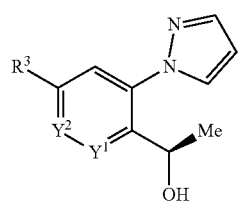

The alcohols in the table below were prepared by reducing the appropriate ethanone according to the procedure described in preparation 47 and the enantiomers separated using the SFC conditions described.

48 [A,B]

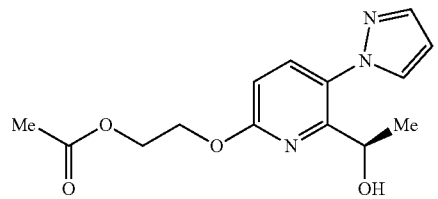

2-({6-[(1R)-1-hydroxyethyl]-5-(1H-pyrazol-1-yl)pyridin-2-yl}oxy)ethyl acetate, Column: Chiralpak AY, 75% CO₂, 25% EtOH, Peak 1 isolated, 180 mg, 45.5% yield; ¹HNMR (400 MHz, CDCl₃) δ: 1.37 (d, 3H), 2.12 (s, 3H), 4.37-4.42 (m, 1H), 4.44-4.49 (m, 2H), 4.61-4.65 (m, 2H), 4.77-4.79 (m, 1H), 5.31 (d, 1H), 6.50 (dd, 1H), 6.80 (d, 1H), 7.58 (d, 1H), 7.63 (d, 1H), 7.74 (d, 1H).

49 [C]

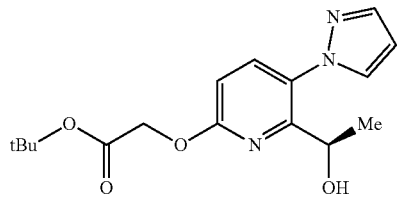

tert-butyl ({6-[(1R)-1-hydroxyethyl]-5-(1H-pyrazol-1-yl)pyridin-2-yl}oxy)acetate, Column: ChiralPak IC-H, 80% CO₂, 20% (0.1% aq NH₃ in IPA), Peak 2 isolated as a colorless oil, 224 mg, 86.2%; ¹H NMR (400 MHz, CDCl₃) δ: 1.34 (d, 3H), 1.49 (s, 9H), 4.33-4.35 (m, 1H), 4.70-5.00 (m, 3H), 6.50 (d, 1H), 6.90 (d, 1H), 7.51-7.67 (m, 2H), 7.74 (d, 1H).

50 [C]

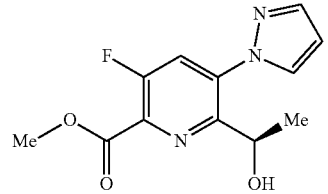

methyl 3-fluoro-6-[(1R)-1-hydroxyethyl]-5-(1H-pyrazol-1-yl)pyridine-2-carboxylate, Column: C2, 80% CO₂, 20% IPA, Peak 2 isolated as a yellow solid, 445 mg, 46%; ¹H NMR (400 MHz, CDCl₃): δ: 1.41 (d, 3H), 4.03 (s, 3H), 4.34-4.79 (m, 1H), 5.13-5.18 (m, 1H), 6.59 (dd, 1H), 7.61 (d, 1H), 7.83 (dd, 2H).

[A] MeOH was used as the reaction solvent
[B] only 0.6 eq of NaBH₄ was used in the reaction
[C] only 0.8 eq of NaBH₄ was used in the reaction Preparation 51 methyl 6-[(1R)-1-hydroxyethyl]-5-(1H-pyrazol-1-yl)pyridine-2-carboxylate

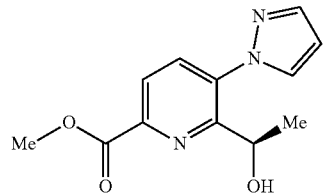 [SMILES: COC(=O)c1ccc(-n2cccn2)c([C@@H](C)O)n1]

To a solution of methyl 6-acetyl-5-(1H-pyrazol-1-yl)pyridine-2-carboxylate (Preparation 37, 800 mg, 3.26 mmol) in THF (8 mL) and MeOH (8 mL) was added NaBH$_4$ (98.7 mg, 2.61 mmol) portion wise, and the reaction mixture stirred at 0° C. for 5 mins. The reaction was quenched with aq NaHCO$_3$ (20 mL) and extracted with EtOAc (3×20 mL). The combined organic layers were washed with brine (50 mL) and dried over Na$_2$SO$_4$, filtered and evaporated under reduced pressure. The residue was purified by column chromatography (silica gel) eluting with EtOAc: pet. ether (10:90 to 80:20) to afford a colorless oil, 690 mg, 85.5%. This was further purified by SFC using a Lux Cellulose-2, eluting with 25% (0.1% aq NH$_3$ in IPA) to provide the title compound, as Peak 2, 353 mg, 42.7%. $^1$H NMR (400 MHz, CDCl$_3$) δ: 1.35 (d, 3H), 4.02 (s, 3H), 4.78 (d, 1H), 5.18-5.20 (m, 1H), 6.51-6.63 (m, 1H), 7.73-7.87 (m, 3H), 8.16 (d, 1H).

Preparation 52

(1R)-1-[6-bromo-3-(1H-pyrazol-1-yl)pyridin-2-yl]ethanol

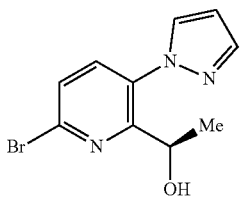 [SMILES: C[C@@H](O)c1nc(Br)ccc1-n1cccn1]

1-[6-Bromo-3-(1H-pyrazol-1-yl)pyridin-2-yl]ethanone (Preparation 34, 50.0 g, 190 mmol) was solubilised in warm (50° C.) DMSO (40 mL) and the resulting solution allowed to cool to rt. A solution of D+ glucose (40.8 g, 225 mmol) in 0.1 M pH 7 buffer (500 mL) was added to a 2 L reactor with pH control, rinsing in with additional buffer (100 mL). A solution of NADP+ (250 mg), GDH-CDX901 (250 mg) and KRED101 (5.0 g) in buffer (200 mL) was added, rinsing in with additional buffer (150 mL) and the mixture stirred at 30° C. The solution of 1-[6-bromo-3-(1H-pyrazol-1-yl)pyridin-2-yl]ethanone was added in approximately 10.0 mL aliquots and the reaction mixture stirred at 30° C. The pH of the reaction mixture was monitored and adjusted by the addition of 2N NaOH to maintain a pH of 7.0 until no further addition was required. 10% IPA/iPrOAc (600 mL) was added and the mixture stirred for 1 hr. The reactor was drained and rinsed with additional 10% IPA/iPrOAc (300 mL). Celite® (40 g) was added, the mixture stirred vigorously for 0.5 hr, and then filtered through a H$_2$O-wetted pad of Celite®, washing through with 10% IPA/iPrOAc (100 mL). The filtrate was separated, the aqueous layer stirred with 10% IPA/iPrOAc (30 mL) and filtered again through Celite®. The combined organic extracts were washed with brine, dried (Na$_2$SO$_4$), filtered and concentrated under reduced pressure, azeotroping with heptane. The resulting product was dried under vacuum to afford the title compound as a solid, 47 g. $^1$H NMR (400 MHz, CDCl$_3$) δ: 1.39 (d, 3H), 4.98 (q, 1H), 6.57 (s, 1H), 7.28-7.7.82 (m, 4H). RT=4.43 mins. HPLC analytical conditions: XBridge C18 4.6 mm×150 mm×5p. MeCN:H$_2$O from 5:95 to 100:0 over 7 mins at 1.5 mL/min Preparation 53

(1R)-1-[5-fluoro-3-(1H-pyrazol-1-yl)pyridin-2-yl]ethanol

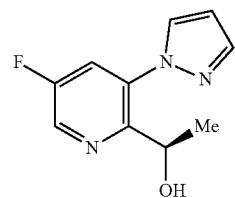

1-[5-Fluoro-3-(1H-pyrazol-1-yl)pyridin-2-yl]ethanone (Preparation 40, 100 g, 487 mmol) was warmed at 50° C. in DMSO (40 mL) until a solution was obtained, then the solution cooled. Glucose (106 g, 406 mmol) and pH 7 potassium phosphate buffer (0.1 M, 800 mL) were added, and the mixture stirred at 30° C. until a solution was obtained. The pH was adjusted to 6.5, NADP+ (500 mg), GDH-CDX901 (500 mg) and KRED101 (5.0 g) were added as solids washing in with buffer (200 mL). The mixture was stirred for 5 mins and then 1-[5-fluoro-3-(1H-pyrazol-1-yl)pyridin-2-yl]ethanone solution was added in 10 mL doses in conjunction with 2M NaOH so as to maintain the pH at 6.5. Once 280 mL of 2M NaOH had been added, the reaction mixture was stirred at rt for 18 hrs. The mixture was diluted with EtOAc (800 mL) and stirred for an hr. Celite® (50 g) was added, the mixture stirred for 230 mins, then filtered through a H$_2$O wet pad of Celite®, washing through with EtOAc and the filtrate separated. The aqueous phase was extracted with EtOAc (2×400 mL), the combined organic extracts washed with brine, dried over Na$_2$SO$_4$ and evaporated under reduced pressure to afford the title compound as a pale yellow solid, 99.6 g. $^1$H NMR (400 MHZ, CDCl$_3$) δ: 1.36 (d, 3H), 4.47-4.49 (m, 1H), 4.98-5.02 (m, 1H), 6.55 (s, 1H), 7.48-7.83 (m, 3H), 8.56 (s, 1H).

Preparation 54

1-[5-fluoro-3-(1H-pyrazol-1-yl)pyridin-2-yl]ethanol

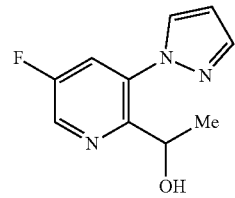

To a solution of 5-fluoro-3-(1H-pyrazol-1-yl)picolinonitrile (Preparation 35, 3.59 g, 19.08 mmol) in THF (90.9 mL) at 0° C., was added MeMgBr (3M in 2-MeTHF, 19.1 mL, 57.2 mmol), the reaction mixture allowed to warm to rt and stirred for 30 mins. The reaction was neutralized with 6N HCl, and extracted with EtOAc. The aqueous layer was quenched with saturated aq Na$_2$CO$_3$ solution and extracted with EtOAc (3×). The combined organic extracts were washed with brine, dried over Na$_2$SO$_4$, filtered and evaporated under reduced pressure. The residue was dissolved in MeOH (87.4 mL), the solution cooled to 0° C. and NaBH$_4$ (1.08 g, 28.6 mmol) added and the reaction mixture stirred at rt for 18 hrs. The mixture was quenched with 1N HCl, then saturated Na₂CO₃ added and the mixture extracted with EtOAc (3×) The combined organic layers were washed with brine, and dried over Na₂SO₄. The solvent was evaporated under reduced pressure to give the crude compound as a yellow oil, 2.55 g, 64.5%. ¹H NMR (400 MHz, CDCl₃) δ: 1.31-1.41 (m, 3H), 4.45-4.46 (m, 1H), 4.99-5.02 (m, 1H), 6.50-6.59 (m, 1H), 7.47 (dd, 1H), 7.71-7.83 (m, 2H), 8.53 (d, 1H).

Preparation 55

(1R)-1-[6-methoxy-3-(1H-pyrazol-1-yl)pyridin-2-yl]ethanol

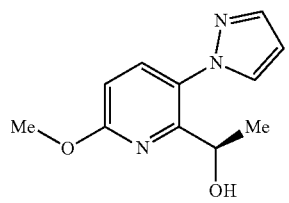 [SMILES: COc1ccc(-n2cccn2)c([C@@H](C)O)n1]

To a solution of NaH (60% in mineral oil, 2.16 g, 54.0 mmol) in MeOH (30 mL) was added (1R)-1-[6-bromo-3-(1H-pyrazol-1-yl)pyridin-2-yl]ethanol (Preparation 52, 1.81 g, 6.75 mmol) and the solution stirred for 20 mins at rt, and then at 60° C. for 16 hrs. The cooled reaction mixture was concentrated in vacuo and the residue, purified by column chromatography (silica gel), eluting with EtOAc: pet. ether (0:100 to 50:50) to afford the title compound as a white solid, 1.36 g, 91%. LCMS m/z=220 [M+H]⁺

Preparation 56

(1R)-1-[6-({[tert-butyl(dimethyl)silyl]oxy}methyl)-3-(1H-pyrazol-1-yl)pyridin-2-yl]ethanol

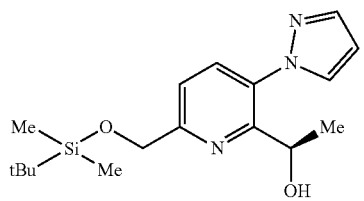 [SMILES: C[C@@H](O)c1nc(CO[Si](C)(C)C(C)(C)C)ccc1-n1cccn1]

To a colorless solution of methyl 6-[(1R)-1-hydroxyethyl]-5-(1H-pyrazol-1-yl)pyridine-2-carboxylate (Preparation 51, 50.00 mg, 0.202 mmol) in MeOH (4.0 mL) was added LiBH₄ (2.0 M in THF, 0.404 mL, 0.81 mmol) at rt and the reaction mixture stirred for 3 hrs. The reaction was neutralized using 10% AcOH/MeOH to pH 7-8 and concentrated in vacuo to give a yellow gum, 44.34 mg. To a yellow solution of this gum (40.00 mg, 0.182 mmol) and imidazole (14.9 mg, 0.22 mmol) in DCM (2.0 mL) was added TBDMSCl (30.2 mg, 0.20 mmol) at rt and the reaction mixture stirred for 18 hrs. The reaction mixture was diluted with DCM and H₂O (6 mL), the layers separated, the organic phase separated and the aqueous layer extracted with DCM (5 mL). The combined organic phases were concentrated in vacuo and the residue purified by column chromatography on silica gel eluting with EtOAC:pet. ether (0:100 to 40:60) to afford the title compound as a yellow gum, 35 mg, 58%. LCMS m/z=334 [M+H]⁺

Preparation 57

1-[3-(1H-pyrazol-1-yl)pyridin-2-yl]ethyl Methanesulfonate

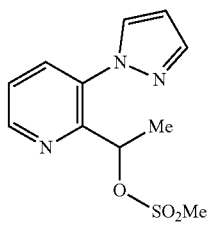

MsCl (218.0 mg, 1.90 mmol) was added to a solution of 1-[3-(1H-pyrazol-1-yl)pyridin-2-yl]ethanol (Preparation 46, 300.0 mg, 1.59 mmol) and Et₃N (321.0 mg, 3.17 mmol) in DCM (10 mL) at 0° C. and the reaction mixture stirred at 0° C. for 30 mins. The reaction was quenched with H₂O (5 mL) and extracted with DCM (2×10 mL). The combined organic layers were washed with aq NaHCO₃ (2×5 mL), dried over Na₂SO₄, filtered and concentrated in vacuo to give the title compound as a yellow oil, 420.0 mg, 99.1%. LCMS m/z=268 [M+H]⁺

Preparation 58

1-[5-fluoro-3-(1H-pyrazol-1-yl)pyridin-2-yl]ethyl Methanesulfonate

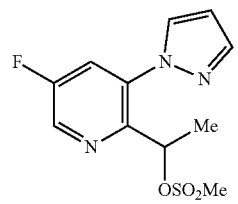

The title compound was obtained as an off-white solid in 97% yield from 1-[5-fluoro-3-(1H-pyrazol-1-yl)pyridin-2-yl]ethanol (Preparation 54) by following the procedure described in preparation 57. LCMS m/z=286 [M+H]⁺

Preparation 59

(1R)-1-[5-fluoro-3-(1H-pyrazol-1-yl)pyridin-2-yl]ethyl Methanesulfonate

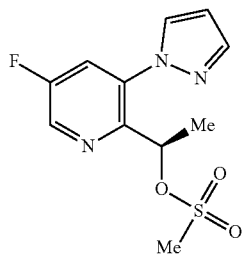

The title compound was obtained as an oil in quantitative yield from (1R)-1-[5-fluoro-3-(1H-pyrazol-1-yl)pyridin-2-yl]ethanol (Preparation 53) by following the procedure described in preparation 57. $^1$H NMR (400 MHz, CDCl$_3$) δ: 1.77 (d, 3H), 2.84 (s, 3H), 6.01 (q, 2H), 7.42-7.45 (m, 2H), 7.79-7.81 (m, 2H), 8.62 (s, 1H).

Preparation 60

1-[6-carbamoyl-3-(1H-pyrazol-1-yl)pyridin-2-yl]ethyl Methanesulfonate

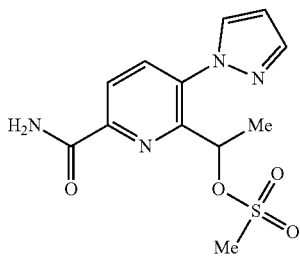 [SMILES: CC(OS(C)(=O)=O)c1nc(C(N)=O)ccc1-n1cccn1]

MsCl (0.3 mL, 4 mmol) was added to an ice-cooled solution of 6-(1-hydroxyethyl)-5-(1H-pyrazol-1-yl)pyridine-2-carboxamide (Preparation 47, 260 mg, 1.12 mmol) and DIPEA (0.8 mL, 4 mmol) in dry DCM (20 mL) and the reaction mixture stirred at 20° C. for 30 mins. The reaction was quenched with H$_2$O (20 mL) and extracted with DCM (2×20 mL). The organic layers were separated, washed with aq NaHCO$_3$ (20 mL), dried over Na$_2$SO$_4$, filtered and evaporated under reduced pressure to provide the title compound as a yellow oil, 350 mg, which was used without further purification. LCMS m/z=311 [M+H]$^+$

Preparation 61

5-bromo-1-(tetrahydro-2H-pyran-2-yl)-1H-indazole-6-carboxylic Acid

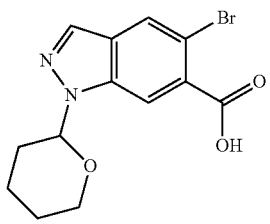 [SMILES: O=C(O)c1cc2c(cnn2C2CCCCO2)cc1Br]

To a solution of methyl 5-bromo-1-(tetrahydro-2H-pyran-2-yl)-1H-indazole-6 carboxylate (J. Med. Chem. 57(12); 5129-5140; 2014. 35 g, 100 mmol) in MeOH (250 mL) and THF (100 mL) was added 2N NaOH (258 mL, 516 mmol) and the reaction mixture stirred at 50° C. for 2 hrs. The yellow solution was concentrated in vacuo to remove MeOH and the pH of the solution carefully adjusted to ~6 using 2N HCl. The resulting solid was collected by filtration and dried under high vacuum to provide the title compound as a white solid, 32.0 g, 95%. $^1$H NMR (400 MHz, MeOD-d$_4$) δ: 1.68-1.85 (m, 3H), 2.06-2.16 (m, 2H), 2.45-2.52 (m, 1H), 3.80-3.87 (m, 1H), 3.98-4.03 (m, 1H), 5.87 (dd, 1H), 8.09 (s, 1H), 8.12 (s, 1H), 8.14 (s, 1H).

Preparation 62 methyl 5-bromo-1-{[2-(trimethylsilyl)ethoxy]methyl}-1H-indazole-6-carboxylate

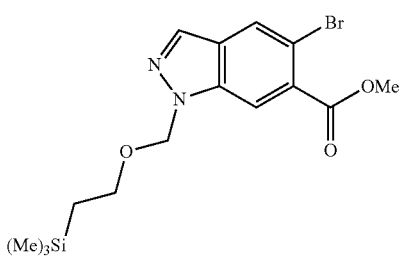

To a suspension of methyl 5-bromo-1H-indazole-6-carboxylate (28 g, 110 mmol) in THF (500 mL) was added NaH (5.71 g, 143 mmol, 60% in mineral oil) in portions at 0° C. and the suspension stirred for 30 mins. SEM-Cl (22.0 g, 132 mmol) was added and the reaction mixture stirred at rt for 16 hrs. The yellow suspension was diluted with H$_2$O (600 mL) and extracted with EtOAc (3×600 mL). The combined organic extracts were washed with brine (1200 mL), dried over Na$_2$SO$_4$, and concentrated in vacuo to give crude product as a yellow oil. This was purified by column chromatography (silica gel) eluting with EtOAc:pet. ether (0:100 to 10:90) to provide the title compound as a yellow oil, 15.8 g, 37%. $^1$H NMR (400 MHz, CDCl$_3$) δ: −0.04 (s, 9H), 0.88-0.92 (m, 2H), 3.53-3.57 (m, 2H), 3.98 (s, 3H), 5.77 (s, 2H), 8.02 (s, 1H), 8.05 (s, 1H), 8.06 (s, 1H).

Preparation 63

5-bromo-1-{[2-(trimethylsilyl)ethoxy]methyl}-1H-indazole-6-carboxylic Acid

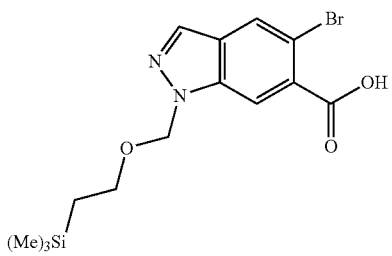

To a solution of methyl 5-bromo-1-{[2-(trimethylsilyl)ethoxy]methyl}-1H-indazole-6-carboxylate (Preparation 62, 11.4 g, 29.6 mmol) in MeOH (250 mL) was added 2N NaOH (88.8 mL, 178 mmol) and the reaction mixture stirred at 50° C. for 3 hrs. The cooled solution was concentrated in vacuo, and the pH of the residue adjusted to 6 using 1N HCl. The resulting mixture was filtered, and the solid dried to afford the title compound as a yellow solid, 11.0 g. $^1$H NMR (400 MHz, MeOD-$d_4$) δ: 0.02 (s, 9H), 0.95 (dd, 2H), 3.68 (dd, 2H), 5.78 (s, 2H), 8.11 (s, 1H), 8.12 (s, 1H), 8.46 (s, 1H).

Preparation 64

1-[5-bromo-1-(tetrahydro-2H-pyran-2-yl)-1H-indazol-6-yl]ethanone

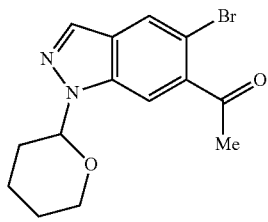 [SMILES: CC(=O)c1cc2c(cnn2C2CCCCO2)cc1Br]

To a solution of 5-bromo-1-(tetrahydro-2H-pyran-2-yl)-1H-indazole-6-carboxylic acid (Preparation 61, 32.0 g, 98.4 mmol) in THF (400 mL) was added HATU (44.9 g, 118 mmol) and N,O-dimethylhydroxylamine hydrochloride (10.6 g, 108 mmol) and the white suspension stirred at rt for 20 mins. Et$_3$N (29.9 g, 295 mmol) was added and the reaction mixture stirred at rt for 16 hrs. The yellow suspension was diluted with saturated aq NH$_4$Cl (400 mL) and extracted with EtOAc (3×400 mL). The combined organic extracts were washed with brine (1200 mL), dried over Na$_2$SO$_4$, and concentrated in vacuo to give a yellow gum. This was purified by column chromatography eluting with EtOAc: pet. ether (20:80 to 70:30) to afford the title compound as a yellow gum, 38.0 g. The gum was dissolved in THF (500 mL), the solution cooled to −70° C., MeMgBr (103 mL, 310 mmol, 3M in Et$_2$O) added drop wise, the suspension stirred for 30 mins, then allowed to warm to rt and stirred for 16 hrs. H$_2$O (400 mL) was added drop wise to quench the reaction, the mixture diluted with EtOAc (400 mL), then filtered through Celite® and separated. The organic phase was dried over Na$_2$SO$_4$, and concentrated in vacuo to give crude product as a yellow gum. This was purified by column chromatography eluting with EtOAc: pet. ether (0:100 to 50:50) to afford the title compound as a colorless gum, 19.5 g, 58%. $^1$H NMR (400 MHz, MeOD-$d_4$) δ: 1.68-1.86 (m, 3H), 2.03-2.16 (m, 2H), 2.46-2.55 (m, 1H), 2.68 (s, 3H), 3.81-3.84 (m, 1H), 3.97-4.03 (m, 1H), 5.87-5.89 (m, 1H), 7.89 (s, 1H), 8.10 (s, 2H).

Preparation 65

1-(5-bromo-1-{[2-(trimethylsilyl)ethoxy]methyl}-1H-indazol-6-yl)ethanone

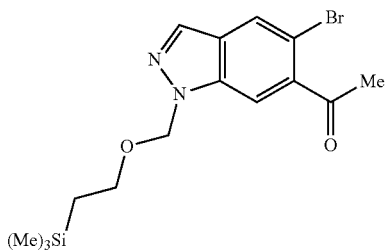

The title compound was obtained as a yellow oil, 4.5 g, 46%, from 5-bromo-1-{[2-(trimethylsilyl)ethoxy]methyl}-1H-indazole-6-carboxylic acid (Preparation 63), by following the procedure described in Preparation 64. $^1$H NMR (400 MHz, CDCl$_3$) δ: 0.03 (s, 9H), 0.96 (t, 2H), 2.67 (s, 3H), 3.62 (t, 2H), 5.73 (s, 2H), 7.88 (s, 1H), 7.98 (s, 1H), 8.10 (s, 1H).

Preparation 66

1-[5-(1H-pyrazol-1-yl)-1-(tetrahydro-2H-pyran-2-yl)-1H-indazol-6-yl]ethanone

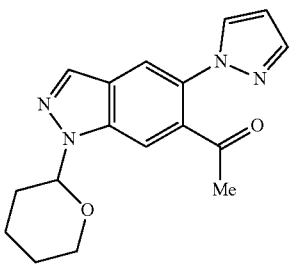 [SMILES: CC(=O)c1cc2c(cnn2C2CCCCO2)cc1-n1cccn1]

To a solution of 1-[5-bromo-1-(tetrahydro-2H-pyran-2-yl)-1H-indazol-6-yl]ethanone, (Preparation 64, 19.5 g, 60.3 mmol) in DMF (300 mL) was added 1H-pyrazole (6.16 g, 90.49 mmol), (R,R)-(−)-N,N'-dimethyl-1,2-cyclohexanediamine (858 mg, 6.03 mmol), CuI (1720 mg, 9.05 mmol) and K$_2$CO$_3$ (2.5 g, 181 mmol) and the suspension stirred at 130° C. for 16 hrs. The cooled black suspension was diluted with H$_2$O (500 mL), extracted with EtOAc (3×500 mL), the combined organic extracts washed with brine (1000 mL), dried over Na$_2$SO$_4$, and concentrated in vacuo. The crude product was purified by column chromatography (silica gel) eluting with EtOAc:pet. ether (20:80 to 60:40) to provide the title compound as a yellow gum, 15.5 g, 82.8%. LCMS m/z=311 [M+H]$^+$

Preparation 67

1-[5-(1H-pyrazol-1-yl)-1-{[2-(trimethylsilyl)ethoxy]methyl}-1H-indazol-6-yl]ethanone

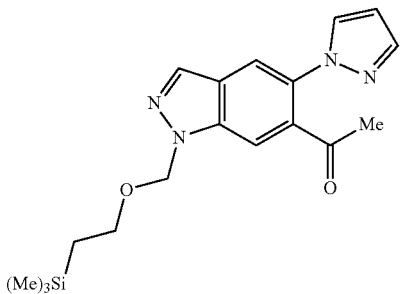

The title compound was obtained as a yellow solid 3.3 g, 76% from 1-(5-bromo-1-{[2-(trimethylsilyl)ethoxy]methyl}-1H-indazol-6-yl)ethanone (Preparation 65), by following the procedure described in preparation 66. LCMS m/z=357 [M+H]$^+$

Preparation 68

1-[5-(1H-pyrazol-1-yl)-1H-indazol-6-yl]ethanone

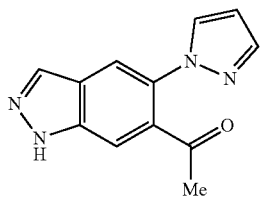 [SMILES: CC(=O)c1cc2[nH]ncc2cc1-n1cccn1]

A suspension of 1-[5-(1H-pyrazol-1-yl)-1-(tetrahydro-2H-pyran-2-yl)-1H-indazol-6-yl]ethanone (Preparation 66, 5.0 g, 16.11 mmol) in 4M HCl in dioxane (100 mL) was stirred at rt for 2 hrs. The mixture was filtered, the solid washed with EtOAc and dried in vacuo to afford the title compound (crude) as an off white solid which was used without further purification. $^1$H NMR (400 MHz, DMSO-d$_6$) δ: 1.91 (s, 3H), 6.55 (dd, 1H), 7.67-7.77 (m, 2H), 7.97 (s, 1H), 8.25 (dd, 2H).

Preparation 69

Methyl [6-acetyl-5-(1H-pyrazol-1-yl)-1H-indazol-1-yl]acetate

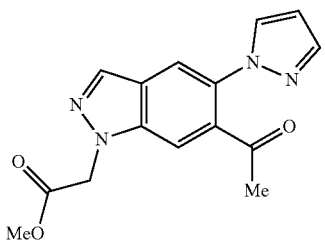 [SMILES: COC(=O)Cn1ncc2cc(-n3cccn3)c(C(C)=O)cc21]

Cs$_2$CO$_3$ (29.8 g, 91.7 mmol) and methyl bromoacetate (9.3 g, 60.8 mmol) were added to a solution of 1-[5-(1H-pyrazol-1-yl)-1H-indazol-6-yl]ethanone (Preparation 68, 6.9 g, 30.50 mmol) in DMF (100 mL) and the reaction mixture stirred at rt for 48 hrs. Additional Cs$_2$CO$_3$ (15 g, 46.2 mmol) and methyl bromoacetate (4.5 g, 29.42 mmol) were added and the reaction mixture stirred for a further 16 hrs. The mixture was filtered, washing through with EtOAc. H$_2$O (250 mL) was added, the layers separated, the aqueous phase extracted with EtOAc (3×150 mL), the combined organic layers washed with H$_2$O (2×100 mL), brine (200 mL), then dried over anhydrous Na$_2$SO$_4$, filtered and concentrated in vacuo. The crude product was purified by column chromatography (silica gel) twice, eluting with EtOAc:pet. ether (0:100 to 60:40) to afford the title compound as a white solid, 5.2 g, 57.2%. $^1$H NMR (400 MHz, CDCl$_3$) δ: 1.93 (s, 3H), 3.79 (s, 3H), 5.25 (s, 2H), 6.54 (dd, 1H), 7.62 (s, 1H), 7.73-7.84 (m, 3H), 8.16 (d, 1H).

Preparation 70 tert-butyl [6-acetyl-5-(1H-pyrazol-1-yl)-1H-indazol-1-yl]acetate

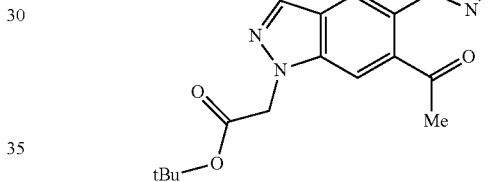

The title compound was obtained as a light yellow solid, in 62.8% yield (632 mg) from 1-[5-(1H-pyrazol-1-yl)-1H-indazol-6-yl]ethanone (Preparation 68) and t-butyl bromoacetate following a similar procedure to that described in Preparation 69. $^1$H NMR (400 MHz, CDCl$_3$) δ: 1.46 (s, 9H), 1.93 (s, 3H), 5.13 (s, 2H), 6.54 (s, 1H), 7.62 (s, 1H), 7.76-7.79 (m, 2H), 7.81 (s, 1H), 8.16 (s, 1H).

Preparation 71

Methyl [6-acetyl-5-(1H-pyrazol-1-yl)-2H-indazol-2-yl]acetate

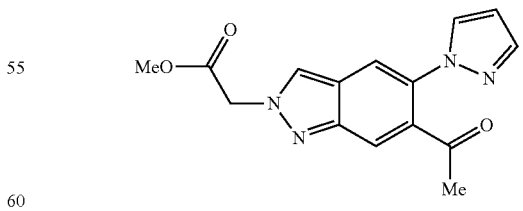

To a solution of 1-[5-(1H-pyrazol-1-yl)-1H-indazol-6-yl]ethanone (Preparation 68, 2.3 g, 10.17 mmol) in THF (20 mL) was added N,N-dicyclohexylmethylamine (3.97 g, 20.3 mmol) and methyl bromoacetate (3.11 g, 20.3 mmol) and the reaction mixture stirred at 70° C. for 18 hrs. The cooled reaction mixture was filtered, washed with EtOAc, H$_2$O (20 mL) added and the layers separated. The aqueous phase was extracted with EtOAc (2×35 mL), the combined organic layers dried over Na₂SO₄, filtered and concentrated in vacuo. The crude product was purified by column chromatography (silica gel) eluting with EtOAc:pet. ether (0:100 to 70:30) to give two products. The first eluting product was triturated with MeOH and MTBE to afford the title compound as an off-white solid, 929 mg, 24.3%. ¹H NMR (400 MHz, CDCl₃) δ: 2.09 (s, 3H), 3.83 (s, 3H), 5.28 (s, 2H), 6.49 (dd, 1H), 7.72-7.74 (m, 3H), 7.98 (s, 1H), 8.13 (d, 1H).

Preparation 72

5-Bromo-1H-pyrazolo[3,4-b]pyridine 7-oxide

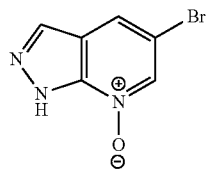

To a suspension of 5-bromo-1H-pyrazolo[3,4-b]pyridine (95 g, 480 mmol) in anhydrous EtOAc (1920 mL) was added m-CPBA (166 g, 816 mmol) at rt over 30 mins, and the reaction mixture then stirred at 45° C. to 50° C. for 5 hrs. The cooled reaction mixture was filtered, the solid washed with EtOAc (2×50 mL) and dried under vacuum to afford the title compound as a light brown solid, 93.6 g, 91%. ¹H NMR (400 MHz, DMSO-d₆) δ: 8.14 (s, 1H), 8.24 (s, 1H), 8.68 (s, 1H), 14.69 (br s, 1H).

Preparation 73

5-bromo-1H-pyrazolo[3,4-b]pyridine-6-carbonitrile

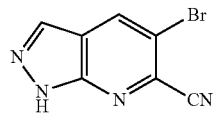 [SMILES: N#Cc1nc2[nH]ncc2cc1Br]

To a suspension of 5-bromo-1H-pyrazolo[3,4-b]pyridine 7-oxide (Preparation 72, 46.6 g, 210 mmol) in MeCN (1050 mL) was added Et₃N (58.3 mL, 420 mmol) and TMSCN (52.5 mL, 420 mmol) and the reaction mixture stirred at 80° C. for 16 hrs. The cooled reaction mixture was concentrated in vacuo and the residue suspended in MTBE for 60 hrs. The resulting solid was filtered off, washing through with MTBE (2×30 mL) and dried under vacuum to afford the title compound as a red solid, 89.9%. ¹H NMR (400 MHz, DMSO-d₆) δ: 8.31 (s, 1H), 8.87 (s, 1H), 14.34 (br s, 1H).

Preparation 74

1-(5-bromo-1H-pyrazolo[3,4-b]pyridin-6-yl)ethanone

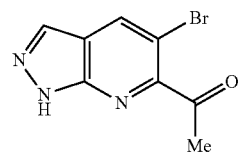 [SMILES: CC(=O)c1nc2[nH]ncc2cc1Br]

To a solution of 5-bromo-1H-pyrazolo[3,4-b]pyridine-6-carbonitrile (Preparation 73, 25.0 g, 100 mmol) in THF (500 mL) was added a solution of MeMgBr (3.0 M in Et₂O, 101 mL, 303 mmol) at 0° C. over 40 mins. The reaction mixture was allowed to warm to 20° C. and stirred for a further 3 hrs. The reaction mixture was poured over aq 6 M HCl (120 mL) in ice-water (300 mL) and the resulting black solution was stirred for 50 mins. The solution was neutralised using aq 10M NaOH and the layers separated. The aqueous layer was extracted with EtOAc (3×250 mL), the combined organic phases were dried over Na₂SO₄, filtered and concentrated in vacuo to afford the title compound as a red solid, 84.9%. ¹H NMR (400 MHz, DMSO-d₆) δ: 2.67 (s, 3H), 8.24 (s, 1H), 8.68-8.74 (m, 1H), 14.15 (br s, 1H).

Preparation 75

1-[5-(1H-pyrazol-1-yl)-1H-pyrazolo[3,4-b]pyridin-6-yl]ethanone

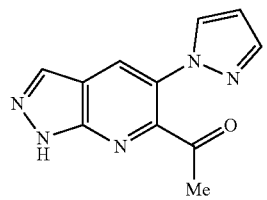 [SMILES: CC(=O)c1nc2[nH]ncc2cc1-n1cccn1]

A suspension of 1-(5-bromo-1H-pyrazolo[3,4-b]pyridin-6-yl)ethanone (Preparation 74, 29.6 g, 110 mmol), 1H-pyrazole (18.1 g, 266 mmol), Cs₂CO₃ (72.3 g, 222 mmol), and (R,R)-(−)-N,N'-dimethyl-1,2-cyclohexanediamine (12.6 g, 88.8 mmol) in DMF (185 mL) was purged with N2. CuI (4.23 g, 22.2 mmol) was added and the mixture stirred vigorously at 130° C. in a sealed vessel for 4 hrs. The cooled reaction mixture was diluted with H₂O (600 mL) the mixture filtered and the filtrate separated. The aqueous layer was extracted with EtOAc (5×150 mL), the combined organic layers were washed with H₂O (50 mL), dried over Na₂SO₄, filtered and evaporated under reduced pressure. The resulting black oil was purified by flash column chromatography on silica gel eluting with EtOAc: pet. ether (0:100 to 100:0) to afford the title compound as a yellow solid, 4.6 g, and additional crude product, ~8.1 g. This was stirred in MTBE (10 mL) for 15 mins, the solid filtered off, washed with MTBE and dried to afford additional title compound, 5.1 g as a white solid. ¹H NMR (400 MHz, CDCl₃) δ: 2.60 (s, 3H), 6.52 (dd, 1H), 7.72-7.79 (m, 2H), 8.21-8.23 (m, 2H), 11.80 (br s, 1H).

Preparation 76

1-[5-(1H-pyrazol-1-yl)-1-{[2-(trimethylsilyl)ethoxy]methyl}-1H-pyrazolo[3,4-b]pyridin-6-yl]ethanone

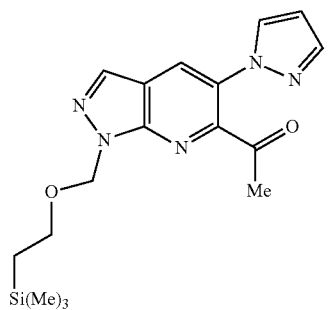

To a solution of 1-[5-(1H-pyrazol-1-yl)-1H-pyrazolo[3,4-b]pyridin-6-yl]ethanone (Preparation 75, 19.35 g, 85.16 mmol) and N,N-dicyclohexylmethylamine (29.2 mL, 136 mmol) in anhydrous DMF (426 mL) was added SEM-Cl (21.1 mL, 119 mmol) over 10 mins at 0° C. and the reaction mixture stirred at rt for 40 hrs. The mixture was diluted with H$_2$O (1500 mL), and extracted with EtOAc (5×300 mL). The combined organic layers were washed with H$_2$O (50 mL), brine (50 mL), dried over Na$_2$SO$_4$, filtered and concentrated in vacuo. The crude product was purified by column chromatography silica gel column eluting with EtOAc:pet. ether (0:100 to 50:50) twice, to afford the title compound as an orange oil, 19.85 g. $^1$H NMR (400 MHz, CDCl$_3$) δ: −0.01-−0.04 (m, 9H), 0.94-1.01 (m, 2H), 2.70 (s, 3H), 3.70-3.75 (m, 2H), 5.95 (s, 2H), 6.52 (d, 1H), 7.74 (d, 1H), 7.77 (d, 1H), 8.19 (s, 1H), 8.21 (s, 1H)

Preparation 77 methyl [6-acetyl-5-(1H-pyrazol-1-yl)-1H-pyrazolo[3,4-b]pyridin-1-yl]acetate

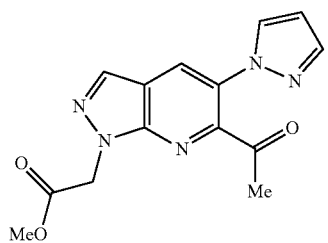 [SMILES: COC(=O)Cn1ncc2cc(-n3cccn3)c(C(C)=O)nc21]

To a solution of 1-[5-(1H-pyrazol-1-yl)-1H-pyrazolo[3,4-b]pyridin-6-yl]ethanone (Preparation 75, 400 mg, 1.6 mmol) in anhydrous THF (5 mL) was added N,N-dicyclohexylmethylamine (0.68 mL, 3.17 mmol) and methyl bromoacetate (0.3 mL, 3.17 mmol) and the reaction mixture stirred at 70° C. for 18 hrs. The cooled reaction mixture was filtered, washed with EtOAc (10 mL), H$_2$O (10 mL) added, and the layers separated. The aqueous layer was extracted with EtOAc (2×30 mL), the combined organic layers dried over Na$_2$SO$_4$, filtered and concentrated in vacuo. The crude product was purified by column chromatography (silica gel) eluting with EtOAc:pet. ether (0:100 to 70:30) to provide the title compound as a white solid, (as peak 1), 120 mg, 25%. $^1$H NMR (400 MHz, CDCl$_3$) δ: 2.64 (s, 3H), 3.81 (s, 3H), 5.40 (s, 2H), 6.52 (dd, 1H), 7.75 (dd, 2H), 8.21 (d, 2H).

Preparation 78

1-[5-(1H-pyrazol-1-yl)-1-(tetrahydro-2H-pyran-2-yl)-1H-pyrazolo[3,4-b]pyridin-6-yl]ethanone

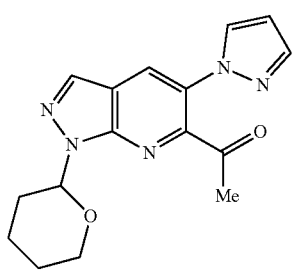

To a solution of 1-[5-(1H-pyrazol-1-yl)-1H-pyrazolo[3,4-b]pyridin-6-yl]ethanone (Preparation 75, 2.69 g, 11.8 mmol) in THF (60 mL) was added 2,3-dihydropyran (5.00 g, 59.4 mmol) followed by pTsOH (299.7 mg, 1.74 mmol) and the reaction mixture stirred at 50° C. for 3 hrs. The reaction mixture was concentrated in vacuo to remove the majority of the solvent and the residue taken up in brine (30 mL) and extracted with EtOAc (3×30 mL). The combined organic layers were dried over MgSO$_4$, filtered, and evaporated under reduced pressure to give a dark oil. This was purified by flash column chromatography on silica gel eluting with EtOAc: pet. ether (0:100 to 49:51) to afford the title compound as a yellow oil 2.39 g, 64.8%. $^1$H NMR (400 MHz, CDCl$_3$) δ: 1.65-1.70 (m, 1H), 1.82-1.88 (m, 2H), 2.02-2.05 (m, 1H), 2.19-2.20 (m, 1H), 2.64-2.66 (m, 4H), 3.82-3.86 (m, 1H), 4.14-4.18 (m, 1H), 6.20 (dd, 1H), 6.50 (s, 1H), 7.74 (d, 1H), 8.16 (s, 1H), 8.20 (s, 1H).

Preparation 79

5-bromo-2-nitro-5-(1H-pyrazol-1-yl)aniline

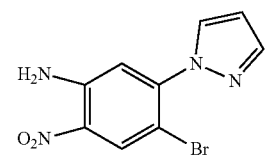 [SMILES: Nc1cc(-n2cccn2)c(Br)cc1[N+](=O)[O-]]

To a suspension of 4-bromo-5-fluoro-2-nitroaniline (10.0 g, 4.55 mmol) and 1H-pyrazole (5.79 g, 85.1 mmol) in DMF (200 mL) was added K$_2$CO$_3$ (17.6 g, 128 mmol) and the reaction mixture stirred at 100° C. for 4 hrs. The cooled mixture was concentrated in vacuo, the residue diluted with DCM (250 mL) and washed with saturated aq NaHCO$_3$ solution (2×80 mL). The organic phase was dried over Na$_2$SO$_4$, filtered and concentrated in vacuo. The crude product was purified by recrystallization from EtOAc/pet. ether to afford the title product as a yellow solid, 8.0 g, 66%. $^1$H NMR (400 MHz, CDCl$_3$) δ: 6.38 (br s, 2H), 7.32 (s, 1H), 7.77 (s, 1H), 8.08 (s, 1H).

Preparation 80

1-[4-amino-5-nitro-2-(1H-pyrazol-1-yl)phenyl]ethanone

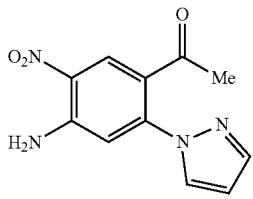 [SMILES: CC(=O)c1cc([N+](=O)[O-])c(N)cc1-n1cccn1]

Step 1

4-bromo-5-chloro-2-nitroaniline

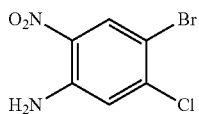

A mixture of 5-chloro-2-nitroaniline (23.40 g, 135.6 mmol) and N-bromosuccinimide (24.10 g, 136.0 mmol) in acetic acid (400 mL) was stirred at 130° C. for 1 h. The reaction mixture was poured into water (400 mL). The precipitate was collected by filtration and washed with petroleum ether (5×50 mL). The filter cake was then dried in vacuo for 3 h to give 29 g (85%) of the title compound as a light brown solid. $^1$H NMR (400 MHz, DMSO-$d_6$) 8.24 (s, 1H), 7.63 (br s, 2H), 7.29 (s, 1H).

Step 2

N-(4-bromo-5-chloro-2-nitrophenyl)acetamide

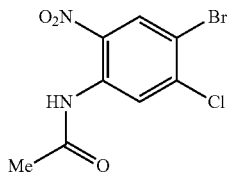 [SMILES: CC(=O)Nc1cc(Cl)c(Br)cc1[N+](=O)[O-]]

4-bromo-5-chloro-2-nitroaniline (11.0 g, 43.7 mmol) in acetic acid (200 mL) was heated at 120° C. Then, acetic anhydride (8.93 g, 87.5 mmol) was added dropwise. The brown solution was stirred at 120° C. for 10 h. The reaction mixture was concentrated under reduced pressure to remove most of the acetic acid and then saturated aqueous sodium bicarbonate was added to adjust the pH to ~7. The mixture was then extracted with ethyl acetate (2×100 mL). The combined organic layers were washed with water (50 mL), brine (50 mL), dried over sodium sulfate, filtered, and concentrated under reduced pressure to give 14 g of a yellow solid containing the title compound, which was taken on to the next step without further purification. $^1$H NMR (400 MHz, DMSO-$d_6$) δ 2.09 (s, 3H), 7.97 (s, 1H), 8.34 (s, 1H), 10.38 (br s, 1H).

Step 3

N-(5-chloro-4-(1-ethoxyvinyl)-2-nitrophenyl)acetamide

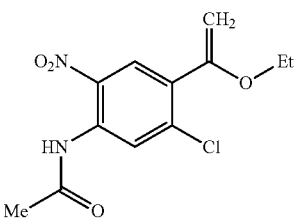 [SMILES: C=C(OCC)c1cc([N+](=O)[O-])c(NC(C)=O)cc1Cl]

To a solution of N-(4-bromo-5-chloro-2-nitrophenyl)acetamide (14 g) and Pd(PPh$_3$)$_4$ (2.52 g 2.18 mmol) in 1,4-dioxane (200 mL) was added tri-butyl(1-ethoxyvinyl)stannane (15.80 g, 43.6 mmol) under a nitrogen atmosphere. The reaction mixture was evacuated with N$_2$ (×3) and then stirred at 100° C. for 16 h. The reaction mixture was cooled to rt and concentrated under reduced pressure. The resulting black oil was poured into water (50 mL) and extracted with ethyl acetate (3×100 mL). The combined organic layers were dried over anhydrous Na$_2$SO$_4$, filtered and concentrated to give the title compound as a black oil, which was taken on to the next step without additional purification. LCMS m/z 284.9 [M+H]$^+$.

Step 4

N-(4-acetyl-5-chloro-2-nitrophenyl)acetamide

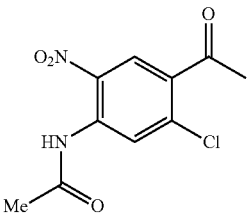 [SMILES: CC(=O)Nc1cc(Cl)c(C(C)=O)cc1[N+](=O)[O-]]

To a solution of N-(5-chloro-4-(1-ethoxyvinyl)-2-nitrophenyl)acetamide in ethyl acetate (60 mL) was added 4 N HCl (aq) (120 mmol, 30 mL). The mixture was stirred at rt for 1 h. The reaction mixture was then extracted with ethyl acetate (3×80 mL). The combined organic layers were washed with saturated aqueous NaHCO$_3$ (25 mL), water (50 mL), brine (50 mL), dried over anhydrous Na$_2$SO$_4$, filtered, and concentrated under reduced pressure to give a black oil. The black oil was then purified via flash chromatography (silica gel) eluting with a gradient of petroleum ether:ethyl acetate (100:0 to 40:60, then 0:100) to deliver 11 g of a black oil. This oil was then re-purified via flash chromatography (silica gel) eluting with a gradient of petroleum ether:ethyl acetate (100:0 to 70:30) to afford a black solid which was triturated with MTBE (2×15 mL) to afford 6.5 g of a brown solid. This solid was then purified via flash chromatography (silica gel) eluting with petroleum ether:ethyl acetate (100:0 to 60:40) to afford a solid. This solid was triturated with MTBE (3×15 mL, then 3×5 mL) to furnish 4.88 g (44% for 3 steps) of title compound as a yellow solid. LCMS m/z=257

[M+H]+. 1H NMR (400 MHz, DMSO-d6) δ 2.12 (s, 3H), 2.63 (s, 3H), 7.93 (s, 1H), 8.36 (s, 1H), 10.53 (s, 1H).

Step 5

1-[4-amino-5-nitro-2-(1H-pyrazol-1-yl)phenyl]ethanone

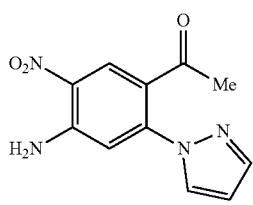 [SMILES: CC(=O)c1cc([N+](=O)[O-])c(N)cc1-n1cccn1]

To a mixture of N-(4-acetyl-5-chloro-2-nitrophenyl)acetamide (4.63 g, 18.04 mmol), 1H-pyrazole (1.60 g, 23.5 mmol), t-BuOK (4.05 g, 36.1 mmol), CuI (687 mg, 3.61 mmol) and 1,10-phenanthroline (650 mg, 3.61 mmol) was added DMF (100 mL). N2 was bubbled through the suspension for 10 mins and the reaction mixture stirred at 110° C. for 16 hrs. The cooled suspension was filtered and the filtrate diluted with EtOAc (150 mL) and water (300 mL). The aqueous phase was extracted with EtOAc (2×150 mL), the combined organic layers were washed with brine (2×150 mL), dried over Na2SO4, filtered and concentrated in vacuo. The crude product was purified by column chromatography on silica gel eluting with EtOAc: pet. ether (100:0 to 50:50) to afford the title compound as a yellow solid, 1.85 g, 41.6%. LCMS m/z=247 [M+H]+

Preparation 81

5-bromo-5-(1H-pyrazol-1-yl)benzene-1,2-diamine

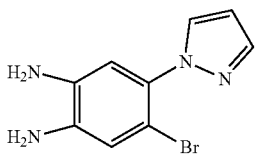 [SMILES: Nc1cc(Br)c(-n2cccn2)cc1N]

To a solution of 4-bromo-2-nitro-5-(1H-pyrazol-1-yl)aniline (Preparation 79, 8.0 g, 28.0 mmol) in THF (150.0 mL), EtOH (150.0 mL) and H2O (50.0 mL) was added iron powder (9.47 g, 10.0 mmol) and NH4Cl (3.02 g, 56.5 mmol), and the reaction mixture heated at 95° C. for 2 hrs. The cooled mixture was diluted with EtOH, filtered through Celite® until no further color came through the filter, and concentrated in vacuo. The residue was dissolved in EtOAc (250 mL), washed with H2O (80 mL), brine (80 mL), dried (Na2SO4), filtered and concentrated to afford the title compound as a brown oil, 7 g, 98% yield. 1H NMR (400 MHz, MeOD-d4) δ: 6.45 (dd, 1H), 6.76 (s, 1H), 6.95 (s, 1H), 7.64 (d, 1H), 7.73 (d, 1H).

Preparation 82

1-[4,5-diamino-2-(1H-pyrazol-1-yl)phenyl]ethanone

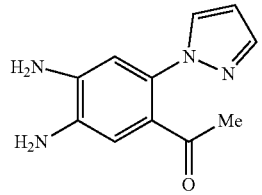 [SMILES: CC(=O)c1cc(N)c(N)cc1-n1cccn1]

To a yellow suspension of 1-[4-amino-5-nitro-2-(1H-pyrazol-1-yl)phenyl]ethanone (Preparation 80, 1.85 g, 7.51 mmol) in MeOH (80 mL) was added wet Pd/C (50% in H2O, 900 mg) and the black suspension stirred at rt for 5 hrs. The mixture was filtered and the filtrate evaporated under reduced pressure to afford the title product as a brown gum, 1600 mg, 98.5%. 1H NMR (400 MHz, CDCl3) δ: 1.82 (s, 3H), 3.47-3.50 (m, 2H), 3.8-3.86 (m, 2H), 6.45 (d, 1H), 6.72 (s, 1H), 7.11 (s, 1H), 7.57 (s, 1H), 7.71 (s, 1H).

Preparation 83

5-bromo-5-(1H-pyrazol-1-yl)-1H-benzimidazole

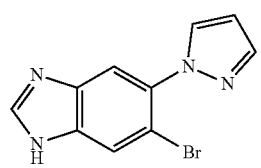 [SMILES: Brc1cc2[nH]cnc2cc1-n1cccn1]

HCl (5 mL) was added to a solution of 4-bromo-5-(1H-pyrazol-1-yl)benzene-1,2-diamine (Preparation 81, 7.0 g, 27.66 mmol) in formic acid (50 mL) and the reaction mixture stirred at 70° C. for 2 hrs. The cooled reaction mixture was evaporated under reduced pressure to afford the title compound as a brown solid. This was used in the next step without further purification, 7.0 g, 96%. 1H NMR (400 MHz, MeOD-d4) δ: 6.63 (dd, 1H), 7.84 (d, 1H), 8.05 (d, 1H), 8.11 (s, 1H), 8.34 (s, 1H), 9.58 (s, 1H).

Preparation 84

1-[2-methyl-5-(1H-pyrazol-1-yl)-1H-benzimidazol-6-yl]ethanone

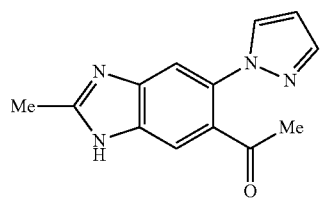 [SMILES: CC(=O)c1cc2[nH]c(C)nc2cc1-n1cccn1]

To a solution of 1-[4,5-diamino-2-(1H-pyrazol-1-yl)phenyl]ethanone (Preparation 82, 1.6 g, 7.40 mmol) and triethyl orthoacetate (3.60 g, 22.2 mmol) in THF (60 mL) was added TsOH (63.7 mg, 0.37 mmol) and the reaction mixture stirred at 60° C. for 16 hrs. The cooled solution was concentrated in vacuo and the residue purified by column chromatography on silica gel eluting with EtOAc:pet. ether (0:100 to 20:80) to yield a yellow gum (2.0 g). It was dissolved in EtOH (35 mL), TsOH (100 mg, 0.58 mmol) was added and the reaction mixture stirred at 85° C. for 2 hrs. The cooled solution was concentrated in vacuo, the resulting solid dissolved in DCM (20 mL), solid NaHCO$_3$ added and the mixture stirred for 10 mins, then filtered. The filtrate was evaporated under reduced pressure to afford the title compound as a brown solid, 1.39 g, 78.2%. $^1$H NMR (400 MHz, CDCl$_3$) δ: 1.90 (s, 3H), 2.62 (s, 3H), 6.55 (d, 1H), 7.60 (s, 1H), 7.70-7.80 (m, 3H).

Preparation 85

1-[5-(1H-pyrazol-1-yl)-1-(tetrahydro-2H-pyran-2-yl)-1H-indazol-6-yl]ethanol

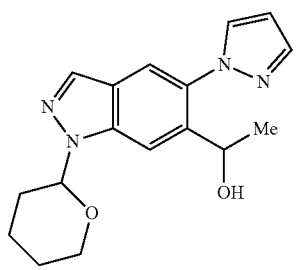 [SMILES: CC(O)c1cc2c(cnn2C2CCCCO2)cc1-n1cccn1]

To a solution of 1-[5-(1H-pyrazol-1-yl)-1-(tetrahydro-2H-pyran-2-yl)-1H-indazol-6-yl]ethanone (Preparation 66, 1.00 g, 3.22 mmol) in dry EtOH (15.0 mL) was added NaBH$_4$ (244 mg, 6.44 mmol) and the reaction mixture stirred at rt for 12 hrs. The mixture was diluted with H$_2$O (500 mL) and extracted with EtOAc (3×500 mL). The combined organic layers were washed with H$_2$O (2×300 mL), dried over Na$_2$SO$_4$, filtered and concentrated in vacuo to give crude product. This was purified by flash chromatography on silica gel eluting with pet. ether: EtOAc (100:0 to 0:100) twice, to provide the title compound as a yellow oil, 900 mg, 89.4%. LCMS m/z=335 [M+Na]$^+$ Preparation 86

1-[5-(1H-pyrazol-1-yl)-1-{[2-(trimethylsilyl)ethoxy]methyl}-1H-indazol-6-yl]ethanol

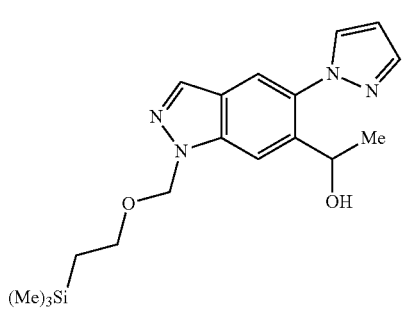

The title compound was obtained as a light yellow gum in 99% yield from 1-[5-(1H-pyrazol-1-yl)-1-{[2-(trimethylsilyl)ethoxy]methyl}-1H-indazol-6-yl]ethanone (Preparation 67) following the procedure described in Preparation 85. $^1$H NMR (400 MHz, MeOD-d$_4$) δ: 0.01 (s, 9H), 0.95 (t, 2H), 1.28 (d, 3H), 3.68 (dt, 2H), 4.73-4.78 (m, 1H), 2.07 (s, 2H), 6.56 (dd, 1H), 7.76-7.77 (m, 2H), 7.91 (d, 1H), 8.01 (s, 1H), 8.51 (s, 1H).

Preparation 87 methyl {6-[(1R)-1-hydroxyethyl]-5-(1H-pyrazol-1-yl)-1H-indazol-1-yl}acetate

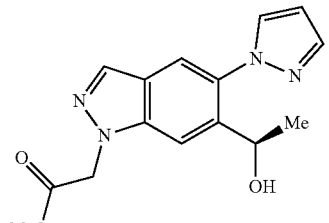

NaBH$_4$ (63.4 mg, 1.68 mmol) was added portion wise to a 0° C. solution of methyl [6-acetyl-5-(1H-pyrazol-1-yl)-1H-indazol-1-yl]acetate (Preparation 69, 1000 mg, 3.35 mmol) in MeOH (40 mL) and the reaction mixture stirred at this temperature for 2 hrs. The reaction was quenched by the addition of 1N HCl to pH 5 and the solution concentrated in vacuo to give a yellow solid. The crude product was purified using column chromatography (silica gel) eluting with EtOAc: pet. ether (0:100 to 80:20) to provide the racemic product. This was further purified by SFC using an AD 250 mm×30 mm 5p column, eluting with 40% (0.1% NH$_3$ (ac) in IPA) at 50 mL/min to provide the title compound as a white solid, 42.5%. RT=4.816 mins [5:95 to 40:60 (0.05% DEA in IPA):CO$_2$ over 5 mins, at a flow rate of 2.5 mL/min]. LCMS m/z=301 [M+H]$^+$ Preparation 88 to 91

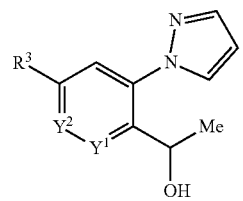

The alcohols in the table below were prepared by reducing the appropriate ethanone according to the method of preparation 87, and then were purified by SFC using the conditions described.

88

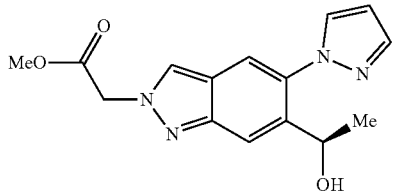

methyl {6-[(1R)-1-hydroxyethyl]-5-(1H-pyrazol-1-yl)-2H-indazol-2-yl}acetate, AS column eluting with 25% (0.1% NH₃ in EtOH), Peak 1, 302 mg, 32.3% as a white solid. ¹H NMR (400 MHz, DMSO-d₆) δ: 1.07 (d, 3H), 3.72 (s, 3H), 4.72-4.76 (m, 1H), 5.23 (d, 1H), 5.48 (s, 2H), 6.48-6.51 (m, 1H), 7.70 (s, 1H), 7.71-7.74 (m, 1H), 7.85 (d, 1H), 8.02 (d, 1H), 8.48 (d, 1H).

89

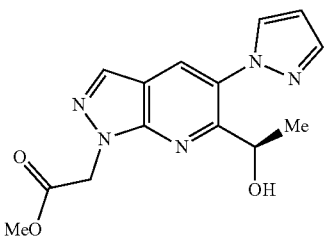 [SMILES: COC(=O)Cn1ncc2cc(-n3cccn3)c([C@@H](C)O)cc21]

methyl {6-[(1R)-1-hydroxyethyl]-5-(1H-pyrazol-1-yl)-1H-pyrazolo[3,4-b]pyridin-1-yl}acetate, Chiralpak IC eluting with 45% (0.1% NH₃ (aq) in MeOH), peak 2, 86 mg, 44% as colourless liquid. ¹H NMR (400 MHz, CDCl₃) δ: 1.35 (d, 3H), 3.80 (s, 3H), 4.64 (br s, 1H), 4.93-4.98 (m, 1H), 5.38 (d, 2H), 6.54 (dd, 1H), 7.70 (d, 1H), 7.80 (d, 1H), 8.04 (s, 1H), 8.15 (s, 1H).

90

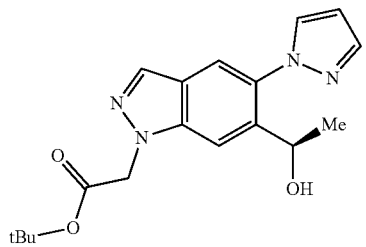

tert-butyl {6-[(1R)-1-hydroxyethyl]-5-(1H-pyrazol-1-yl)-1H-indazol-1-yl}acetate, ChiralTech IC column, eluting with 25% (0.2% NH₃ in MeOH), peak 2, 277 mg, 35.8%. ¹H NMR (400 MHz, CDCl₃) δ: 1.47 (d, 3H), 4.86 (s, 3H), 5.08-5.12 (m, 1H), 6.06 (s, 1H), 7.56 (s, 1H), 7.65 (s, 1H), 7.72 (s, 1H), 7.76 (s, 1H), 8.06 (s, 1H).

91 ᴬ

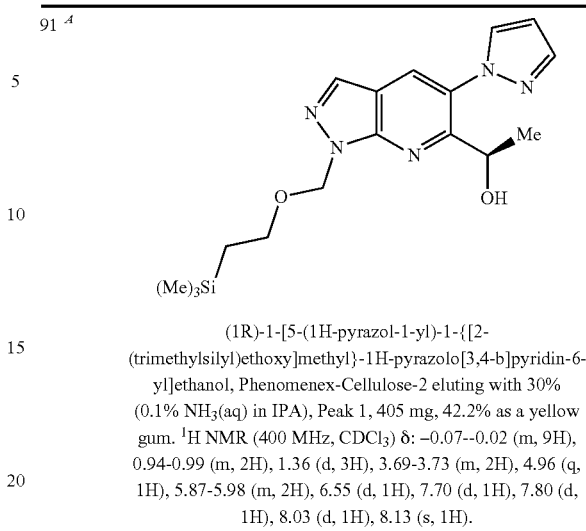

(1R)-1-[5-(1H-pyrazol-1-yl)-1-{[2-(trimethylsilyl)ethoxy]methyl}-1H-pyrazolo[3,4-b]pyridin-6-yl]ethanol, Phenomenex-Cellulose-2 eluting with 30% (0.1% NH₃(aq) in IPA), Peak 1, 405 mg, 42.2% as a yellow gum. ¹H NMR (400 MHz, CDCl₃) δ: −0.07--0.02 (m, 9H), 0.94-0.99 (m, 2H), 1.36 (d, 3H), 3.69-3.73 (m, 2H), 4.96 (q, 1H), 5.87-5.98 (m, 2H), 6.55 (d, 1H), 7.70 (d, 1H), 7.80 (d, 1H), 8.03 (d, 1H), 8.13 (s, 1H).

ᴬ 1 eq NaBH₄ used in the reaction

Preparation 92

1-[1-(2-{[tert-butyl(dimethyl)silyl]oxy}ethyl)-5-(1H-pyrazol-1-yl)-1H-indazol-6-yl]ethanol

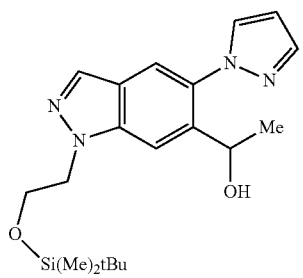

To a 0° C. solution of methyl [6-acetyl-5-(1H-pyrazol-1-yl)-1H-indazol-1-yl]acetate (Preparation 69, 5.10 g, 17.1 mmol) in MeOH (100 mL) was added NaBH₄ (1290 mg, 34.2 mmol) portion wise and the reaction mixture was stirred at rt for 5 hrs. The reaction was quenched by the addition of 3M HCl aq to pH5, the solution concentrated in vacuo and the residue partitioned between EtOAc/H₂O (100 mL/10 mL). The layers were separated and the aqueous extracted with EtOAc (3×10 mL). The combined organic layers were dried over Na₂SO₄ and evaporated under reduced pressure to give a yellow gum. The gum was dissolved in dry DCM (100 mL) the solution cooled to 0° C., then imidazole (2.33 g, 34.2 mmol) and TBDMSCl (2.58 g, 17.1 mmol) added and the reaction mixture stirred at rt for 16 hrs. The reaction mixture was diluted with H₂O (20 mL), extracted with DCM (2×30 mL), the combined organic layers dried over Na₂SO₄ and concentrated in vacuo. The residue was purified by column chromatography (silica gel) eluting with EtOAc:pet. ether (10:90 to 40:60) to afford the title compound, as a white solid, 5.20 g, 78.8%. ¹H NMR (400 MHz, CDCl₃) δ: −0.16 (d, 6H), 0.74 (s, 9H), 1.44 (d, 3H), 4.02-4.12 (m, 2H), 4.55 (t, 2H), 4.72 (br d, 1H), 4.99 (br s, 1H), 6.50 (t, 1H), 7.63 (s, 1H), 7.70 (s, 1H), 7.73 (d, 1H), 7.77 (d, 1H), 8.03 (s, 1H).

Preparation 93

[5-(1H-pyrazol-1-yl)-1-{[2-(trimethylsilyl)ethoxy]methyl}-1H-benzimidazol-6-yl]methanol

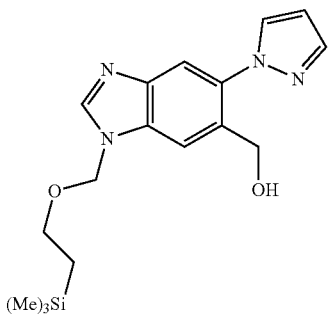

SEM-Cl (5.65 mL, 31.90 mmol) was added drop wise to a solution of 6-bromo-5-(1H-pyrazol-1-yl)-1H-benzimidazole (Preparation 83, 7.0 g, 26.61 mmol) and DIPEA (14.7 mL, 79.80 mmol) in THF (100 mL) at 0° C. and the reaction mixture stirred at 10° C. for 2 hrs. The mixture was diluted with EtOAc (250 mL) and washed with saturated aq NaHCO₃ soln (2×60 mL). The organic phase was dried over Na₂SO₄, filtered and concentrated in vacuo to give an oil. This was purified by flash chromatography on silica gel eluting with EtOAc:pet. ether (0:100 to 30:70) to afford a yellow oil, 8 g, 76.4% as a mixture of isomers. MeOH (100 mL) was added to a suspension of this yellow oil (8 g, 20.34 mmol), Et₃N (8.82 mL, 61.0 mmol) and Pd(dppf)Cl₂ (1.49 g, 2.03 mmol) in DMF (100 mL) and the reaction mixture stirred at 80° C. under a CO atmosphere (50 psi) for 16 hrs. The cooled reaction mixture was concentrated in vacuo and the crude product purified by flash chromatography on silica gel eluting with EtOAc:pet. ether (80:20) to give a yellow oil, 7.0 g, 92.4%. LiAlH₄ (1.1 g, 28.98 mmol) was added to a solution of this oil (7 g, 18.79 mmol) in THF (100 mL) at 0° C. and the reaction mixture allowed to warm to rt over 2 hrs. H₂O (1 mL) was added drop wise, the mixture dried over Na₂SO₄, and stirred at rt for 1 hr. The mixture was filtered and concentrated in vacuo. The crude product was purified by flash chromatography on silica gel eluting with EtOAc:MeOH (100:0 to 95:5) to provide the title compound as a yellow oil, 5.0 g, 77.2%. LCMS m/z=345 [M+H]⁺

Preparation 94

5-(1H-pyrazol-1-yl)-1-{[2-(trimethylsilyl)ethoxy]methyl}-1H-benzimidazole-6-carbaldehyde

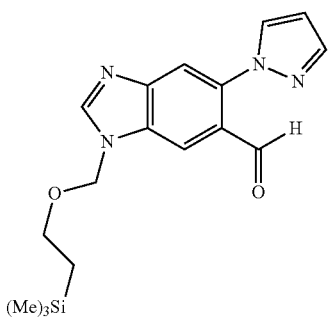

To a solution of [5-(1H-pyrazol-1-yl)-1-{[2-(trimethylsilyl)ethoxy]methyl}-1H-benzimidazol-6-yl]methanol (Preparation 93, 2.5 g, 7.26 mmol) in DCM (20 mL) was added manganese dioxide (IV) (6.31 g, 72.3 mmol), and the mixture stirred at 50° C. for 2 hrs. The insoluble material was filtered off through Celite® and the filtrate was evaporated under reduced pressure to afford the title compound as a light yellow solid, 1.5 g, 60.4%. LCMS m/z=343 [M+H]⁺

Preparation 95

1-[5-(1H-pyrazol-1-yl)-1-{[2-(trimethylsilyl)ethoxy]methyl}-1H-benzimidazol-6-yl]ethanol

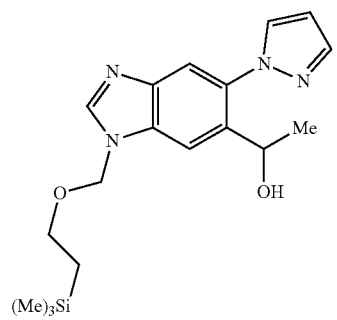

MeMgBr (2.92 mL, 8.76 mmol, 3M in Et₂O) was added drop wise to a solution of 5-(1H-pyrazol-1-yl)-1-{[2-(trimethylsilyl)ethoxy]methyl}-1H-benzimidazole-6-carbaldehyde (Preparation 94, 1.5 g, 4.38 mmol) in THF (20 mL) at −30° C. under Ar(g), and the reaction mixture stirred at rt for 1 hr. The mixture was cooled to 0° C., and quenched by the addition of saturated aq NH₄Cl solution (100 mL) and extracted with EtOAc. The organic layer was washed with saturated aq NaHCO₃ solution (2×100 mL), dried over Na₂SO₄, filtered and concentrated in vacuo. The crude product was purified by flash chromatography on silica gel eluting with EtOAc:pet. ether (90:10) to afford the title compound as a light yellow oil, 1.3 g, 82.9%. LCMS m/z=359 [M+H]⁺

Preparation 96

(1R)-1-{5-(1H-pyrazol-1-yl)-1-[(2S)-tetrahydro-2H-pyran-2-yl]-1H-pyrazolo[3,4-b]pyridin-6-yl}ethanol

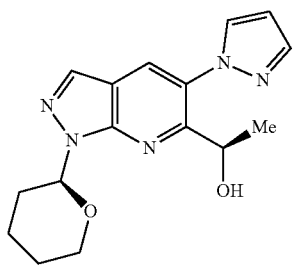 [SMILES: C[C@@H](O)c1nc2c(cnn2[C@@H]2CCCCO2)cc1-n1cccn1]

NaBH₄ (441.5 mg, 11.67 mmol) was added to a solution of 1-[5-(1H-pyrazol-1-yl)-1-(tetrahydro-2H-pyran-2-yl)-1H-pyrazolo[3,4-b]pyridin-6-yl]ethanone (Preparation 78, 2.39 g, 7.68 mmol) in MeOH (50 mL) at 0° C. and the reaction mixture stirred at rt for 4 hrs. The reaction was quenched by the addition of saturated aq NH₄Cl (25 mL) and the mixture concentrated in vacuo to a volume of ~30 mL. The suspension was extracted with EtOAc (3×20 mL), the combined organic layers were dried over MgSO₄, filtered, and evaporated under reduced pressure to give a pale yellow oil. The crude was purified by column chromatography on silica gel to give a pale yellow gum (2.10 g, 87.3% yield). This was further purified by SFC using a Chiralpak AY column, eluting with 30% (0.1% NH₃ (aq) in EtOH) to afford the title compound, peak 3, as a yellow solid, 620.0 mg, 24.8%. ¹H NMR (400 MHz, CDCl₃) δ: 1.32 (d, 3H), 1.64-1.70 (m, 1H), 1.77-1.91 (m, 2H), 2.0-2.07 (m, 1H), 2.14-2.24 (m, 1H), 2.63-2.74 (m, 1H), 3.83 (dt, 1H), 4.12-4.18 (m, 1H), 4.72 (br d, 1H), 5.00 (q, 1H), 6.18 (dd, 1H), 6.53-6.55 (m, 1H), 7.68 (d, 1H), 7.79 (d, 1H) 8.02 (s, 1H), 8.14 (s, 1H)

Preparation 97

2-fluoroquinolin-3-yl acetate

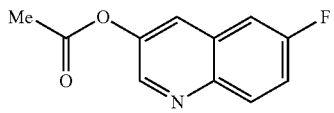 [SMILES: CC(=O)Oc1cnc2ccc(F)cc2c1]

Acetyl chloride (13.7 mL, 192 mmol) was added drop wise to a mixture of 6-fluoro-quinolin-3-ol (28.0 g, 172 mmol) and pyridine (77.7 mL, 961.1 mmol) in DCM (250 mL) while cooling with ice and the reaction mixture stirred at rt for 1 hr. The mixture was diluted with DCM (150 mL), washed with H₂O (100 mL), then 1N HCl (100 mL). The separated organic phase was dried (Na₂SO₄), filtered, and concentrated under reduced pressure to afford a residue. This crude product was purified by column chromatography (silica gel) eluting with EtOAc:pet. ether (0:100 to 100:0) to afford the title compound as an off-white solid, 21.3 g (61%). ¹H NMR (CDCl₃, 400 MHz) δ: 2.46 (s, 3H), 7.48-7.52 (m, 2H), 7.07 (s, 1H), 8.20-8.23 (m, 1H), 8.72 (s, 1H).

Preparation 98

6-bromoquinolin-3-yl acetate

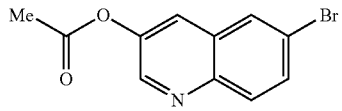

The title compound was obtained as a light yellow solid, 36 g, 56.1% from 6-bromo-quinolin-3-ol following the procedure described in preparation 97. ¹H NMR (400 MHz, CDCl₃) δ: 2.38-2.47 (m, 3H), 7.76-7.83 (m, 1H), 7.89 (d, 1H), 7.96-8.03 (m, 2H), 8.73 (d, 1H).

Preparation 99

5,8-difluoroquinolin-3-yl acetate

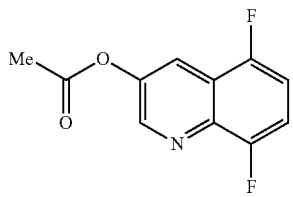 [SMILES: CC(=O)Oc1cnc2c(F)ccc(F)c2c1]

AcCl (2.80 g, 35.6 mmol) was added drop wise to an ice cold suspension of 5,8-difluoro-quinolin-3-ol (5.38 g, 29.70 mmol) and pyridine (4.7 g, 59.4 mmol) in dry DCM (50 mL) and after complete addition, the reaction mixture was stirred at rt for 2 hrs. The reaction mixture was poured into H₂O (50 mL) and extracted with DCM (2×50 mL). The combined organic layers were dried over Na₂SO₄ and evaporated under reduced pressure to give crude product. This was re-dissolved in EtOAc (100 mL), washed sequentially with citric acid aq (10 mL), H₂O (10 mL) and brine (10 mL) then dried over Na₂SO₄, filtered and evaporated under reduced pressure to provide the title compound, 6.63 g as a light yellow solid. ¹H NMR (400 MHz, CDCl₃) δ: 2.45 (s, 3H), 7.21-7.25 (m, 1H), 7.32-7.36 (m, 1H), 8.21 (d, 1H), 8.82 (d, 1H).

Preparation 100

6-bromo-1-oxidoquinolin-3-yl Acetate

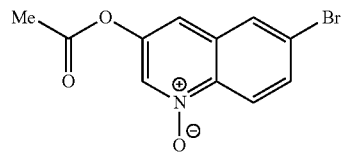

m-CPBA (18.7 g, 108 mmol) was added portion wise to an ice-cooled solution of 6-bromoquinolin-3-yl acetate (Preparation 98, 16 g, 60.13 mmol) in DCM (300 mL), and the reaction mixture stirred at rt for 15 hrs. The resulting suspension was filtered and the filtrate diluted with DCM (500 mL), washed with saturated Na₂S₂O₃ solution (800 mL), saturated Na₂CO₃ solution (400 mL) and brine (100 mL), then dried over anhydrous Na₂SO₄, filtered and evaporated under reduced pressure, to provide the title compound as a light yellow solid, 16 g, 94%. ¹H NMR (400 MHz, CDCl₃) δ: 2.38 (s, 3H), 7.49 (d, 1H), 7.79 (dd, 1H), 8.00 (d, 1H), 8.39 (d, 1H), 8.56 (d, 1H)

Preparation 101

6-fluoro-1-oxidoquinolin-3-yl Acetate

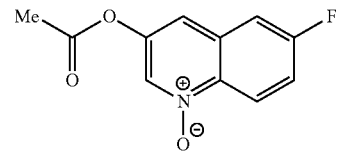 [SMILES: CC(=O)Oc1cc2cc(F)ccc2[n+]([O-])c1]

To a solution of 6-fluoroquinolin-3-yl acetate (Preparation 97, 41.0 g, 200 mmol) in DCM (400 mL) was added m-CPBA (48.7 g, 240 mmol) in portions at 0° C. with stirring and after complete addition, the solution was stirred at rt for 16 hrs. The suspension was filtered and the filtrate evaporated under reduced pressure. The crude product was purified by column chromatography eluting with EtOAc:pet. ether:MeOH:DCM (70:30:0:0 to 0:0:10:90) to afford the title compound as a yellow solid, 41 g, 90%. LCMS m/z=180 [M+H]$^+$ Preparation 102

5,8-difluoro-1-oxidoquinolin-3-yl acetate

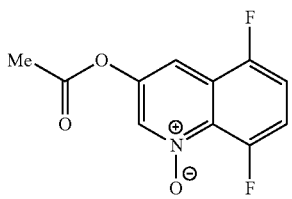 [SMILES: CC(=O)Oc1cc2c(F)ccc(F)c2[n+]([O-])c1]

To a solution of 5,8-difluoroquinolin-3-yl acetate (Preparation 99, 2.5 g, 11.2 mmol) in dry DCM (100 mL) was added m-CPBA (4.83 g, 27.99 mmol) in portions at 0° C. with stirring and after complete addition, the solution was stirred at rt for 60 hrs. The light yellow solution was poured into aq $Na_2CO_3$ (1.5 g in 50 mL $H_2O$) and extracted with DCM (2×50 mL). The combined organic layers were washed with saturated $Na_2S_2O_3$ aq (2×10 mL), brine (10 mL), dried over $Na_2SO_4$ and the solvent evaporated to give crude product (3 g) as brown solid. This was purified by column chromatography (silica gel), eluting with EtOAc:pet. ether (0:100 to 100:0) to provide the title compound, 600 mg as a light yellow solid. LCMS m/z=240 [M+H]$^+$ Preparation 103

6-bromoquinolin-3-ol 1-oxide

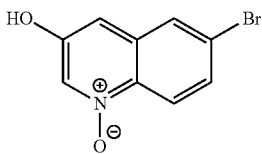 [SMILES: [O-][n+]1cc(O)cc2cc(Br)ccc21]

$K_2CO_3$ (4.09 mg, 296 mmol) was added in one portion to a suspension of 6-bromo-1-oxidoquinolin-3-yl acetate (Preparation 100, 25.17 g, 89.23 mmol) in anhydrous MeOH (472 mL) and the resulting suspension stirred at 80° C. for 16 hrs. The cooled suspension was evaporated under reduced pressure and the residue diluted with $H_2O$ (400 mL), and then neutralized with 1N HCl (~350 mL). The resulting precipitate was collected by filtration, rinsed with $H_2O$ (50 mL) and dried in vacuo to afford the title compound as a light yellow solid, 86%. $^1$H NMR (400 MHz, DMSO-$d_6$) 7.15 (d, 1H), 7.60 (dd, 1H), 8.17 (d, 1H), 8.24-8.31 (m, 2H).

Preparation 104

5,8-Difluoroquinolin-3-ol 1-oxide

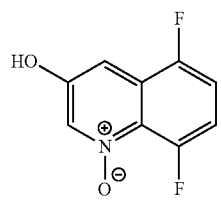

The title compound was obtained as a beige solid (450 mg) in 91% yield from 5,8-difluoro-1-oxidoquinolin-3-yl acetate (Preparation 102) by following the procedure described in preparation 103. LCMS m/z=198 [M+H]$^+$ Preparation 105 tert-butyl (6-fluoro-3-hydroxyquinolin-2-yl)carbamate

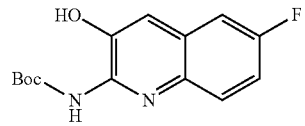 [SMILES: CC(C)(C)OC(=O)Nc1nc2ccc(F)cc2cc1O]

To an ice-cooled solution of 6-fluoro-1-oxidoquinolin-3-yl acetate (Preparation 101, 35.0 g, 158 mmol), tert-butyl N-(diethoxyphosphoryl)carbamate (52.1 g, 206 mmol) and DIPEA (61.6 g, 475 mmol) in DCM (600 mL) was added a solution of TsCl (45.3 g, 237 mmol) in DCM (200 mL) over 20 mins and the reaction mixture stirred at this temperature for 1.5 hrs. The reaction mixture was stirred for a further 17 hrs at rt, diluted with DCM (700 mL) and washed with saturated aq citric acid (500 mL). The organic phase was concentrated in vacuo and purified by column chromatography (silica gel) eluting with EtOAc:pet. ether (5:95 to 80:20) to afford a yellow gum, 72 g, 99%. $K_2CO_3$ (43.6 g, 316 mmol) was added to a mixture of 2-[(tert-butoxycarbonyl)(diethoxyphosphoryl)amino]-6-fluoroquinolin-3-yl acetate (Preparation 105, 72.0 g, 160 mmol) in MeOH (720 mL) and the reaction mixture stirred at rt for 16 hrs. The yellow suspension was concentrated in vacuo, diluted with $H_2O$ (500 mL), then neutralized with 1N HCl aq to pH 7 at 0° C. The resulting precipitate was collected by filtration and the residue triturated with MTBE (200 mL) and stirred for 10 mins. The suspension was filtered and washed with MTBE (2×50 mL). The solid was dried in vacuo to provide the title compound as an off-white solid, 30 g, 68%. LCMS m/z=279 [M+H]$^+$

Preparation 106

2-fluoro-3[(4-methoxybenzyl)oxy]quinolin-2-amine

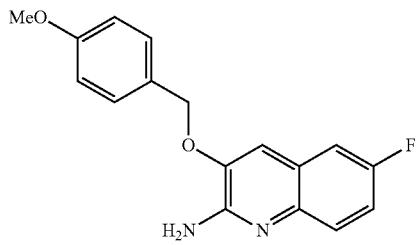 [SMILES: COc1ccc(COc2cc3cc(F)ccc3nc2N)cc1]

To a solution of 2-amino-5-fluorobenzaldehyde (2 g, 14.38 mmol) and 2-[(4-methoxybenzyl)oxy]acetonitrile (Preparation 231, 2.8 g, 15.8 mmol) in DMSO (20 mL) was slowly added t-BuOK (2.42 g, 21.6 mmol) and the reaction mixture stirred at rt for 3 hrs. The reaction was repeated in 18 batches. The combined reaction mixtures were diluted with H$_2$O (800 mL) and extracted with EtOAc (2×800 mL). The combined organic layer was washed with H$_2$O (2×1.5 L) and brine (1.5 L), then dried (Na$_2$SO$_4$), filtered, and concentrated in vacuo. The residue was recrystallized from EtOAc:DCM:pet. ether (2:1:10, 200 mL) to afford the title compound as a yellow solid, 24 g, 29.5%. The filtrate was concentrated in vacuo and the residue purified by column chromatography on silica gel, eluting with EtOAc:DCM 0:100 to 20:80) and then recrystallized from (EtOAc:DCM: pet. ether=2:1:10, 100 mL) to afford additional product, 6.2 g, 7.6%. LCMS m/z=299 [M+H]$^+$

Preparation 107

5-bromo-3-[(4-methoxybenzyl)oxy]quinolin-2-amine

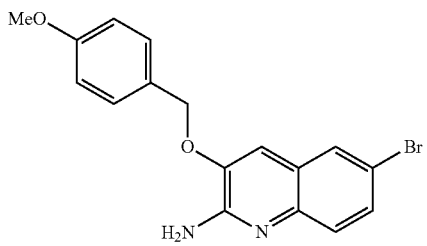 [SMILES: COc1ccc(COc2cc3cc(Br)ccc3nc2N)cc1]

The title compound was obtained as a yellow solid in 42% yield (49 g), from 2-amino-5-bromobenzaldehyde and 2-[(4-methoxybenzyl)oxy]acetonitrile (Preparation 231), by following the procedure described in Preparation 106. LCMS m/z=359 [M+H]$^+$

Preparation 108

7-chloro-6-fluoro-3-[(4-methoxybenzyl)oxy]quinolin-2-amine

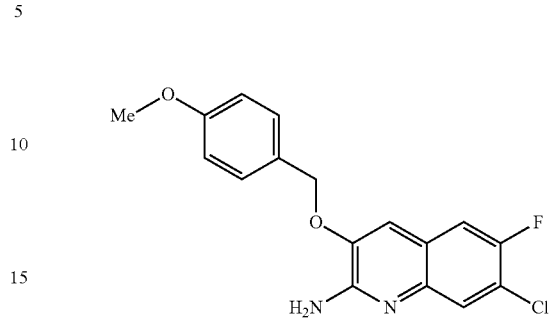

t-BuOK (4.85 g, 43.2 mmol) was added to a solution of 2-amino-4-chloro-5-fluorobenzaldehyde (5 g, 28.81 mmol) and 2-[(4-methoxybenzyl)oxy]acetonitrile (Preparation 231, 6.13 g, 34.6 mmol) in DMSO (50 mL) and the reaction mixture stirred at 50° C. for 4 hrs. The mixture was diluted with EtOAC (200 mL) and washed with brine (3×100 mL), dried over Na$_2$SO$_4$, filtered and the filtrate was evaporated under reduced pressure. The residue was treated with EtOAc (10 mL), the resulting solid filtered off and dried to afford the title compound as a yellow solid, 1.98 g, 20.7%.

LCMS m/z=333 [M+H]$^+$

Preparations 109 to 112

The compounds in the table below were prepared from 2-[(4-methoxybenzyl)oxy]acetonitrile (Preparation 231) and the appropriate benzaldehyde by following the procedure described in Preparation 108.

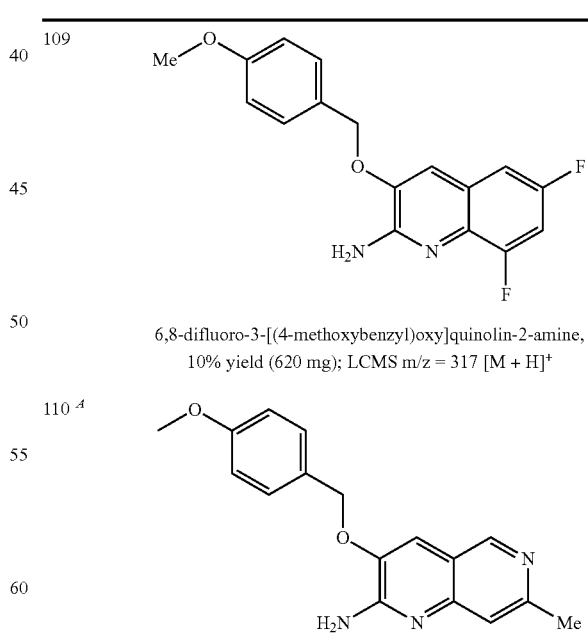

109

6,8-difluoro-3-[(4-methoxybenzyl)oxy]quinolin-2-amine, 10% yield (620 mg); LCMS m/z = 317 [M + H]$^+$

110 $^A$

3-[(4-methoxybenzyl)oxy]-7-methyl-1,6-naphthyridin-2-amine, 100 mg, 46%, as a yellow solid.
LCMS m/z = 296.1 [M + H]$^+$.

111 [B]

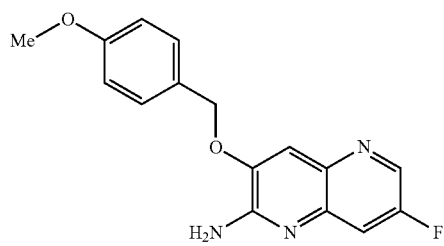

7-fluoro-3-[(4-methoxybenzyl)oxy]-1,5-naphthyridin-
2-amine, 155 mg, 14.5% as a light brown solid.
LCMS m/z = 300 [M + H]$^+$

112 [B,C]

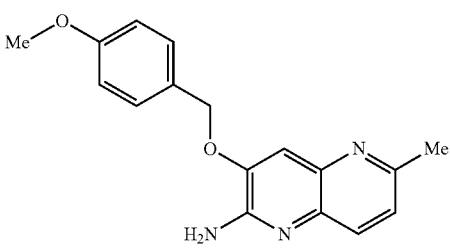

3-[(4-methoxybenzyl)oxy]-6-methyl-1,5-naphthyridin-
2-amine, 1.64 g, 43.6% as a yellow solid.
LCMS m/z = 296 [M + H]$^+$

[A] 1 eq of tBuOK was used in the reaction
[B] purified by column chromatography eluting with EtOAc/pet. ether (20:80 to 90:10)
[C] 1.2 eq tBuOK was used in the reaction Preparation 113

6-bromo-7-fluoro-3-[(4-methoxybenzyl)oxy]quino-
lin-2-amine

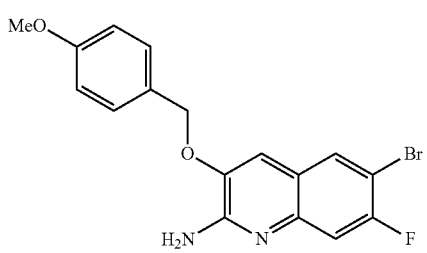 [SMILES: COc1ccc(COc2cc3cc(Br)c(F)cc3nc2N)cc1]

A mixture of 2-amino-5-bromo-4-fluorobenzaldehyde (5.0 g, 22.93 mmol), 2-[(4-methoxybenzyl)oxy]acetonitrile (Preparation 231, 4.88 g, 27.5 mmol) and tBuOK (27.5 mL, 1M, 27.5 mmol) in dry DMSO (40 mL) was stirred at 50° C. for 1.5 hrs. The mixture was diluted with brine (100 mL) and extracted with EtOAc (3×200 mL), the combined organic extracts dried over Na$_2$SO$_4$ and concentrated in vacuo. The residue was purified by silica gel chromatography eluting with pet. ether:EtOAc (100:0 to 50:50) to afford the title compound as a yellow solid, 1.4 g, 16%. LCMS m/z=377 [M+H]$^+$ Preparation 114

6-bromo-8-fluoro-3-[(4-methoxybenzyl)oxy]quino-
lin-2-amine

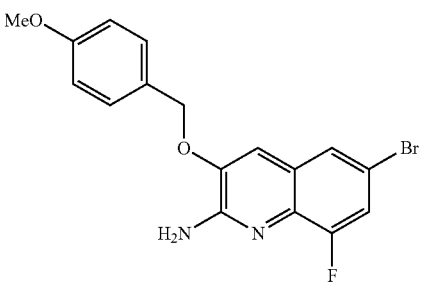 [SMILES: COc1ccc(COc2cc3cc(Br)cc(F)c3nc2N)cc1]

The title compound was obtained as a yellow solid in (4.1 g, 18%) from 2-amino-5-bromo-3-fluorobenzaldehyde and 2-[(4-methoxybenzyl)oxy]acetonitrile (Preparation 231) by following the procedure described in Preparation 113. LCMS m/z=377 [M+H]$^+$ Preparation 115

3-[(4-methoxybenzyl)oxy]-1,5-naphthyridin-2-amine

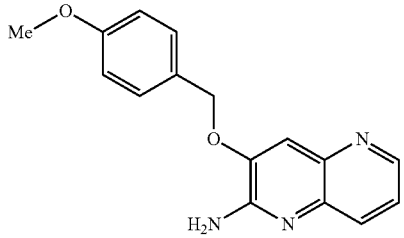 [SMILES: COc1ccc(COc2cc3ncccc3nc2N)cc1]

The title compound was obtained as a black oil in 52% yield, 3.6 g, from 3-aminopicolinaldehyde and 2-[(4-methoxybenzyl)oxy]acetonitrile (Preparation 231) by following the procedure described in Preparation 113. LCMS m/z=282 [M+H]$^+$ Preparation 116 methyl 2-amino-3-[(4-methoxybenzyl)oxy]quino-
line-6-carboxylate

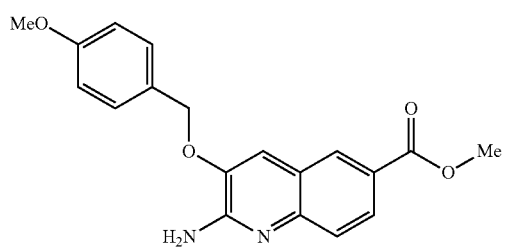 [SMILES: COC(=O)c1ccc2nc(N)c(OCc3ccc(OC)cc3)cc2c1]

To a solution of 6-bromo-3-[(4-methoxybenzyl)oxy]quinolin-2-amine (Preparation 107, 24.5 g, 68.2 mmol), Et$_3$N (47.5 mL, 341 mmol) and Pd(dppf)Cl$_2$ (4.99 g, 6.82 mmol) in DMF (250 mL) was added MeOH (700 mL) and the reaction mixture stirred at 80° C. under an atmosphere of CO (50 psi) for 16 hrs. The cooled reaction mixture was filtered and the filtrate concentrated in vacuo. The residue was suspended in H$_2$O (500 mL), the solids filtered off, washing through with H$_2$O (2×50 mL) and dried under vacuum to provide the title compound as a brown solid, 91%. LCMS m/z=339 [M+H]$^+$ Preparation 117 methyl 2-amino-7-fluoro-3-[(4-methoxybenzyl)oxy]quinoline-6-carboxylate

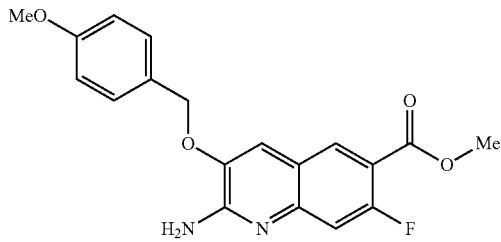 [SMILES: COC(=O)c1cc2cc(OCc3ccc(OC)cc3)c(N)nc2cc1F]

MeOH (10 mL) was added to a mixture of 6-bromo-7-fluoro-3-[(4-methoxybenzyl)oxy]quinolin-2-amine (Preparation 113, 1.47 g, 4.00 mmol), Et$_3$N (789 mg, 7.79 mmol), Pd(OAc)$_2$ (87.5 mg, 0.390 mmol) and DPPP (161 mg, 0.39 mmol) in DMF (10 mL) and the reaction mixture stirred at 80° C. under a CO atmosphere (50 psi) for 16 hrs. The cooled reaction mixture was filtered and the filtrate evaporated under reduced pressure to afford the title compound as a brown solid, 900 mg, 65%. LCMS m/z=357 [M+H]$^+$ Preparation 118 methyl 2-amino-8-fluoro-3-[(4-methoxybenzyl)oxy]quinoline-6-carboxylate

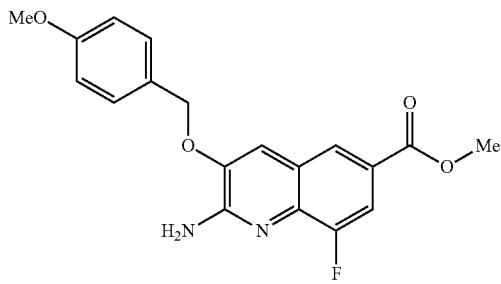 [SMILES: COC(=O)c1cc(F)c2nc(N)c(OCc3ccc(OC)cc3)cc2c1]

MeOH (50 mL) was added to a mixture of 6-bromo-8-fluoro-3-[(4-methoxybenzyl)oxy]quinolin-2-amine (Preparation 114, 1500 mg, 3.98 mmol), Et$_3$N (805 mg, 7.95 mmol), Pd(OAc)$_2$ (89.3 mg, 0.40 mmol) and DPPP (164 mg, 0.40 mmol) in DMF (50 mL) and the reaction mixture stirred at 80° C. under a CO atmosphere (50 psi) for 16 hrs. The cooled mixture was concentrated in vacuo, the residue suspended in EtOAc (20 mL) and the resulting solid filtered off. The solid was suspended in EtOAc (20 mL) again, the suspension filtered and the solid dried in vacuo to provide the title compound as a red solid, 900 mg, 63.5%. LCMS m/z=357 [M+H]$^+$ Preparation 119

2-{6-fluoro-3-[(4-methoxybenzyl)oxy]quinolin-2-yl}-1H-isoindole-1,3(2H)-dione

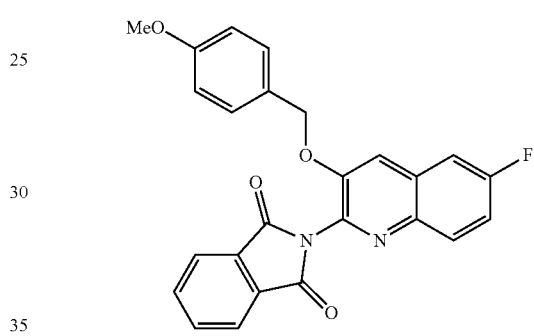

To a mixture of 6-fluoro-3-[(4-methoxybenzyl)oxy]quinolin-2-amine (Preparation 106, 2.4 g, 80.45 mmol), Et$_3$N (32.60 g, 322 mmol) and DMAP (9.83 g, 80.5 mmol) in dry dioxane (600 mL) at 20° C. was added drop wise, phthaloyl dichloride (24.5 g, 121 mmol) and the reaction mixture stirred at 90° C. for 15 hrs. The cooled reaction mixture was concentrated in vacuo and the residue partitioned between H$_2$O (1000 mL) and DCM (2×1100 mL). The combined organic layers were washed with H$_2$O (2×1000 mL), dried (Na$_2$SO$_4$), filtered, and concentrated in vacuo to provide a brown solid. This was suspended in DCM (~200 mL), stirred for 30 mins then filtered, washed with H$_2$O (100 mL) and dried in vacuo to provide the title compound as a pale yellow solid, 11 g, 32%. The filtrate was concentrated in vacuo and purified by column chromatography eluting with (EtOAc:DCM:THF 40:40:1): pet. ether (0:100 to 30:70) to give a brown oil, which was recrystallized from pet. ether:DCM (10:1) to give additional product (6.2 g, 18%) as a yellow solid.

LCMS m/z=429 [M+H]$^+$

Preparations 120 to 125

The phthalimides in the table below were prepared from the appropriate amine and phthaloyl chloride by following the procedure described in preparation 119.

143

120 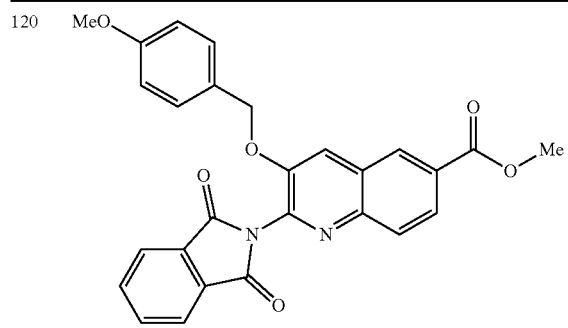

methyl 2-(1,3-dioxo-1,3-dihydro-2H-isoindol-2-yl)-3-[(4-methoxybenzyl)oxy]quinoline-6-carboxylate, brown solid, 60.5%. $^1$H NMR (400 MHz, DMSO-$d_6$) δ: 3.70 (s, 3H), 3.96 (s, 3H), 5.25 (s, 2H), 6.86 (d, 2H), 7.30 (d, 2H) , 7.95-8.01 (m, 2H), 8.05-8.15 (m, 4H), 8.43 (s, 1H), 8.72 (s, 1H)

121 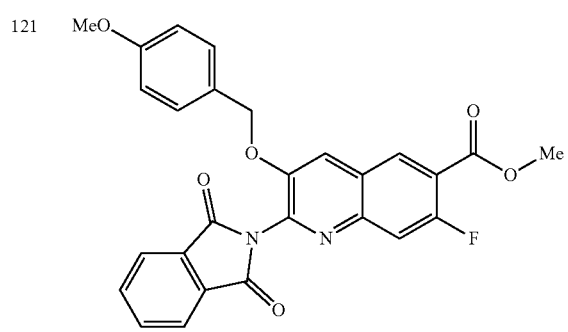

methyl 2-(1,3-dioxo-1,3-dihydro-2H-isoindol-2-yl)-7-fluoro-3-[(4-methoxybenzyl)oxy]quinoline-6-carboxylate, (700 mg, 62.5%) as a yellow solid. LCMS m/z = 487 [M + H]$^+$ 122 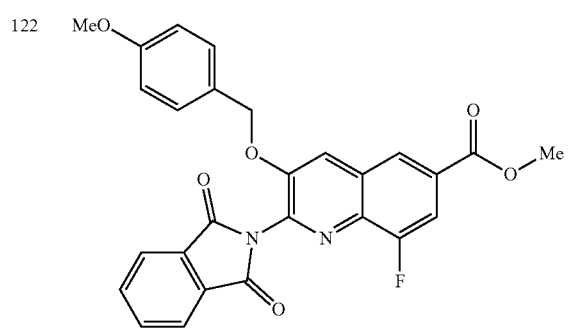

methyl 2-(1,3-dioxo-1,3-dihydro-2H-isoindol-2-yl)-8-fluoro-3-[(4-methoxybenzyl)oxy]quinoline-6-carboxylate, 3.0 g, 44% as a yellow solid. LCMS m/z = 487 [M + H]$^+$ 144
-continued 123 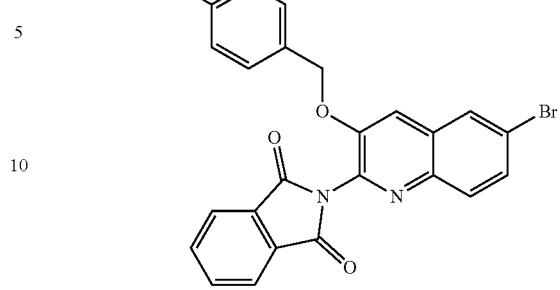

2-{6-bromo-3-[(4-methoxybenzyl)oxy]quinolin-2-yl}-1H-isoindole-1,3(2H)-dione, 4.7 g, 57.5% as a yellow solid. $^1$H NMR (400 MHz, DMSO-$d_6$) δ: 3.70 (s, 3H), 5.22 (s, 2H), 6.85 (d, 2H), 7.28 (d, 2H), 7.81 (dd, 1H), 7.91-8.00 (m, 3H), 8.01-8.09 (m, 2H), 8.16 (s, 1H), 8.28 (d, 1H)

124 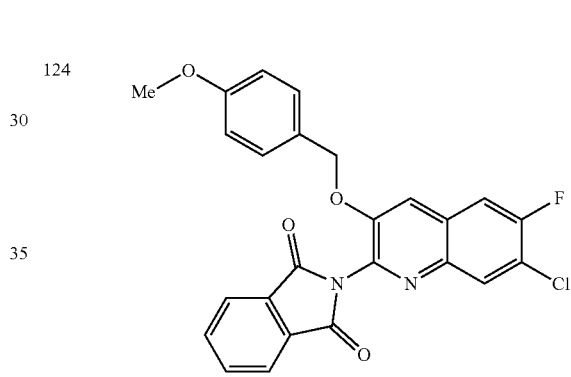

2-{7-chloro-6-fluoro-3-[(4-methoxybenzyl)oxy]quinolin-2-yl}-1H-isoindole-1,3(2H)-dione, 960 mg, 86.3% as a yellow solid. LCMS m/z = 485 [M + Na]$^+$ 125 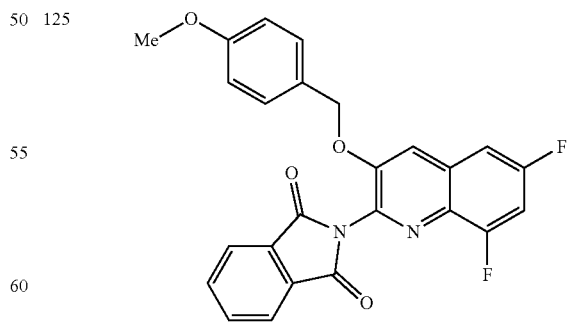

2-{6,8-difluoro-3-[(4-methoxybenzyl)oxy]quinolin-2-yl}-1H-isoindole-1,3(2H)-dione, 2.4 g, 74% as a yellow solid. LCMS m/z = 469 [M + Na]$^+$

Preparation 126

2-(1,3-dioxo-1,3-dihydro-2H-isoindol-2-yl)-3-[(4-methoxybenzyl)oxy]quinoline-6-carbonitrile

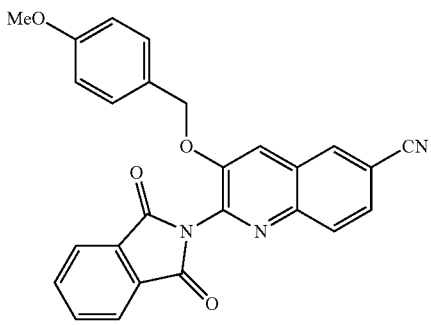 [SMILES: COc1ccc(COc2cc3cc(C#N)ccc3nc2N2C(=O)c3ccccc3C2=O)cc1]

Pd$_2$(dba)$_3$ (880 mg, 0.96 mmol) and BINAP (1.2 g, 1.92 mmol) was added to a suspension of 2-{6-bromo-3-[(4-methoxybenzyl)oxy]quinolin-2-yl}-1H-isoindole-1,3(2H)-dione (Preparation 123, 4.7 g, 9.61 mmol) and Zn(CN)$_2$ (2.4 g, 20.44 mmol) in DMF (60 mL), the mixture degassed with N2, and the reaction mixture stirred at 100° C. for 18 hrs. The cooled suspension was diluted with DCM (100 mL), washed with H$_2$O (2×100 mL), dried over Na$_2$SO$_4$, filtered and dried in vacuo. The residue was purified by column chromatography (silica gel) eluting with EtOAc:DCM (10:90 to 100:0) to afford the title compound as a yellow solid, 1.2 g, 28.7%. $^1$H NMR (400 MHz, DMSO-d$_6$) δ: 3.70 (s, 3H), 5.26 (s, 2H), 6.86 (d, 2H), 7.29 (d, 2H), 7.95-8.10 (m, 5H), 8.17 (d, 1H), 8.29 (s, 1H), 8.64 (d, 1H)

Preparation 127

2-(6-fluoro-3-hydroxyquinolin-2-yl)-1H-isoindole-1,3(2H)-dione

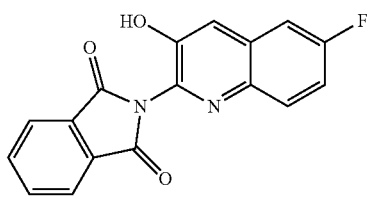 [SMILES: O=C1c2ccccc2C(=O)N1c1nc2ccc(F)cc2cc1O]

To a solution of 2-{6-fluoro-3-[(4-methoxybenzyl)oxy]quinolin-2-yl}-1H-isoindole-1,3(2H)-dione (Preparation 119, 17.20 g, 40.15 mmol) in DCM (18 mL) was added TFA (18 mL) at 15° C. and the reaction mixture stirred for 17 hrs. H$_2$O (50 mL) was added and the mixture stirred for 15 mins. The resulting precipitate was filtered off, washed with H$_2$O (20 mL) and DCM (2×20 mL) then dried under vacuum to afford the title compound as a pale yellow solid, 11.3 g, 91%. LCMS m/z=309 [M+H]$^+$

Preparations 128 to 133

The compounds in the table below were prepared from the appropriate quinoline by following the procedure described in preparation 127.

| | |
|---|---|
| 128 | 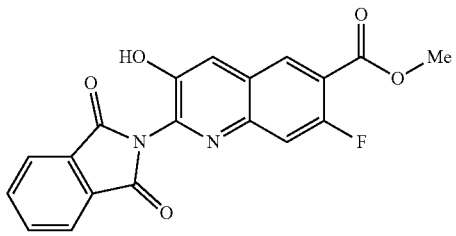 methyl 2-(1,3-dioxo-1,3-dihydro-2H-isoindol-2-yl)-3-hydroxyquinoline-6-carboxylate, yellow solid in 59.9% yield (13.8 g). LCMS m/z = 349 [M + H]$^+$ |
| 129 | 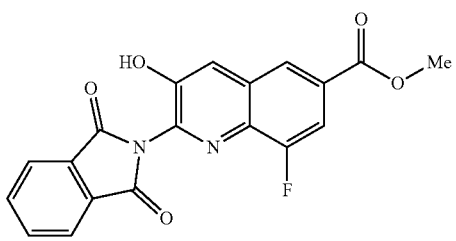 methyl 2-(1,3-dioxo-1,3-dihydro-2H-isoindol-2-yl)-3-hydroxy-7-fluoroquinoline-6-carboxylate, 430 mg, 81.6% as a yellow solid. LCMS m/z = 367 [M + H]$^+$ |
| 130 | methyl 2-(1,3-dioxo-1,3-dihydro-2H-isoindol-2-yl)-3-hydroxy-8-fluoroquinoline-6-carboxylate, 2.01 g, 88% as a white solid. $^1$H NMR (400 MHz, CDCl$_3$) δ: 4.03 (s, 3H), 6.92-6.94 (m, 1H), 7.86-7.90 (m, 4H), 8.04 (d, 1H), 8.25 (d, 1H). |
| 131 | 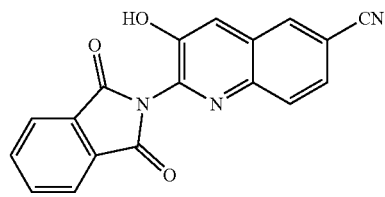 2-(1,3-dioxo-1,3-dihydro-2H-isoindol-2-yl)-3-hydroxyquinoline-6-carbonitrile, 670 mg, 77.1%, as a light yellow solid. LCMS m/z = 316 [M + H]$^+$ |
| 132 $^A$ | 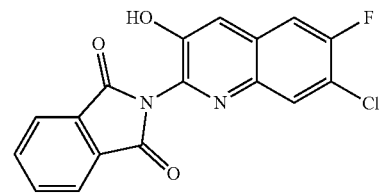 2-(7-chloro-6-fluoro-3-hydroxyquinolin-2-yl)-1H-isoindole-1,3(2H)-dione, 612 mg, yield: 85.9% as a pale yellow solid. LCMS m/z = 343 [M + H]$^+$ |

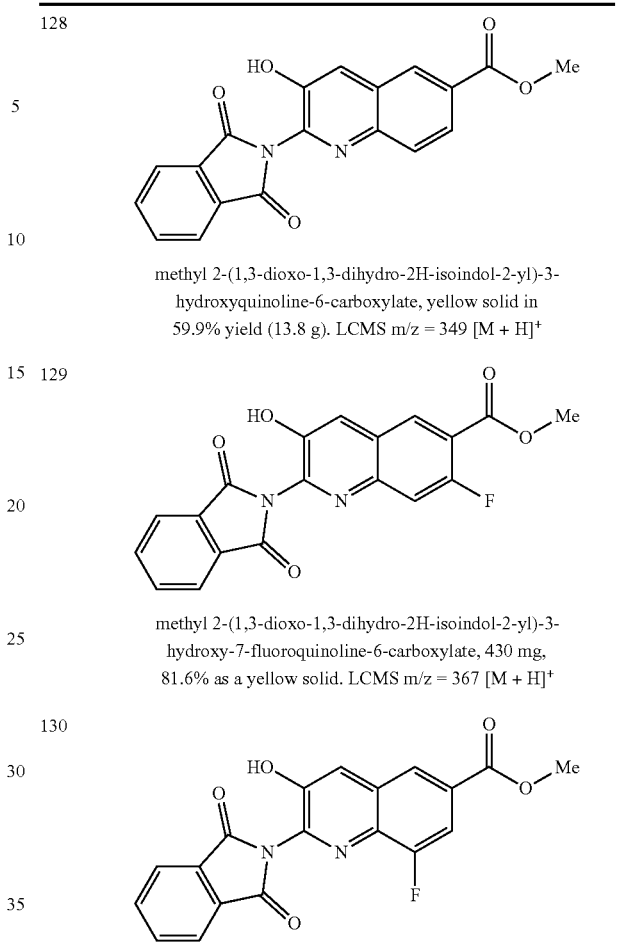

133

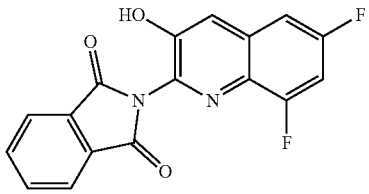

2-(6,8-difluoro-3-hydroxyquinolin-2-yl)-1H-isoindole-
1,3(2H)-dione, 1440 mg, 82% as a pale yellow solid.
¹H NMR (400 MHz, DMSO-d₆) δ: 7.52-7.62 (m, 1H),
7.64-7.70 (m, 1H), 7.87 (d, 1H), 7.93-8.09 (m, 4H),
11.35 (s, 1H).

*A* DCM/NaHCO₃ work-up. Recrystallised from DCM/pet. ether

Preparation 134

2-amino-6-fluoroquinolin-3-ol

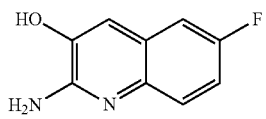

Pd(OH)₂ (47.1 mg, 0.067 mmol) was added to a solution of 6-fluoro-3-[(4-methoxybenzyl)oxy]quinolin-2-amine (Preparation 106, 200 mg, 0.67 mmol) in MeOH (10 mL) and the reaction mixture stirred at rt under an atmosphere of H₂ for 18 hrs. The reaction mixture was filtered and the filtrate was concentrated in vacuo to afford the title compound as a brown solid. ¹H NMR (400 MHz, DMSO-d₆) δ: 6.32 (br s, 2H), 7.12-7.24 (m, 2H), 7.55 (dd, 1H), 7.70-7.80 (m, 1H).

Preparation 135

2-amino-6-bromoquinolin-3-ol

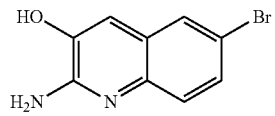

A solution of 6-bromo-3-[(4-methoxybenzyl)oxy]quinolin-2-amine (Preparation 107, 97 mg, 0.27 mmol) in DCM (2 mL) and TFA (2 mL) was stirred at rt for 2 hrs. The reaction mixture was evaporated under reduced pressure and the residue suspended in EtOAc (5 mL) and neutralised using aq NaHCO₃. The layers were separated, the organic phase dried and evaporated under reduced pressure to afford the title compound as a yellow solid, 583 mg, 88% yield. LCMS m/z=240 [M+H]⁺

Preparation 136

6-bromo-2-(tert-butylamino)quinolin-3-ol

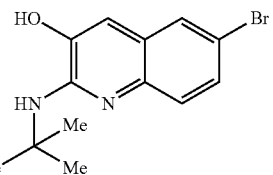

To a solution of 6-bromo-1-oxidoquinolin-3-yl acetate (Preparation 100, 2.53 g, 8.94 mmol) and t-butylamine (0.92 mL, 8.74 mmol) in DCM (100 mL) at 0° C., was added Ts₂O (8.75 g, 26.8 mmol) portion wise so as to maintain the reaction mixture temperature <5° C. and the reaction mixture stirred for 20 mins. Additional t-butylamine (1.0 equiv) and Ts₂O (0.5 equiv) were added and the reaction mixture stirred for 30 mins. The reaction mixture was washed with 1N NaOH (10 mL) and H₂O (10 mL), then dried over MgSO₄, filtered, and concentrated in vacuo. The product was dissolved in MeOH (60 mL), K₂CO₃ (2.79 g, 17.9 mmol) added and the reaction mixture stirred at rt for 18 hrs. The mixture was concentrated in vacuo, the residue suspended in DCM and filtered. The filtrate was poured into cold H₂O, saturated NH₄Cl was added and the mixture extracted with DCM (4×50 mL). The combined organic extracts were dried over Na₂SO₄, filtered and concentrated in vacuo. The crude product was purified on ISCO® eluting with 9:1 DCM/MeOH to afford a yellow foam, 1.0 g, 37.9%. ¹H NMR (400 MHz, CDCl₃) δ: 1.53-1.65 (m, 9H), 6.93 (s, 1H), 7.34-7.41 (m, 1H), 7.46 (d, 1H), 7.51 (d, 1H)

Preparation 137

2-amino-7-fluoro-1,5-naphthyridin-3-ol
Trifluoroacetate

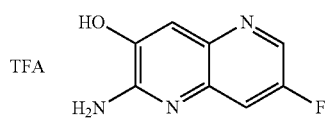

A solution of 7-fluoro-3-[(4-methoxybenzyl)oxy]-1,5-naphthyridin-2-amine (Preparation 111, 155 mg, 0.518 mmol) in TFA (4 mL) was stirred at rt for 16 hrs. The brown solution was concentrated in vacuo, azeotroping with EtOAc and the product dried in vacuo to afford the title compound as a brown solid, 92.8 mg, 100%. LCMS m/z=180 [M+H]⁺

Preparation 138

2-amino-7-methyl-1,6-naphthyridin-3-ol
Trifluoroacetate

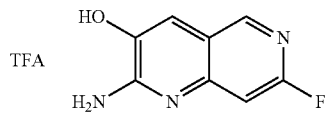 [SMILES: Nc1nc2cc(F)ncc2cc1O]

The title compound was obtained in 88% yield (990 mg) from 3-[(4-methoxybenzyl)oxy]-7-methyl-1,6-naphthyridin-2-amine (Preparation 110) by following the procedure described in Preparation 137. $^1$H NMR (400 MHz, DMSO-$d_6$) δ: 2.60 (s, 3H), 7.32 (s, 1H), 7.45 (s, 1H), 7.75 (br s, 1H), 8.36 (s, 1H), 8.99 (s, 1H), 11.61 (br s, 1H).

Preparation 139

2-amino-1,5-naphthyridin-3-ol Trifluoroacetate

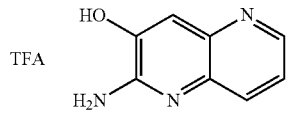

The title compound was obtained in 92% yield (3.5 g) from 3-[(4-methoxybenzyl)oxy]-1,5-naphthyridin-2-amine (Preparation 115) by following the procedure described in Preparation 137. LCMS m/z=276 [M+H]$^+$ Preparation 140

2-amino-7-chloro-6-fluoroquinolin-3-ol

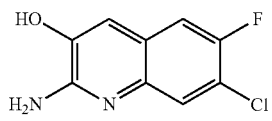

A solution of 7-chloro-6-fluoro-3-[(4-methoxybenzyl)oxy]quinolin-2-amine (Preparation 108, 1 g, 3.01 mmol) in DCM (4 mL) and TFA (4 mL) was stirred at rt for 1 hr. The mixture was concentrated in vacuo, the residue washed with aq NaHCO$_3$ solution, and the resulting solid, filtered off and dried to afford the title compound as a gray solid, 600 mg, 94%. LCMS m/z=213 [M+H]$^+$ Preparation 141 tert-butyl (3-hydroxy-7-methyl-1,6-naphthyridin-2-yl)carbamate

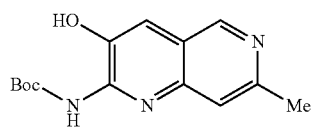 [SMILES: Cc1cc2nc(NC(=O)OC(C)(C)C)c(O)cc2cn1]

To a solution of 2-amino-7-methyl-1,6-naphthyridin-3-ol trifluoroacetate (Preparation 138, 970 mg, 3.35 mmol) in THF (10 mL) and H$_2$O (3 mL) was added NaOH (537 mg, 13.4 mmol), DMAP (82 mg, 0.671 mmol) and Boc$_2$O (952 mg, 4.36 mmol) and the reaction mixture stirred at rt for 16 hrs. The reaction was neutralized with 1N HCl to pH=6 and the mixture extracted with EtOAc (2×20 mL). The combined organic extracts were dried over Na$_2$SO$_4$ and concentrated in vacuo. The residue was purified using a column chromatography column (silica gel) eluting with MeOH: DCM (0:100 to 6:94) to afford the title compound as a yellow solid, 500 mg, 54%. LCMS m/z=276 [M+H]$^+$ Preparation 142 tert-butyl (3-hydroxy-1,5-naphthyridin-2-yl)carbamate

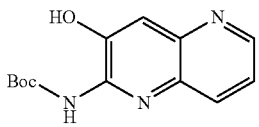 [SMILES: CC(C)(C)OC(=O)Nc1nc2cccnc2cc1O]

The title compound was obtained as a brown solid, 710 mg, 21.4%, from 2-amino-1,5-naphthyridin-3-ol trifluoroacetate (Preparation 139) by following the procedure described in Preparation 141. $^1$H NMR (400 MHz, DMSO-$d_6$) δ: 1.48 (s, 9H), 7.47-7.50 (m, 2H), 8.10 (d, 1H), 8.70 (br s, 1H), 8.86 (s, 1H), 11.00-11.46 (m, 1H).

Preparation 143 tert-butyl (7-fluoro-3-hydroxy-1,5-naphthyridin-2-yl)carbamate

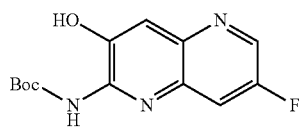 [SMILES: CC(C)(C)OC(=O)Nc1nc2cc(F)cnc2cc1O]

To a solution of 2-amino-7-fluoro-1,5-naphthyridin-3-ol trifluoroacetate (Preparation 137, 92.8 mg, 0.518 mmol) in THF (5 mL) and H$_2$O (1 mL) was added NaOH aq to adjust the pH to 9, then, DMAP (12.7 mg, 0.104 mmol) and Boc$_2$O (147 mg, 0.67 mmol) were added and the reaction mixture stirred at 20° C. for 4 hrs. The reaction mixture was concentrated in vacuo and the residue purified by column chromatography (silica gel) eluting with MeOH:DCM (0:100 to 5:95) to afford the title compound as a light yellow solid, 65 mg, 45%. $^1$H NMR (400 MHz, DMSO-$d_6$) δ: 1.49 (s, 9H), 6.76 (br s, 1H), 7.54 (s, 1H), 8.79 (d, 1H), 8.98-8.90 (m, 1H), 11.29 (br s, 1H).

Preparation 144 tert-butyl (3-hydroxy-6-methyl-1,5-naphthyridin-2-yl)carbamate

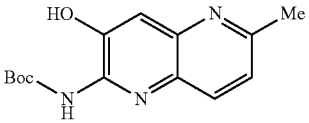

To a suspension of 3-[(4-methoxybenzyl)oxy]-6-methyl-1,5-naphthyridin-2-amine (Preparation 112, 1.64 g, 5.55 mmol) in DCM (7.0 mL) was added TFA (7.0 mL, 94 mmol) at rt and the reaction mixture stirred at 25° C. for 7 hrs. The brown solution was concentrated in vacuo and co-evaporated with MeOH (20 mL) and EtOAc (20 mL) to afford a yellow solid, 1.61 g. This was dissolved in THF (14 mL) and H₂O (3 mL), NaOH (666 mg, 16.7 mmol), DMAP (136 mg, 1.11 mmol) and Boc₂O (970 mg, 4.44 mmol) were added and the resulting brown solution stirred at 25° C. for 4 hrs. Additional NaOH (222 mg, 5.55 mmol) in H₂O (3 mL) and Boc₂O (606 mg, 2.78 mmol) were added and the reaction mixture stirred at 25° C. for 16 hrs. The reaction was neutralized with 1N HCl, then extracted with EtOAc (3×50 mL). The combined organic layers were dried over Na₂SO₄, concentrated in vacuo and the crude purified by column chromatography (silica gel) eluting with MeOH:DCM (0:100 to 5:95) to afford the title compound as a yellow solid, 400 mg, 26.2%. ¹H NMR (400 MHz, DMSO-d₆) δ: 1.47 (s, 9H), 2.60 (s, 3H), 7.24-7.55 (m, 2H), 7.98 (d, 1H), 8.84 (s, 1H), 11.04 (br s, 1H).

Preparations 145 to 153

To a solution of the appropriate alcohol (1 eq), quinolinol (1 eq) and PPh₃ (3 eq) in dry THF (10-12.5 mL/mmol) was added DIAD (3 eq) dropwise at 0° C. and the reaction mixture stirred at 25° C. for 15 hrs. The reaction mixture was concentrated in vacuo to afford the crude product which was purified by silica gel chromatography eluting with pet. ether:EtOAc at an appropriate gradient to afford the title compound.

145 ᴬ methyl 3-[(1S)-1-{[2-(1,3-dioxo-1,3-dihydro-2H-isoindol-2-yl)-6-fluoroquinolin-3-yl]oxy}ethyl]-4-(1H-pyrazol-1-yl) benzoate, pale yellow oil, 4700 mg, 91%.
LCMS m/z = 537 [M + H]⁺

146 ᴮ,ᶜ

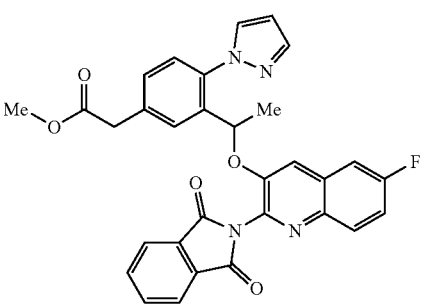

methyl {3-[1-{[2-(1,3-dioxo-1,3-dihydro-2H-isoindol-2-yl)-6-fluoroquinolin-3-yl]oxy}ethyl]-4-(1H-pyrazol-1-yl)phenyl}acetate, 186 mg, 73%.
LCMS m/z = 551 [M + H]⁺

147

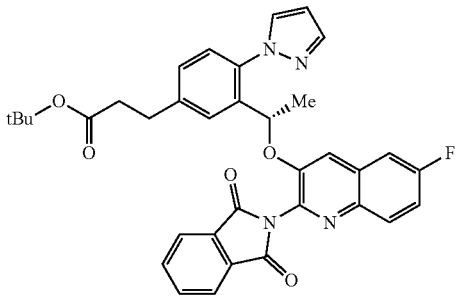

tert-butyl 3-{3-[(1S)-1-{[2-(1,3-dioxo-1,3-dihydro-2H-isoindol-2-yl)-6-fluoroquinolin-3-yl]oxy}ethyl]-4-(1H-pyrazol-1-yl)phenyl}propanoate,
yellow oil in quantitative yield.
LCMS m/z = 607 [M + H]⁺

148

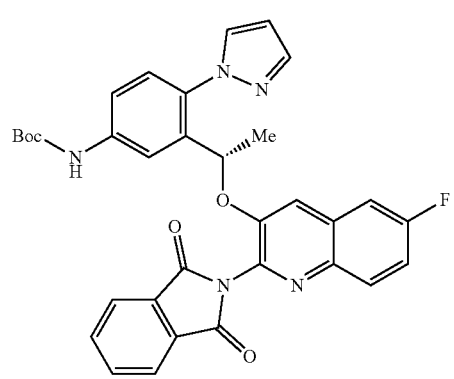

tert-butyl {3-[(1S)-1-{[2-(1,3-dioxo-1,3-dihydro-2H-isoindol-2-yl)-6-fluoroquinolin-3-yl]oxy}ethyl]-4-(1H-pyrazol-1-yl)phenyl}carbamate, 70 mg, 61% as a yellow liquid. LCMS m/z = 594 [M + H]⁺

149

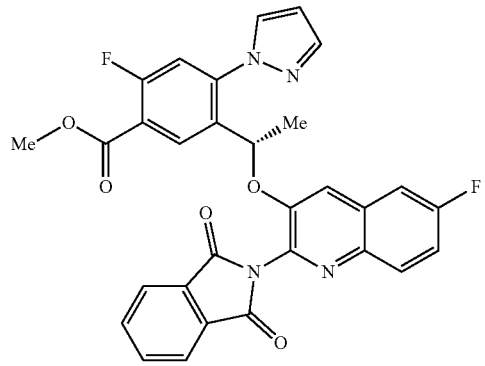

methyl 5-[(1S)-1-{[2-(1,3-dioxo-1,3-dihydro-2H-isoindol-2-yl)-6-fluoroquinolin-3-yl]oxy}ethyl]-2-fluoro-4-(1H-pyrazol-1-yl)benzoate, 341 mg, 92.9% as a yellow gum.
LCMS m/z = 577 [M + Na]⁺

150

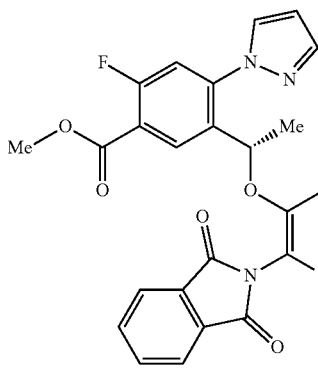

methyl 5-[(1S)-1-{[2-(1,3-dioxo-1,3-dihydro-2H-isoindol-
2-yl)-6,8-difluoroquinolin-3-yl]oxy}ethyl]-2-fluoro-4-(1H-
pyrazol-1-yl)benzoate, quantitative yield as yellow gum.
LCMS m/z = 573 [M + H]$^+$

151 $^D$

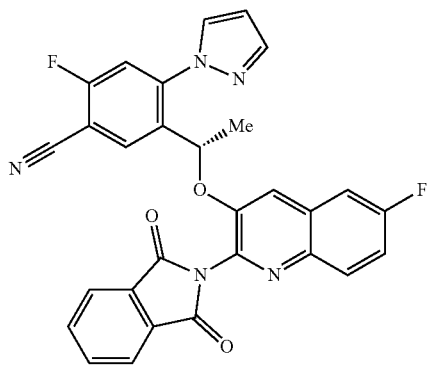

5-[(1S)-1-{[2-(1,3-dioxo-1,3-dihydro-2H-isoindol-2-yl)-
6-fluoroquinolin-3-yl]oxy}ethyl)-2-fluoro-4-(1H-pyrazol-
1-yl)benzonitrile, 280 mg, 86.2% as a yellow solid.
LCMS m/z = 522 [M + H]$^+$

152 $^B$

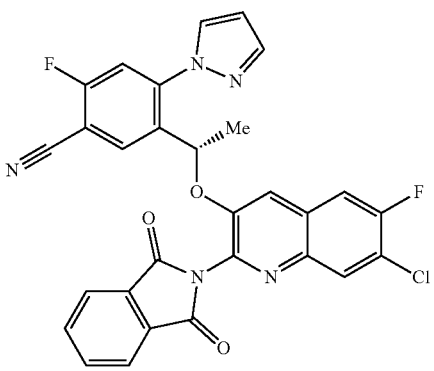

5-[(1S)-1-{[7-chloro-2-(1,3-dioxo-1,3-dihydro-2H-
isoindol-2-yl)-6-fluoroquinolin-3-yl]oxy}ethyl]-2-
fluoro-4-(1H-pyrazol-1-yl)benzonitrile, 180 mg,
68.1% as a yellow oil. LCMS m/z = 556 [M + H]$^+$

153 $^E$

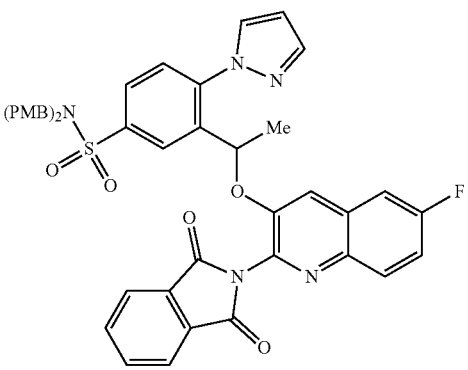

3-[1-{[2-(1,3-dioxo-1,3-dihydro-2H-isoindol-2-yl)-6-
fluoroquinolin-3-yl]oxy}ethyl]-N,N-bis(4-methoxybenzyl)-
4-(1H-pyrazol-1-yl)benzenesulfonamide, 53 mg, 43%.
LCMS m/z = 799 [M + H]$^+$ $^A$ 1.5 eq Et$_3$N added to reaction mixture
$^B$ 1.2 eq of DIAD and PPh$_3$ were used in the reaction
$^C$ H$_2$O/EtOAc work up was also conducted
$^D$ aq NH$_4$Cl/DCM work up was also conducted
$^E$ 1.7 eq DIAD and PPh$_3$ was used in the reaction Preparation 154 tert-butyl {3-[(1S)-1-({2-[(tert-butoxycarbonyl)
amino]-6-fluoroquinolin-3-yl}oxy)ethyl]-4-(1H-
pyrazol-1-yl)phenoxy}acetate

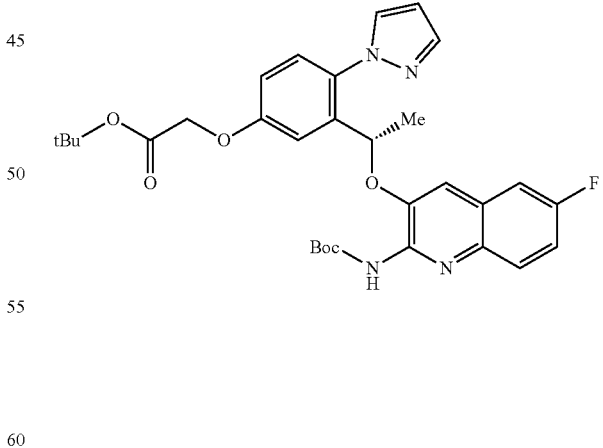

The title compound was prepared as a yellow liquid, 93 mg, from tert-butyl {3-[(2R)-1-hydroxyethyl]-4-(1H-pyrazol-1-yl)phenoxy}acetate (Preparation 24) and tert-butyl (6-fluoro-3-hydroxyquinolin-2-yl)carbamate (Preparation 105) by following the procedure described for Preparations 145 to 153. LCMS m/z=579 [M+H]$^+$

Preparation 155 tert-butyl (3-{(1S)-1-[5-cyano-2-(1H-pyrazol-1-yl)phenyl]ethoxy}-6-fluoroquinolin-2-yl)carbamate

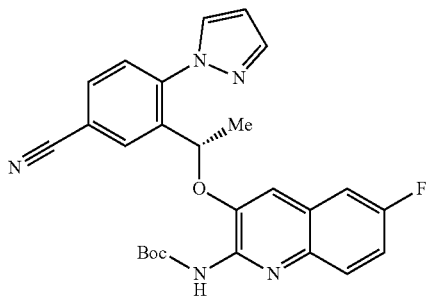 [SMILES: C[C@H](Oc1cc2cc(F)ccc2nc1NC(=O)OC(C)(C)C)c1cc(C#N)ccc1-n1cccn1]

The title compound was prepared from tert-butyl (6-fluoro-3-hydroxyquinolin-2-yl)carbamate (Preparation 105) and 3-[(1R)-1-hydroxyethyl]-4-(1H-pyrazol-1-yl)benzonitrile (Preparation 31) as a brown oil, 170 mg, 95.2%, following the procedure described for Preparations 145 to 153. LCMS m/z=496 [M+Na]$^+$

Preparation 156

3-(1-{[6-bromo-2-(tert-butylamino)quinolin-3-yl]oxy}ethyl)-4-(1H-pyrazol-1-yl)benzonitrile

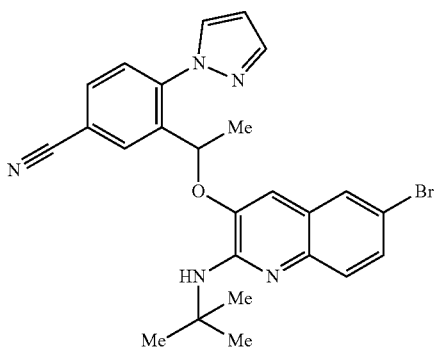 [SMILES: CC(Oc1cc2cc(Br)ccc2nc1NC(C)(C)C)c1cc(C#N)ccc1-n1cccn1]

The title compound was prepared as a gray solid, 100 mg, 21.7%, from 3-(1-hydroxyethyl)-4-(1H-pyrazol-1-yl)benzonitrile (Preparation 30) and 6-bromo-2-(tert-butylamino)quinolin-3-ol (Preparation 136) by following a similar procedure to that described for Preparations 145 to 153, except 1.2 eq of DIAD and PPh$_3$ were used in the reaction. LCMS m/z=492 [M+H]$^+$

Preparation 157 methyl 3-{(1S)-1-[(5,8-difluoro-1-oxidoquinolin-3-yl)oxy]ethyl}-4-(1H-pyrazol-1-yl)benzoate

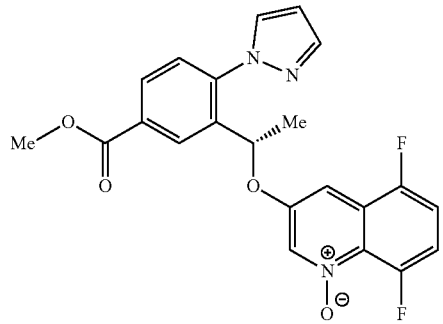 [SMILES: COC(=O)c1ccc(-n2cccn2)c([C@H](C)Oc2cc3c(F)ccc(F)c3[n+]([O-])c2)c1]

To a yellow mixture of 5,8-difluoroquinolin-3-ol 1-oxide (Preparation 104, 300 mg, 1.52 mmol), methyl 3-[(1R)-1-hydroxyethyl]-4-(1H-pyrazol-1-yl)benzoate (Preparation 28, 330 mg, 1.34 mmol) and Ph$_3$P resin (1390 mg, 4.18 mmol) in dry THF (14 mL) and DMF (2.4 mL) was added DIAD (846 mg, 4.18 mmol) drop wise at rt. The mixture was purged with N$_2$, stirred at rt for 30 mins and then heated at 50° C. for 16 hrs. The cooled reaction mixture was concentrated in vacuo and the residue purified by column chromatography (silica gel) eluting with EtOAc:pet. ether (0:100 to 60:40) to afford the title compound as a yellow gum, 47.5%. LCMS m/z=426 [M+H]$^+$

Preparation 158 methyl 3-{(1S)-1-[(6,8-difluoroquinolin-3-yl)oxy]ethyl}-4-(1H-pyrazol-1-yl)benzoate

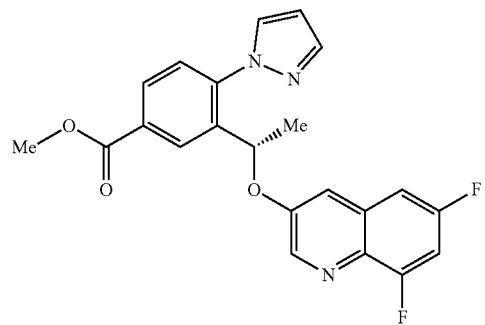 [SMILES: COC(=O)c1ccc(-n2cccn2)c([C@H](C)Oc2cnc3c(F)cc(F)cc3c2)c1]

A mixture of allyl palladium chloride dimer (674 mg, 1.84 mmol) and (S)-1-[(R$_P$)-2-(dicyclohexylphosphino)ferrocenyl]ethyldi-tert-butylphosphine (2.66 g, 4.80 mmol) in toluene (250 mL) was stirred for 20 mins. 3-Bromo-6,8-difluoroquinoline (18.04 g, 73.9 mmol) and methyl 3-[(1S)-1-hydroxyethyl]-4-(1H-pyrazol-1-yl)benzoate (Preparation 27, 20.04 g, 81.4 mmol) were added and the reaction mixture stirred until a solution was obtained. Cs$_2$CO$_3$ (49.9 g, 153 mmol) was added and the reaction mixture stirred at 105° C. (internal temperature) for 22 hrs. The reaction mixture was then allowed to cool to rt. The residue was partitioned between EtOAc (200 mL) and H$_2$O (200 mL) and the layers separated. The aqueous phase was extracted with EtOAc (2×200 mL) and the combined organic extracts were washed with brine (50 mL), dried (MgSO$_4$), filtered through Celite® and the filtrate concentrated under reduced pressure. The crude material was purified by column chromatography (gold silica gel column) eluting with heptanes:EtOAc (100:0 to 70:30) to afford the title compound as a glass-like solid, 23.1 g, 76.3%. $^1$H NMR (400 MHz, CDCl$_3$) δ: 1.71 (d, 3H), 3.96 (s, 3H), 5.98-6.02 (m, 1H), 6.64 (s, 1H), 7.00-7.45 (m, 4H), 7.83 (s, 1H), 7.92 (s, 1H), 8.17 (d, 1H), 8.36 (s, 1H), 8.70 (s, 1H).

Preparation 159 methyl 3-{(1S)-1-[(6,8-difluoro-1-oxidoquinolin-3-yl)oxy]ethyl}-4-(1H-pyrazol-1-yl)benzoate

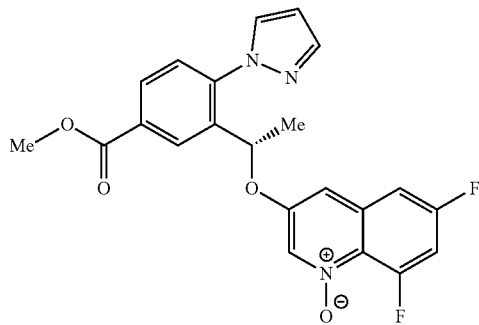 [SMILES: COC(=O)c1ccc(-n2cccn2)c([C@H](C)Oc2cc3cc(F)cc(F)c3[n+]([O-])c2)c1]

m-CPBA (72.47 g, 290 mmol) was added to a solution of methyl 3-{(1S)-1-[(6,8-difluoroquinolin-3-yl)oxy]ethyl}-4-(1H-pyrazol-1-yl)benzoate (Preparation 158, 30.5 g, 74.5 mmol) in DCM (700 mL) and the reaction mixture stirred at rt for 16 hrs. The mixture was cooled to −1.9° C. and saturated Na$_2$SO$_3$ solution (25 mL) added at a rate of 1 mL/min. 2M Na$_2$CO$_3$ solution (400 mL) was added, the mixture stirred for 15 mins and the layers separated. The aqueous phase was extracted with DCM (200 mL), the combined organic extracts washed with brine (250 mL) then dried over MgSO$_4$, filtered, and concentrated in vacuo. The crude product was purified by flash column chromatography on silica gel eluting with EtOAc:heptanes (30:70 to 75:25) to afford the title compound as a pale, orange foam, 17.33 g, 55%. LCMS m/z=426 [M+H]$^+$ Preparation 160

2-(3-{(1S)-1-[5-amino-2-(1H-pyrazol-1-yl)phenyl]ethoxy}-6-fluoroquinolin-2-yl)-1H-isoindole-1,3(2H)-dione

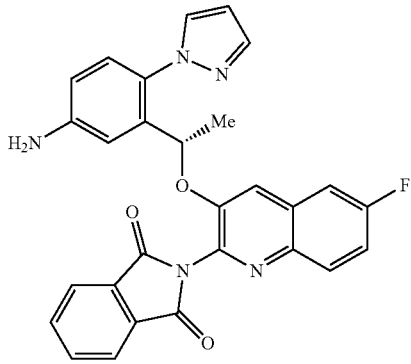 [SMILES: C[C@H](Oc1cc2cc(F)ccc2nc1N1C(=O)c2ccccc2C1=O)c1cc(N)ccc1-n1cccn1]

TFA (1 mL) was added to a solution of tert-butyl {3-[(1S)-1-{[2-(1,3-dioxo-1,3-dihydro-2H-isoindol-2-yl)-6-fluoroquinolin-3-yl]oxy}ethyl]-4-(1H-pyrazol-1-yl)phenyl}carbamate (Preparation 148, 70 mg, 0.1 mmol) in DCM (2 mL) and the reaction mixture stirred at 25° C. for 1 hr. The reaction mixture was evaporated under reduced pressure and the crude suspended in EtOAc (20 mL) and washed with H$_2$O (5 mL), brine (5 mL), dried over Na$_2$SO$_4$ and evaporated under reduced pressure to afford the title compound as a yellow liquid, 50 mg, 98%. LCMS m/z=572 [M+H]$^+$ Preparation 161

5-[(1S)-1-{[2-(1,3-dioxo-1,3-dihydro-2H-isoindol-2-yl)-6-fluoroquinolin-3-yl]oxy}ethyl]-2-fluoro-4-(1H-pyrazol-1-yl)benzamide

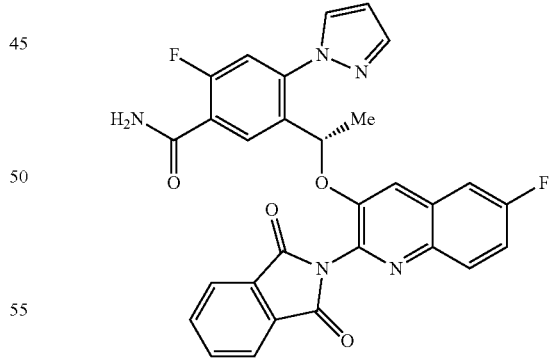

K$_2$CO$_3$ (213 mg, 1.54 mmol) was added to a solution of 5-[(1S)-1-{[2-(1,3-dioxo-1,3-dihydro-2H-isoindol-2-yl)-6-fluoroquinolin-3-yl]oxy}ethyl]-2-fluoro-4-(1H-pyrazol-1-yl)benzonitrile (Preparation 151, 230 mg, 0.441 mmol) in DMSO (7.5 mL), and the mixture stirred for 10 mins. H$_2$O$_2$ (1.5 mL) was added and the reaction mixture stirred for 1 hr. Water (100 mL) was added and the aqueous mixture extracted with DCM (3×90 mL). The combined organic extracts were washed with brine (100 mL), dried over Na₂SO₄, filtered and concentrated in vacuo to provide the title compound as a yellow oil, 182 mg, 76.5%. LCMS m/z=548 [M+H₂O]+

Preparation 162

5-[(1S)-1-{[7-chloro-2-(1,3-dioxo-1,3-dihydro-2H-isoindol-2-yl)-6-fluoroquinolin-3-yl]oxy}ethyl]-2-fluoro-4-(1H-pyrazol-1-yl)benzamide

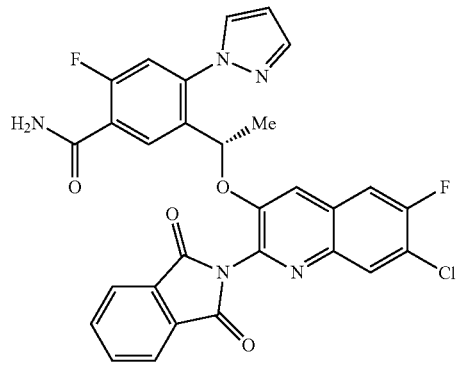 [SMILES: C[C@H](Oc1cc2cc(F)c(Cl)cc2nc1N1C(=O)c2ccccc2C1=O)c1cc(C(N)=O)c(F)cc1-n1cccn1]

The title compound was obtained as a yellow oil in 97% yield, 160 mg, from 5-[(1S)-1-{[7-chloro-2-(1,3-dihydro-2H-isoindol-2-yl)-6-fluoroquinolin-3-yl]oxy}ethyl]-2-fluoro-4-(1H-pyrazol-1-yl)benzonitrile (Preparation 152) by following the procedure described in Preparation 161. LCMS m/z=592 [M+H]⁺

Preparation 163

3-{(1S)-1-[(2-amino-6-fluoroquinolin-3-yl)oxy]ethyl}-4-(1H-pyrazol-1-yl)benzohydrazide

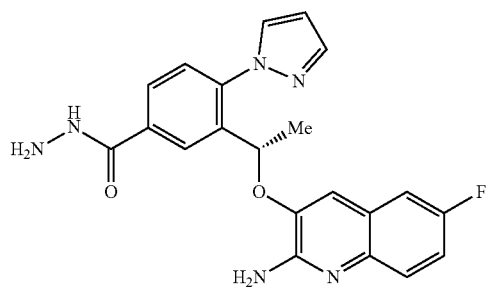 [SMILES: C[C@H](Oc1cc2cc(F)ccc2nc1N)c1cc(C(=O)NN)ccc1-n1cccn1]

To a solution of methyl 3-[(1S)-1-{[2-(1,3-dioxo-1,3-dihydro-2H-isoindol-2-yl)-6-fluoroquinolin-3-yl]oxy}ethyl]-4-(1H-pyrazol-1-yl)benzoate (Preparation 145, 300 mg, 0.56 mmol) in MeOH (15 mL) was added hydrazine hydrate (1.5 mL, 15 mmol), and the reaction mixture stirred at 15° C. for 60 hrs. The reaction mixture was concentrated in vacuo and the residue purified by HPLC using an Agela Durashell C18 column and eluting with 0.05% aq NH₄OH: MeCN (30:70 to 60:40) to provide the title compound as a white solid, 96 mg, 42%. LCMS m/z=407 [M+H]⁺

Preparation 164 tert-butyl (6-fluoro-3-{(1S)-1-[5-(N-hydroxycarbamimidoyl)-2-(1H-pyrazol-1-yl)phenyl]ethoxy}quinolin-2-yl)carbamate

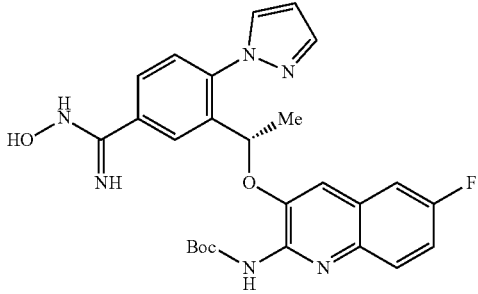 [SMILES: C[C@H](Oc1cc2cc(F)ccc2nc1NC(=O)OC(C)(C)C)c1cc(C(=N)NO)ccc1-n1cccn1]

To a solution of tert-butyl (3-{(1S)-1-[5-cyano-2-(1H-pyrazol-1-yl)phenyl]ethoxy}-6-fluoroquinolin-2-yl)carbamate (Preparation 155, 170 mg, 0.36 mmol) in anhydrous MeOH (2 mL) and THF (2 mL) was added NH₂OH.HCl (37.4 mg, 0.54 mmol) and Et₃N (109 mg, 1.08 mmol) at rt and the reaction mixture stirred for 20 hrs at 80° C. The cooled reaction mixture was quenched with H₂O (10 mL) and extracted with EtOAc (3×20 mL). The combined organic layers were washed with brine (10 mL), dried over Na₂SO₄, filtered, and concentrated in vacuo to give crude product. This was purified by column chromatography (silica gel), eluting with MeOH:DCM (0:100 to 5:95) to afford the title compound as a colorless oil, 156 mg, 85.8%. LCMS m/z=507 [M+H]⁺

Preparation 165 methyl 3-{(1S)-1-[(2-chloro-5,8-difluoroquinolin-3-yl)oxy]ethyl}-4-(1H-pyrazol-1-yl)benzoate

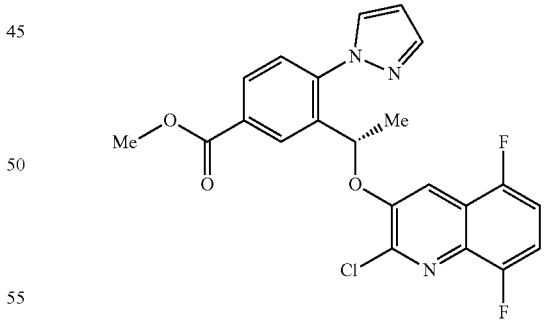

A solution of TsCl (194 mg, 1.02 mmol) in DCM (2 mL) was added to an ice-cooled solution of methyl 3-{(1S)-1-[(5,8-difluoro-1-oxidoquinolin-3-yl)oxy]ethyl}-4-(1H-pyrazol-1-yl)benzoate (Preparation 157, 360 mg, 0.846 mmol) and DIPEA (219 mg, 1.69 mmol) in DCM (6 mL) and the solution stirred at rt for 18 hrs. The reaction mixture was concentrated in vacuo and the residue purified by column chromatography (silica gel) eluting with EtOAc:pet. ether (0:100 to 20:80) to afford the title compound, 70.1%. LCMS m/z=444 [M+H]⁺

161

Preparation 166 methyl 3-[(1S)-1-({5,8-difluoro-2-[(4-methoxyben-zyl)amino]quinolin-3-yl}oxy)ethyl]-4-(1H-pyrazol-1-yl)benzoate

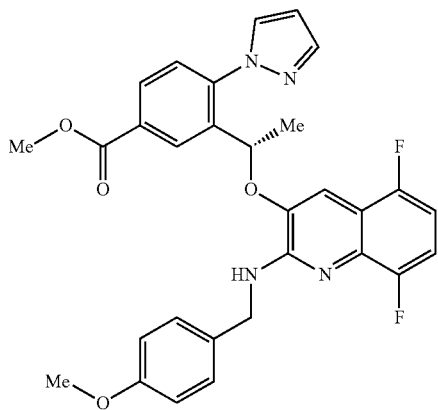 [SMILES: COC(=O)c1ccc(-n2cccn2)c([C@H](C)Oc2cc3c(F)ccc(F)c3nc2NCc2ccc(OC)cc2)c1]

To a solution of methyl 3-{(1S)-1-[(2-chloro-5,8-difluoroquinolin-3-yl)oxy]ethyl}-4-(1H-pyrazol-1-yl)benzoate (Preparation 165, 300 mg, 0.68 mmol) in THF (8 mL) was added PMB-NH$_2$ (464 mg, 3.38 mmol) and DIPEA (0.353 mL, 2.03 mmol) and the reaction mixture heated at 70° C. for 40 hrs. The cooled reaction mixture was concentrated under reduced pressure and the residue purified by column chromatography (silica gel) eluting with EtOAc:pet. ether (0:100 to 20:80) to afford the title compound as a yellow gum, 240 mg, 65.2%. LCMS m/z=567 [M+Na]$^+$ Preparations 167 to 180

To a solution of the appropriate alcohol (1 eq), and quinolinol (1 eq) and PPh$_3$ (3 eq) in dry THF (10-12.5 mL/mmol) was added DIAD (3 eq) drop wise at 0° C. and the reaction mixture stirred at 25° C. for 15 hrs. The reaction mixture was concentrated in vacuo to afford the crude product which was purified by silica gel chromatography eluting with pet. ether:EtOAc at an appropriate gradient to afford the title compound.

167

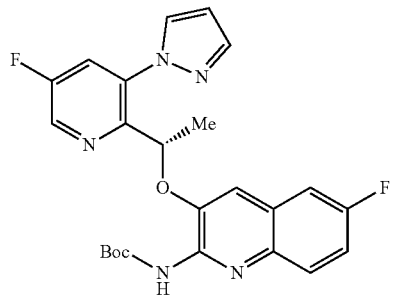

tert-butyl (6-fluoro-3-{(1S)-1-[5-fluoro-3-(1H-pyrazol-1-yl)pyridin-2-yl]ethoxy}quinolin-2-yl)carbamate, 250 mg, 99% yield as a yellow gum. LCMS m/z = 368 [M − Boc]$^+$

162

-continued

168

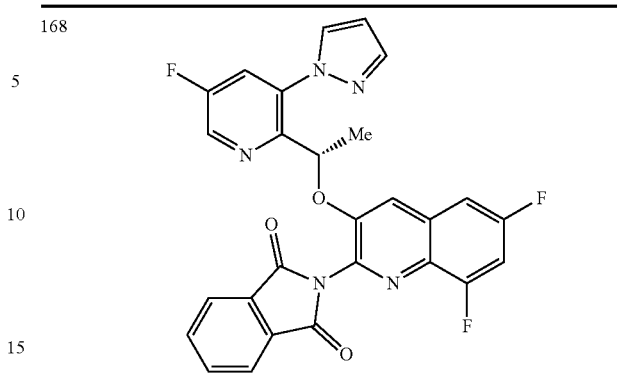

2-(6,8-difluoro-3-{(1S)-1-[5-fluoro-3-(1H-pyrazol-1-yl)pyridin-2-yl]ethoxy}quinolin-2-yl)-1H-isoindole-1,3(2H)-dione, light yellow oil, 120 mg, 96%. LCMS m/z = 538 [M + H]$^+$

169

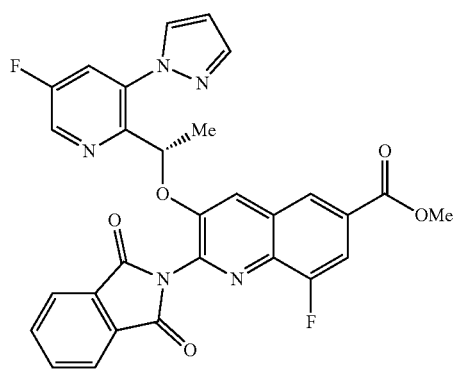

methyl 2-(1,3-dioxo-1,3-dihydro-2H-isoindol-2-yl)-8-fluoro-3-{(1S)-1-[5-fluoro-3-(1H-pyrazol-1-yl)pyridin-2-yl]ethoxy}quinoline-6-carboxylate, white solid, 1.188 g, 78.3%. $^1$H NMR (400 MHz, CDCl$_3$) δ: 1.66 (d, 3H), 4.03 (s, 3H), 4.14 (q, 1H), 5.94-5.97 (m, 1H), 6.50 (d, 1H), 7.46 (dd, 1H), 7.57 (s, 1H), 7.74-8.04 (m, 6H), 8.22 (s, 1H), 8.48 (d, 1H).

170

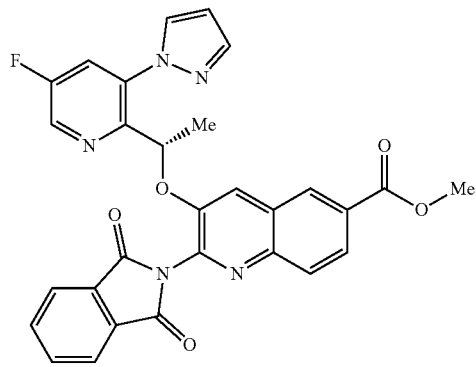

methyl 2-(1,3-dioxo-1,3-dihydro-2H-isoindol-2-yl)-3-{(1S)-1-[5-fluoro-3-(1H-pyrazol-1-yl)pyridin-2-yl]ethoxy}quinoline-6-carboxylate, 5.16 g, 83% as a yellow foam. $^1$H NMR (400 MHz, CDCl$_3$) δ: 1.64 (d, 3H), 4.00 (s, 3H), 4.15 (q, 1H), 5.88 (q, 1H), 6.42 (s, 1H), 7.42-8.18 (m, 9H), 8.43 (dd, 2H).

171

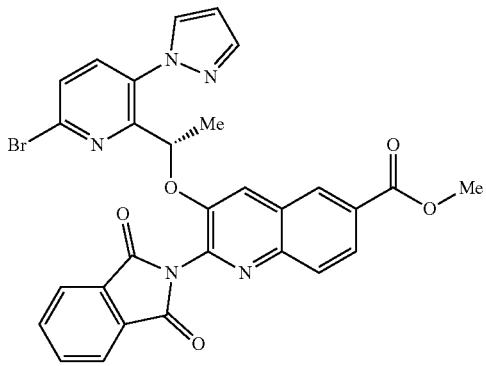

methyl 3-{(1S)-1-[6-bromo-3-(1H-pyrazol-1-yl)pyridin-2-yl]ethoxy}-2-(1,3-dioxo-1,3-dihydro-2H-isoindol-2-yl)quinoline-6-carboxylate, yellow oil in quantitative yield. LCMS m/z = 600 [M + H]+

172

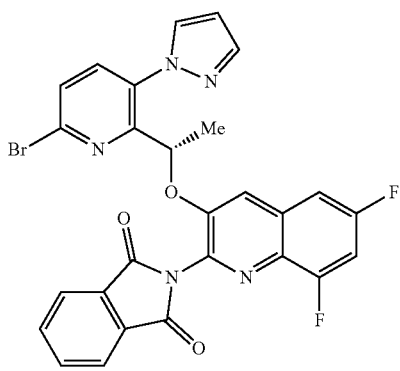

2-(3-{(1S)-1-[6-bromo-3-(1H-pyrazol-1-yl)pyridin-2-yl]ethoxy}-6,8-difluoroquinolin-2-yl)-1H-isoindole-1,3(2H)-dione, light yellow oil in quantitative yield. LCMS m/z = 578 [M + H]+

173

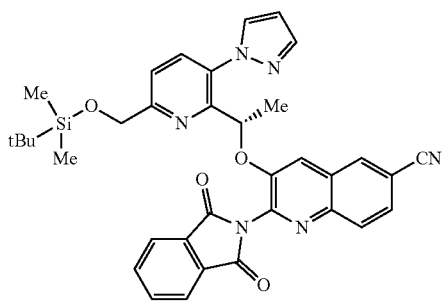

3-{(1S)-1-[6-({[tert-butyl(dimethyl)silyl]oxy}methyl)-3-(1H-pyrazol-1-yl)pyridin-2-yl]ethoxy}-2-(1,3-dioxo-1,3-dihydro-2H-isoindol-2-yl)quinoline-6-carbonitrile, yellow gum in quantitative yield. LCMS m/z = 631 [M + H]+

174 B

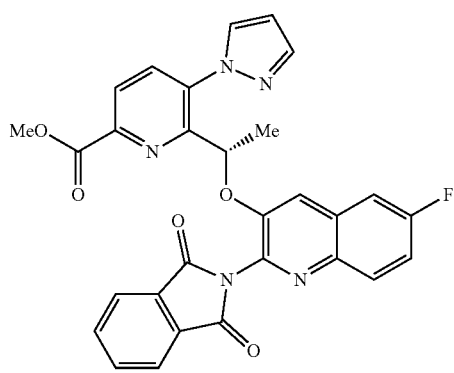

methyl 6-[(1S)-1-{[2-(1,3-dioxo-1,3-dihydro-2H-isoindol-2-yl)-6-fluoroquinolin-3-yl]oxy}ethyl]-5-(1H-pyrazol-1-yl)pyridine-2-carboxylate, 120 mg, 92% as a colorless oil. LCMS m/z = 538, 560 [M + H]+, [M + Na]+

175

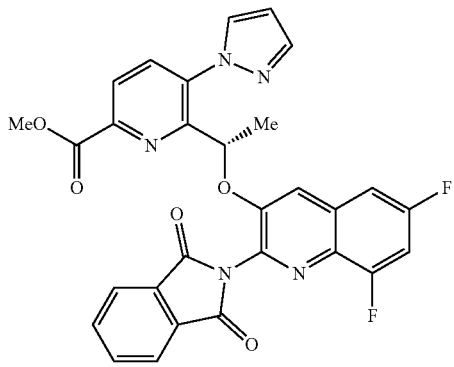

2-(6,8-difluoro-3-{(1S)-1-[6-methoxy-3-(1H-pyrazol-1-yl)pyridin-2-yl]ethoxy}quinolin-2-yl)-1H-isoindole-1,3(2H)-dione, 1030 mg, 84.9% as a yellow solid. 1H NMR (400 MHz, DMSO-d6) δ: 1.53 (d, 3H), 3.58 (s, 3H), 5.63 (q, 1H), 6.57 (d, 1H), 6.86 (d, 1H), 7.47 (dd, 1H), 7.62-7.72 (m, 2H), 7.77 (d, 1H), 7.86 (d, 1H), 7.98-8.02 (m, 3H), 8.06-8.10 (m, 2H).

176

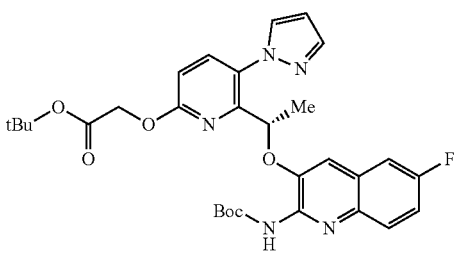

tert-butyl ({6-[(1S)-1-({2-[(tert-butoxycarbonyl)amino]-6-fluoroquinolin-3-yl}oxy)ethyl]-5-(1H-pyrazol-1-yl)pyridin-2-yl}oxy)acetate, quantitative yield, as a light yellow oil. LCMS m/z = 580 [M + H]+

177

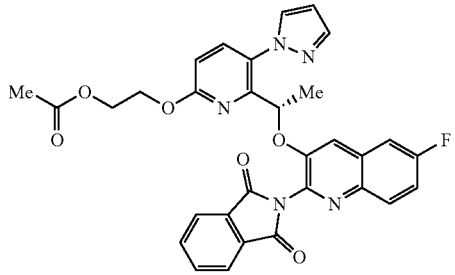

2-({6-[(1S)-1-{[2-(1,3-dioxo-1,3-dihydro-2H-isoindol-2-yl)-6-fluoroquinolin-3-yl]oxy}ethyl]-5-(1H-pyrazol-1-yl)pyridin-2-yl}oxy)ethyl acetate, 130 mg, 93% as a yellow gum.
LCMS m/z = 582 [M + H]⁺

178

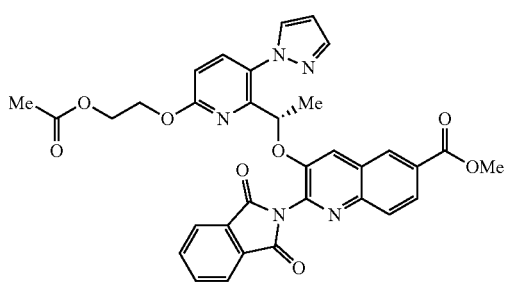

methyl 3-[(1S)-1-{6-[2-(acetyloxy)ethoxy]-3-(1H-pyrazol-1-yl)pyridin-2-yl}ethoxy]-2-(1,3-dioxo-1,3-dihydro-2H-isoindol-2-yl)quinoline-6-carboxylate, (yield), as a light yellow oil. LCMS m/z = 644 [M + Na]⁺

179

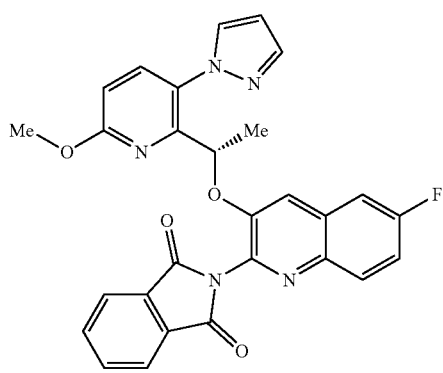

2-(6-fluoro-3-{(1S)-1-[6-methoxy-3-(1H-pyrazol-1-yl)pyridin-2-yl]ethoxy}quinolin-2-yl)-1H-isoindole-1,3(2H)-dione, quantitative yield as a yellow solid.
LCMS m/z = 532 [M + Na]⁺

180

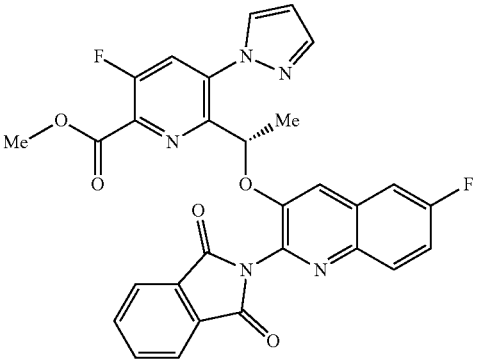

methyl 6-[(1S)-1-{[2-(1,3-dioxo-1,3-dihydro-2H-isoindol-2-yl)-6-fluoroquinolin-3-yl]oxy}ethyl]-3-fluoro-5-(1H-pyrazol-1-yl)pyridine-2-carboxylate, 73 mg, 50% as a yellow solid.
LCMS m/z = 578 [M + Na]⁺

---

$^A$ 1.2 eq of DIAD and PPh₃ were used in the reaction
$^B$ 4 eq Et₃N was added to the reaction mixture Preparations 181 to 84

To a solution of (1R)-1-[6-bromo-3-(1H-pyrazol-1-yl)pyridin-2-yl]ethanol (Preparation 52) (1 eq) and the appropriate quinolinol (1 eq) and PPh₃ (3 eq) in dry THF (10-12.5 mL/mmol) was added DIAD (3 eq) drop wise at 0° C. and the reaction mixture stirred at 25° C. for 15 hrs. The reaction mixture was concentrated in vacuo to afford the crude product which was purified by silica gel chromatography eluting with pet. ether:EtOAc at an appropriate gradient to afford the title compound.

181

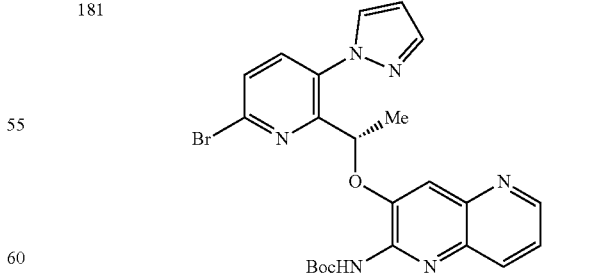

tert-butyl (3-{(1S)-1-[6-bromo-3-(1H-pyrazol-1-yl)pyridin-2-yl]ethoxy}-1,5-naphthyridin-2-yl)carbamate, 270 mg, 69% as a green gum.
LCMS m/z = 413 [M − Boc]⁺

182

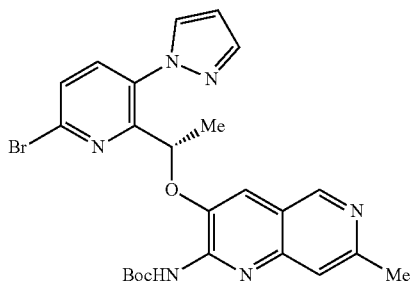

tert-butyl (3-{(1S)-1-[6-bromo-3-(1H-pyrazol-1-yl)pyridin-2-yl]ethoxy}-7-methyl-1,6-naphthyridin-2-yl)carbamate, 90 mg, 79%, as a colorless oil. LCMS m/z = 527 [M + H]⁺

183

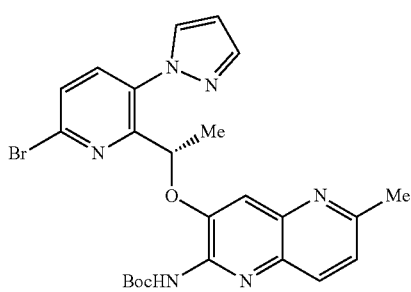

tert-butyl (3-{(1S)-1-[6-bromo-3-(1H-pyrazol-1-yl)pyridin-2-yl]ethoxy}-6-methyl-1,5-naphthyridin-2-yl)carbamate, yellow solid in quantitative yield. LCMS m/z = 527 [M + H]⁺

184

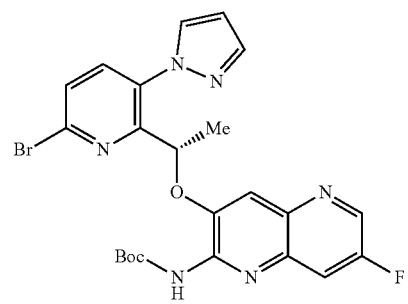

tert-butyl (3-{(1S)-1-[6-bromo-3-(1H-pyrazol-1-yl)pyridin-2-yl]ethoxy}-7-fluoro-1,5-naphthyridin-2-yl)carbamate, 85 mg, 69% as light yellow solid. LCMS m/z = 531 [M + H]⁺

Preparation 185

5,8-difluoro-3-{(1S)-1-[5-fluoro-3-(1H-pyrazol-1-yl)pyridin-2-yl]ethoxy}quinoline 1-oxide

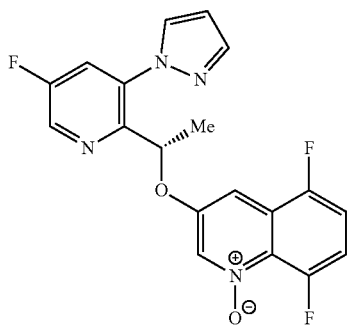 [SMILES: C[C@H](Oc1cc2c(F)ccc(F)c2[n+](O)c1)c1ncc(F)cc1-n1cccn1]

DIAD (903 mg, 4.46 mmol) was added dropwise to a suspension of 5,8-difluoroquinolin-3-ol 1-oxide (Preparation 104, 400.0 mg, 2.03 mmol), (1R)-1-[5-fluoro-3-(1H-pyrazol-1-yl)pyridin-2-yl]ethanol (Preparation 53, 420 mg, 2.03 mmol) and Ph₃P resin (1490 mg, 4.46 mmol) in dry THF (10 mL)/DMF (1.0 mL), the mixture purged with N2 and the reaction mixture stirred at rt for 5 mins, then at 50° C. for 18 hrs. The cooled mixture was concentrated in vacuo and the residue purified by column chromatography (silica gel) eluting with MeOH:DCM (0:100 to 95:5) to afford the title compound as a yellow gum, 650 mg, 83%.

LCMS m/z=387 [M+H]⁺

Preparation 186

5-bromo-N-tert-butyl-3-{1-[5-fluoro-3-(1H-pyrazol-1-yl)pyridin-2-yl]ethoxy}quinolin-2-amine

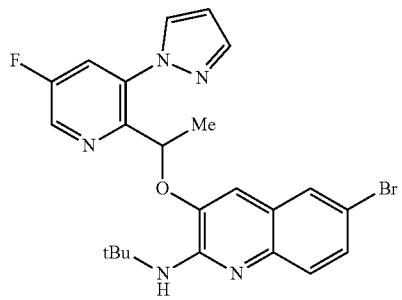 [SMILES: CC(Oc1cc2cc(Br)ccc2nc1NC(C)(C)C)c1ncc(F)cc1-n1cccn1]

A solution of PPh₃ (709 mg, 2.70 mmol) and DIAD (546 mg, 2.70 mmol) in THF (10.7 mL) was cooled to 0° C., then a solution of 1-[5-fluoro-3-(1H-pyrazol-1-yl)pyridin-2-yl]ethanol (Preparation 54, 400 mg, 1.93 mmol) and 6-bromo-2-(tert-butylamino)quinolin-3-ol (Preparation 136, 627 mg, 2.12 mmol) in THF (10.7 mL) was added. The reaction mixture was stirred at 0° C. for 5 mins and at rt for 18 hrs then filtered and the filtrate concentrated in vacuo. The crude product was purified by ISCO column chromatography on silica gel eluting with hexanes:EtOAc (15:85 to 50:50) to afford the title compound as a yellow solid, 830 mg, 89%.
¹H NMR (CDCl₃, 400 MHz) δ: 1.54 (s, 9H), 1.79 (d, 3H), 5.45 (s, 1H), 5.79 (q, 1H), 6.52-6.56 (m, 1H), 6.58 (t, 1H), 7.34-7.41 (m, 2H), 7.41-7.48 (m, 2H), 7.63 (d, 1H), 7.84-7.89 (m, 1H), 8.59 (d, 1H).

Preparation 187 methyl 2-(1,3-dioxo-1,3-dihydro-2H-isoindol-2-yl)-7-fluoro-3-{1-[5-fluoro-3-(1H-pyrazol-1-yl)pyridin-2-yl]ethoxy}quinoline-6-carboxylate

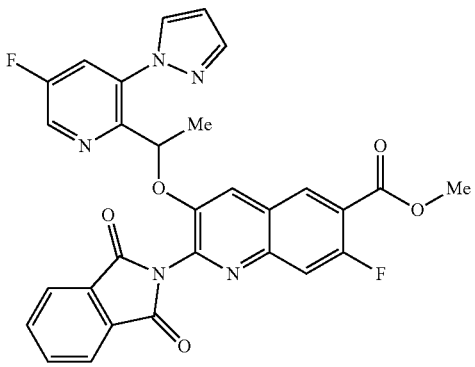 [SMILES: COC(=O)c1cc2cc(OC(C)c3ncc(F)cc3-n3cccn3)c(N3C(=O)c4ccccc4C3=O)nc2cc1F]

To a solution of methyl 2-(1,3-dioxo-1,3-dihydro-2H-isoindol-2-yl)-3-hydroxy-7-fluoroquinoline-6-carboxylate (Preparation 129, 120 mg, 0.328 mmol) in dry THF (2 mL) was added 1-[5-fluoro-3-(1H-pyrazol-1-yl)pyridin-2-yl]ethanol (Preparation 54, 81.5 mg, 0.39 mmol) and PPh$_3$ (172 mg, 0.66 mmol). The reaction mixture was stirred at 0° C., DIAD (132 mg, 0.655 mmol) added drop wise and the reaction mixture stirred at 20° C. for 16 hrs. The reaction mixture was diluted with EtOAc (10 mL), washed with brine (3×5 mL), the combined organic layers dried over Na$_2$SO$_4$, filtered, and concentrated in vacuo. The crude residue was purified by chromatography on silica gel eluting with pet. ether:EtOAc (100:0 to 30:70) to afford the title compound as a white solid, 150 mg, 82.4%. LCMS m/z=578 [M+Na]$^+$ Preparation 188 tert-butyl (3-{(1S)-1-[6-bromo-3-(1H-pyrazol-1-yl)pyridin-2-yl}ethoxyl-6-fluoroquinolin-2-yl)carbamate

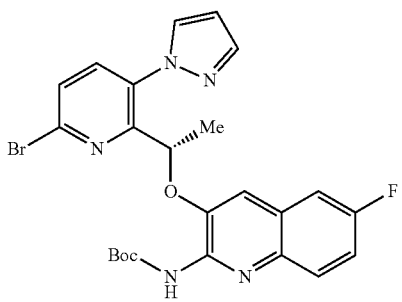 [SMILES: C[C@H](Oc1cc2cc(F)ccc2nc1NC(=O)OC(C)(C)C)c1nc(Br)ccc1-n1cccn1]

To a cooled (−6° C.) suspension of (1R)-1-[6-bromo-3-(1H-pyrazol-1-yl)pyridin-2-yl]ethanol (Preparation 52, 12.0 g, 43.12 mmol) and PPh$_3$ (13.80 g, 52.6 mmol) in THF (120 mL) was added DIAD (9.34 mL, 47.4 mmol) dropwise so as to maintain the internal temperature below 3° C. The reaction mixture was stirred for 10 mins at −6° C., then a solution of tert-butyl (6-fluoro-3-hydroxyquinolin-2-yl)carbamate (Preparation 105, 11.60 g, 43.1 mmol) in THF (40 mL) added dropwise over 15 mins. The reaction mixture was allowed to warm slowly to rt and stirred for 17 hrs. The reaction mixture was partitioned between MTBE (120 mL) and 1N NaOH (80 mL), the layers separated and the aqueous phase extracted with MTBE (120 mL). The combined organic phases were washed with 1N NaOH (80 mL), then brine (80 mL) and dried over MgSO$_4$. The mixture was filtered through a Celite® pad, washing through with MTBE (120 mL), and the filtrate concentrated under reduced pressure. The residue was azeotroped with Et$_2$O and then purified using the CombiFlash Rf (Gold silica gel column) eluting with EtOAc:DCM (0:100 to 20:80) to afford the title compound. LCMS m/z=528 [M+H]$^+$ Preparation 189

3-{(1S)-1-[6-bromo-3-(1H-pyrazol-1-yl)pyridin-2-yl]ethoxy}-6-fluoroquinolin-2-amine

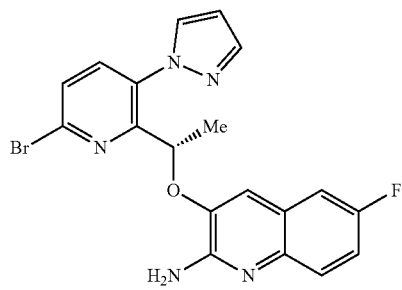 [SMILES: C[C@H](Oc1cc2cc(F)ccc2nc1N)c1nc(Br)ccc1-n1cccn1]

TFA (10 mL, 187 mmol) was added drop wise to a solution of tert-butyl (3-{(1S)-1-[6-bromo-3-(1H-pyrazol-1-yl)pyridin-2-yl]ethoxy}-6-fluoroquinolin-2-yl)carbamate (Preparation 188, 9.9 g, 18.74 mmol) in DCM (50 mL) and the reaction mixture stirred at rt for 17 hrs. Additional TFA (2 mL) was added and the reaction mixture stirred for a further 24 hrs. The solution was concentrated under reduced pressure and the residue azeotroped with DCM (20 mL) and heptane (200 mL). The crude material was partitioned between 1N NaOH (150 mL) and DCM (100 mL) and the layers separated. The aqueous phase was extracted with DCM (100 mL), the combined organic layers dried over MgSO$_4$, filtered and concentrated under reduced pressure. The product was recrystallized from hot EtOAc/heptane to afford the title compound as a white solid, 6.71 g. $^1$HNMR (400 MHz, CDCl$_3$) δ: 1.84 (d, 3H), 5.16 (br s, 2H), 5.82-5.87 (m, 1H), 6.60 (s, 1H), 6.74 (s, 1H), 6.98-7.00 (m, 1H), 7.12-7.18 (m, 2H), 7.52-7.58 (m, 2H), 7.62 (s, 1H), 7.88 (s, 1H).

Preparation 190

2-(tert-butylamino)-3-{1-[5-fluoro-3-(1H-pyrazol-1-yl)pyridin-2-yl]ethoxy}quinoline-6-carbonitrile

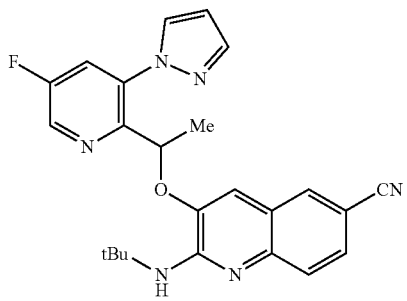 [SMILES: CC(Oc1cc2cc(C#N)ccc2nc1NC(C)(C)C)c1ncc(F)cc1-n1cccn1]

To a solution of 6-bromo-N-tert-butyl-3-{1-[5-fluoro-3-(1H-pyrazol-1-yl)pyridin-2-yl]ethoxy}quinolin-2-amine (Preparation 186, 600 mg, 1.24 mmol) in t-BuOH (6 mL) and H$_2$O (6 mL) was added K$_3$Fe(CN)$_6$ (209 mg, 0.495 mmol), polymer bound Pd(PPh$_3$)$_4$(71.6 mg, 0.062 mmol) and Polycat® 5 catalyst (1M, 0.31 mL, 0.31 mmol), the system purged with N2 for 2 mins and then stirred at 85° C. for 18 hrs. The cooled reaction mixture was filtered through Celite®, washing through with EtOAc. The filtrate was washed with brine and H$_2$O, dried over Na$_2$SO$_4$ and concentrated in vacuo. The crude product was purified on a silica gel cartridge eluting with heptane:EtOAc (50:50) to afford the title compound as a white solid. LCMS m/z=431 [M+H]$^+$

Preparation 191

5-bromo-3-{1-[3-(1H-pyrazol-1-yl)pyridin-2-yl]ethoxy}quinolin-2-amine

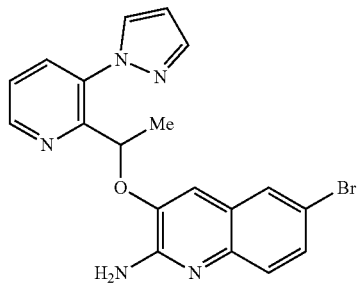

A suspension of 1-[3-(1H-pyrazol-1-yl)pyridin-2-yl]ethyl methanesulfonate (Preparation 57, 376.0 mg, 1.41 mmol), 2-amino-6-bromoquinolin-3-ol (Preparation 135, 280.0 mg, 1.17 mmol) and Cs$_2$CO$_3$ (763.0 mg, 2.34 mmol) in MeCN (15 mL) was stirred at 60° C. for 16 hrs. The cooled reaction mixture was concentrated in vacuo and the resulting yellow solid purified by flash silica gel chromatography eluting with DCM:MeOH (100:0 to 85:15) to afford the title product as a yellow solid, 360.0 mg, 74.9%. LCMS m/z=411 [M+H]$^+$

Preparation 192

2-amino-3-{1-[3-(1H-pyrazol-1-yl)pyridin-2-yl]ethoxy}quinoline-6-carbonitrile

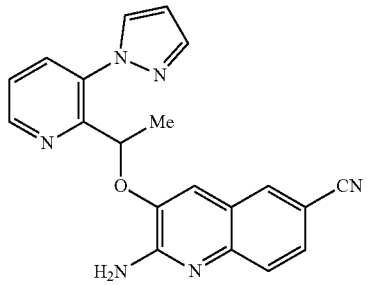 [SMILES: CC(Oc1cc2cc(C#N)ccc2nc1N)c1ncccc1-n1cccn1]

Nitrogen was bubbled through a mixture of 6-bromo-3-{1-[3-(1H-pyrazol-1-yl)pyridin-2-yl]ethoxy}quinolin-2-amine (Preparation 191, 360 mg, 0.88 mmol), Pd$_2$(dba)$_3$ (121.0 mg, 0.132 mmol), tBuXPhos (123.0 mg, 0.26 mmol), Zn(CN)$_2$ (155.0 mg, 1.32 mmol) and TMEDA (20.4 mg, 0.175 mmol), in anhydrous DMF (10 mL), the reaction tube sealed and the reaction mixture heated to 160° C. under microwave irradiation for 1.5 hrs. The cooled mixture was concentrated in vacuo and the residue purified by column chromatography (silica gel) eluting with DCM:MeOH (100:0 to 92:8) to afford the title product as a yellow solid, 270.0 mg, 86.3%. LCMS m/z=357 [M+H]$^+$

Preparation 193

2-amino-3-{(1S)-1-[6-hydroxy-3-(1H-pyrazol-1-yl)pyridin-2-yl]ethoxy}quinoline-6-carboxylic Acid

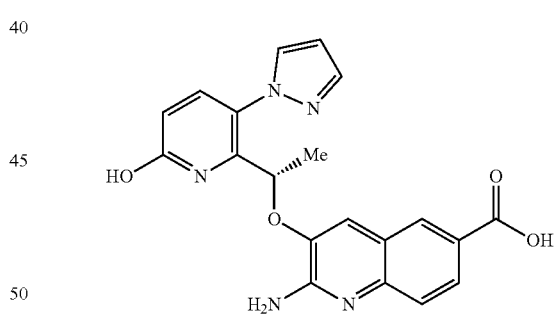

To a solution of methyl 3-{(1S)-1-[6-bromo-3-(1H-pyrazol-1-yl)pyridin-2-yl]ethoxy}-2-(1,3-dioxo-1,3-dihydro-2H-isoindol-2-yl)quinoline-6-carboxylate (Preparation 171, 670 mg, 1.12 mmol) and KOH (188 mg, 3.36 mmol) in 1,4-dioxane/H$_2$O (40 mL/20 mL) was added tBuXPhos (47.5 mg, 0.112 mmol) and Pd$_2$(dba)$_3$ (51.3 mg, 0.056 mmol) under N2. The mixture was degassed with N2 and the reaction mixture stirred at 90° C. for 3 hrs. The mixture was concentrated in vacuo to remove organic solvent and the pH adjusted to 6 with 1N HCl. The mixture was extracted with DCM (3×20 mL) and washed with H$_2$O (5 mL) and brine (5 mL). The mixture was filtered and the filter cake washed with MTBE (2×10 mL) then dried under vacuum to afford the title compound as a brown solid, 438 mg.

LCMS m/z=392 [M+H]$^+$

Preparation 194

1-(2-amino-3-{(1S)-1-[6-hydroxy-3-(1H-pyrazol-1-yl)pyridin-2-yl]ethoxy}quinolin-6-yl)ethanone

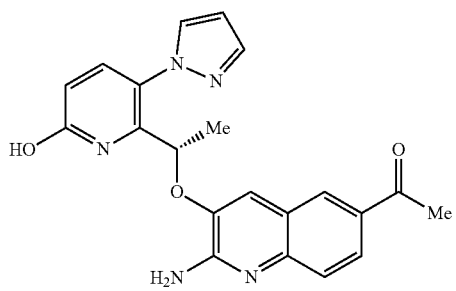 [SMILES: CC(=O)c1ccc2nc(N)c(O[C@@H](C)c3nc(O)ccc3-n3cccn3)cc2c1]

To a solution of 2-amino-3-{(1S)-1-[6-hydroxy-3-(1H-pyrazol-1-yl)pyridin-2-yl]ethoxy}quinoline-6-carboxylic acid (Preparation 193, 150 mg, 0.38 mmol) in DMF (3 mL) was added MeNHOMe HCl (77.1 mg, 0.58 mmol), DIPEA (297 mg, 2.3 mmol) and HATU (291 mg, 0.767 mmol) and the reaction mixture stirred at rt for 1 hr. The mixture was quenched with $H_2O$ (5 mL) and extracted with EtOAc:THF (v:v=3:1, 5×15 mL). The combined organic phases were dried over $Na_2SO_4$, filtered and concentrated in vacuo to give a yellow gum. This was dissolved in THF (10 mL), the solution cooled to 0° C., MeMgBr (4 mL, 3M in $Et_2O$) added and the reaction mixture stirred at rt for 1 hr. The suspension was quenched with 1N HCl (3 mL) and concentrated in vacuo. The residue was partitioned between $H_2O$ (15 mL) and EtOAc/THF, (V/V=2/1, 40 mL), the layers separated and the organic extract dried over $Na_2SO_4$, filtered and evaporated under reduced pressure to afford the title compound as a yellow gum, 150 mg. LCMS m/z=390 $[M+H]^+$

Preparation 195

2-amino-7-fluoro-3-{1-[5-fluoro-3-(1H-pyrazol-1-yl)pyridin-2-yl]ethoxy}quinoline-6-carboxylic Acid

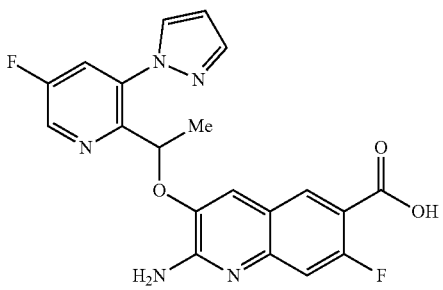 [SMILES: CC(Oc1cc2cc(C(=O)O)c(F)cc2nc1N)c1ncc(F)cc1-n1cccn1]

To a solution of methyl 2-(1,3-dioxo-1,3-dihydro-2H-isoindol-2-yl)-7-fluoro-3-{1-[5-fluoro-3-(1H-pyrazol-1-yl)pyridin-2-yl]ethoxy}quinoline-6-carboxylate (Preparation 187, 150 mg, 0.270 mmol) in THF/MeOH/$H_2O$ (2 mL/2 mL/2 mL) was added NaOH (54.0 mg, 1.35 mmol) and the reaction mixture stirred at 20° C. for 12 hrs. The pH of the reaction mixture was adjusted to 6 using aq HCl, the mixture evaporated under reduced pressure and the product dried by lyophilisation to afford a white solid, which was used without further purification, 111 mg. LCMS m/z=412 $[M+H]^+$

Preparation 196

2-fluoro-3-{1-[5-(1H-pyrazol-1-yl)-1-(tetrahydro-2H-pyran-2-yl)-1H-indazol-6-yl]ethoxy}quinolin-2-amine

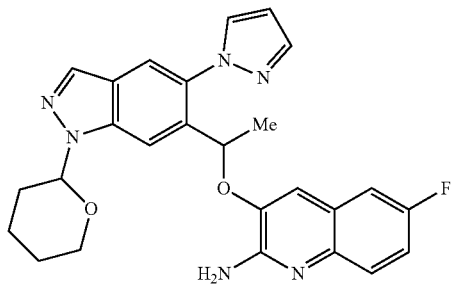 [SMILES: CC(Oc1cc2cc(F)ccc2nc1N)c1cc2c(cnn2C2CCCCO2)cc1-n1cccn1]

MsCl (0.023 mL, 0.298 mmol) was added drop wise to a 0° C. solution of 1-[5-(1H-pyrazol-1-yl)-1-(tetrahydro-2H-pyran-2-yl)-1H-indazol-6-yl]ethanol (Preparation 85, 62 mg, 0.20 mmol) and $Et_3N$ (60.3 mg, 0.60 mmol) in dry DCM (4 mL) and the solution allowed to warm to rt and stirred for 1.5 hrs. The reaction mixture was diluted with DCM (5 mL), quenched with brine (5 mL) and the layers separated. The organic phase was washed with $NaHCO_3$ (5 mL) and brine (5 mL), dried over $Na_2SO_4$ and concentrated in vacuo to give a light yellow oil. A suspension of this oil, 2-amino-6-fluoroquinolin-3-ol (Preparation 134, 40 mg, 0.23 mmol) and $Cs_2CO_3$ (200 mg, 0.615 mmol) in MeCN (5 mL) was stirred at 80° C. for 16 hrs. The reaction mixture was filtered and the filtrate concentrated in vacuo. The residue was purified by flash silica gel column eluting with pet. ether: EtOAc (100:0 to 0:100), to afford the title compound as a light brown oil, 42 mg, 43%. LCMS m/z=473 $[M+H]^+$

Preparation 197

7-chloro-6-fluoro-3-{1-[5-(1H-pyrazol-1-yl)-1-(tetrahydro-2H-pyran-2-yl)-1H-indazol-6-yl]ethoxy}quinolin-2-amine

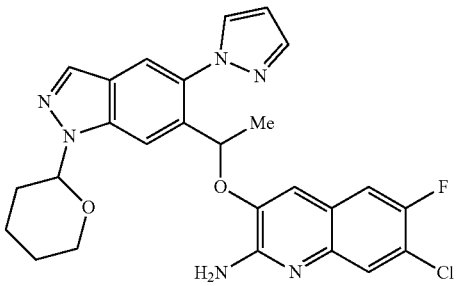 [SMILES: CC(Oc1cc2cc(F)c(Cl)cc2nc1N)c1cc2c(cnn2C2CCCCO2)cc1-n1cccn1]

The title compound was obtained in 35% yield, 50 mg, from 1-[5-(1H-pyrazol-1-yl)-1-(tetrahydro-2H-pyran-2-yl)-1H-indazol-6-yl]ethanol (Preparation 85) and 2-amino-7- chloro-6-fluoroquinolin-3-ol (Preparation 140) by following the procedure described in Preparation 196. LCMS m/z=507 [M+H]+

Preparations 198 to 206

To a solution of the appropriate alcohol (1 eq) and quinolinol or naphthyridinol (1 eq) and PPh$_3$ (3 eq) in dry THF (10-12.5 mL/mmol) was added DIAD (3 eq) drop wise at 0° C. and the reaction mixture stirred at 25° C. for 15 hrs. The reaction mixture was concentrated in vacuo to afford the crude product which was purified by silica gel chromatography eluting with pet. ether:EtOAc at an appropriate gradient to afford the title compound.

198

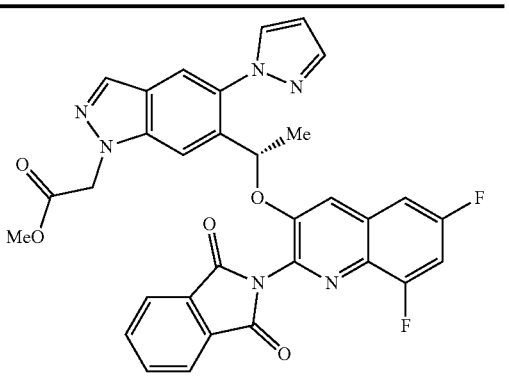

methyl {6-[(1S)-1-{[2-(1,3-dioxo-1,3-dihydro-2H-isoindol-2-yl)-6,8-difluoroquinolin-3-yl]oxy}ethyl]-5-(1H-pyrazol-1-yl)-1H-indazol-1-yl}acetate, yellow gum in quantitative yield.
LCMS m/z = 631 [M + Na]+

199

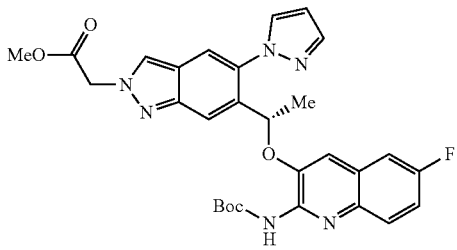

methyl {6-[(1S)-1-({2-[(tert-butoxycarbonyl)amino]-6-fluoroquinolin-3-yl}oxy)ethyl]-5-(1H-pyrazol-1-yl)-2H-indazol-2-yl}acetate, light yellow oil, in quantitative yield.
LCMS m/z = 561 [M + H]+

200

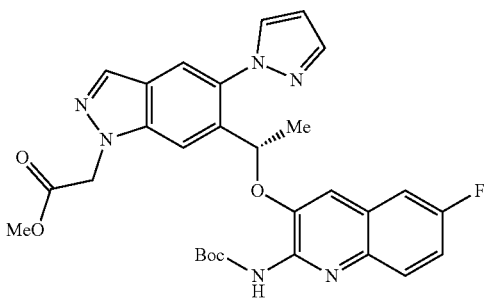

methyl {6-[(1S)-1-({2-[(tert-butoxycarbonyl)amino]-6-fluoroquinolin-3-yl}oxy)ethyl]-5-(1H-pyrazol-1-yl)-1H-indazol-1-yl}acetate, 170 mg, 91% as a light yellow oil.
LCMS m/z = 561 [M + H]+

201

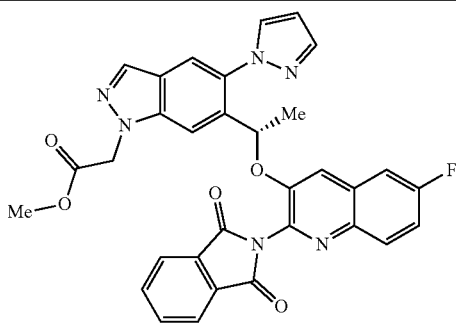

methyl {6-[(1S)-1-{[2-(1,3-dioxo-1,3-dihydro-2H-isoindol-2-yl)-6-fluoroquinolin-3-yl]oxy}ethyl]-5-(1H-pyrazol-1-yl)-1H-indazol-1-yl}acetate, 295 mg, as a green gum.
LCMS m/z = 591 [M + H]+

202

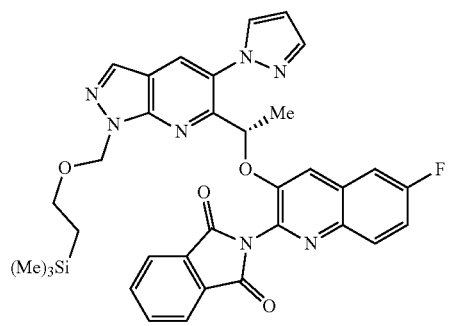

2-(6-fluoro-3-{(1S)-1-[5-(1H-pyrazol-1-yl)-1-{[2-(trimethylsilyl)ethoxy]methyl}-1H-pyrazolo[3,4-b]pyridin-6-yl]ethoxy}quinolin-2-yl)-1H-isoindole-1,3(2H)-dione, a pale yellow gum in quantitative yield.
LCMS m/z = 672 [M + Na]+

203

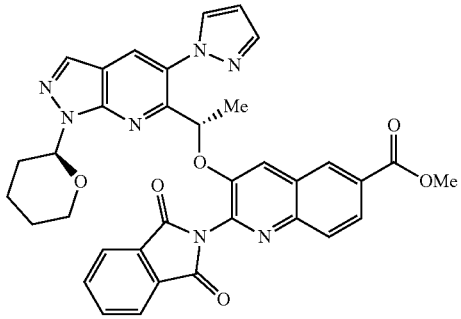

methyl 2-(1,3-dioxo-1,3-dihydro-2H-isoindol-2-yl)-3-[(1S)-1-{5-(1H-pyrazol-1-yl)-1-[(2S)-tetrahydro-2H-pyran-2-yl]-1H-pyrazolo[3,4-b]pyridin-6-yl]ethoxy]quinoline-6-carboxylate, a yellow gum in quantitative yield.
LCMS m/z = 644 [M + H]+

204

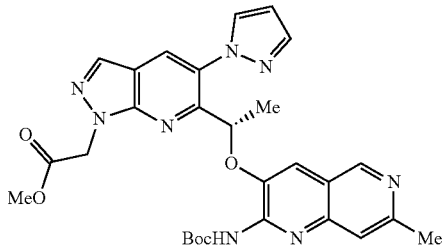

methyl {6-[(1S)-1-({2-[(tert-butoxycarbonyl)amino]-7-methyl-1,6-naphthyridin-3-yl}oxy)ethyl]-5-(1H-pyrazol-1-yl)-1H-pyrazolo[3,4-b]pyridin-1-yl}acetate, a yellow liquid in quantitative yield. LCMS m/z = 559 [M + H]+

205

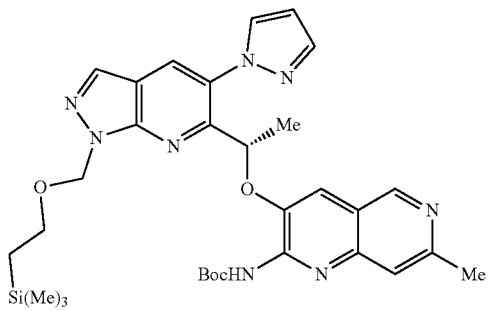

tert-butyl (7-methyl-3-{(1S)-1-[5-(1H-pyrazol-1-yl)-1-{[2-(trimethylsilyl)ethoxy]methyl}-1H-pyrazolo[3,4-b]pyridin-6-yl]ethoxy}-1,6-naphthyridin-2-yl)carbamate, a yellow gum in quantitative yield. LCMS m/z = 617 [M + H]+

206

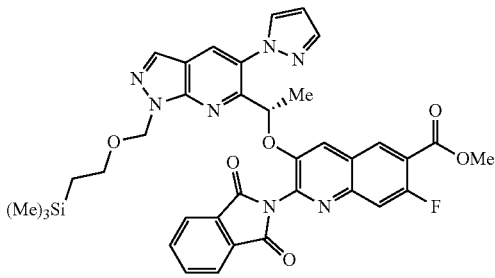

methyl 2-(1,3-dioxo-1,3-dihydro-2H-isoindol-2-yl)-7-fluoro-3-{(1S)-1-[5-(1H-pyrazol-1-yl)-1-{[2-(trimethylsilyl)ethoxy]methyl}-1H-pyrazolo[3,4-b]pyridin-6-yl]ethoxy}quinoline-6-carboxylate, a green gum. LCMS m/z = 730 [M + Na]+

*A* 1.5 eq of DIAD and PPh3 used in the reaction

Preparation 207 tert-butyl {6-[(1S)-1-{[2-(1,3-dioxo-1,3-dihydro-2H-isoindol-2-yl)-6-fluoroquinolin-3-yl]oxy}ethyl]-5-(1H-pyrazol-1-yl)-1H-indazol-1-yl}acetate

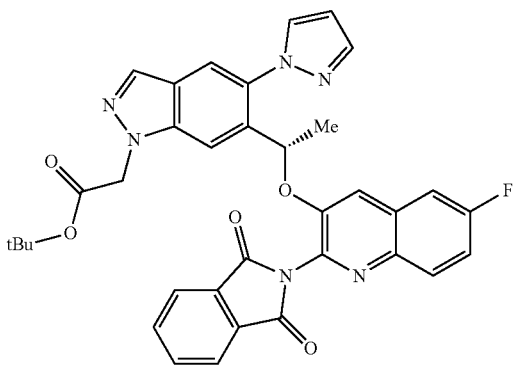 [SMILES: C[C@H](Oc1cc2cc(F)ccc2nc1N1C(=O)c2ccccc2C1=O)c1cc2c(cnn2CC(=O)OC(C)(C)C)cc1-n1cccn1]

DIAD (86.3 mg, 0.427 mmol) in THF (0.5 mL) was added drop wise to a solution of PPh3 (112 mg, 0.43 mmol) in THF (2 mL) in an ice/acetone bath and the solution stirred at 0° C. for 5 mins. A suspension of 2-(6-fluoro-3-hydroxyquinolin-2-yl)-1H-isoindole-1,3(2H)-dione (Preparation 127, 101 mg, 0.328 mmol) in THF (0.7 mL), followed by methyl {6-[(1R)-1-hydroxyethyl]-5-(1H-pyrazol-1-yl)-2H-indazol-2-yl}acetate (Preparation 90, 112 mg, 0.328 mmol) in THF (0.3 mL) was added and the reaction mixture allowed to warm to rt and stirred for 16 hrs. The mixture was diluted with EtOAc, washed with H2O (10 mL), 1N NaOH (10 mL) and brine (10 mL) then dried over MgSO4, filtered and concentrated in vacuo. The crude product was purified by silica gel chromatography eluting with EtOAc:heptane (0:100 to 50:50) to afford the title compound as a white solid, 147.9 mg. LCMS m/z=633 [M+H]+

Preparations 208 to 210

To a solution of the appropriate alcohol (1 eq) and quinolinol or naphthyridinol (1 eq) and PPh3 (3 eq) in dry THF (10-12.5 mL/mmol) was added DIAD (3 eq) drop wise at 0° C. and the reaction mixture stirred at 25° C. for 15 hrs. The reaction mixture was concentrated in vacuo to afford the crude product which was purified by silica gel chromatography eluting with pet. ether:EtOAc at an appropriate gradient to afford the title compound

208 *A*

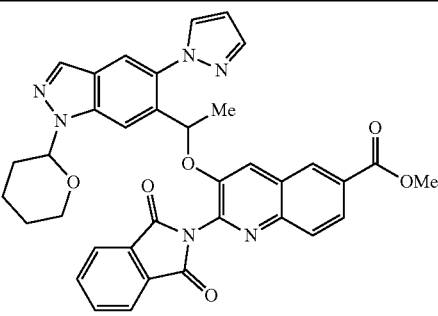

methyl 2-(1,3-dioxo-1,3-dihydro-2H-isoindol-2-yl)-3-{1-[5-(1H-pyrazol-1-yl)-1-(tetrahydro-2H-pyran-2-yl)-1H-indazol-6-yl]ethoxy}quinoline-6-carboxylate, 65 mg, 32% as ayellow solid. LCMS m/z = 665 [M + H]+

209 B

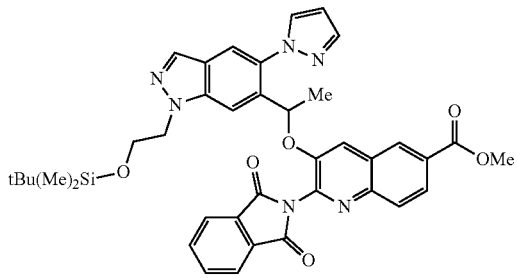

methyl 3-{1-[1-(2-{[tert-butyl(dimethyl)silyl]oxy}ethyl)-5-(1H-pyrazol-1-yl)-1H-indazol-6-yl]ethoxy}-2-(1,3-dioxo-1,3-dihydro-2H-isoindol-2-yl)quinoline-6-carboxylate. 9.50 g, 75.3% as yellow solid. LCMS m/z = 717 [M + H]⁺

210 C,B

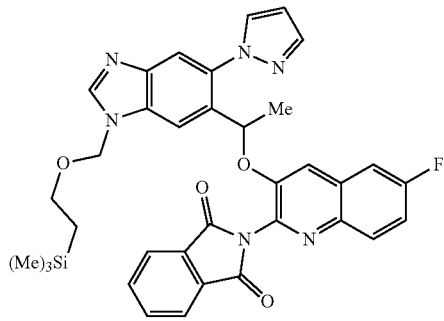

2-(6-fluoro-3-{1-[5-(1H-pyrazol-1-yl)-1-{[2-(trimethylsilyl)ethoxy]methyl}-1H-benzimidazol-6-yl]ethoxy}quinolin-2-yl)-1H-isoindole-1,3(2H)-dione, (421 mg, 100% yield) as a yellow solid. LCMS m/z = 649 [M + H]⁺

[A] 1.2 eq DIAD and PPh₃ used in the reaction
[B] aqueous work-up performed before chromatography
[C] 1.5 eq of DIAD and PPh₃ used in the reaction Preparation 211 methyl 2-(1,3-dioxo-1,3-dihydro-2H-isoindol-2-yl)-7-fluoro-3-{1-[5-(1H-pyrazol-1-yl)-1-{[2-(trimethylsilyl)ethoxy]methyl}-1H-indazol-6-yl]ethoxy}quinoline-6-carboxylate

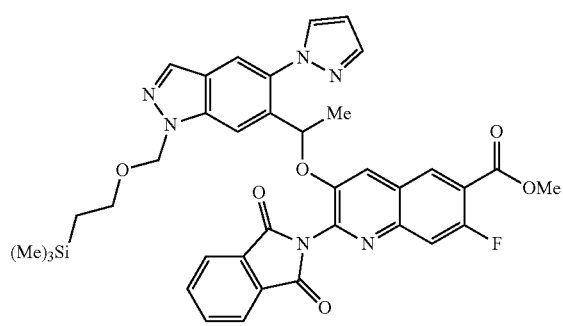

To a solution of 1-[5-(1H-pyrazol-1-yl)-1-{[2-(trimethylsilyl)ethoxy]methyl}-1H-indazol-6-yl]ethanol (Preparation 86, 800 mg, 2.23 mmol) and methyl 2-(1,3-dioxo-1,3-dihydro-2H-isoindol-2-yl)-3-hydroxy-7-fluoroquinoline-6-carboxylate (Preparation 129, 899 mg, 2.45 mmol) in THF (15 mL) was added PPh₃ (878 mg, 3.35 mmol) and DIAD (677 mg, 3.35 mmol) and the reaction mixture stirred at 30° C. for 16 hrs under N2. The yellow solution was diluted with H₂O (15 mL), extracted with EtOAc (3×15 mL) and the combined organic extracts were washed with brine (40 mL), dried over Na₂SO₄, and concentrated in vacuo. The yellow gum was purified by column chromatography eluting with EtOAc: pet. ether (5:95 to 50:50) to afford the title compound as a yellow solid, 1000 mg, 63.4%. LCMS m/z=707 [M+H]⁺

Preparation 212 methyl 2-amino-7-fluoro-3-{1-[5-(1H-pyrazol-1-yl)-1-{[2-(trimethylsilyl)ethoxy]methyl}-1H-indazol-6-yl]ethoxy}quinoline-6-carboxylate

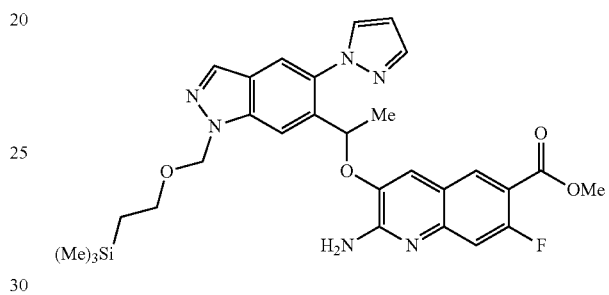

To a suspension of methyl 2-(1,3-dioxo-1,3-dihydro-2H-isoindol-2-yl)-7-fluoro-3-{1-[5-(1H-pyrazol-1-yl)-1-{[2-(trimethylsilyl)ethoxy]methyl}-1H-indazol-6-yl]ethoxy}quinoline-6-carboxylate (Preparation 211, 1000 mg, 1.42 mmol) in EtOH (40 mL) was added hydrazine hydrate (8 mL) and the yellow suspension stirred at 85° C. for 40 mins. The cooled reaction mixture was concentrated in vacuo and the residue suspended in MeOH (15 mL), filtered and the filtrate concentrated in vacuo to provide crude product. This was purified by column chromatography (silica gel), eluting with MeOH:DCM (0:100 to 20:80) to afford the title compound as a yellow solid, 430 mg, 52.7%. LCMS m/z=577 [M+H]⁺

Preparation 213 methyl 2-amino-3-{1-[1-(2-{[tert-butyl(dimethyl)silyl]oxy}ethyl)-5-(1H-pyrazol-1-yl)-1H-indazol-6-yl]ethoxy}quinoline-6-carboxylate

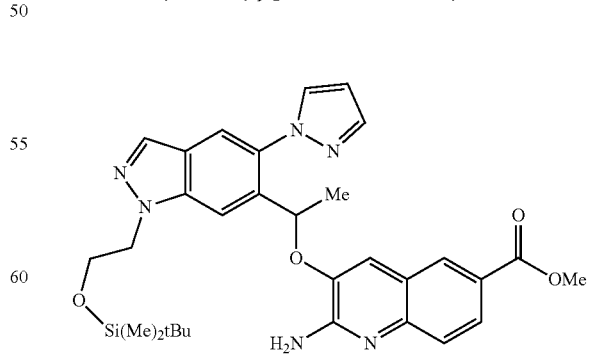

NH₃ gas was bubbled through a solution of methyl 3-{1-[1-(2-{[tert-butyl (dimethyl)silyl]oxy}ethyl)-5-(1H-pyrazol-1-yl)-1H-indazol-6-yl]ethoxy}-2-(1,3-dioxo-1,3-dihydro-2H-isoindol-2-yl)quinoline-6-carboxylate (Preparation 209, 9.5 g, 13.25 mmol) in THF (150 mL) at −60° C. and the reaction mixture stirred at rt in a sealed vessel for 16 hrs. The solution was evaporated under reduced pressure to provide the title compound as a light yellow solid. LCMS m/z=587 [M+H]$^+$ Preparation 214

2-amino-7-fluoro-3-{1-[5-(1H-pyrazol-1-yl)-1-{[2-(trimethylsilyl)ethoxy]methyl}-1H-indazol-6-yl]ethoxy}quinoline-6-carboxylic Acid

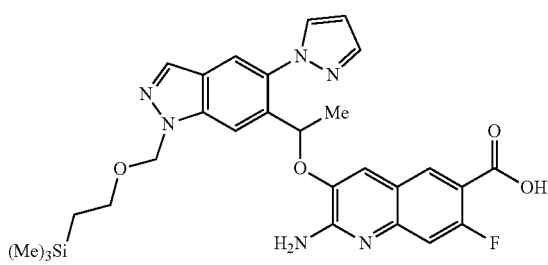

To a solution of methyl 2-amino-7-fluoro-3-{1-[5-(1H-pyrazol-1-yl)-1-{[2-(trimethylsilyl)ethoxy]methyl}-1H-indazol-6-yl]ethoxy}quinoline-6-carboxylate (Preparation 212, 380 mg, 0.66 mmol) in MeOH (3 mL) was added 2N NaOH (3 mL, 6 mmol) and the yellow solution stirred at 15° C. for 80 hrs. Additional 2N NaOH (0.5 mL, 1 mmol) was added and the reaction mixture stirred at 30° C. for a further 4.5 hrs. The mixture was neutralised using 1N HCl and the resulting suspension extracted with EtOAc (3×5 mL). The combined organic extracts were washed with brine (10 mL), dried over Na$_2$SO$_4$ and evaporated under reduced pressure to afford the title compound as a yellow solid, 320 mg, 86.3%. LCMS m/z=563 [M+H]$^+$ Preparation 215

2-amino-3-{1-[1-(2-{[tert-butyl(dimethyl)silyl]oxy}ethyl)-5-(1H-pyrazol-1-yl)-1H-indazol-6-yl]ethoxy}quinoline-6-carboxamide

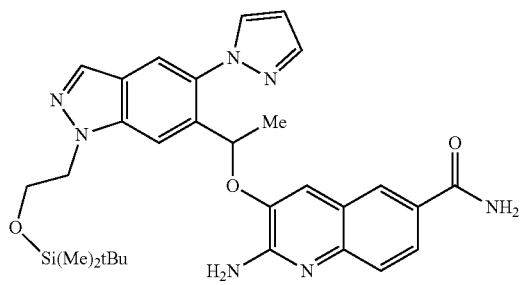

NH$_3$ gas was bubbled through a solution of methyl 2-amino-3-{1-[1-(2-{[tert-butyl(dimethyl)silyl]oxy}ethyl)-5-(1H-pyrazol-1-yl)-1H-indazol-6-yl]ethoxy}quinoline-6-carboxylate (Preparation 213, 7.78 g, 0.86 mmol) in MeOH (70 mL) for 10 mins at −60° C., the reaction mixture then sealed in an autoclave and stirred at 80° C. for 90 hrs. The cooled solution was concentrated in vacuo and the residue was dried in vacuo to give crude product. This was purified by column chromatography (silica gel) eluting with EtOAc:pet. ether (30:70 to 100:0) to provide the title compound as a light yellow solid, 2.2 g, 29%. LCMS m/z=572 [M+H]$^+$ Preparation 216

2-amino-7-fluoro-3-{1-[5-(1H-pyrazol-1-yl)-1-{[2-(trimethylsilyl)ethoxy]methyl}-1H-indazol-6-yl]ethoxy}quinoline-6-carboxamide

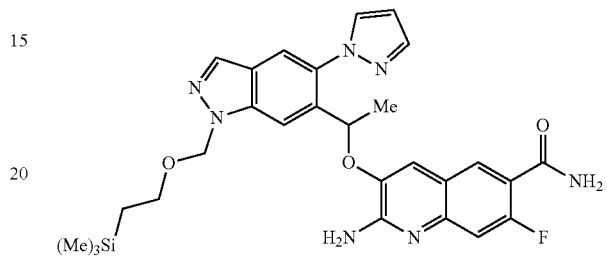

To a yellow solution of 2-amino-7-fluoro-3-{1-[5-(1H-pyrazol-1-yl)-1-{[2-(trimethylsilyl)ethoxy]methyl}-1H-indazol-6-yl]ethoxy}quinoline-6-carboxylic acid (Preparation 214, 310 mg, 0.55 mmol) in THF (3 mL) was added HATU (209 mg, 0.55 mmol) and NH$_4$Cl (29.5 mg, 0.55 mmol) and the mixture stirred at 15° C. for 20 mins. Et$_3$N (167 mg, 1.65 mmol) was added and the reaction mixture stirred for 36 hrs. The yellow suspension was diluted with H$_2$O (8 mL), extracted with EtOAc (3×8 mL), the combined organic extracts washed with brine (20 mL), dried over Na$_2$SO$_4$, and concentrated in vacuo. The crude product was purified by prep-TLC eluting with EtOAc to afford the title compound as a yellow solid, 60 mg, 19%. LCMS m/z=562 [M+H]$^+$ Preparation 217

2-amino-3-{1-[5-(1H-pyrazol-1-yl)-1-(tetrahydro-2H-pyran-2-yl)-1H-indazol-6-yl]ethoxy}quinoline-6-carboxamide

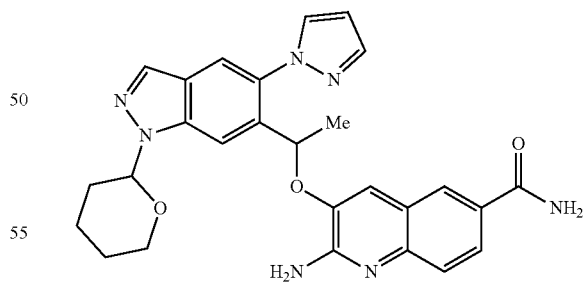

Calcium chloride (518 mg, 4.67 mmol) was added to a solution of methyl 2-(1,3-dioxo-1,3-dihydro-2H-isoindol-2-yl)-3-{1-[5-(1H-pyrazol-1-yl)-1-(tetrahydro-2H-pyran-2-yl)-1H-indazol-6-yl]ethoxy}quinoline-6-carboxylate (Preparation 208, 1.0 g, 1.56 mmol) in methanolic NH$_3$ (30 mL, 7.0 M) and the reaction mixture stirred at 80° C. in a sealed tube for 18 hrs. The cooled reaction mixture was concentrated in vacuo, H$_2$O (10 mL) added and the solution extracted with DCM (3×20 mL). The combined organic extracts were dried over Na₂SO₄, filtered and evaporated under reduced pressure to afford the title compound as a yellow gum, 600 mg, 77.5%. LCMS m/z=498 [M+H]⁺

Preparation 218 tert-butyl (6-fluoro-3-{(1S)-1-[1-(2-hydroxyethyl)-5-(1H-pyrazol-1-yl)-1H-indazol-6-yl]ethoxy}quinolin-2-yl)carbamate

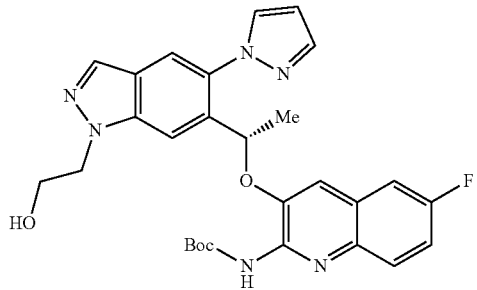 [SMILES: C[C@H](Oc1cc2cc(F)ccc2nc1NC(=O)OC(C)(C)C)c1cc2c(cnn2CCO)cc1-n1cccn1]

To a solution of methyl {6-[(1S)-1-({2-[(tert-butoxycarbonyl)amino]-6-fluoroquinolin-3-yl}oxy)ethyl]-5-(1H-pyrazol-1-yl)-1H-indazol-1-yl}acetate (Preparation 200, 103 mg, 0.184 mmol) in MeOH/THF (1 mL/3 mL) was added NaBH₄ (34.8 mg, 0.92 mmol) by portion at rt. The reaction mixture was stirred at rt for 3 hrs, then additional NaBH₄ (34.8 mg, 0.92 mmol) was added and the reaction mixture stirred for another 3 hrs. The mixture was poured into saturated aq NaHCO₃ and concentrated in vacuo to remove the organic solvent, then extracted with EtOAc (2×15 mL). The combined organic layers were dried over Na₂SO₄, filtered, and concentrated in vacuo. The residue was purified by column chromatography (silica gel) eluting with EtOAc:pet. ether (0:100 to 80:20) to afford the title compound as a light yellow gum, 79 mg, 81%. LCMS m/z=533 [M+H]⁺

Preparation 219

{6-[(1S)-1-({2-[(tert-butoxycarbonyl)amino]-6-fluoroquinolin-3-yl}oxy)ethyl]-5-(1H-pyrazol-1-yl)-2H-indazol-2-yl}acetic Acid

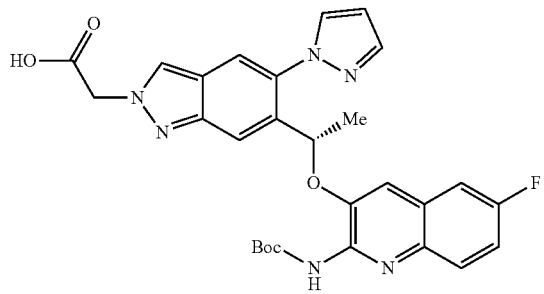 [SMILES: C[C@H](Oc1cc2cc(F)ccc2nc1NC(=O)OC(C)(C)C)c1cc2nn(CC(=O)O)cc2cc1-n1cccn1]

To a solution of methyl {6-[(1S)-1-({2-[(tert-butoxycarbonyl)amino]-6-fluoroquinolin-3-yl}oxy)ethyl]-5-(1H-pyrazol-1-yl)-2H-indazol-2-yl}acetate (Preparation 199, 190 mg, 0.34 mmol) in dry THF/MeOH (3 mL/3 mL) was added 2M NaOH (1.1 mL, 2.2 mmol) and the reaction mixture stirred at rt for 1 hr. The reaction mixture was extracted with EtOAc (3×10 mL), the combined organic extracts washed with H₂O (2×5 mL), the aqueous layers combined and acidified to pH 3-5 using 1 N HCl. This aqueous solution was extracted with EtOAc (3×10 mL), these combined organic layers dried over anhydrous Na₂SO₄, filtered and concentrated in vacuo to afford the title compound as a light yellow gum, 80 mg, 43%. LCMS m/z=547 [M+H]⁺

Preparation 220 tert-butyl (3-{(1S)-1-[1-(2-hydroxyethyl)-5-(1H-pyrazol-1-yl)-1H-pyrazolo[3,4-b]pyridin-6-yl]ethoxy}-7-methyl-1,6-naphthyridin-2-yl)carbamate

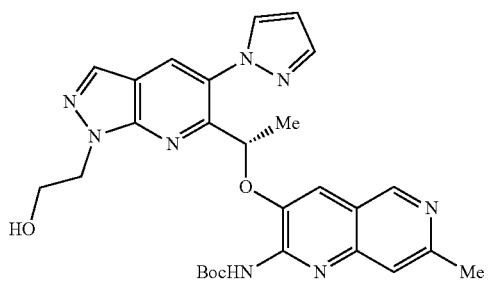 [SMILES: Cc1cc2nc(NC(=O)OC(C)(C)C)c(O[C@@H](C)c3nc4c(cnn4CCO)cc3-n3cccn3)cc2cn1]

To a solution of methyl {6-[(1S)-1-({2-[(tert-butoxycarbonyl)amino]-7-methyl-1,6-naphthyridin-3-yl}oxy)ethyl]-5-(1H-pyrazol-1-yl)-1H-pyrazolo[3,4-b]pyridin-1-yl}acetate (Preparation 204, 120 mg, 0.215 mmol) in anhydrous THF (2 mL) was added LiAlH₄ (16.3 mg, 0.43 mmol) at 0° C. and the reaction mixture stirred for 1 hr. The reaction mixture was quenched by the addition of H₂O (16.3 mL) followed by 15% aqueous NaOH (16.3 mL) and the mixture stirred at rt for 15 mins. The resulting solid was filtered off and the filtrate evaporated under reduced pressure to afford the title compound as a brown solid. LCMS m/z=531 [M+H]⁺

Preparation 221

2-amino-3-[(1S)-1-{5-(1H-pyrazol-1-yl)-1-[(2S)-tetrahydro-2H-pyran-2-yl]-1H-pyrazolo[3,4-b]pyridin-6-yl]ethoxy}quinoline-6-carboxamide

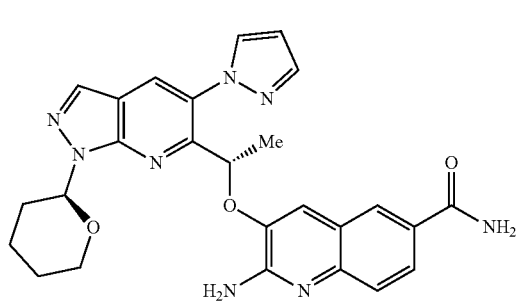 [SMILES: C[C@H](Oc1cc2cc(C(N)=O)ccc2nc1N)c1nc2c(cnn2[C@@H]2CCCCO2)cc1-n1cccn1]

A solution of methyl 2-(1,3-dioxo-1,3-dihydro-2H-isoindol-2-yl)-3-[(1S)-1-{5-(1H-pyrazol-1-yl)-1-[(2S)-tetrahydro-2H-pyran-2-yl]-1H-pyrazolo[3,4-b]pyridin-6-yl}ethoxy]quinoline-6-carboxylate (Preparation 203, 1.25 g, 1.95 mmol) in methanolic NH₃ (25 mL, 7M) was stirred at 80° C. in a sealed tube for 18 hrs. The cooled solution was evaporated under reduced pressure to afford a yellow gum. This was dissolved in fresh methanolic NH₃ (25 mL, 7M) and the reaction mixture stirred in a sealed vessel at 80° C. for 66 hrs. The cooled solution was evaporated under reduced pressure to afford the title compound as a red gum. LCMS m/z=499 [M+H]⁺

Preparation 222

2-amino-7-fluoro-3-{(1S)-1-[5-(1H-pyrazol-1-yl)-1-{[2-(trimethylsilyl)ethoxy]methyl}-1H-pyrazolo[3,4-b]pyridin-6-yl]ethoxy}quinoline-6-carboxamide

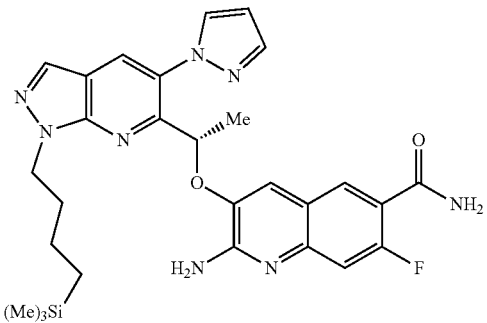

A solution of methyl 2-(1,3-dioxo-1,3-dihydro-2H-isoindol-2-yl)-7-fluoro-3-{(1S)-1-[5-(1H-pyrazol-1-yl)-1-{[2-(trimethylsilyl)ethoxy]methyl}-1H-pyrazolo[3,4-b]pyridin-6-yl]ethoxy}quinoline-6-carboxylate (Preparation 206, 120 mg, 0.17 mmol) in methanolic NH₃ (~8 M, 10 mL) was stirred at 80° C. in a sealed tube for 16 hrs. The cooled reaction mixture was evaporated under reduced pressure to afford the title compound, which was used directly in the next step. LCMS m/z=585 [M+Na]⁺

Preparation 223

2-fluoro-3-{1-[5-(1H-pyrazol-1-yl)-1-{[2-(trimethylsilyl)ethoxy]methyl}-1H-benzimidazol-6-yl]ethoxy}quinolin-2-amine

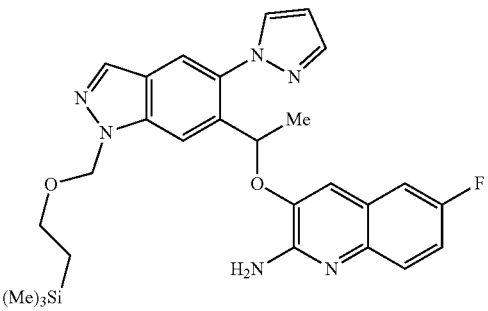

A yellow solution of 2-(6-fluoro-3-{1-[5-(1H-pyrazol-1-yl)-1-{[2-(trimethylsilyl)ethoxy]methyl}-1H-benzimidazol-6-yl]ethoxy}quinolin-2-yl)-1H-isoindole-1,3(2H)-dione (Preparation 210, 421 mg, 0.65 mmol) and N₂H₄.H₂O (3 mL) in EtOH (20 mL) was stirred at 85° C. for 1 hr. The yellow solution was concentrated in vacuo, MeOH (20 mL) added and the yellow solid filtered off. The filtrate was concentrated in vacuo and the yellow oil purified by prep-TLC (DCM:MeOH 20:1) to afford the title compound as a yellow oil, 241 mg, 71.6%. LCMS m/z=519 [M+H]⁺

Preparation 224

2-(6-fluoro-3-{1-[2-methyl-5-(1H-pyrazol-1-yl)-1-{[2-(trimethylsilyl)ethoxy]methyl}-1H-benzimidazol-6-yl]ethoxy}quinolin-2-yl)-1H-isoindole-1,3(2H)-dione

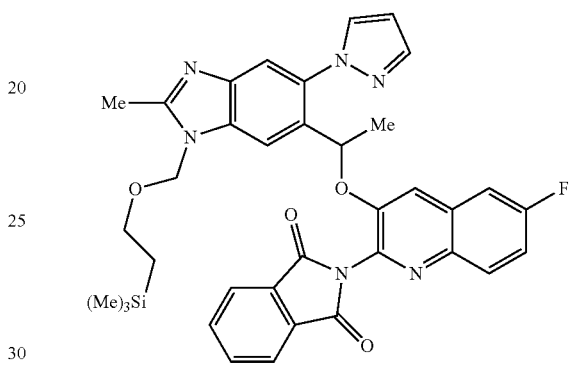

To a yellow solution of 1-[2-methyl-5-(1H-pyrazol-1-yl)-1H-benzimidazol-6-yl]ethanone (Preparation 84, 50 mg, 0.21 mmol) in DMF (2 mL) was added NaH (13.3 mg, 0.333 mmol) and the suspension stirred at 15° C. for 0.5 h. The suspension was cooled to 0° C., SEMCl (55.5 mg, 0.333 mmol) added and the reaction mixture stirred at rt for 1.5 hrs. The suspension was quenched with H₂O (5 mL), diluted with EtOAc (20 mL) and H₂O (15 mL). The separated aqueous phase was extracted with EtOAc (2×15 mL), the combined organic extracts were washed with brine (2×20 mL), dried over Na₂SO₄, filtered and concentrated in vacuo. The crude product was purified by prep-TLC (DCM: MeOH=12:1) to yield a pale yellow oil, 50 mg, 65%. The reaction was repeated so as to obtain 150 mg of product. To a solution of the yellow oil (150 mg, 0.405 mmol) in MeOH (10 mL) was added NaBH₄ (58.2 mg, 1.54 mmol) and the solution stirred at rt for 2 hrs. The reaction mixture was concentrated in vacuo to give a white residue, which was partitioned between DCM (20 mL) and H₂O (15 mL), the layers separated and the aqueous extracted with DCM (2×15 mL). The combined organic extracts were dried over Na₂SO₄, filtered and concentrated in vacuo to give the desired product (145 mg, 96.1%) as a colorless gum. The reaction was repeated so as to obtain 195 mg of product. To a solution of the gum (195 mg, 0.523 mmol), 2-(6-fluoro-3-hydroxyquinolin-2-yl)-1H-isoindole-1,3(2H)-dione (Preparation 127, 194 mg, 0.628 mmol) and PPh₃ (206 mg, 0.785 mmol) in THF (11 mL) was added a solution of DIAD (159 mg, 0.785 mmol) in THF (1 mL) at 0° C. and the reaction mixture then stirred at rt for 16 hrs. The solution was concentrated in vacuo and the residue purified by column chromatography on silica gel eluting with MeOH (NH₄OH):DCM (0-1.3%) to afford the title compound as a pale yellow gum, 230 mg, 66.3%. LCMS m/z=663 [M+H]⁺

Preparation 225

2-fluoro-3-{1-[2-methyl-5-(1H-pyrazol-1-yl)-1-{[2-(trimethylsilyl)ethoxy]methyl}-1H-benzimidazol-6-yl]ethoxy}quinolin-2-amine

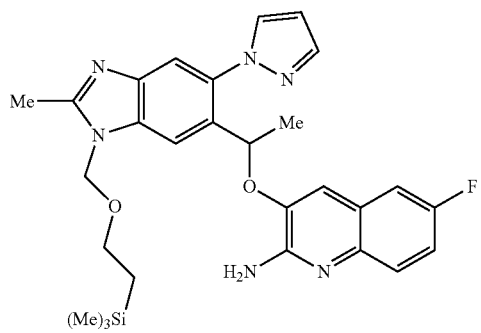

To a yellow solution of 2-(6-fluoro-3-{1-[2-methyl-5-(1H-pyrazol-1-yl)-1-{[2-(trimethylsilyl)ethoxy]methyl}-1H-benzimidazol-6-yl]ethoxy}quinolin-2-yl)-1H-isoindole-1,3(2H)-dione (Preparation 224, 230 mg, 0.347 mmol) in EtOH (5 mL) was added N2H4.H2O (3 mL) and the yellow solution stirred at 85° C. for 1 hr. The solution was concentrated in vacuo, the gum was suspended in MeOH (5 mL) and the white solids were filtered off. The filtrate was concentrated in vacuo and the product purified by prep-TLC eluting with DCM:MeOH:NH3 (20:1:0.5) to afford the desired product as pale yellow gum, 110 mg, 59.5%. LCMS m/z=533 [M+H]$^+$

Preparation 226

1-(6-bromo-3-(1H-pyrazol-1-yl)pyridin-2-yl)ethan-1,2,2,2-d$_4$-1-ol

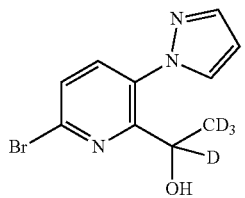 [SMILES: [2H]C([2H])([2H])C([2H])(O)c1nc(Br)ccc1-n1cccn1]

Step 1

To a yellow solution of 1-[6-bromo-3-(1H-pyrazol-1-yl)pyridin-2-yl]ethanone (Preparation 34, 2.1 g 7.9 mmol) in THF (10 mL) was added a solution of LiOD in D$_2$O (3M, 10.5 mL) at 20° C. After 48 hrs, the red solution was extracted with DCM (3×20 mL), dried over Na$_2$SO$_4$, filtered and concentrated in vacuo to give 1-(6-bromo-3-(1H-pyrazol-1-yl)pyridin-2-yl)ethan-1-one-2,2,2-d$_3$ (2.09 g, 98.4%) as a red solid.

Step 2

To a yellow solution of 1-(6-bromo-3-(1H-pyrazol-1-yl)pyridin-2-yl)ethan-1-one-2,2,2-d$_3$ (2.09 g 7.8 mmol) in CD$_3$OD (10.0 mL) was added NaBD$_4$ (260 mg, 6.21 mmol) at 25° C. After 1 hr, the reaction mixture was quenched with acetone (5 mL) and the solvent was removed in vacuo. The residue was purified by column chromatography (20 g silica gel, EtOAc/PE=0~25%~35%) to afford the title compound (1.96 g, 92.7%) as a yellow solid. LCMS m/z=272/274 [M+H]$^+$. $^1$H NMR (400 MHz, DMSO-d$_6$) b 5.33-5.26 (m, 1H), 6.59 (t, 1H), 7.76-7.71 (m, 1H), 7.83 (dd, 2H), 8.20 (d, 1H).

Preparation 227 tert-butyl (3-(1-(6-bromo-3-(1H-pyrazol-1-yl)pyridin-2-yl)ethoxy-1,2,2,2-d$_4$)-6-fluoroquinolin-2-yl)carbamate

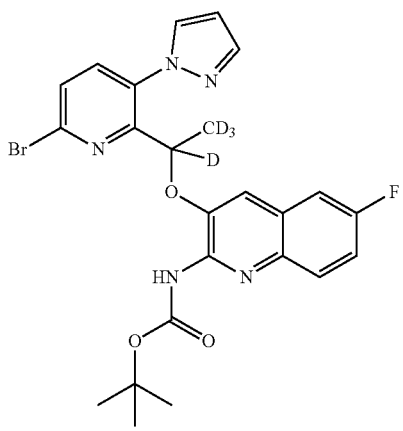 [SMILES: [2H]C([2H])([2H])C([2H])(Oc1cc2cc(F)ccc2nc1NC(=O)OC(C)(C)C)c1nc(Br)ccc1-n1cccn1]

The title compound was obtained as a light yellow solid, 2.8 g, 73%, from tert-butyl (6-fluoro-3-hydroxyquinolin-2-yl)carbamate (Preparation 105) and 1-(6-bromo-3-(1H-pyrazol-1-yl)pyridin-2-yl)ethan-1,2,2,2-d$_4$-1-ol (Preparation 226), by following the procedure described for Preparations 167 to 180. LCMS m/z=530.3/532.3 [M−H]$^-$. $^1$H NMR (300 MHz, CDCl$_3$) E11.60 (s, 6H), 1.65 (s, 3H), 6.57 (s, 1H), 6.97 (s, 1H), 7.04 (dd, 1H), 7.16-.7.24 (m, 1H), 7.45-7.60 (m, 3H), 7.86 (s, 1H), 7.90-7.95 (m, 2H).

Preparation 228 methyl 3-(1-hydroxyethyl-1,2,2,2-d$_4$)-4-(1H-pyrazol-1-yl)benzoate

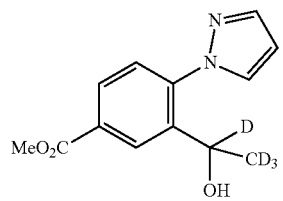 [SMILES: [2H]C([2H])([2H])C([2H])(O)c1cc(C(=O)OC)ccc1-n1cccn1]

Step 1

To a suspension of methyl 3-[(1S)-1-hydroxyethyl]-4-(1H-pyrazol-1-yl)benzoate (Preparation 27, 1.20 g, 4.92 mmol) in D$_2$O (24 mL) at rt, was added NaOD (40% wt in D₂O, 1 mL, 14.75 mmol) and THF (6 mL). After stirring overnight at rt, LCMS analysis showed formation of the desired intermediate. Then, NaBD₄ (210 mg, 4.92 mmol) was added in one portion at rt. After stirring for 1 hr, the reaction mixture was cooled with an ice bath, acidified with aqueous 2M HCl and extracted with ethyl acetate (3×). The combined organic layers were dried over Na₂SO₄, filtered and evaporated to afford 3-(1-hydroxyethyl-1,2,2,2-d₄)-4-(1H-pyrazol-1-yl)benzoic acid (1.4 g, quantitative yield) as a white solid.

Step 2

To a solution of 3-(1-hydroxyethyl-1,2,2,2-d₄)-4-(1H-pyrazol-1-yl)benzoic acid (1.40 g, 4.92 mmol) in methanol (25 mL) at rt, was added sulfuric acid 95% concentrated (5-6 drops). The resulting solution was heated under reflux for 10 hrs, cooled to rt and evaporated to dryness. The residue was dissolved in ethyl acetate, washed with saturated NaHCO₃, dried over Na₂SO₄, filtered and evaporated. The crude product was then purified on silica gel (4 g, elution with 0 to 20% ethyl acetate in heptane) to afford the title compound (1.1 g, 89%) as a colorless oil. LCMS m/z=251.2 [M+H]⁺. ¹H NMR (300 MHz, CDCl₃) δ 3.95 (s, 3H), 6.53 (t, 1H), 7.36 (d, 1H), 7.78 (d, 2H), 8.05 (d, 1H), 8.30 (d, 1H).

Preparation 229 methyl 3-(1-((2-(1,3-dioxoisoindolin-2-yl)-6,8-difluoroquinolin-3-yl)oxy)ethyl-1,2,2,2-d₄)-4-(1H-pyrazol-1-yl)benzoate

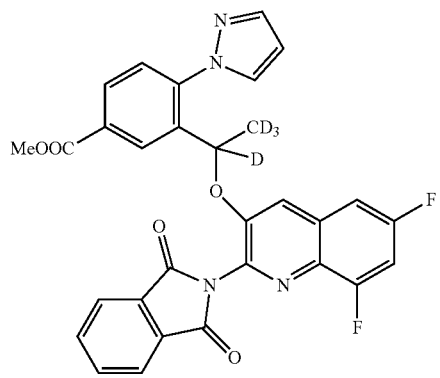 [SMILES: [2H]C([2H])([2H])C([2H])(Oc1cc2cc(F)cc(F)c2nc1N1C(=O)c2ccccc2C1=O)c1cc(C(=O)OC)ccc1-n1cccn1]

The title compound was obtained as a light yellow solid, 1.35 g, 74%, from 2-(6,8-difluoro-3-hydroxyquinolin-2-yl)-1H-isoindole-1,3(2H)-dione (Preparation 133) and methyl 3-(1-hydroxyethyl-1,2,2,2-d₄)-4-(1H-pyrazol-1-yl)benzoate (Preparation 228), by following the procedure described for Preparations 145 to 153. LCMS m/z=580.8 [M+Na]⁺.

Preparation 230

(S)-3-(1-((2-(1,3-dioxoisoindolin-2-yl)-6,8-difluoroquinolin-3-yl)oxy)ethyl)-4-(1H-pyrazol-1-yl)benzonitrile

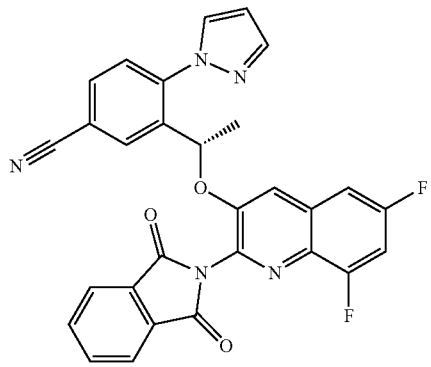 [SMILES: C[C@H](Oc1cc2cc(F)cc(F)c2nc1N1C(=O)c2ccccc2C1=O)c1cc(C#N)ccc1-n1cccn1]

The title compound was obtained as a yellow gum, 940 mg, 96%, from 2-(6,8-difluoro-3-hydroxyquinolin-2-yl)-1H-isoindole-1,3(2H)-dione (Preparation 133) and 3-[(1R)-1-hydroxyethyl]-4-(1H-pyrazol-1-yl)benzonitrile (Preparation 31), by following the procedure described for Preparations 145 to 153. LCMS m/z 522.2 [M+1]⁺

Preparation 231

2-[(4-methoxybenzyl)oxy]acetonitrile

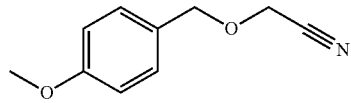

A solution of (4-methoxyphenyl)methanol (75 g, 540 mmol) in anhydrous THF (100 mL) was added dropwise to a suspension of sodium hydride (16.9 g, 706 mmol) in anhydrous THF (500 mL) at 0° C. The resulting mixture was stirred at 0° C. for 2 hrs and then treated dropwise with a solution of 2-bromoacetonitrile (78.1 g, 651 mmol) in anhydrous THF (154 mL) over 1 hr. The resulting reaction mixture was stirred at rt for 16 hrs. Saturated aqueous ammonium chloride (200 mL) was then added cautiously. After complete addition, the mixture was filtered. EtOAc (250 mL) was added, and the layers were separated. The aqueous layer was then extracted with EtOAc (2×250 mL). The combined organic layers were washed with brine (50 mL), dried (Na₂SO₄), filtered, and concentrated under reduced pressure. The crude product was then purified by flash chromatography (silica gel) eluting with a gradient of petroleum ether:ethyl acetate (100:0 to 80:20) to afford 60.8 g (63%) of the title compound as a light yellow liquid.

LCMS m/z=200.1 [M+Na]. ¹H NMR (400 MHz, CDCl₃) δ 3.81 (s, 3H), 4.19 (s, 2H), 4.58 (s, 2H), 6.90 (d, 2H), 7.28 (d, 2H).

Biological Assays

In Vitro Studies
Binding Affinity, Kd (uM)

The binding affinity for compounds to purified sickle cell hemoglobin (HbS) was determined using Surface Plasmon Resonance (SPR). Patient Sickle Cell blood was obtained from Boston Children's Hospital in accordance with Institutional Review Board protocols. HbS was obtained from the blood of homozygous S/S patients, and purified using the method described in: Antonini and Brunori, Hemoglobin and Myoglobin in their Reactions with Ligands. Amsterdam, London, North-Holland Publishing Company, 1971. Whole blood was separated into red blood cell and plasma components by centrifugation, after which the plasma was decanted and discarded. Packed red blood cells were washed with normal saline (0.9% NaCl) and then lysed by 2:1 dilution with cold deionized water. The hemolysate was centrifuged to remove cellular debris, and further purified with the addition of Drabkin's Buffer (2.8 M potassium phosphate), and centrifugation with Celite®. Organic phosphates (2,3-BPG) were removed via gel filtration with Sephadex® G-25. HbS and wild-type hemoglobin, hemoglobin A (HbA), were separated by cation exchange chromatography, using diethylaminoethyl (DEAE)-Sepharose® fast flow, and eluted using a pH gradient from pH 8.5-pH 7.5. Purity of the resulting HbS and HbA was determined by native gel electrophoresis and HbS fractions used further.

To stabilize the tetrameric structure of hemoglobin, HbS was crosslinked between the beta subunits (Lys82-Lys82) using bis(3,5-dibromosalicyl) fumarate, as described in: Shibayama N. et al, J Am Chem Soc 2014, 136, 13, 5097-5105 and Shibayama N. et al, Biochemistry 1991, 39, 33, 8158-8165). Crosslinked HbS was subsequently biotynylated and captured on a custom made Streptavidin sensor to achieve protein density of 4000 to 5000 resonance units (RUs) on the surface. Compound binding to HbS using SPR was tested on Sierra Sensors MASS-1 instrument. The running buffer contained 100 mM Potassium Phosphate, pH 7.5, 0.005% Tween-20, 1 mM ethylenediaminetetraacetic acid (EDTA), 0.1 mg/mL bovine serum albumin with 1% DMSO. Compound samples were injected at a flow rate of 30 µL/min for 2 minutes association and at least 5 minutes of dissociation time. A 2- or 3-fold dilution series containing at least 4 concentrations were tested for each compound. The dose range was selected based on the activity of the compounds in biochemical assays, when available. Multiple blank injections of running buffer were run before and after each compound series to allow blank subtraction for compound data in the analysis software. Positive controls were run in each experiment to monitor and maintain the activity of HbS on the surface. A DMSO curve was run at the beginning of each data set to apply an excluded volume correction to the data during analysis. The data were processed and analyzed using Sierra Sensors and Scrubber 2.0 software. The binding affinities (dissociation constant Kd) were calculated by fitting the sensorgrams to a 1:1 binding model. Kd (uM) values for compounds of the invention are presented in Table 4 that follows.

'R'-'T' Assay (Delay in Oxygenation, and Hence Polymerization, of HbS), $IC_{50}$ (uM)

Conversion from oxy (R, relaxed state) to deoxy (T, tense state) HbS in the presence of compound was performed to determine the ability of compounds to stabilize the oxy (R) state under deoxygenating conditions. The assay run was similar to the 'Oxygen dissociation assay' described in Oksenberg et al, Br J Haematology, 2016, 175, 141-153.

Assay ready compound plates were prepared by first preparing a master serial dilution plate from a 30 mM initial compound stock in 100% DMSO. From this master serial dilution plate, 167 nL of the desired compound concentration was delivered to the assay ready plates using acoustical dispensing. Plates were frozen at −20° C. until needed. Purified HbS-O$_2$ (i.e. oxy HbS) was diluted to 3 uM in 100 mM potassium phosphate buffer, pH=7.4. 50 uL of 3 uM stock solution was added to each well of the assay ready plate and mechanically mixed eight times. Following mixing the plates were covered and incubated at room temperature for one hour with moderate shaking. Following incubation, the plates were placed in a deoxygenated environment (<1% O$_2$) for two hours, and the conversion to deoxy HbS monitored as a function of time. Oxygenated and deoxygenated forms of hemoglobin were detected using the absorbance of the Soret peaks at 415 and 430 nm respectively, and absorbance measurements (optical density, OD) were taken at 0, 90 and 120 minutes. Background absorbance for correction was collected at 700 nm.

Data were analyzed by first subtracting baseline absorbance at 700 nm from 415 nm and 430 nm data at each timepoint, and then taking the ratio of 415/430 nm data (Ratio=$[(OD_{415}-OD_{700})/(OD_{430}-OD_{700})]$. The effect at each timepoint was calculated using the ratios from the previous calculation at time 0 and each time point of interest (Effect$^{time\ x}$=Ratio$^{time\ x}$/Ratio$^{time\ 0}$). Percent effect was calculated by comparing the effects of compound versus HbS only with the effects observed by the positive control compound tucaresol (percent effect=$[(effect^{time\ x}$ compound−effect$^{time\ x}$ HbS)/(effect$^{time\ x}$ tucaresol−effect$^{time\ x}$ HbS)]×100). Data were reported as the percent effect for a single point. Calculations to determine the concentration of compound for 50% inhibition ($IC_{50}$ (uM)) of the HbS 'R'-'T' conversion were based on the percent effect at varying compound concentration. IC50 (uM) values for compounds of the invention are presented in Table 4 below.

TABLE 4

In Vitro Study Data

| Ex | Kd | n | $IC_{50}$ | n |
|---|---|---|---|---|
| 1 | 0.020 | 2 | 4.50 | 4 |
| 2 | 0.021 | 2 | 6.82 | 2 |
| 3 | 0.067 | 1 | 5.06 | 3 |
| 4 | 0.100 | 8 | 4.92 | 6 |
| 5 | 0.014 | 2 | 4.38 | 2 |
| 6 | 0.035 | 4 | 4.48 | 2 |
| 7 | 0.126 | 2 | NT | |
| 8 | 0.271 | 2 | 7.18 | 2 |
| 9 | 0.087 | 4 | 4.72 | 4 |
| 10 | 0.211 | 4 | 5.86 | 2 |
| 11 | 0.061 | 4 | 4.35 | 2 |
| 12 | 0.038 | 4 | 4.48 | 2 |
| 13 | 0.065 | 6 | 4.33 | 2 |
| 14 | 0.041 | 2 | 4.30 | 2 |
| 15 | 0.063 | 2 | 3.89 | 2 |
| 16 | 0.188 | 2 | 3.60 | 2 |
| 17 | 0.014 | 3 | 5.05 | 4 |
| 18 | 0.194 | 2 | 7.16 | 2 |
| 19 | 0.064 | 6 | 4.50 | 4 |
| 20 | NT | | NT | |
| 21 | 0.037 | 8 | 4.62 | 9 |
| 22 | 0.172 | 2 | 5.40 | 2 |
| 23 | 0.043 | 2 | 4.01 | 2 |
| 24 | 0.015 | 2 | 4.66 | 2 |
| 25 | 0.067 | 2 | 4.78 | 2 |
| 26 | 0.138 | 2 | 4.91 | 2 |
| 27 | 0.183 | 4 | 5.36 | 4 |
| 28 | 0.157 | 2 | 6.56 | 1 |

TABLE 4-continued

In Vitro Study Data

| Ex | Kd | n | IC$_{50}$ | n |
|---|---|---|---|---|
| 29 | 0.067 | 2 | 4.58 | 3 |
| 30 | 1.510 | 1 | 6.25 | 2 |
| 31 | 0.069 | 4 | 4.96 | 4 |
| 32 | 0.057 | 2 | 4.75 | 4 |
| 33 | 0.034 | 2 | 4.30 | 2 |
| 34 | 0.121 | 2 | 5.53 | 2 |
| 35 | 0.068 | 2 | 3.93 | 2 |
| 36 | 0.160 | 2 | 7.71 | 2 |
| 37 | 0.579 | 2 | 6.77 | 4 |
| 38 | 0.045 | 2 | 3.62 | 2 |
| 39 | 0.464 | 2 | 6.22 | 2 |
| 40 | 0.164 | 2 | 5.27 | 2 |
| 41 | 0.044 | 2 | 3.83 | 2 |
| 42 | 0.142 | 2 | 5.26 | 5 |
| 43 | 0.020 | 2 | 4.63 | 2 |
| 44 | 0.063 | 4 | 4.40 | 4 |
| 45 | 0.185 | 2 | 5.58 | 2 |
| 46 | 0.102 | 2 | 5.22 | 2 |
| 47 | 0.384 | 2 | 6.32 | 2 |
| 48 | 0.253 | 2 | 4.71 | 2 |
| 49 | 0.178 | 2 | 6.39 | 2 |
| 50 | 1.334 | 2 | 100.00 | 1 |
| 51 | 6.884 | 2 | 52.09 | 2 |
| 52 | 10.000 | 2 | 100.00 | 2 |
| 53 | 0.016 | 6 | 4.25 | 4 |
| 54 | 0.892 | 2 | 11.23 | 2 |
| 55 | 0.406 | 2 | 5.71 | 2 |
| 56 | 0.053 | 1 | 5.68 | 2 |
| 57 | 0.184 | 2 | 4.84 | 2 |
| 58 | 0.034 | 3 | 4.80 | 4 |
| 59 | 0.047 | 2 | 4.50 | 2 |
| 60 | 0.055 | 4 | 4.11 | 2 |
| 61 | 0.036 | 2 | 5.45 | 4 |
| 62 | 0.040 | 2 | NT | |
| 63 | 0.152 | 2 | 8.36 | 2 |
| 64 | 0.220 | 2 | 5.73 | 2 |
| 65 | 0.015 | 3 | 6.17 | 2 |
| 66 | NT | | NT | |
| 67 | 0.009 | 6 | 3.71 | 4 |
| 68 | 0.015 | 4 | 4.61 | 4 |
| 69 | 0.010 | 4 | 4.67 | 6 |
| 70 | 0.013 | 4 | 4.60 | 4 |
| 71 | 0.048 | 2 | 4.61 | 2 |
| 72 | 0.011 | 2 | 3.03 | 2 |
| 73 | 0.020 | 2 | 4.51 | 2 |
| 74 | 0.059 | 6 | 4.28 | 4 |
| 75 | 0.036 | 2 | 3.76 | 1 |
| 76 | 0.014 | 4 | 28.88 | 2 |
| 77 | 0.195 | 2 | 6.30 | 2 |
| 80 | 0.036 | 2 | NT | |

NT Not Tested

Co-Crystallization with HbA

The binding of the compound of Example 58 to hemoglobin (Hb) was further investigated through co-crystallization experiments. Given the structural and functional similarity of HbS and HbA, and the large quantity of material needed for structural studies, purified HbA was utilized for these studies.

HbA with Example 58 was crystallized according to published protocols (Lee et al. "Crowning proteins: modulating the protein surface properties using crown ethers", Angew Chem Int Ed Engl 2014; 53(48):13054-13058). Briefly, 20 mg/mL HbA in 20 mM Tris-HCl (pH 8.0) was mixed with equal volume of 50 mM 18-crown-6 solution and incubated at 20° C. for 20 minutes. Example 58 was then added to a final concentration of 1.5 mM and further incubated for an additional 1 hr. Crystallization was performed at 20° C. using hanging drop vapor diffusion method by mixing equal volumes of protein and reservoir solution containing 0.1 M Tris-HCl (pH 8.0), 0.2 M Li$_2$SO$_4$ and 30-32% PEG 3350. Crystals grew to their maximum size in ~2 days and the crystals were further soaked overnight with 10 mM Example 58. Diffraction data were collected at the Argonne National Laboratory Advanced Photon Source, beamline 17-ID. The data was processed using autoPROC (Global Phasing Limited) and the structure was solved using 3WHM (PDB code) as a starting model. Model building and refinement were carried out using COOT (Emsley P, Cowtan K. "Coot: model-building tools for molecular graphics", Acta Crystallogr D Biol Crystallogr 2004; 60(Pt 12 Pt 1):2126-32) and BUSTER (Global Phasing Limited). The final resolution of the structure was 1.85 angstroms (Å).

High-resolution (1.85 Å) co-crystal structure of Example 58 in complex with human HbA indicates that Ex 58 binds to the oxygenated (R state) conformation of Hb, and does so in a ditopic manner, with a compound to Hb tetramer stoichiometry of 2:1. These structural studies are consistent with the data reported in Table 4 above as regards binding interaction and the proposed mechanism of action for compounds of the invention, i.e. stabilization of the oxy (R state) of HbS and hence delay in polymerisation.

HbS Polymerization Assay

This assay is used to determine the degree of inhibition of polymerization of HbS by compounds of the invention at varying degrees of HbS occupancy. The method used for the assay was adapted from that described in He and Russell (He, Z. and J. E. Russell, "A high-Throughput Microplate Method for Assessing Aggregation of Deoxygenated Hemoglobin S Heterotetramers in Vitro", Anal Biochem 306(2): 349-352 (2002)).

Purified HbS was exchanged into 1.25 M potassium phosphate, pH=7.4 and concentrated to 1.1 mM. The hemoglobin concentration was fixed at 0.15 mM, and the HbS was diluted to the appropriate concentration using 1.25 M potassium phosphate, pH=7.4. The compound of the invention was added to 0.15 mM HbS in the following concentrations: 0.03 mM (10%), 0.075 mM (25%) and 0.15 mM (50%). As these compounds are ditopic binders, the concentration was doubled to calculate the % coverage, ie. 0.15*0.5=0.075*2=0.15. DMSO concentrations were matched for all compound concentrations, as well as no-compound control, and HbA. Following incubation, 33.5 μL of HbS solution was added to each well of a Costar 96-well half area plate. To induce deoxygenation, 16.5 μL of 1 M sodium dithionite, prepared in 1.25 M potassium phosphate, was added to each well for a final assay concentration of 330 mM, and mixed thoroughly. Fifty μL of mineral oil was overlaid over the solution in each well to prevent reoxygenation, and the plate was placed at 4° C. for five minutes. Following cold incubation, the plates were placed in a spectrophotometer that had been equilibrated at 37° C., to initiate the polymerization process (temperature jump). The reaction was monitored at 700 nm for 40 minutes, with data points collected every 30 seconds. Four wells were used for each condition, and the data averaged at every point for analysis. Data was analyzed using Graph Pad Prism, and the data was fit to a Boltzman sigmoidal equation, in which V50 (t1/2) was taken as the delay time. The percent change was calculated using the DMSO as the initial delay time. Error in percent change was compounded using the V50 errors generated when fit to the Boltzman sigmoidal equation.

Delay in HbS polymerization, as measured by increasing delay time as a function of % HbS occupancy (% HbS Occ), is reported in Table 5 below as the increase in delay time (DT) for 10%, 25% and 50% HbS occupancy (n=3).

TABLE 5

Increase in Delay Time of HbS Polymerization

| Ex | Increase in DT for 10% HbS Occ | Increase in DT for 25% HbS Occ | Increase in DT for 50% HbS Occ |
|---|---|---|---|
| 21 | NT | 64 ± 6% | NT |
| 58 | 18 ± 5% | 70 ± 8% | 74 ± 21% |

NT Not Tested

The high concentration dependence of HbS polymerization accounts for the non-linearity of the effects at higher HbS occupancy levels.

Whole Blood Oxygen Affinity Assay

Oxygen affinity is a marker of the ability of Hb to bind and release oxygen in solution. It can be determined in whole blood by measuring the percentage of oxygenated and deoxygenated Hb present at a given oxygen concentration. Oxygen affinity is expressed as the p50, the partial pressure of oxygen at which 50% of the Hb in solution has oxygen bound, or the p20, the partial pressure of oxygen at which 20% of the Hb in solution has oxygen bound. Stabilization of the oxygenated state of Hb in whole blood is demonstrated by shifts in the p20 and p50 values toward lower partial pressures of oxygen.

To determine the effects of compounds of the invention on oxygen affinity the p50 and p20 were measured in human, dog, and mouse whole blood using a Hemeox Analyzer (TCS Scientific). The blood was spiked with a compound of the invention to a concentration of 1 mM and incubated for 1 hour at 25 C with constant rotation. A concentration of 1 mM of compound was selected to approximate 20% hemoglobin occupancy in whole blood. Controls with the same concentration of DMSO, but no compound were incubated in the same way at the same time. Following incubation, samples were immediately assayed for oxygen affinity using the Hemox analyzer. Fifty μL of blood sample was diluted into 5 mL of hemox buffer (TCS Scientific), which had been pre-incubated to 37 C. Following dilution, samples were loaded into the analysis chamber, and fully oxygenated using compressed air. Once samples had reached an $pO_2$ of >150 torr, the measurement was initiated by switching to N2, and the percent oxyhemoglobin as a function of partial pressure was recorded. The p20 and p50 of each sample were recorded from the instrument readout. Data are reported as the percent (%) change relative to DMSO according to the following calculations:

$$\left[\frac{p20_{Ex} - p20_{DMSO}}{p20_{DMSO}}\right]*100 \ \&\ \left[\frac{p50_{Ex} - p50_{DMSO}}{p50_{DMSO}}\right]*100$$

Compounds of the invention reduced the p20 and p50 in whole blood from human, dog, and mouse, as set out in Table 6 below (samples were collected with at least an n of 2).

TABLE 6

Reduction in p20 and p50 (%)

| | Reduction in p20 (%) | | | Reduction in p50 (%) | | |
|---|---|---|---|---|---|---|
| Ex | Human | Dog | Mouse | Human | Dog | Mouse |
| 4 | 40 ± 4 | | | 7 ± 3 | | |
| 21 | 25 ± 9 | | | 14 ± 10 | | |

TABLE 6-continued

Reduction in p20 and p50 (%)

| | Reduction in p20 (%) | | | Reduction in p50 (%) | | |
|---|---|---|---|---|---|---|
| Ex | Human | Dog | Mouse | Human | Dog | Mouse |
| 27 | 70 ± 4 | | | 26 ± 1 | | |
| 58 | 24 ± 19 | 10 ± 6 | 11 ± 2 | 12 ± 9 | 6 ± 6 | 5 ± 3 |
| 61 | 14 ± 8 | | | 1 ± 6 | | |

In Vivo Studies

Mouse Model

The effect of the compounds of the invention was evaluated in-male sickle Townes mice in a single dose study. Compounds of the invention were administered in amounts set out in Tables 7, 8 and 9 that follow by oral gavage. Control mice received vehicle. Blood (50 μL) was drawn at 0.5 h, 1 h, 4 h, 7 h, 10 h, and 24 h. To measure exposure in whole blood, 20 μL sample was used. Blood drawn at 0.5 h was also evaluated for cell sickling.

Red Blood Cells (RBCs) from treated animals were diluted to ~$10^7$ cells/mL with 300 μL Hemeox solution in a 24-well plate and incubated in a hypoxia chamber, 5% $CO_2$ and 3% $O_2$ for 4 h. Cells were then fixed at room temperature for 30 minutes in sickling fixative solution and stained with TER119 alexa 488 conjugated antibody (BioLegend) for 30 minutes at room temperature, washed and plated at 50,000 cells/well with 200 μL of hemox buffer (TCS Scientific). Data were visualized using Graph Pad Prism (Version 5). Results are expressed as mean±standard error of the mean (SEM). Statistical analysis was made using a non-parametric one-way analysis of variance (ANOVA) followed by a Dunnett's multiple comparison. Significance was accepted when p<0.01.

For the chronic dosing study, 6-8 mice (Townes SCD mice) were dosed twice per day (BID) with either vehicle or compounds of the invention in vehicle in amounts set out in Tables 7, 8 and 9 that follow. Following 15 days of dosing, blood samples were collected from all animals to run in the Hemeox analyzer to generate oxygen affinity curves, complete blood analysis was performed using Idexx hematology Analyzer, and cell sickling assessed as described before. Soluble Vascular Adhesion Molecule 1 levels (sVCAM1) were assessed by Enzyme linked immunosorbent assay (ELISA) from R&D systems. Results are presented below in Tables 7, 8 and 9.

TABLE 7

Summary of In Vivo Pharmacological Results for the compound of Example 21
Response following a Single Dose of Example 21 at 0.5 h in SCD Mice (n = 3)

| Dose (mg/kg) | Blood Exposure (μM) | % Change in RBC Sickling |
|---|---|---|
| 30 | 14.7 | 2.03 |
| 100 | 302.8 | -0.02 |
| 300 | 1136.4 | 24.6 |
| 900 | 1502.7 | 29.0 |

Response Following BID Dosing of Example 21
(200 mg/kg) for 15 Days (n = 6-8)

| Parameter | Change |
|---|---|
| RBC sickling | 30.8 ± 14.5% decrease |
| p20 | 76.1 ± 13.9% decrease |

TABLE 7-continued

| | |
|---|---|
| p50 | 26.2 ± 9.7% decrease |
| Hb | 43.7 ± 9.83% increase |
| Hematocrit | 29.1 ± 11.2% increase |
| Reticulocytes | 32.7 ± 9.37% decrease |
| RBCs | 44.6 ± 9.04% increase |
| sVCAM 1 | 6.57 ± 3.75% decrease |

TABLE 8

Summary of In Vivo Pharmacological
Results for the compound of Example 27
Response following a Single Dose of
Example 27 at 0.5 h in SCD Mice (n = 3)

| Dose (mg/kg) | Blood Exposure (μM) | % Change in RBC Sickling |
|---|---|---|
| 5 | 7.4 | NT |
| 50 | 208 | NT |

Response Following BID Dosing of Example 27
(100 mg/kg) for 15 Days (n = 4-5)

| Parameter | Change |
|---|---|
| RBC sickling | 19.2 ± 5.4% decrease |
| p20 | 10.8 ± 3.8% decrease |
| p50 | 7.89 ± 3.36% decrease |
| Hb | 54.4 ± 8.7% increase |
| Hematocrit | 42.0 ± 12.7% increase |
| Reticulocytes | 18.4 ± 5.5% decrease |
| RBCs | 51.9 ± 8.3% increase |

NT = Not Tested

TABLE 9

Summary of In Vivo Pharmacological Results for
the compound of Example 58
Response following a Single Dose of Example 58
at 0.5 h in SCD Mice (n = 3)

| Dose (mg/kg) | Blood Exposure (μM) | % Change in RBC Sickling |
|---|---|---|
| 10 | 35.8 | −6.2 |
| 40 | 285 | 4.6 |
| 220 | 1450 | 50.8 |
| 490 | 2870 | 48.3 |

Response Following BID Dosing of Example 58
(200 mg/kg) for 15 Days (n = 6-8) *

| Parameter | Change |
|---|---|
| RBC sickling | 37.8 ± 9.0% decrease |
| p20 | 84.4 ± 2.6% decrease |
| p50 | 53.7 ± 21.2% decrease |
| Hb | 42.4 ± 4.2% increase |
| Hematocrit | 30.9 ± 0.7% increase |
| Reticulocytes | 54.7 ± 2.4% decrease |
| RBCs | 39.2 ± 9.3% increase |
| sVCAM1 | 9.98 ± 7.1% decrease |

* n = 6-7 were included the above calculations.

The invention claimed is:

1. A compound of formula (I)

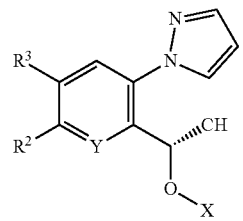

(I)

or a tautomer thereof, or a pharmaceutically acceptable salt of said compound or tautomer thereof, wherein X is an amino substituted naphthyridine or quinoline selected from

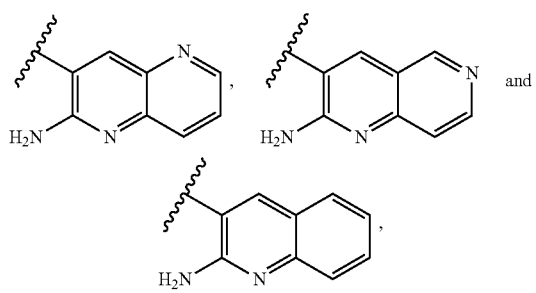

wherein the right-hand-side ring of said naphthyridine is optionally substituted by $R^1$, and wherein the right-hand-side ring of said quinoline is optionally independently substituted by one or two $R^1$;

Y is CH or N;

each $R^1$ is independently halogen; CN; $(C_1$-$C_4)$alkyl, optionally substituted by OH; or $CONR^4R^5$;

$R^2$ and $R^3$ together with the carbon atoms to which they are attached form a 5-membered heteroaryl containing one or two N, optionally substituted by $R^6$; or $R^2$ is H; OH; $(C_1$-$C_4)$alkyl, optionally substituted by OH or $CO_2R^4$; $(C_1$-$C_4)$alkyloxy, optionally substituted by OH or $CO_2R^4$; $CO_2R^4$; $CONR^4R^5$; $SO_2NR^4R^4$; $NR^4SO_2(C_1$-$C_4)$alkyl; or oxadiazolone;

$R^3$ is H or halogen;

each $R^4$ is independently H or $(C_1$-$C_4)$alkyl;

each $R^5$ is independently H; $(C_1$-$C_4)$alkyl, optionally substituted by OH, $O(C_1$-$C_4)$alkyl or $CO_2R^4$; $SO_2(C_1$-$C_4)$alkyl; or $(C_3$-$C_6)$cycloalkyl, optionally substituted by OH; and $R^6$ is $(C_1$-$C_4)$alkyl, optionally substituted by OH, $CO_2R^4$ or $CONR^4R^5$.

2. A compound of claim 1 or a tautomer thereof, or a pharmaceutically acceptable salt of said compound or tautomer thereof, wherein X is an amino substituted quinoline selected from

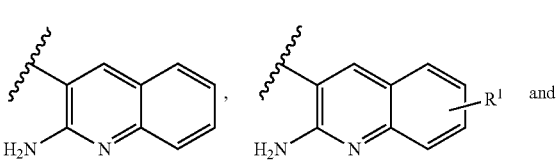

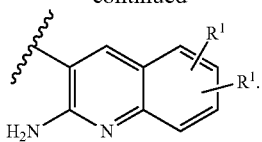

3. A compound of claim 2 or a tautomer thereof, or a pharmaceutically acceptable salt of said compound or tautomer thereof, wherein X is an amino substituted quinoline selected from

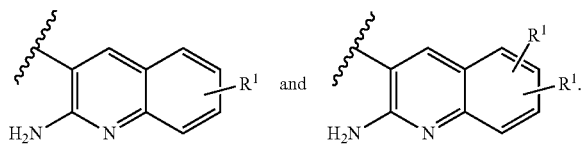

4. A compound of claim 3 or a tautomer thereof, or a pharmaceutically acceptable salt of said compound or tautomer thereof, wherein X is the amino substituted quinoline

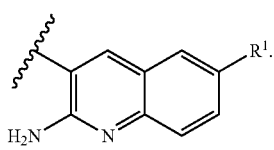

5. A compound of claim 3 or a tautomer thereof, or a pharmaceutically acceptable salt of said compound or tautomer thereof, wherein X is the amino substituted quinoline

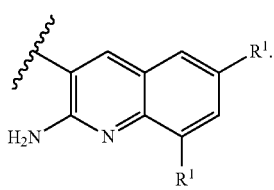

6. A compound of claim 1 or a tautomer thereof, or a pharmaceutically acceptable salt of said compound or tautomer thereof, wherein X is an amino substituted naphthyridine selected from

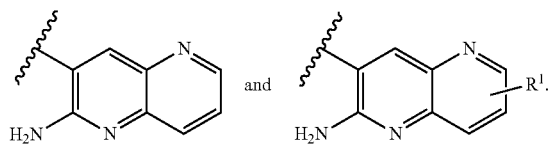

7. A compound of claim 1 or a tautomer thereof, or a pharmaceutically acceptable salt of said compound or tautomer thereof, wherein each $R^1$ is independently F, C, Br, CN, $CH_3$ or $CONH_2$.

8. A compound of claim 7 or a tautomer thereof, or a pharmaceutically acceptable salt of said compound or tautomer thereof, wherein each $R^1$ is independently F, Cl or $CONH_2$.

9. A compound of claim 1 or a tautomer thereof, or a pharmaceutically acceptable salt of said compound or tautomer thereof, wherein Y is CH.

10. A compound of claim 1 or a tautomer thereof, or a pharmaceutically acceptable salt of said compound or tautomer thereof, wherein Y is N.

11. A compound of claim 9 or claim 10 or a tautomer thereof, or a pharmaceutically acceptable salt of said compound or tautomer thereof, wherein $R^2$ and $R^3$ together with the carbon atoms to which they are attached form a 5-membered heteroaryl selected from

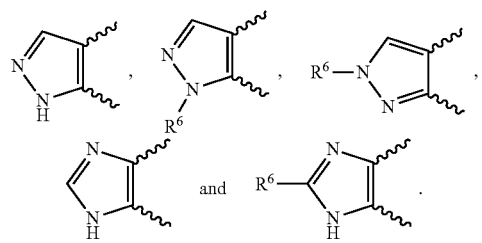

12. A compound of claim 11 or a tautomer thereof, or a pharmaceutically acceptable salt of said compound or tautomer thereof, wherein $R^2$ and $R^3$ together with the carbon atoms to which they are attached form a pyrazolyl selected from

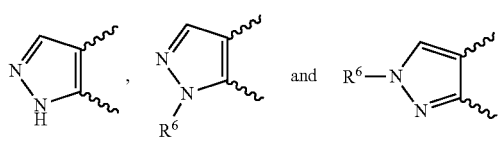

13. A compound of claim 9 or a tautomer thereof, or a pharmaceutically acceptable salt of said compound or tautomer thereof, wherein $R^2$ is $(C_1-C_4)$alkyl substituted by $CO_2R^4$; $(C_1-C_4)$alkyloxy substituted by $CO_2R^4$; $CO_2R^4$; $CONR^4R^5$; $SO_2NR^4R^4$; or oxadiazolone.

14. A compound of claim 10 or a tautomer thereof, or a pharmaceutically acceptable salt of said compound or tautomer thereof, wherein $R^2$ is H; OH; $(C_1-C_4)$alkyl substituted by OH; $(C_1-C_4)$alkyloxy; $(C_1-C_4)$alkyloxy substituted by OH or $CO_2R^4$; $CO_2R^4$; or $CONR^4R^5$.

15. A compound of claim 1 or a tautomer thereof, or a pharmaceutically acceptable salt of said compound or tautomer thereof, wherein $R^3$ is H or F.

16. A compound of claim 1 or a tautomer thereof, or a pharmaceutically acceptable salt of said compound or tautomer thereof, wherein $R^4$ is H or methyl.

17. A compound of claim 1 or a tautomer thereof, or a pharmaceutically acceptable salt of said compound or tautomer thereof, wherein $R^5$ is H or methyl.

18. A compound according to claim 1, or a pharmaceutically acceptable salt thereof, selected from:
3-{(1S)-1-[(2-amino-6,8-difluoroquinolin-3-yl)oxy]ethyl}-4-(1H-pyrazol-1-yl)benzoic acid;
6-{(1S)-1-[(2-amino-6-fluoroquinolin-3-yl)oxy]ethyl}-5-(1H-pyrazol-1-yl)pyridin-2-ol;
(S)-6-(1-((2-amino-6-fluoroquinolin-3-yl)oxy)ethyl)-5-(1H-pyrazol-1-yl)pyridin-2(1H)-one; and
2-amino-7-fluoro-3-{(1S)-1-[5-(1H-pyrazol-1-yl)-1H-pyrazolo[3,4-b]pyridin-6-yl]ethoxy}quinoline-6-carboxamide.

19. A compound that is (S)-6-(1-((2-amino-6-fluoroquinolin-3-yl)oxy)ethyl)-5-(1H-pyrazol-1-yl)pyridin-2(1H)-one or a tautomer thereof, or a pharmaceutically acceptable salt of said compound or tautomer thereof.

20. A compound that is (S)-6-(1-((2-amino-6-fluoroquinolin-3-yl)oxy)ethyl)-5-(1H-pyrazol-1-yl)pyridin-2(1H)-one or a tautomer thereof.

21. A compound that is (S)-6-(1-((2-amino-6-fluoroquinolin-3-yl)oxy)ethyl)-5-(1H-pyrazol-1-yl(pyridin-2(1H)-one or a pharmaceutically acceptable salt thereof.

22. A compound that is (S)-6-(1-((2-amino-6-fluoroquinolin-3-yl)oxy)ethyl)-5-(1H-pyrazol-1-yl)pyridin-2(1H)-one.

23. A pharmaceutical composition comprising a compound according to claim 19 or a tautomer thereof, or a pharmaceutically acceptable salt of said compound or tautomer thereof, and a pharmaceutically acceptable excipient.

24. The pharmaceutical composition according to claim 23 further comprising one or more additional therapeutic agents.

25. A method of treating sickle cell disease in a human or animal, comprising administering to said human or animal a therapeutically effective amount of a compound according to claim 19 or a tautomer thereof, or a pharmaceutically acceptable salt thereof of said compound or tautomer.

26. A pharmaceutical composition comprising a compound according to claim 18, or a pharmaceutically acceptable salt thereof, in combination with pharmaceutically acceptable excipient.

27. The compound 6-{(1S)-1-[(2-amino-6-fluoroquinolin-3-yl)oxy]ethyl}-5-(1H-pyrazol-1-yl)pyridin-2-ol, or a pharmaceutically acceptable salt thereof.

28. The compound 6-{(1S)-1-[(2-amino-6-fluoroquinolin-3-yl)oxy]ethyl}-5-(1H-pyrazol-1-yl)pyridin-2-ol.

\* \* \* \* \*